US012807684B2

(12) United States Patent
Weiner et al.

(10) Patent No.: US 12,807,684 B2
(45) Date of Patent: Nov. 24, 2026

(54) DNA ANTIBODY CONSTRUCTS FOR USE AGAINST HIV

(71) Applicants: The Wistar Institute of Anatomy and Biology, Philadelphia, PA (US); INOVIO PHARMACEUTICALS, INC., Plymouth Meeting, PA (US)

(72) Inventors: David Weiner, Merion, PA (US); Megan Wise, Glenside, PA (US)

(73) Assignees: The Wistar Institute of Anatomy and Biology, Philadelphia, PA (US); Inovio Pharmaceuticals, Inc., Plymouth Meeting, PA (US)

( * ) Notice: Subject to any disclaimer, the term of this patent is extended or adjusted under 35 U.S.C. 154(b) by 66 days.

(21) Appl. No.: 18/526,819

(22) Filed: Dec. 1, 2023

(65) Prior Publication Data

US 2024/0124559 A1 Apr. 18, 2024

Related U.S. Application Data

(63) Continuation of application No. 16/497,945, filed as application No. PCT/US2018/024520 on Mar. 27, 2018, now Pat. No. 11,845,787.

(60) Provisional application No. 62/477,277, filed on Mar. 27, 2017, provisional application No. 62/477,217, filed on Mar. 27, 2017.

(51) Int. Cl.
*A61K 39/10* (2006.01)
*A61P 31/18* (2006.01)
*C07K 16/10* (2026.01)
*C07K 16/114* (2026.01)

(52) U.S. Cl.
CPC ............ *C07K 16/114* (2026.01); *A61P 31/18* (2018.01); *C07K 2317/55* (2013.01); *C07K 2317/76* (2013.01)

(58) Field of Classification Search
CPC ................................ A61K 39/42; A61P 31/18
See application file for complete search history.

(56) References Cited

U.S. PATENT DOCUMENTS

| | | | | |
|---|---|---|---|---|
| 8,333,971 B2 | 12/2012 | Goldenberg | | |
| 11,129,905 B2 * | 9/2021 | Yang | .................. | A61K 47/6881 |
| 2007/0264265 A1 | 11/2007 | Goldenberg | | |
| 2012/0020988 A1 | 1/2012 | Auer | | |
| 2015/0152167 A1 | 6/2015 | Ho | | |

FOREIGN PATENT DOCUMENTS

| | | | | |
|---|---|---|---|---|
| WO | WO2016/054296 * | 4/2016 | ............. | A61K 39/00 |
| WO | 2016089862 A1 | 6/2016 | | |

OTHER PUBLICATIONS

Sok et al. (PNAS, 2014, vol. 111, p. 17624-17629).*
Muthumani et al. (Human Vaccines and Immunotherapeutics, 2013, p. 2253-2262 in IDS on Sep. 4, 2025).*
Muthumani et al., 2013, "Optimized and enhanced DNA plasmid vector based in vivo construction of a neutralizing antiHIV-1 envelope glycoprotein Fab," Human Vaccines & Immunotherapeutics, 9:10, 2253-2262.
Pardi et al. 2017, "Administration of nucleoside-modified mRNA encoding broadly neutralizing antibody protects humanized mice from HIV-1 challenge," Nature Communications, 8:14630 (pp. 1-8).
Silva et al., "The S228P mutation prevents in vivo and in vitro IgG4 Fab-arm exchange as demonstrated using a combination of novel quantitative immunoassays and physiological matrix preparation", J Biol Chem., (Feb. 27, 2015), vol. 290, No. 9, pp. 5462-5469, XP055299482.

* cited by examiner

*Primary Examiner* — Agnieszka Boesen
(74) *Attorney, Agent, or Firm* — Riverside Law LLP

(57) ABSTRACT

Disclosed herein is a composition including a recombinant nucleic acid sequence that encodes an antibody to an HIV antigen. Also disclosed herein is a method of generating a synthetic antibody in a subject by administering the composition to the subject. The disclosure also provides a method of preventing and/or treating an HIV infection in a subject using said composition and method of generation.

13 Claims, 15 Drawing Sheets

Specification includes a Sequence Listing.

B

A

| | Tier | Clade | Chuang: VRC01 $IC_{50}$ (μg/ml) | Huang: PGT128 $IC_{50}$ (μg/ml) | Chuang: PG9 $IC_{50}$ (μg/ml) | Chuang: 3BNC117 $IC_{50}$ (μg/ml) | Chuang: NIH45-46 $IC_{50}$ (μg/ml) |
|---|---|---|---|---|---|---|---|
| CAP210.0 | 2 | C | >50 | >50 | 0.087 | 8.16 | >50 |
| DU172 | 2 | C | >50 | 0.044 | 0.262 | 0.289 | >50 |
| Q168ENV | 2 | A1 | 0.150 | >50 | 0.106 | 0.050 | 0.138 |
| Q461ENV | 2 | A1 | 0.339 | >50 | 3.010 | 0.069 | 0.212 |
| QH0692 | 2 | B | 1.840 | 0.046 | >50 | 0.275 | 0.991 |
| WITO | 2 | B | 0.110 | >50 | 0.023 | 0.030 | 0.037 |
| ZM249 | 2 | C | 0.062 | 10.7 | 0.033 | 0.039 | 0.038 |

B

| | | | VRC01 | | PGT128 | | PG9 | | 3BNC117 | | NIH45-46 | |
|---|---|---|---|---|---|---|---|---|---|---|---|---|
| | Tier | Clade | IgG1 | IgG4 | IgG1 | IgG4 | IgG1 | IgG4 | IgG1 | IgG4 | IgG1 | IgG4 |
| CAP210.0 | 2 | C | >20 | >20 | >20 | >20 | 0.35 | 0.357 | >20 | >20 | >20 | >20 |
| DU172 | 2 | C | >20 | >20 | 0.025 | 0.029 | 0.15 | 0.192 | 0.303 | 0.435 | >20 | >20 |
| Q168ENV | 2 | A1 | 0.219 | 0.233 | >20 | >20 | 0.009 | 0.011 | 0.046 | 0.087 | 0.066 | 0.128 |
| Q461ENV | 2 | A1 | 0.439 | 0.56 | >20 | >20 | 0.301 | 0.434 | 0.062 | 0.109 | 0.121 | 0.23 |
| QH0692 | 2 | B | >20 | >20 | 0.018 | 0.024 | >20 | >20 | 0.303 | 0.435 | 0.52 | 0.69 |
| WITO | 2 | B | 0.399 | 0.451 | >20 | >20 | 0.006 | 0.008 | 0.089 | 0.117 | 0.133 | 0.255 |
| ZM249 | 2 | C | 0.121 | 0.116 | >20 | >20 | 0.131 | 0.4 | 0.126 | 0.217 | 0.022 | 0.033 |

Figure 11 A - Figure 11B

SEQUENCE LISTING

```
Sequence total quantity: 152
SEQ ID NO: 1            moltype = AA  length = 727
FEATURE                 Location/Qualifiers
REGION                  1..727
                        note = 3BNC117 human IgG1 antibody
source                  1..727
                        mol_type = protein
                        organism = synthetic construct
SEQUENCE: 1
MDWTWRILFL VAAATGTHAQ VQLLQSGAAV TKPGASVRVS CEASGYNIRD YFIHWWRQAP  60
GQGLQWVGWI NPKTGQPNNP RQFQGRVSLT RHASWDFDTF SFYMDLKALR SDDTAVYFCA  120
RQRSDYWDFD VWGSGTQVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSCDKTHT CPPCPAPELL GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GKRGRKRRSG  480
SGATNFSLLK QAGDVEENPG PMVLQTQVFI SLLLWISGAY GDIQMTQSPS SLSASVGDTV  540
TITCQANGYL NWYQQRRGKA PKLLIYDGSK LERGVPSRFS GRRWGQEYNL TINNLQPEDI  600
ATYFCQVYEF VVPGTRLDLK RTVAAPSVFI FPPSDEQLKS GTASVVCLLN NFYPREAKVQ  660
WKVDNALQSG NSQESVTEQD SKDSTYSLSS TLTLSKADYE KHKVYACEVT HQGLRSPVTK  720
SFNRGEC                                                           727

SEQ ID NO: 2            moltype = DNA  length = 2205
FEATURE                 Location/Qualifiers
misc_feature            1..2205
                        note = 3BNC117 human IgG1 antibody
source                  1..2205
                        mol_type = other DNA
                        organism = synthetic construct
SEQUENCE: 2
ggatccgcca ccatggattg gacatggaga attctgtttc tggtcgccgc cgctaccgga  60
actcacgctc aggtgcagct gctgcagtca ggggccgcag tgacaaagcc aggggcaagt  120
gtccgcgtgt catgcgaggc cagcggctac aacatccggg actatttcat tcactggtgg  180
cgacaggcac ctggacaggg actgcagtgg gtggggtgga tcaatccaaa gaccggccag  240
cccaacaatc ctaggcagtt ccagggcaga gtgagcctga cccggcatgc ttcctgggac  300
tttgatacat tctcttttta catggacctg aaggcactga ggagtgacga taccgccgtg  360
tacttctgcg ctagacagcg gtcagattat tgggactttg acgtgtgggg cagcggaact  420
caggtcaccg tgagctccgc cagtacaaag ggaccttcag tgtttccact ggctccctct  480
agtaaaagca catccggcgg aactgccgct ctgggatgtc tggtgaagga ctacttccct  540
gagccagtca ccgtgtcctg gaactctgga gctctgacta gcggggtcca cacctttcca  600
gcagtgctgc agtcaagcgg cctgtactcc ctgtcctctg tggtcactgt ccccagttca  660
agcctgggaa ctcagaccta tatctgcaac gtgaatcaca agccaagtaa taccaaagtc  720
gacaagaaag tggagcccaa gtcctgtgat aaaacacata cttgccctcc ctgtccagct  780
cctgaactgc tgggcggccc aagcgtgttc ctgtttccac ccaagcctaa agacactctg  840
atgatttcta gaacccctga ggtcacatgc gtggtcgtgg acgtgagcca cgaggacccc  900
gaagtcaagt tcaactggta cgtggatggc gtcgaagtgc ataatgccaa gaccaaaccc  960
cgagaggaac agtacaactc tacttatagg gtcgtgagtg tcctgaccgt gctgcaccag  1020
gactggctga acggcaagga gtataagtgc aaagtgtcca ataaggctct gccagcaccc  1080
atcgaaaaaa caatttctaa ggccaaagga cagcctagag agccacaggt gtacactctg  1140
cctccatccc gggacgaact gacaaagaac caggtctctc tgacttgtct ggtgaaagga  1200
ttctatccca gcgatatcgc tgtggagtgg gaatccaatg ggcagcctga gaacaattac  1260
aagaccacac cccctgtgct ggacagtgat gggtcattct ttctgtattc caagctgaca  1320
gtggacaaat ctcggtggca gcagggcaac gtcttttctt gcagtgtgat gcatgaagcc  1380
ctgcacaatc attacacaca gaagtcactg agcctgtccc caggaaagcg aggacgaaaa  1440
aggagatctg ggagtggcgc tactaacttc tctctgctga aacaggcagg agatgtggag  1500
gaaaatcctg ggccaatggt cctgcagacc caggtgttta tctcactgct gctgtggatt  1560
agcggcgcat atggagacat ccagatgaca cagagccctt cctctctgtc agcaagcgtc  1620
ggcgataccg tgacaattac ttgtcaggcc aacggctacc tgaattggta tcagcagcgg  1680
cgcggaaagg ctcccaaact gctgatctac gacggctcca agctggagcg cggagtgcct  1740
agccgattct ccgggcgaag gtggggacag gagtataacc tgactatcaa caatctgcag  1800
cctgaagata ttgccaccta cttctgccag gtgtatgagt ttgtcgtgcc agggaccagg  1860
ctggacctga agagaacagt cgcagccccc agcgtgttca tctttccacc ctcagatgag  1920
cagctgaaat ccggaaccgc ctctgtggtg tgcctgctga acaacttcta cccacgcgaa  1980
gccaaggtcc agtggaaagt ggacaacgct ctgcagtctg gcaatagtca ggagtcagtg  2040
acagaacagg acagcaagga ttccacttat tctctgagtt caaccctgac actgtccaaa  2100
gcagattacg agaagcacaa agtgtatgcc tgcgaggtca cccaccaggg gctgcggtca  2160
ccagtcacaa agtccttcaa cagaggggaa tgctgataac tcgag                 2205

SEQ ID NO: 3            moltype = AA  length = 472
FEATURE                 Location/Qualifiers
REGION                  1..472
                        note = 3BNC117 human IgG1 antibody (heavy chain) (mod1)
source                  1..472
                        mol_type = protein
                        organism = synthetic construct
SEQUENCE: 3
MDWTWRILFL VAAATGTHAQ VQLLQSGAAV TKPGASVRVS CEASGYNIRD YFIHWWRQAP  60
```

```
GQGLQWVGWI NPKTGQPNNP RQFQGRVSLT RHASWDFDTF SFYMDLKALR SDDTAVYFCA  120
RQRSDYWDFD VWGSGTQVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSCDKTHT CPPCPAPELL GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 4            moltype = DNA  length = 1440
FEATURE                 Location/Qualifiers
misc_feature            1..1440
                        note = 3BNC117 human IgG1 antibody (heavy chain) (mod1)
source                  1..1440
                        mol_type = other DNA
                        organism = synthetic construct
SEQUENCE: 4
ggatccgcca ccatggattg gacatggaga attctgtttc tggtcgccgc cgctaccgga  60
actcacgctc aggtgcagct gctgcagtca ggggccgcag tgacaaagcc aggggcaagt  120
gtccgcgtgt catgcgaggc cagcggctac aacatccggg actatttcat tcactggtgg  180
cgacaggcac ctggacaggg actgcagtgg gtggggtgga tcaatccaaa gaccggccag  240
cccaacaatc ctaggcagtt ccagggcaga gtgagcctga cccggcatgc ttcctgggac  300
tttgatacat tctcttttta catggacctg aaggcactga ggagtgacga taccgccgtg  360
tacttctgcg ctagacagcg gtcagattat tgggactttg acgtgtgggg cagcggaact  420
caggtcaccg tgagctccgc cagtacaaag ggaccttcag tgtttccact ggctccctct  480
agtaaaagca catccggcgg aactgccgct ctgggatgtc tggtgaagga ctacttccct  540
gagccagtca ccgtgtcctg gaactctgga gctctgacta gcggggtcca cacctttcca  600
gcagtgctgc agtcaagcgg cctgtactcc ctgtcctctg tggtcactgt ccccagttca  660
agcctgggaa ctcagaccta tatctgcaac gtgaatcaca agccaagtaa taccaaagtc  720
gacaagaaag tggagcccaa gtcctgtgat aaaacacata cttgccctcc ctgtccagct  780
cctgaactgc tgggcggccc aagcgtgttc ctgtttccac ccaagcctaa agacactctg  840
atgatttcta gaacccctga ggtcacatgc gtggtcgtgg acgtgagcca cgaggacccc  900
gaagtcaagt tcaactggta cgtggatggc gtcgaagtgc ataatgccaa gaccaaaccc  960
cgagaggaac agtacaactc tacttatagg gtcgtgagtg tcctgaccgt gctgcaccag  1020
gactggctga acggcaagga gtataagtgc aaagtgtcca ataaggctct gccagcaccc  1080
atcgaaaaaa caatttctaa ggccaaagga cagcctagag agccacaggt gtacactctg  1140
cctccatccc gggacgaact gacaaagaac caggtctctc tgacttgtct ggtgaaagga  1200
ttctatccca gcgatatcgc tgtggagtgg gaatccaatg ggcagcctga gaacaattac  1260
aagaccacac cccctgtgct ggacagtgat gggtcattct ttctgtattc caagctgaca  1320
gtggacaaat ctcggtggca gcagggcaac gtcttttctt gcagtgtgat gcatgaagcc  1380
ctgcacaatc attacacaca gaagtcactg agcctgtccc caggaaagtg ataactcgag  1440

SEQ ID NO: 5            moltype = AA  length = 226
FEATURE                 Location/Qualifiers
REGION                  1..226
                        note = 3BNC117 human IgG1 antibody (light chain) (mod1)
source                  1..226
                        mol_type = protein
                        organism = synthetic construct
SEQUENCE: 5
MVLQTQVFIS LLLWISGAYG DIQMTQSPSS LSASVGDTVT ITCQANGYLN WYQQRRGKAP  60
KLLIYDGSKL ERGVPSRFSG RRWGQEYNLT INNLQPEDIA TYFCQVYEFV VPGTRLDLKR  120
TVAAPSVFIF PPSDEQLKSG TASVVCLLNN FYPREAKVQW KVDNALQSGN SQESVTEQDS  180
KDSTYSLSST LTLSKADYEK HKVYACEVTH QGLRSPVTKS FNRGEC                226

SEQ ID NO: 6            moltype = DNA  length = 702
FEATURE                 Location/Qualifiers
misc_feature            1..702
                        note = 3BNC117 human IgG1 antibody (light chain) (mod1)
source                  1..702
                        mol_type = other DNA
                        organism = synthetic construct
SEQUENCE: 6
ggatccgcca ccatggtcct gcagacccag gtgtttatct cactgctgct gtggattagc  60
ggcgcatatg gagacatcca gatgacacag agcccttcct ctctgtcagc aagcgtcggc  120
gataccgtga caattacttg tcaggccaac ggctacctga attggtatca gcagcggcgc  180
ggaaaggctc ccaaactgct gatctacgac ggctccaagc tggagcgcgg agtgcctagc  240
cgattctccg ggcgaaggtg gggacaggag tataacctga ctatcaacaa tctgcagcct  300
gaagatattg ccacctactt ctgccaggtg tatgagtttg tcgtgccagg gaccaggctg  360
gacctgaaga gaacagtcgc agcccccagc gtgttcatct ttccaccctc agatgagcag  420
ctgaaatccg gaaccgcctc tgtggtgtgc ctgctgaaca acttctaccc acgcgaagcc  480
aaggtccagt ggaaagtgga caacgctctg cagtctggca atagtcagga gtcagtgaca  540
gaacaggaca gcaaggattc cacttattct ctgagttcaa ccctgacact gtccaaagca  600
gattacgaga agcacaaagt gtatgcctgc gaggtcaccc accaggggct gcggtcacca  660
gtcacaaagt ccttcaacag aggggaatgc tgataactcg ag                    702

SEQ ID NO: 7            moltype = AA  length = 724
FEATURE                 Location/Qualifiers
REGION                  1..724
                        note = 3BNC117 human IgG4 (mod 2)
```

-continued

```
source                  1..724
                        mol_type = protein
                        organism = synthetic construct
SEQUENCE: 7
MDWTWRILFL VAAATGTHAQ VQLLQSGAAV TKPGASVRVS CEASGYNIRD YFIHWWRQAP  60
GQGLQWVGWI NPKTGQPNNP RQFQGRVSLT RHASWDFDTF SFYMDLKALR SDDTAVYFCA  120
RQRSDYWDFD VWGSGTQVTV SSASTKGPSV FPLAPCSRST SESTAALGCL VKDYFPEPVT  180
VSWNSGALTS GVHTFPAVLQ SSGLYSLSSV VTVPSSSLGT KTYTCNVDHK PSNTKVDKRV  240
ESKYGPPCPS CPAPEFLGGP SVFLFPPKPK DTLMISRTPE VTCVVVDVSQ EDPEVQFNWY  300
VDGVEVHNAK TKPREEQFNS TYRVVSVLTV LHQDWLNGKE YKCKVSNKGL PSSIEKTISK  360
AKGQPREPQV YTLPPSQEEM TKNQVSLTCL VKGFYPSDIA VEWESNGQPE NNYKTTPPVL  420
DSDGSFFLYS RLTVDKSRWQ EGNVFSCSVM HEALHNHYTQ KSLSLSLGKR GRKRRSGSGA  480
TNFSLLKQAG DVEENPGPMV LQTQVFISLL LWISGAYGDI QMTQSPSSLS ASVGDTVTIT  540
CQANGYLNWY QQRRGKAPKL LIYDGSKLER GVPSRFSGRR WGQEYNLTIN NLQPEDIATY  600
FCQVYEFVVP GTRLDLKRTV AAPSVFIFPP SDEQLKSGTA SVVCLLNNFY PREAKVQWKV  660
DNALQSGNSQ ESVTEQDSKD STYSLSNTLT LSKADYEKHK VYACEVTHQG LSSPVTKSFN  720
RGEC                                                              724

SEQ ID NO: 8            moltype = DNA  length = 2196
FEATURE                 Location/Qualifiers
misc_feature            1..2196
                        note = 3BNC117 human IgG4 (mod 2)
source                  1..2196
                        mol_type = other DNA
                        organism = synthetic construct
SEQUENCE: 8
ggatccgcca ccatggactg gacctggcgc atcctgttcc tggtggcagc agcaaccgga  60
acacacgcac aggtgcagct gctgcagagc ggagcagcag tgacaaagcc aggagcatct  120
gtgagggtga gctgcgaggc atccggctac aacatccgcg attacttcat ccactggtgg  180
aggcaggcac caggacaggg actgcagtgg gtgggctgga tcaatcctaa gaccggccag  240
cctaacaatc caaggcagtt ccagggacgc gtgagcctga ccaggcacgc ctcctgggac  300
tttgatacat tctcttttta catggacctg aaggccctgc gcagcgacga taccgccgtg  360
tacttctgtg cccggcagag gagcgattat tgggactttg acgtgtgggg ctctggcacc  420
caggtgacag tgagctccgc ctccacaaag ggaccaagcg tgttcccact ggcaccttgc  480
agcaggtcca cctctgagag cacagccgcc ctgggctgtc tggtgaagga ctacttccct  540
gagccagtga ccgtgagctg gaactccggc gccctgacca gcggagtgca cacatttccc  600
gccgtgctgc agtctagcgg cctgtactcc ctgtcctctg tggtgaccgt gcctagctcc  660
tctctgggca ccaagacata tacctgcaac gtggaccaca agccaagcaa tacaaaggtg  720
gataagagag tggagtccaa gtacggccct ccctgccctt cttgtccagc acctgagttc  780
ctgggcggcc cttccgtgtt cctgtttcca cccaagccaa aggacaccct gatgatctct  840
cggacccccg aggtgacatg cgtggtggtg gacgtgagcc aggaggaccc cgaggtgcag  900
ttcaactggt acgtggatgg cgtggaggtg cacaatgcca agacaaagcc cagagaggag  960
cagtttaact ctacctaccg ggtggtgagc gtgctgacag tgctgcacca ggactggctg  1020
aacggcaagg agtataagtg caaggtgtcc aataagggcc tgcctagctc catcgagaag  1080
accatctcta aggcaaaggg acagccacgc gagccacagg tgtacacact gcctccaagc  1140
caggaggaga tgaccaagaa ccaggtgtcc ctgacatgtc tggtgaaggg cttctatcca  1200
agcgacatcg ccgtggagtg ggagtccaat ggccagcccg agaacaatta caagaccaca  1260
ccccctgtgc tggactctga tggcagcttc tttctgtata gcagactgac cgtggataag  1320
tcccggtggc aggagggcaa cgtgttttcc tgctctgtga tgcacgaggc cctgcacaat  1380
cactacaccc agaagagcct gtccctgtct ctgggcaaga ggggcagaaa gaggagaagc  1440
ggctccggcg ccacaaactt cagcctgctg aagcaggcag gcgacgtgga ggagaatcca  1500
ggacccatgg tgctgcagac ccaggtgttt atctccctgc tgctgtggat ctctggcgcc  1560
tatggcgaca tccagatgac acagtccccc tctagcctgt ctgccagcgt gggcgataca  1620
gtgaccatca catgtcaggc caacggctac ctgaattggt atcagcagag gaggggcaag  1680
gcaccaaagc tgctgatcta cgacggcagc aagctggaga gaggcgtgcc ctcccggttc  1740
tctggcagga gatggggcca ggagtataac ctgaccatca acaatctgca gcctgaggat  1800
atcgccacat acttctgcca ggtgtatgag tttgtggtgc ctggcacccg cctggacctg  1860
aagaggacag tggccgcccc aagcgtgttc atctttccac ccagcgatga gcagctgaag  1920
tctggcaccg ccagcgtggt gtgcctgctg aacaatttct acccaagaga ggccaaggtg  1980
cagtggaagg tggacaacgc cctgcagagc ggcaattccc aggagtctgt gaccgagcag  2040
gacagcaagg attccacata ttccctgtct aacaccctga cactgagcaa ggccgattac  2100
gagaagcaca aggtgtatgc atgcgaggtg acccaccagg gactgtcctc tcctgtgaca  2160
aagtccttta atcggggcga gtgttgataa ctcgag                            2196

SEQ ID NO: 9            moltype = AA  length = 724
FEATURE                 Location/Qualifiers
REGION                  1..724
                        note = 3BNC117 human IgG4 (S228P) (mod 3)
source                  1..724
                        mol_type = protein
                        organism = synthetic construct
SEQUENCE: 9
MDWTWRILFL VAAATGTHAQ VQLLQSGAAV TKPGASVRVS CEASGYNIRD YFIHWWRQAP  60
GQGLQWVGWI NPKTGQPNNP RQFQGRVSLT RHASWDFDTF SFYMDLKALR SDDTAVYFCA  120
RQRSDYWDFD VWGSGTQVTV SSASTKGPSV FPLAPCSRST SESTAALGCL VKDYFPEPVT  180
VSWNSGALTS GVHTFPAVLQ SSGLYSLSSV VTVPSSSLGT KTYTCNVDHK PSNTKVDKRV  240
ESKYGPPCPP CPAPEFLGGP SVFLFPPKPK DTLMISRTPE VTCVVVDVSQ EDPEVQFNWY  300
VDGVEVHNAK TKPREEQFNS TYRVVSVLTV LHQDWLNGKE YKCKVSNKGL PSSIEKTISK  360
AKGQPREPQV YTLPPSQEEM TKNQVSLTCL VKGFYPSDIA VEWESNGQPE NNYKTTPPVL  420
```

```
DSDGSFFLYS RLTVDKSRWQ EGNVFSCSVM HEALHNHYTQ KSLSLSLGKR GRKRRSGSGA  480
TNFSLLKQAG DVEENPGPMV LQTQVFISLL LWISGAYGDI QMTQSPSSLS ASVGDTVTIT  540
CQANGYLNWY QQRRGKAPKL LIYDGSKLER GVPSRFSGRR WGQEYNLTIN NLQPEDIATY  600
FCQVYEFVVP GTRLDLKRTV AAPSVFIFPP SDEQLKSGTA SVVCLLNNFY PREAKVQWKV  660
DNALQSGNSQ ESVTEQDSKD STYSLSNTLT LSKADYEKHK VYACEVTHQG LSSPVTKSFN  720
RGEC                                                               724

SEQ ID NO: 10          moltype = DNA  length = 2196
FEATURE                Location/Qualifiers
misc_feature           1..2196
                       note = 3BNC117 human IgG4 (S228P) (mod 3)
source                 1..2196
                       mol_type = other DNA
                       organism = synthetic construct
SEQUENCE: 10
ggatccgcca ccatggactg gacctggcgc atcctgttcc tggtggcagc agcaaccgga  60
acacacgcac aggtgcagct gctgcagagc ggagcagcag tgacaaagcc aggagcatct  120
gtgagggtga gctgcgaggc atccggctac aacatccgcg attacttcat ccactggtgg  180
aggcaggcac caggacaggg actgcagtgg gtgggctgga tcaatcctaa gaccggccag  240
cctaacaatc caaggcagtt ccagggacgc gtgagcctga ccaggcacgc ctcctgggac  300
tttgatacat tctcttttta catggacctg aaggccctgc gcagcgacga taccgccgtg  360
tacttctgtg cccggcagag gagcgattat tgggactttg acgtgtgggg ctctggcacc  420
caggtgacag tgagctccgc ctccacaaag ggaccaagcg tgttcccact ggcaccttgc  480
agcaggtcca cctctgagag cacagccgcc ctgggctgtc tggtgaagga ctacttccct  540
gagccagtga ccgtgagctg gaactccggc gccctgacca gcggagtgca cacatttccc  600
gccgtgctgc agtctagcgg cctgtactcc ctgtcctctg tggtgaccgt gcctagctcc  660
tctctgggca ccaagacata tacctgcaac gtggaccaca agccaagcaa tacaaaggtg  720
gataagagag tggagtccaa gtacggccct ccctgccctc cctgtccagc acctgagttc  780
ctgggcggcc cttccgtgtt cctgtttcca cccaagccaa aggacaccct gatgatctct  840
cggacccccg aggtgacatg cgtggtggtg gacgtgagcc aggaggaccc cgaggtgcag  900
ttcaactggt acgtggatgg cgtggaggtg cacaatgcca agacaaagcc cagagaggag  960
cagtttaact ctacctaccg ggtggtgagc gtgctgacag tgctgcacca ggactggctg  1020
aacggcaagg agtataagtg caaggtgtcc aataagggcc tgcctagctc catcgagaag  1080
accatctcta aggcaaaggg acagccacgc gagccacagg tgtacacact gcctccaagc  1140
caggaggaga tgaccaagaa ccaggtgtcc ctgacatgtc tggtgaaggg cttctatcca  1200
agcgacatcg ccgtggagtg ggagtccaat ggccagcccg agaacaatta caagaccaca  1260
ccccctgtgc tggactctga tggcagcttc tttctgtata gcagactgac cgtggataag  1320
tcccggtggc aggagggcaa cgtgttttcc tgctctgtga tgcacgaggc cctgcacaat  1380
cactacaccc agaagagcct gtccctgtct ctgggcaaga ggggcagaaa gaggagaagc  1440
ggctccggcg ccacaaactt cagcctgctg aagcaggcag gcgacgtgga ggagaatcca  1500
ggacccatgg tgctgcagac ccaggtgttt atctccctgc tgctgtggat ctctggcgcc  1560
tatggcgaca tccagatgac acagtccccc tctagcctgt ctgccagcgt gggcgataca  1620
gtgaccatca catgtcaggc caacggctac ctgaattggt atcagcagag gaggggcaag  1680
gcaccaaagc tgctgatcta cgacggcagc aagctggaga gaggcgtgcc ctcccggttc  1740
tctggcagga gatggggcca ggagtataac ctgaccatca acaatctgca gcctgaggat  1800
atcgccacat acttctgcca ggtgtatgag tttgtggtgc ctggcacccg cctggacctg  1860
aagaggacag tggccgcccc aagcgtgttc atctttccac ccagcgatga gcagctgaag  1920
tctggcaccg ccagcgtggt gtgcctgctg aacaatttct acccaagaga ggccaaggtg  1980
cagtggaagg tggacaacgc cctgcagagc ggcaattccc aggagtctgt gaccgagcag  2040
gacagcaagg attccacata ttccctgtct aacaccctga cactgagcaa ggccgattac  2100
gagaagcaca aggtgtatgc atgcgaggtg acccaccagg gactgtcctc tcctgtgaca  2160
aagtccttta atcggggcga gtgttgataa ctcgag                            2196

SEQ ID NO: 11          moltype = AA  length = 469
FEATURE                Location/Qualifiers
REGION                 1..469
                       note = 3BNC117 human IgG4 (heavy chain) (mod 4)
source                 1..469
                       mol_type = protein
                       organism = synthetic construct
SEQUENCE: 11
MDWTWRILFL VAAATGTHAQ VQLLQSGAAV TKPGASVRVS CEASGYNIRD YFIHWWRQAP  60
GQGLQWVGWI NPKTGQPNNP RQFQGRVSLT RHASWDFDTF SFYMDLKALR SDDTAVYFCA  120
RQRSDYWDFD VWGSGTQVTV SSASTKGPSV FPLAPCSRST SESTAALGCL VKDYFPEPVT  180
VSWNSGALTS GVHTFPAVLQ SSGLYSLSSV VTVPSSSLGT KTYTCNVDHK PSNTKVDKRV  240
ESKYGPPCPP CPAPEFLGGP SVFLFPPKPK DTLMISRTPE VTCVVVDVSQ EDPEVQFNWY  300
VDGVEVHNAK TKPREEQFNS TYRVVSVLTV LHQDWLNGKE YKCKVSNKGL PSSIEKTISK  360
AKGQPREPQV YTLPPSQEEM TKNQVSLTCL VKGFYPSDIA VEWESNGQPE NNYKTTPPVL  420
DSDGSFFLYS RLTVDKSRWQ EGNVFSCSVM HEALHNHYTQ KSLSLSLGK             469

SEQ ID NO: 12          moltype = DNA  length = 1431
FEATURE                Location/Qualifiers
misc_feature           1..1431
                       note = 3BNC117 human IgG4 (heavy chain) (mod 4)
source                 1..1431
                       mol_type = other DNA
                       organism = synthetic construct
SEQUENCE: 12
ggatccgcca ccatggactg gacctggcgc atcctgttcc tggtggcagc agcaaccgga  60
```

```
acacacgcac aggtgcagct gctgcagagc ggagcagcag tgacaaagcc aggagcatct  120
gtgagggtga gctgcgaggc atccggctac aacatccgcg attacttcat ccactggtgg  180
aggcaggcac caggacaggg actgcagtgg gtgggctgga tcaatcctaa gaccggccag  240
cctaacaatc caaggcagtt ccagggacgc gtgagcctga ccaggcacgc ctcctgggac  300
tttgatacat tctcttttta catggacctg aaggccctgc gcagcgacga taccgccgtg  360
tacttctgtg cccggcagag gagcgattat tgggactttg acgtgtgggg ctctggcacc  420
caggtgacag tgagctccgc ctccacaaag ggaccaagcg tgttcccact ggcaccttgc  480
agcaggtcca cctctgagag cacagccgcc ctgggctgtc tggtgaagga ctacttccct  540
gagccagtga ccgtgagctg gaactccggc gccctgacca gcggagtgca cacatttccc  600
gccgtgctgc agtctagcgg cctgtactcc ctgtcctctg tggtgaccgt gcctagctcc  660
tctctgggca ccaagacata tacctgcaac gtggaccaca agccaagcaa tacaaaggtg  720
gataagagag tggagtccaa gtacggccct ccctgccctc cctgtccagc acctgagttc  780
ctgggcggcc cttccgtgtt cctgtttcca cccaagccaa aggacaccct gatgatctct  840
cggacccccg aggtgacatg cgtggtggtg gacgtgagcc aggaggaccc cgaggtgcag  900
ttcaactggt acgtggatgg cgtggaggtg cacaatgcca agacaaagcc cagagaggag  960
cagtttaact ctacctaccg ggtggtgagc gtgctgacag tgctgcacca ggactggctg  1020
aacggcaagg agtataagtg caaggtgtcc aataagggcc tgcctagctc catcgagaag  1080
accatctcta aggcaaaggg acagccacgc gagccacagg tgtacacact gcctccaagc  1140
caggaggaga tgaccaagaa ccaggtgtcc ctgacatgtc tggtgaaggg cttctatcca  1200
agcgacatcg ccgtggagtg ggagtccaat ggccagcccg agaacaatta caagaccaca  1260
ccccctgtgc tggactctga tggcagcttc tttctgtata gcagactgac cgtggataag  1320
tcccggtggc aggagggcaa cgtgttttcc tgctctgtga tgcacgaggc cctgcacaat  1380
cactacaccc agaagagcct gtccctgtct ctgggcaagt gataactcga g           1431

SEQ ID NO: 13          moltype = AA  length = 226
FEATURE                Location/Qualifiers
REGION                 1..226
                       note = 3BNC117 human IgG4 (light chain)(mod 4)
source                 1..226
                       mol_type = protein
                       organism = synthetic construct
SEQUENCE: 13
MVLQTQVFIS LLLWISGAYG DIQMTQSPSS LSASVGDTVT ITCQANGYLN WYQQRRGKAP  60
KLLIYDGSKL ERGVPSRFSG RRWGQEYNLT INNLQPEDIA TYFCQVYEFV VPGTRLDLKR  120
TVAAPSVFIF PPSDEQLKSG TASVVCLLNN FYPREAKVQW KVDNALQSGN SQESVTEQDS  180
KDSTYSLSNT LTLSKADYEK HKVYACEVTH QGLSSPVTKS FNRGEC                226

SEQ ID NO: 14          moltype = DNA  length = 702
FEATURE                Location/Qualifiers
misc_feature           1..702
                       note = 3BNC117 human IgG4 (light chain)(mod 4)
source                 1..702
                       mol_type = other DNA
                       organism = synthetic construct
SEQUENCE: 14
ggatccgcca ccatggtgct gcagacccag gtgtttatct ccctgctgct gtggatctct  60
ggcgcctatg gcgacatcca gatgacacag tccccctcta gcctgtctgc cagcgtgggc  120
gatacagtga ccatcacatg tcaggccaac ggctacctga attggtatca gcagaggagg  180
ggcaaggcac caaagctgct gatctacgac ggcagcaagc tggagagagg cgtgccctcc  240
cggttctctg gcaggagatg gggccaggag tataacctga ccatcaacaa tctgcagcct  300
gaggatatcg ccacatactt ctgccaggtg tatgagtttg tggtgcctgg cacccgcctg  360
gacctgaaga ggacagtggc cgccccaagc gtgttcatct ttccacccag cgatgagcag  420
ctgaagtctg gcaccgccag cgtggtgtgc ctgctgaaca atttctaccc aagagaggcc  480
aaggtgcagt ggaaggtgga caacgccctg cagagcggca attcccagga gtctgtgacc  540
gagcaggaca gcaaggattc cacatattcc ctgtctaaca ccctgacact gagcaaggcc  600
gattacgaga agcacaaggt gtatgcatgc gaggtgaccc accagggact gtcctctcct  660
gtgacaaagt cctttaatcg gggcgagtgt tgataactcg ag                    702

SEQ ID NO: 15          moltype = AA  length = 744
FEATURE                Location/Qualifiers
REGION                 1..744
                       note = PGT128 Human IgG1
source                 1..744
                       mol_type = protein
                       organism = synthetic construct
SEQUENCE: 15
MDWTWRILFL VAAATGTHAQ PQLQESGPTL VEASETLSLT CAVSGDSTAA CNSFWGWVRQ  60
PPGKGLEWVG SLSHCASYWN RGWTYHNPSL KSRLTLALDT PKNLVFLKLN SVTAADTATY  120
YCARFGGEVL RYTDWPKPAW VDLWGRGTLV TVSSASTKGP SVFPLAPSSK STSGGTAALG  180
CLVKDYFPEP VTVSWNSGAL TSGVHTFPAV LQSSGLYSLS SVVTVPSSSL GTQTYICNVN  240
HKPSNTKVDK KVEPKSCDKT HTCPPCPAPE LLGGPSVFLF PPKPKDTLMI SRTPEVTCVV  300
VDVSHEDPEV KFNWYVDGVE VHNAKTKPRE EQYNSTYRVV SVLTVLHQDW LNGKEYKCKV  360
SNKALPAPIE KTISKAKGQP REPQVYTLPP SRDELTKNQV SLTCLVKGFY PSDIAVEWES  420
NGQPENNYKT TPPVLDSDGS FFLYSKLTVD KSRWQQGNVF SCSVMHEALH NHYTQKSLSL  480
SPGKRGRKRR SGSGATNFSL LKQAGDVEEN PGPMAWTPLF LFLLTCCPGG SNSQSALTQP  540
PSASGSPGQS ITISCTGTSN NFVSWYQQHA GKAPKLVIYD VNKRPSGVPD RFSGSKSGNT  600
ASLTVSGLQT DDEAVYYCGS LVGNWDVIFG GGTKLTVLGQ PKAAPSVTLF PPSSEELQAN  660
KATLVCLISD FYPGAVTVAW KADSSPVKAG VETTTPSKQS NNKYAASSYL SLTPEQWKSH  720
KSYSCQVTHE GSTVEKTVAP TECS                                        744
```

```
SEQ ID NO: 16          moltype = DNA  length = 2256
FEATURE                Location/Qualifiers
misc_feature           1..2256
                       note = PGT128 Human IgG1
source                 1..2256
                       mol_type = other DNA
                       organism = synthetic construct
SEQUENCE: 16
ggatccgcca ccatggactg gacctggaga atcctgttcc tggtggcagc agcaacagga  60
acccacgcac agccacagct gcaggagtcc ggacccaccc tggtggaggc ctccgagaca  120
ctgtctctga cctgcgccgt gagcggcgat tccacagcag cctgtaactc cttctgggga  180
tgggtgcgcc agccccctgg caagggcctg gagtgggtgg gctctctgag ccactgcgcc  240
agctactgga acaggggctg gacctatcac aatccctctc tgaagagcag actgaccctg  300
gccctggaca cacctaagaa cctggtgttc ctgaagctga atagcgtgac cgccgccgat  360
acagccacct actattgtgc caggtttggc ggcgaggtgc tgagatacac agactggcca  420
aagccagcat gggtggatct gtggggaagg ggcacactgg tgaccgtgag ctccgcctcc  480
accaagggac caagcgtgtt cccactggca ccttctagca agtccacatc tggcggcacc  540
gccgccctgg gatgcctggt gaaggactac ttccctgagc cagtgacagt gtcctggaac  600
tctggcgccc tgacctctgg cgtgcacaca tttcccgccg tgctgcagtc ctctggcctg  660
tacagcctga gctccgtggt gaccgtgcct tctagctccc tgggcacaca gacctatatc  720
tgcaacgtga atcacaagcc tagcaataca aaggtggaca agaaggtgga gccaaagtcc  780
tgtgataaga cacacacctg cccaccctgt ccagcacctg agctgctggg cggcccttcc  840
gtgttcctgt ttcctccaaa gccaaaggac accctgatga tctcccggac acctgaggtg  900
acctgcgtgg tggtggacgt gtctcacgag gaccccgagg tgaagtttaa ctggtacgtg  960
gatggcgtgg aggtgcacaa tgccaagacc aagcccaggg aggagcagta caactctacc  1020
tatagagtgg tgagcgtgct gacagtgctg caccaggatt ggctgaacgg caaggagtat  1080
aagtgcaagg tgagcaataa ggccctgcca gcccccatcg agaagaccat ctccaaggca  1140
aagggacagc cacgggagcc acaggtgtac acactgcccc cttcccgcga cgagctgacc  1200
aagaaccagg tgtctctgac atgtctggtg aagggcttct atccaagcga tatcgccgtg  1260
gagtgggagt ccaatggcca gcccgagaac aattacaaga ccacaccacc cgtgctggac  1320
agcgatggct ccttctttct gtattccaag ctgaccgtgg acaagtctag gtggcagcag  1380
ggcaacgtgt ttagctgctc cgtgatgcac gaggccctgc acaatcacta cacccagaag  1440
tctctgagcc tgtcccctgg caagagggga aggaagagga gatctggcag cggcgccaca  1500
aacttcagcc tgctgaagca ggccggcgat gtggaggaga atcctggccc aatggcctgg  1560
acccctctgt tcctgttcct gctgacatgc tgtcctggcg gctccaactc tcagagcgcc  1620
ctgacccagc ctccatccgc ctctggcagc cctggacaga gcatcacaat ctcctgtaca  1680
ggcaccagca acaatttcgt gagctggtac cagcagcacg caggcaaggc accaaagctg  1740
gtcatctacg acgtgaacaa gcggccttcc ggcgtgccag atcgcttctc cggctctaag  1800
agcggcaata cagcctctct gaccgtgagc ggcctgcaga ccgacgatga ggccgtgtac  1860
tattgcggca gcctggtggg caactgggac gtgatcttcg gcggcggaac aaagctgacc  1920
gtgctgggac agccaaaggc agcaccttcc gtgaccctgt ttcccccttc tagcgaggag  1980
ctgcaggcca ataaggccac cctggtgtgc ctgatcagcg acttctaccc tggagcagtg  2040
acagtggcat ggaaggccga ttcctctcca gtgaaggccg gcgtggagac cacaaccccc  2100
tctaagcaga gcaacaataa gtacgccgcc agctcctatc tgtctctgac cccagagcag  2160
tggaagagcc acaagtccta ttcttgccag gtgacacacg agggctctac agtggagaag  2220
accgtggccc ccacagagtg tagctgataa ctcgag                             2256

SEQ ID NO: 17          moltype = AA  length = 484
FEATURE                Location/Qualifiers
REGION                 1..484
                       note = PGT128 HUMAN IgG1- (HEAVY CHAIN) (MOD 1)
source                 1..484
                       mol_type = protein
                       organism = synthetic construct
SEQUENCE: 17
MDWTWRILFL VAAATGTHAQ PQLQESGPTL VEASETLSLT CAVSGDSTAA CNSFWGWVRQ  60
PPGKGLEWVG SLSHCASYWN RGWTYHNPSL KSRLTLALDT PKNLVFLKLN SVTAADTATY  120
YCARFGGEVL RYTDWPKPAW VDLWGRGTLV TVSSASTKGP SVFPLAPSSK STSGGTAALG  180
CLVKDYFPEP VTVSWNSGAL TSGVHTFPAV LQSSGLYSLS SVVTVPSSSL GTQTYICNVN  240
HKPSNTKVDK KVEPKSCDKT HTCPPCPAPE LLGGPSVFLF PPKPKDTLMI SRTPEVTCVV  300
VDVSHEDPEV KFNWYVDGVE VHNAKTKPRE EQYNSTYRVV SVLTVLHQDW LNGKEYKCKV  360
SNKALPAPIE KTISKAKGQP REPQVYTLPP SRDELTKNQV SLTCLVKGFY PSDIAVEWES  420
NGQPENNYKT TPPVLDSDGS FFLYSKLTVD KSRWQQGNVF SCSVMHEALH NHYTQKSLSL  480
SPGK                                                               484

SEQ ID NO: 18          moltype = DNA  length = 1476
FEATURE                Location/Qualifiers
misc_feature           1..1476
                       note = PGT128 HUMAN IgG1- (HEAVY CHAIN) (MOD 1)
source                 1..1476
                       mol_type = other DNA
                       organism = synthetic construct
SEQUENCE: 18
ggatccgcca ccatggactg gacctggaga atcctgttcc tggtggcagc agcaacagga  60
acccacgcac agccacagct gcaggagtcc ggacccaccc tggtggaggc ctccgagaca  120
ctgtctctga cctgcgccgt gagcggcgat tccacagcag cctgtaactc cttctgggga  180
tgggtgcgcc agccccctgg caagggcctg gagtgggtgg gctctctgag ccactgcgcc  240
agctactgga acaggggctg gacctatcac aatccctctc tgaagagcag actgaccctg  300
```

```
gccctggaca cacctaagaa cctggtgttc ctgaagctga atagcgtgac cgccgccgat  360
acagccacct actattgtgc caggtttggc ggcgaggtgc tgagatacac agactggcca  420
aagccagcat gggtggatct gtggggaagg ggcacactgg tgaccgtgag ctccgcctcc  480
accaagggac caagcgtgtt cccactggca ccttctagca agtccacatc tggcggcacc  540
gccgccctgg gatgcctggt gaaggactac ttccctgagc cagtgacagt gtcctggaac  600
tctggcgccc tgacctctgg cgtgcacaca tttcccgccg tgctgcagtc ctctggcctg  660
tacagcctga gctccgtggt gaccgtgcct tctagctccc tgggcacaca gacctatatc  720
tgcaacgtga atcacaagcc tagcaataca aaggtggaca agaaggtgga gccaaagtcc  780
tgtgataaga cacacacctg cccaccctgt ccagcacctg agctgctggg cggcccttcc  840
gtgttcctgt ttcctccaaa gccaaaggac accctgatga tctcccggac acctgaggtg  900
acctgcgtgg tggtggacgt gtctcacgag gaccccgagg tgaagtttaa ctggtacgtg  960
gatggcgtgg aggtgcacaa tgccaagacc aagcccaggg aggagcagta caactctacc  1020
tatagagtgg tgagcgtgct gacagtgctg caccaggatt ggctgaacgg caaggagtat  1080
aagtgcaagg tgagcaataa ggccctgcca gcccccatcg agaagaccat ctccaaggca  1140
aagggacagc cacgggagcc acaggtgtac acactgcccc cttcccgcga cgagctgacc  1200
aagaaccagg tgtctctgac atgtctggtg aagggcttct atccaagcga tatcgccgtg  1260
gagtgggagt ccaatggcca gcccgagaac aattacaaga ccacaccacc cgtgctggac  1320
agcgatggct ccttcttct gtattccaag ctgaccgtgg acaagtctag gtggcagcag  1380
ggcaacgtgt ttagctgctc cgtgatgcac gaggccctgc acaatcacta cacccagaag  1440
tctctgagcc tgtcccctgg caagtgataa ctcgag                            1476

SEQ ID NO: 19           moltype = AA  length = 231
FEATURE                 Location/Qualifiers
REGION                  1..231
                        note = PGT128 human IgG1- (light chain) (mod 1)
source                  1..231
                        mol_type = protein
                        organism = synthetic construct
SEQUENCE: 19
MAWTPLFLFL LTCCPGGSNS QSALTQPPSA SGSPGQSITI SCTGTSNNFV SWYQQHAGKA  60
PKLVIYDVNK RPSGVPDRFS GSKSGNTASL TVSGLQTDDE AVYYCGSLVG NWDVIFGGGT  120
KLTVLGQPKA APSVTLFPPS SEELQANKAT LVCLISDFYP GAVTVAWKAD SSPVKAGVET  180
TTPSKQSNNK YAASSYLSLT PEQWKSHKSY SCQVTHEGST VEKTVAPTEC S           231

SEQ ID NO: 20           moltype = DNA  length = 717
FEATURE                 Location/Qualifiers
misc_feature            1..717
                        note = PGT128 human IgG1- (light chain) (mod 1)
source                  1..717
                        mol_type = other DNA
                        organism = synthetic construct
SEQUENCE: 20
ggatccgcca ccatggcctg gacccctctg ttcctgttcc tgctgacatg ctgtcctggc  60
ggctccaact ctcagagcgc cctgacccag cctccatccg cctctggcag ccctggacag  120
agcatcacaa tctcctgtac aggcaccagc aacaatttcg tgagctggta ccagcagcac  180
gcaggcaagg caccaaagct ggtcatctac gacgtgaaca agcggccttc cggcgtgcca  240
gatcgcttct ccggctctaa gagcggcaat acagcctctc tgaccgtgag cggcctgcag  300
accgacgatg aggccgtgta ctattgcggc agcctggtgg gcaactggga cgtgatcttc  360
ggcggcggaa caaagctgac cgtgctggga cagccaaagg cagcaccttc cgtgaccctg  420
tttccccctt ctagcgagga gctgcaggcc aataaggcca ccctggtgtg cctgatcagc  480
gacttctacc ctggagcagt gacagtggca tggaaggccg attcctctcc agtgaaggcc  540
ggcgtggaga ccacaacccc ctctaagcag agcaacaata agtacgccgc cagctcctat  600
ctgtctctga ccccagagca gtggaagagc cacaagtcct attcttgcca ggtgacacac  660
gagggctcta cagtggagaa gaccgtggcc cccacagagt gtagctgata actcgag     717

SEQ ID NO: 21           moltype = AA  length = 741
FEATURE                 Location/Qualifiers
REGION                  1..741
                        note = PGT128 human IgG4 (mod 2)
source                  1..741
                        mol_type = protein
                        organism = synthetic construct
SEQUENCE: 21
MDWTWRILFL VAAATGTHAQ PQLQESGPTL VEASETLSLT CAVSGDSTAA CNSFWGWVRQ  60
PPGKGLEWVG SLSHCASYWN RGWTYHNPSL KSRLTLALDT PKNLVFLKLN SVTAADTATY  120
YCARFGGEVL RYTDWPKPAW VDLWGRGTLV TVSSASTKGP SVFPLAPCSR STSESTAALG  180
CLVKDYFPEP VTVSWNSGAL TSGVHTFPAV LQSSGLYSLS SVVTVPSSSL GTKTYTCNVD  240
HKPSNTKVDK RVESKYGPPC PSCPAPEFLG GPSVFLFPPK PKDTLMISRT PEVTCVVVDV  300
SQEDPEVQFN WYVDGVEVHN AKTKPREEQF NSTYRVVSVL TVLHQDWLNG KEYKCKVSNK  360
GLPSSIEKTI SKAKGQPREP QVYTLPPSQE EMTKNQVSLT CLVKGFYPSD IAVEWESNGQ  420
PENNYKTTPP VLDSDGSFFL YSRLTVDKSR WQEGNVFSCS VMHEALHNHY TQKSLSLSLG  480
KRGRKRRSGS GATNFSLLKQ AGDVEENPGP MAWTPLFLFL LTCCPGGSNS QSALTQPPSA  540
SGSPGQSITI SCTGTSNNFV SWYQQHAGKA PKLVIYDVNK RPSGVPDRFS GSKSGNTASL  600
TVSGLQTDDE AVYYCGSLVG NWDVIFGGGT KLTVLGQPKA APSVTLFPPS SEELQANKAT  660
LVCLISDFYP GAVTVAWKAD SSPVKAGVET TTPSKQSNNK YAASSYLSLT PEQWKSHKSY  720
SCQVTHEGST VEKTVAPTEC S                                            741

SEQ ID NO: 22           moltype = DNA  length = 2247
FEATURE                 Location/Qualifiers
```

```
misc_feature          1..2247
                      note = PGT128 human IgG4 (mod 2)
source                1..2247
                      mol_type = other DNA
                      organism = synthetic construct
SEQUENCE: 22
ggatccgcca ccatggactg gacctggaga atcctgttcc tggtggcagc agcaacagga  60
acccacgcac agccccagct gcaggagtcc ggccctacac tggtggaggc cagcgagacc  120
ctgtccctga catgcgccgt gtctggcgat agcaccgcag catgtaactc cttctgggga  180
tgggtgcgcc agcccctgg caagggcctg gagtgggtgg gctctctgag ccactgcgcc  240
agctactgga acaggggctg gacctatcac aatccatccc tgaagtctag actgacactg  300
gccctggaca cccccaagaa cctggtgttc ctgaagctga atagcgtgac agccgccgat  360
acagccacct actattgtgc caggtttggc ggcgaggtgc tgagatacac cgactggcca  420
aagccagcat gggtggatct gtggggaagg ggcaccctgg tgacagtgag ctccgccagc  480
acaaagggcc cttccgtgtt tcctctggcc ccatgctccc gctctaccag cgagtccaca  540
gccgccctgg gatgtctggt gaaggactat ttccctgagc cagtgaccgt gagctggaac  600
tccggcgccc tgacatccgg agtgcacacc tttccagccg tgctgcagtc tagcggcctg  660
tactctctgt cctctgtggt gacagtgcca agctcctctc tgggcacaaa gacctataca  720
tgcaacgtgg accacaagcc ctccaatacc aaggtggata agagggtgga gtctaagtac  780
ggcccaccct gcccaagctg tccagcacct gagttcctgg gcggcccaag cgtgttcctg  840
tttcctccaa agcccaagga caccctgatg atcagcagaa cccccgaggt gacatgcgtg  900
gtggtggacg tgtcccagga ggaccccgag gtgcagttca actggtacgt ggatggcgtg  960
gaggtgcaca atgccaagac caagccacgg gaggagcagt ttaattccac ataccgcgtg  1020
gtgtctgtgc tgaccgtgct gcaccaggac tggctgaacg gcaaggagta taagtgcaag  1080
gtgtctaata agggcctgcc cagctccatc gagaagacaa tcagcaaggc aaagggacag  1140
ccccgggagc ctcaggtgta caccctgccc ccttctcagg aggagatgac aaagaaccag  1200
gtgagcctga cctgtctggt gaagggcttc tatccttccg acatcgccgt ggagtgggag  1260
tctaatggcc agccagagaa caattacaag accacaccac ccgtgctgga ctctgatggc  1320
agcttctttc tgtatagccg gctgaccgtg gataagtccc gctggcagga gggcaacgtg  1380
ttttcttgca gcgtgatgca cgaggccctg cacaatcact acacacagaa gtccctgtct  1440
ctgagcctgg gcaagagggg aaggaagagg agatccggct ctggcgccac caacttcagc  1500
ctgctgaagc aggcaggcga cgtggaggag aatccaggac ccatggcctg gacacctctg  1560
ttcctgtttc tgctgacctg ctgtccaggc ggcagcaact cccagtctgc cctgacacag  1620
cctccaagcg cctccggctc tccaggacag tctatcacca tcagctgtac cggcacatct  1680
aacaattttg tgagctggta ccagcagcac gcaggcaagg cacctaagct ggtcatctac  1740
gacgtgaaca agaggccatc cggcgtgccc gatagattca gcggctccaa gtctggcaat  1800
accgcctccc tgacagtgtc tggcctgcag acagacgatg aggccgtgta ctattgcggc  1860
agcctggtgg gcaactggga tgtgatcttc ggcggcggaa ccaagctgac agtgctggga  1920
cagcctaagg cagcaccatc cgtgaccctg tttcccccctt ctagcgagga gctgcaggcc  1980
aataaggcca ccctggtgtg cctgatcagc gacttctacc ctggagcagt gaccgtggca  2040
tggaaggccg attcctctcc cgtgaaggcc ggcgtggaga ccacaacccc ttccaagcag  2100
tctaacaata agtacgccgc cagctcctat ctgagcctga cacctgagca gtggaagtcc  2160
cacaagagct attcctgcca ggtgacccac gagggctcca ccgtggagaa gacagtggcc  2220
ccaaccgagt gttcttgata actcgag                                      2247

SEQ ID NO: 23         moltype = AA  length = 741
FEATURE               Location/Qualifiers
REGION                1..741
                      note = PGT128 human IgG4mut (S228P) (mod3)
source                1..741
                      mol_type = protein
                      organism = synthetic construct
SEQUENCE: 23
MDWTWRILFL VAAATGTHAQ PQLQESGPTL VEASETLSLT CAVSGDSTAA CNSFWGWVRQ  60
PPGKGLEWVG SLSHCASYWN RGWTYHNPSL KSRLTLALDT PKNLVFLKLN SVTAADTATY  120
YCARFGGEVL RYTDWPKPAW VDLWGRGTLV TVSSASTKGP SVFPLAPCSR STSESTAALG  180
CLVKDYFPEP VTVSWNSGAL TSGVHTFPAV LQSSGLYSLS SVVTVPSSSL GTKTYTCNVD  240
HKPSNTKVDK RVESKYGPPC PPCPAPEFLG GPSVFLFPPK PKDTLMISRT PEVTCVVVDV  300
SQEDPEVQFN WYVDGVEVHN AKTKPREEQF NSTYRVVSVL TVLHQDWLNG KEYKCKVSNK  360
GLPSSIEKTI SKAKGQPREP QVYTLPPSQE EMTKNQVSLT CLVKGFYPSD IAVEWESNGQ  420
PENNYKTTPP VLDSDGSFFL YSRLTVDKSR WQEGNVFSCS VMHEALHNHY TQKSLSLSLG  480
KRGRKRRSGS GATNFSLLKQ AGDVEENPGP MAWTPLFLFL LTCCPGGSNS QSALTQPPSA  540
SGSPGQSITI SCTGTSNNFV SWYQQHAGKA PKLVIYDVNK RPSGVPDRFS GSKSGNTASL  600
TVSGLQTDDE AVYYCGSLVG NWDVIFGGGT KLTVLGQPKA APSVTLFPPS SEELQANKAT  660
LVCLISDFYP GAVTVAWKAD SSPVKAGVET TTPSKQSNNK YAASSYLSLT PEQWKSHKSY  720
SCQVTHEGST VEKTVAPTEC S                                            741

SEQ ID NO: 24         moltype = DNA  length = 2247
FEATURE               Location/Qualifiers
misc_feature          1..2247
                      note = PGT128 human IgG4mut (S228P) (mod3)
source                1..2247
                      mol_type = other DNA
                      organism = synthetic construct
SEQUENCE: 24
ggatccgcca ccatggactg gacctggaga atcctgttcc tggtggcagc agcaacagga  60
acccacgcac agccccagct gcaggagtcc ggccctacac tggtggaggc cagcgagacc  120
ctgtccctga catgcgccgt gtctggcgat agcaccgcag catgtaactc cttctgggga  180
tgggtgcgcc agcccctgg caagggcctg gagtgggtgg gctctctgag ccactgcgcc  240
```

```
agctactgga acaggggctg gacctatcac aatccatccc tgaagtctag actgacactg  300
gccctggaca cccccaagaa cctggtgttc ctgaagctga atagcgtgac agccgccgat  360
acagccacct actattgtgc caggtttggc ggcgaggtgc tgagatacac cgactggcca  420
aagccagcat gggtggatct gtggggaagg ggcaccctgg tgacagtgag ctccgccagc  480
acaaagggcc cttccgtgtt tcctctggcc ccatgctccc gctctaccag cgagtccaca  540
gccgccctgg gatgtctggt gaaggactat ttccctgagc cagtgaccgt gagctggaac  600
tccggcgccc tgacatccgg agtgcacacc tttccagccg tgctgcagtc tagcggcctg  660
tactctctgt cctctgtggt gacagtgcca agctcctctc tgggcacaaa gacctataca  720
tgcaacgtgg accacaagcc ctccaatacc aaggtggata agagggtgga gtctaagtac  780
ggcccaccct gcccaccctg tccagcacct gagttcctgg gcggcccaag cgtgttcctg  840
tttcctccaa agcccaagga caccctgatg atcagcagaa cccccgaggt gacatgcgtg  900
gtggtggacg tgtcccagga ggaccccgag gtgcagttca actggtacgt ggatggcgtg  960
gaggtgcaca atgccaagac caagccacgg gaggagcagt ttaattccac ataccgcgtg  1020
gtgtctgtgc tgaccgtgct gcaccaggac tggctgaacg gcaaggagta taagtgcaag  1080
gtgtctaata agggcctgcc cagctccatc gagaagacaa tcagcaaggc aaagggacag  1140
ccccgggagc ctcaggtgta caccctgccc ccttctcagg aggagatgac aaagaaccag  1200
gtgagcctga cctgtctggt gaagggcttc tatccttccg acatcgccgt ggagtgggag  1260
tctaatggcc agccagagaa caattacaag accacaccac ccgtgctgga ctctgatggc  1320
agcttctttc tgtatagccg gctgaccgtg gataagtccc gctggcagga gggcaacgtg  1380
ttttcttgca gcgtgatgca cgaggccctg cacaatcact acacacagaa gtccctgtct  1440
ctgagcctgg gcaagagggg aaggaagagg agatccggct ctggcgccac caacttcagc  1500
ctgctgaagc aggcaggcga cgtggaggag aatccaggac ccatggcctg gacacctctg  1560
ttcctgtttc tgctgacctg ctgtccaggc ggcagcaact cccagtctgc cctgacacag  1620
cctccaagcg cctccggctc tccaggacag tctatcacca tcagctgtac cggcacatct  1680
aacaattttg tgagctggta ccagcagcac gcaggcaagg cacctaagct ggtcatctac  1740
gacgtgaaca agaggccatc cggcgtgccc gatagattca gcggctccaa gtctggcaat  1800
accgcctccc tgacagtgtc tggcctgcag acagacgatg aggccgtgta ctattgcggc  1860
agcctggtgg gcaactggga tgtgatcttc ggcggcggaa ccaagctgac agtgctggga  1920
cagcctaagg cagcaccatc cgtgaccctg tttcccccctt ctagcgagga gctgcaggcc  1980
aataaggcca ccctggtgtg cctgatcagc gacttctacc ctggagcagt gaccgtggca  2040
tggaaggccg attcctctcc cgtgaaggcc ggcgtggaga ccacaacccc ttccaagcag  2100
tctaacaata agtacgccgc cagctcctat ctgagcctga cacctgagca gtggaagtcc  2160
cacaagagct attcctgcca ggtgacccac gagggctcca ccgtggagaa gacagtggcc  2220
ccaaccgagt gttcttgata actcgag                                     2247

SEQ ID NO: 25          moltype = AA  length = 481
FEATURE                Location/Qualifiers
REGION                 1..481
                       note = PGT128 human IgG4-heavy chain (mod 4)
source                 1..481
                       mol_type = protein
                       organism = synthetic construct
SEQUENCE: 25
MDWTWRILFL VAAATGTHAQ PQLQESGPTL VEASETLSLT CAVSGDSTAA CNSFWGWVRQ  60
PPGKGLEWVG SLSHCASYWN RGWTYHNPSL KSRLTLALDT PKNLVFLKLN SVTAADTATY  120
YCARFGGEVL RYTDWPKPAW VDLWGRGTLV TVSSASTKGP SVFPLAPCSR STSESTAALG  180
CLVKDYFPEP VTVSWNSGAL TSGVHTFPAV LQSSGLYSLS SVVTVPSSSL GTKTYTCNVD  240
HKPSNTKVDK RVESKYGPPC PPCPAPEFLG GPSVFLFPPK PKDTLMISRT PEVTCVVVDV  300
SQEDPEVQFN WYVDGVEVHN AKTKPREEQF NSTYRVVSVL TVLHQDWLNG KEYKCKVSNK  360
GLPSSIEKTI SKAKGQPREP QVYTLPPSQE EMTKNQVSLT CLVKGFYPSD IAVEWESNGQ  420
PENNYKTTPP VLDSDGSFFL YSRLTVDKSR WQEGNVFSCS VMHEALHNHY TQKSLSLSLG  480
K                                                                 481

SEQ ID NO: 26          moltype = DNA  length = 1467
FEATURE                Location/Qualifiers
misc_feature           1..1467
                       note = PGT128 human IgG4-heavy chain (mod 4)
source                 1..1467
                       mol_type = other DNA
                       organism = synthetic construct
SEQUENCE: 26
ggatccgcca ccatggactg gacctggaga atcctgttcc tggtggcagc agcaacagga  60
acccacgcac agccccagct gcaggagtcc ggccctacac tggtggaggc cagcgagacc  120
ctgtccctga catgcgccgt gtctggcgat agcaccgcag catgtaactc cttctgggga  180
tgggtgcgcc agccccctgg caagggcctg gagtgggtgg gctctctgag ccactgcgcc  240
agctactgga acaggggctg gacctatcac aatccatccc tgaagtctag actgacactg  300
gccctggaca cccccaagaa cctggtgttc ctgaagctga atagcgtgac agccgccgat  360
acagccacct actattgtgc caggtttggc ggcgaggtgc tgagatacac cgactggcca  420
aagccagcat gggtggatct gtggggaagg ggcaccctgg tgacagtgag ctccgccagc  480
acaaagggcc cttccgtgtt tcctctggcc ccatgctccc gctctaccag cgagtccaca  540
gccgccctgg gatgtctggt gaaggactat ttccctgagc cagtgaccgt gagctggaac  600
tccggcgccc tgacatccgg agtgcacacc tttccagccg tgctgcagtc tagcggcctg  660
tactctctgt cctctgtggt gacagtgcca agctcctctc tgggcacaaa gacctataca  720
tgcaacgtgg accacaagcc ctccaatacc aaggtggata agagggtgga gtctaagtac  780
ggcccaccct gcccaccctg tccagcacct gagttcctgg gcggcccaag cgtgttcctg  840
tttcctccaa agcccaagga caccctgatg atcagcagaa cccccgaggt gacatgcgtg  900
gtggtggacg tgtcccagga ggaccccgag gtgcagttca actggtacgt ggatggcgtg  960
gaggtgcaca atgccaagac caagccacgg gaggagcagt ttaattccac ataccgcgtg  1020
gtgtctgtgc tgaccgtgct gcaccaggac tggctgaacg gcaaggagta taagtgcaag  1080
```

```
gtgtctaata agggcctgcc cagctccatc gagaagacaa tcagcaaggc aaagggacag  1140
ccccgggagc ctcaggtgta caccctgccc ccttctcagg aggagatgac aaagaaccag  1200
gtgagcctga cctgtctggt gaagggcttc tatccttccg acatcgccgt ggagtgggag  1260
tctaatggcc agccagagaa caattacaag accacaccac ccgtgctgga ctctgatggc  1320
agcttctttc tgtatagccg gctgaccgtg gataagtccc gctggcagga gggcaacgtg  1380
ttttcttgca gcgtgatgca cgaggccctg cacaatcact acacacagaa gtccctgtct  1440
ctgagcctgg gcaagtgata actcgag                                      1467

SEQ ID NO: 27           moltype = AA  length = 231
FEATURE                 Location/Qualifiers
REGION                  1..231
                        note = PGT128 human IgG4-light chain (mod 4)
source                  1..231
                        mol_type = protein
                        organism = synthetic construct
SEQUENCE: 27
MAWTPLFLFL LTCCPGGSNS QSALTQPPSA SGSPGQSITI SCTGTSNNFV SWYQQHAGKA  60
PKLVIYDVNK RPSGVPDRFS GSKSGNTASL TVSGLQTDDE AVYYCGSLVG NWDVIFGGGT  120
KLTVLGQPKA APSVTLFPPS SEELQANKAT LVCLISDFYP GAVTVAWKAD SSPVKAGVET  180
TTPSKQSNNK YAASSYLSLT PEQWKSHKSY SCQVTHEGST VEKTVAPTEC S           231

SEQ ID NO: 28           moltype = DNA  length = 717
FEATURE                 Location/Qualifiers
misc_feature            1..717
                        note = PGT128 human IgG4-light chain (mod 4)
source                  1..717
                        mol_type = other DNA
                        organism = synthetic construct
SEQUENCE: 28
ggatccgcca ccatggcctg gacacctctg ttcctgtttc tgctgacctg ctgtccaggc  60
ggcagcaact cccagtctgc cctgacacag cctccaagcg cctccggctc tccaggacag  120
tctatcacca tcagctgtac cggcacatct aacaattttg tgagctggta ccagcagcac  180
gcaggcaagg cacctaagct ggtcatctac gacgtgaaca agaggccatc cggcgtgccc  240
gatagattca gcggctccaa gtctggcaat accgcctccc tgacagtgtc tggcctgcag  300
acagacgatg aggccgtgta ctattgcggc agcctggtgg gcaactggga tgtgatcttc  360
ggcggcggaa ccaagctgac agtgctggga cagcctaagg cagcaccatc cgtgaccctg  420
tttcccccctt ctagcgagga gctgcaggcc aataaggcca ccctggtgtg cctgatcagc  480
gacttctacc ctggagcagt gaccgtggca tggaaggccg attcctctcc cgtgaaggcc  540
ggcgtggaga ccacaacccc ttccaagcag tctaacaata agtacgccgc cagctcctat  600
ctgagcctga cacctgagca gtggaagtcc cacaagagct attcctgcca ggtgacccac  660
gagggctcca ccgtggagaa gacagtggcc ccaaccgagt gttcttgata actcgag     717

SEQ ID NO: 29           moltype = AA  length = 750
FEATURE                 Location/Qualifiers
REGION                  1..750
                        note = PG9 IgG1
source                  1..750
                        mol_type = protein
                        organism = synthetic construct
SEQUENCE: 29
MDWTWRILFL VAAATGTHAQ RLVESGGGVV QPGSSLRLSC AASGFDFSRQ GMHWVRQAPG  60
QGLEWVAFIK YDGSEKYHAD SVWGRLSISR DNSKDTLYLQ MNSLRVEDTA TYFCVREAGG  120
PDYRNGYNYY DFYDGYYNYH YMDVWGKGTT VTVSSASTKG PSVFPLAPSS KSTSGGTAAL  180
GCLVKDYFPE PVTVSWNSGA LTSGVHTFPA VLQSSGLYSL SSVVTVPSSS LGTQTYICNV  240
NHKPSNTKVD KKAEPKSCDK THTCPPCPAP ELLGGPSVFL FPPKPKDTLM ISRTPEVTCV  300
VVDVSHEDPE VKFNWYVDGV EVHNAKTKPR EEQYNSTYRV VSVLTVLHQD WLNGKEYKCK  360
VSNKALPAPI EKTISKAKGQ PREPQVYTLP PSRDELTKNQ VSLTCLVKGF YPSDIAVEWE  420
SNGQPENNYK TTPPVLDSDG SFFLYSKLTV DKSRWQQGNV FSCSVMHEAL HNHYTQKSLS  480
LLPGKRGRKR RSGSGATNFS LLKQAGDVEE NPGPMAWTPL FLFLLTCCPG GSNSQSALTQ  540
PASVSGSPGQ SITISCNGTS NDVGGYESVS WYQQHPGKAP KVVIYDVSKR PSGVSNRFSG  600
SKSGNTASLT ISGLQAEDEG DYYCKSLTST RRRVFGTGTK LTVLGQPKAA PSVTLFPPSS  660
EELQANKATL VCLISDFYPG AVTVAWKADS SPVKAGVETT TPSKQSNNKY AASSYLSLTP  720
EQWKSHKSYS CQVTHEGSTV EKTVAPTECS                                  750

SEQ ID NO: 30           moltype = DNA  length = 2274
FEATURE                 Location/Qualifiers
misc_feature            1..2274
                        note = PG9 IgG1
source                  1..2274
                        mol_type = other DNA
                        organism = synthetic construct
SEQUENCE: 30
ggatccgcca ccatggactg gacttggaga atcctgttcc tggtcgccgc cgctaccggg  60
actcacgctc agaggctggt ggagagtggg ggaggggtcg tgcagccagg cagctccctg  120
cgactgagtt gcgccgcttc agggttcgac ttttcccgac agggaatgca ctgggtcagg  180
caggcacctg gacagggact ggagtgggtg gcttttatca agtacgacgg aagtgaaaaa  240
tatcatgccg attcagtgtg ggggcggctg tcaattagcc gcgacaacag taaggatacc  300
ctgtacctgc agatgaatag cctgcgggtc gaggacacag ctacttattt ctgcgtgcgc  360
gaagcaggcg gaccagatta ccgaaacggg tataattact atgactttta cgatggctac  420
```

```
tataactacc actatatgga cgtgtggggc aagggaacca cagtcacagt gtctagtgca  480
tcaactaaag gacccagcgt gttcccccctg gccccttcaa gcaagtccac ttctgggggc  540
accgcagccc tgggatgtct ggtgaaggat tacttccctg agccagtcac cgtgagttgg  600
aactcaggcg ccctgactag cggagtccat acctttcctg ctgtgctgca gtcctctggg  660
ctgtactccc tgagttcagt ggtcactgtg ccaagctcct ctctgggcac ccagacatat  720
atctgcaacg tgaatcacaa gcctagcaat accaaagtcg acaagaaagt ggaaccaaag  780
tcctgtgata aaactcatac ctgccctccc tgtccagcac ctgagctgct gggagggcct  840
tccgtgttcc tgtttccacc caagccaaaa gacacactga tgatttctag gacaccagaa  900
gtcacttgcg tggtcgtgga cgtgagccac gaggaccccg aagtcaagtt taactggtac  960
gtggatggcg tcgaggtgca taatgccaag accaaacccc gcgaggaaca gtacaactcc  1020
acatataggg tcgtgtctgt cctgactgtg ctgcaccagg actggctgaa cggcaaggag  1080
tataagtgca aagtgtccaa taaggcactg ccagcccccca tcgagaaaac catttctaag  1140
gccaaaggac agccaagaga accccaggtg tacacactgc ctccatcccg ggacgagctg  1200
actaagaacc aggtctctct gacctgtctg gtgaaaggct tctatccctc tgatatcgct  1260
gtggagtggg aaagtaatgg acagcctgaa aacaattaca agactacccc tcccgtgctg  1320
gacagcgatg ggtccttctt tctgtatagc aagctgacag tggacaaatc cagatggcag  1380
cagggcaacg tctttagttg ctcagtgatg cacgaggccc tgcacaatca ttacacacag  1440
aaaagcctgt ccctgtctcc cggcaagagg ggaagaaaaa ggagaagtgg gtcaggcgca  1500
actaacttca gcctgctgaa gcaggccgga gatgtggagg aaaatcctgg gccaatggct  1560
tggacccctc tgttcctgtt cctgctgaca tgctgtcctg gcggaagcaa ctcccagtct  1620
gcactgaccc agccagcaag cgtgagcggg agcccaggcc agagcatcac catttcctgt  1680
aacggcacat ccaatgacgt gggcggctac gagtccgtgt cttggtatca gcagcatcct  1740
ggaaaggccc caaaagtcgt gatctacgat gtcagcaaaa gaccttctgg ggtgagtaac  1800
cggttcagtg gatcaaagag cggggaatacc gcttctctga caattagtgg cctgcaggca  1860
gaggacgaag gagattacta ttgcaagtca ctgacaagca ctcggcgccg agtcttcgga  1920
accgggacaa agctgactgt gctgggccag cccaaagctg caccttctgt gaccctgttt  1980
ccacccagtt cagaggaact gcaggctaac aaggccaccc tggtgtgcct gatcagcgac  2040
ttctaccctg gcgctgtcac tgtggcctgg aaggctgata gctccccagt caaagcagga  2100
gtggaaacaa ctacccccctc caagcagtct aacaacaagt acgccgcttc tagttatctg  2160
tcactgaccc cagagcagtg gaagtctcac aaatcctatt cttgtcaggt cacccatgaa  2220
gggagcactg tggagaaaac cgtcgcacca accgaatgtt cctgataact cgag        2274
```

```
SEQ ID NO: 31          moltype = AA  length = 747
FEATURE                Location/Qualifiers
REGION                 1..747
                       note = PG9 human IgG4
source                 1..747
                       mol_type = protein
                       organism = synthetic construct
SEQUENCE: 31
MDWTWRILFL VAAATGTHAQ RLVESGGGVV QPGSSLRLSC AASGFDFSRQ GMHWVRQAPG  60
QGLEWVAFIK YDGSEKYHAD SVWGRLSISR DNSKDTLYLQ MNSLRVEDTA TYFCVREAGG  120
PDYRNGYNYY DFYDGYYNYH YMDVWGKGTT VTVSSASTKG PSVFPLAPCS RSTSESTAAL  180
GCLVKDYFPE PVTVSWNSGA LTSGVHTFPA VLQSSGLYSL SSVVTVPSSS LGTKTYTCNV  240
DHKPSNTKVD KRVESKYGPP CPSCPAPEFL GGPSVFLFPP KPKDTLMISR TPEVTCVVVD  300
VSQEDPEVQF NWYVDGVEVH NAKTKPREEQ FNSTYRVVSV LTVLHQDWLN GKEYKCKVSN  360
KGLPSSIEKT ISKAKGQPRE PQVYTLPPSQ EEMTKNQVSL TCLVKGFYPS DIAVEWESNG  420
QPENNYKTTP PVLDSDGSFF LYSRLTVDKS RWQEGNVFSC SVMHEALHNH YTQKSLSLSL  480
GKRGRKRRSG SGATNFSLLK QAGDVEENPG PMAWTPLFLF LLTCCPGGSN SQSALTQPAS  540
VSGSPGQSIT ISCNGTSNDV GGYESVSWYQ QHPGKAPKVV IYDVSKRPSG VSNRFSGSKS  600
GNTASLTISG LQAEDEGDYY CKSLTSTRRR VFGTGTKLTV LGQPKAAPSV TLFPPSSEEL  660
QANKATLVCL ISDFYPGAVT VAWKADSSPV KAGVETTTPS KQSNNKYAAS SYLSLTPEQW  720
KSHKSYSCQV THEGSTVEKT VAPTECS                                    747
```

```
SEQ ID NO: 32          moltype = DNA  length = 2265
FEATURE                Location/Qualifiers
misc_feature           1..2265
                       note = PG9 human IgG4
source                 1..2265
                       mol_type = other DNA
                       organism = synthetic construct
SEQUENCE: 32
ggatccgcca ccatggactg gacctggcgc atcctgtttc tggtggcagc agcaacagga  60
acccacgcac agaggctggt ggagagcggc ggcggcgtgg tgcagcctgg cagctccctg  120
agactgtcct gcgcagcatc tggcttcgac ttcagcaggc agggcatgca ctgggtgcgg  180
caggcaccag gacagggact ggagtgggtg gccttcatca agtacgacgg ctctgagaag  240
tatcacgcag atagcgtgtg gggccgcctg tccatctcta gggacaacag caaggatacc  300
ctgtacctgc agatgaattc cctgcgcgtg gaggacacag ccacctattt ctgcgtgagg  360
gaggccggcg gaccagatta caggaacggc tataattact atgactttta cgatggctac  420
tataactacc actatatgga cgtgtggggc aagggcacca cagtgacagt gtctagcgcc  480
tccaccaagg gaccaagcgt gttccctctg gcaccatgca gcaggtccac ctctgagagc  540
acagccgccc tgggctgtct ggtgaaggat tatttccctg agccagtgac cgtgagctgg  600
aattccggcg ccctgacatc cggagtgcac acctttcctg ccgtgctgca gtcctctggc  660
ctgtacagcc tgagctccgt ggtgacagtg ccctctagct ccctgggcac aaagacctat  720
acatgcaacg tggaccacaa gccttccaat accaaggtgg ataagagagt ggagagcaag  780
tacggccctc cctgcccatc ctgtccagca cctgagttcc tgggcggccc aagcgtgttc  840
ctgtttccac ccaagcccaa ggacacactg atgatcagcc ggacccctga ggtgacatgc  900
gtggtggtgg acgtgtccca ggaggacccc gaggtgcagt tcaactggta cgtggatggc  960
gtggaggtgc acaatgccaa gaccaagccc agagaggagc agtttaacag cacataccgg  1020
```

-continued

```
gtggtgtccg tgctgaccgt gctgcaccag gactggctga acggcaagga gtataagtgc  1080
aaggtgtcta ataagggcct gccttctagc atcgagaaga caatcagcaa ggcaaaggga  1140
cagccccggg agcctcaggt gtacaccctg cctccatctc aggaggagat gacaaagaac  1200
caggtgagcc tgacctgtct ggtgaagggc ttttatccat ctgacatcgc cgtggagtgg  1260
gagagcaatg gccagcccga gaacaattac aagaccacac cccctgtgct ggactctgat  1320
ggcagcttct ttctgtattc ccgcctgact gtggataagt ctaggtggca ggagggcaac  1380
gtgttttcct gctctgtgat gcacgaggcc ctgcacaatc actacacaca gaagagcctg  1440
tccctgtctc tgggcaagag aggaaggaag aggagaagcg gctccggagc aaccaacttc  1500
agcctgctga agcaggcagg cgacgtggag gagaatccag gacccatggc ctggacacct  1560
ctgttcctgt ttctgctgac ctgctgtcca ggcggctcta acagccagtc cgccctgacc  1620
cagccagcat ctgtgagcgg ctcccctggc cagagcatca caatctcctg taacggcacc  1680
tccaatgacg tgggcggcta cgagtctgtg agctggtatc agcagcaccc aggcaaggcc  1740
cccaaggtgg tcatctacga tgtgagcaag agaccctccg gcgtgtctaa ccggttctcc  1800
ggctctaaga gcggcaatac cgcctctctg acaatcagcg gactgcaggc agaggacgag  1860
ggcgattact attgcaagag cctgacctcc acacggcgca gggtgttcgg aaccggcaca  1920
aagctgacag tgctgggaca gcctaaggca gcaccatccg tgaccctgtt tccaccctcc  1980
tctgaggagc tgcaggccaa caaggccacc ctggtgtgcc tgatcagcga cttctaccct  2040
ggagcagtga ccgtggcatg gaaggcagat agctccccag tgaaggcagg agtggagacc  2100
acaacccctt ctaagcagag caacaataag tacgccgcct ctagctatct gtccctgaca  2160
ccagagcagt ggaagtctca caagtcctat tcttgccagg tgacccacga gggctccacc  2220
gtggagaaga cagtggcccc caccgagtgt tcttgataac tcgag                 2265

SEQ ID NO: 33          moltype = AA  length = 733
FEATURE                Location/Qualifiers
REGION                 1..733
                       note = NIH45-46human IgG1 antibody
source                 1..733
                       mol_type = protein
                       organism = synthetic construct
SEQUENCE: 33
MDWTWRILFL VAAATGTHAQ VRLSQSGGQM KKPGESMRLS CRASGYEFLN CPINWIRLAP  60
GRRPEWMGWL KPRGGAVNYA RKFQGRVTMT RDVYSDTAFL ELRSLTSDDT AVYFCTRGKY  120
CTARDYYNWD FEHWGRGAPV TVSSASTKGP SVFPLAPSSK STSGGTAALG CLVKDYFPEP  180
VTVSWNSGAL TSGVHTFPAV LQSSGLYSLS SVVTVPSSSL GTQTYICNVN HKPSNTKVDK  240
KVEPKSCDKT HTCPPCPAPE LLGGPSVFLF PPKPKDTLMI SRTPEVTCVV VDVSHEDPEV  300
KFNWYVDGVE VHNAKTKPRE EQYNSTYRVV SVLTVLHQDW LNGKEYKCKV SNKALPAPIE  360
KTISKAKGQP REPQVYTLPP SRDELTKNQV SLTCLVKGFY PSDIAVEWES NGQPENNYKT  420
TPPVLDSDGS FFLYSKLTVD KSRWQQGNVF SCSVMHEALH NHYTQKSLSL SPGKRGRKRR  480
SGSGATNFSL LKQAGDVEEN PGPMVLQTQV FISLLLWISG AYGEIVLTQS PATLSLSPGE  540
TAIISCRTSQ SGSLAWYQQR PGQAPRLVIY SGSTRAAGIP DRFSGSRWGA DYNLSISNLE  600
SGDFGVYYCQ QYEFFGQGTK VQVDIKRTVA APSVFIFPPS DEQLKSGTAS VVCLLNNFYP  660
REAKVQWKVD NALQSGNSQE SVTEQDSKDS TYSLSSTLTL SKADYEKHKV YACEVTHQGL  720
RSPVTKSFNR GEC                                                    733

SEQ ID NO: 34          moltype = DNA  length = 2223
FEATURE                Location/Qualifiers
misc_feature           1..2223
                       note = NIH45-46human IgG1 antibody
source                 1..2223
                       mol_type = other DNA
                       organism = synthetic construct
SEQUENCE: 34
ggatccgcca ccatggactg gacctggcgc atcctgttcc tggtggcagc agcaaccgga  60
acacacgcac aggtgaggct gtcccagtct ggcggccaga tgaagaagcc tggagagtct  120
atgaggctga gctgcagggc atccggatac gagttcctga actgtccaat caattggatc  180
agactggccc ctggcaggag accagagtgg atgggatggc tgaagcctcg gggcggcgcc  240
gtgaactacg caaggaagtt tcagggcaga gtgaccatga cacgggacgt gtatagcgat  300
accgccttcc tggagctgag atctctgacc agcgacgata cagccgtgta cttttgcacc  360
cgcggcaagt attgtacagc cagggactac tataattggg atttcgagca ctggggaagg  420
ggcgccccag tgaccgtgag ctccgcctcc acaaagggac ctagcgtgtt cccactggca  480
ccttctagca agagcacctc cggcggcaca gccgccctgg gatgcctggt gaaggactac  540
ttccctgagc cagtgaccgt gtcctggaac tctggcgccc tgaccagcgg agtgcacaca  600
tttccagccg tgctgcagtc ctctggcctg tactccctga gctccgtggt gaccgtgccc  660
tctagctccc tgggcaccca gacatatatc tgcaacgtga atcacaagcc atctaataca  720
aaggtggaca agaaggtgga gcccaagagc tgtgataaga cccacacatg ccctccctgt  780
ccagcacctg agctgctggg cggcccttcc gtgttcctgt ttccacccaa gccaaaggac  840
acactgatga tctccagaac ccccgaggtg acatgcgtgg tggtggacgt gtctcacgag  900
gaccccgagg tgaagttcaa ctggtacgtg gatggcgtgg aggtgcacaa tgccaagacc  960
aagccaagag aggagcagta caactctacc tatcgggtgg tgagcgtgct gacagtgctg  1020
caccaggatt ggctgaacgg caaggagtat aagtgcaagg tgagcaataa ggccctgcca  1080
gcccccatcg agaagaccat ctccaaggcc aagggccagc caagagagcc ccaggtgtac  1140
acactgcctc caagccggga cgagctgacc aagaaccagg tgtccctgac atgtctggtg  1200
aagggcttct atccttccga tatcgccgtg gagtgggagt ctaatggcca gccagagaac  1260
aattacaaga ccacaccccc tgtgctggac agcgatggct ccttctttct gtatagcaag  1320
ctgaccgtgg acaagtcccg gtggcagcag ggcaacgtgt tttcttgcag cgtgatgcac  1380
gaggccctgc acaatcacta cacccagaag tccctgtctc tgagcccagg caagagggga  1440
agaaagcggc gctccggctc tggagccaca aacttcagcc tgctgaagca ggccggcgat  1500
gtggaggaga atcctggccc aatggtgctg cagacccagg tgtttatctc cctgctgctg  1560
tggatctctg gcgcctacgg cgagatcgtg ctgacccagt ctccagccac actgagcctg  1620
```

-continued

```
tccccaggag agaccgcaat catctcctgt cgcacatctc agagcggctc cctggcatgg  1680
taccagcaga gaccaggaca ggcccctcgg ctggtcatct actctggcag cacaagggcc  1740
gcaggcatcc ccgaccgctt ctccggctct aggtggggcg ccgattacaa cctgagcatc  1800
tccaatctgg agagcggcga ctttggcgtg tactattgcc agcagtatga gttctttggc  1860
cagggcacca aggtgcaggt ggacatcaag cgcacagtgg ccgcccccag cgtgttcatc  1920
tttccaccca gcgatgagca gctgaagtct ggcaccgcca gcgtggtgtg cctgctgaac  1980
aatttctacc ctagggaggc caaggtgcag tggaaggtgg acaacgccct gcagtctggc  2040
aatagccagg agtccgtgac cgagcaggac tctaaggata gcacatattc cctgtctagc  2100
accctgacac tgtccaaggc cgattacgag aagcacaagg tgtatgcatg cgaggtgacc  2160
caccagggac tgcgcagccc cgtgacaaag tcctttaaca ggggcgagtg ttgataactc  2220
gag                                                                2223

SEQ ID NO: 35          moltype = AA  length = 730
FEATURE                Location/Qualifiers
REGION                 1..730
                       note = NIH45-46human IgG4 antibody
source                 1..730
                       mol_type = protein
                       organism = synthetic construct
SEQUENCE: 35
MDWTWRILFL VAAATGTHAQ VRLSQSGGQM KKPGESMRLS CRASGYEFLN CPINWIRLAP  60
GRRPEWMGWL KPRGGAVNYA RKFQGRVTMT RDVYSDTAFL ELRSLTSDDT AVYFCTRGKY  120
CTARDYYNWD FEHWGRGAPV TVSSASTKGP SVFPLAPCSR STSESTAALG CLVKDYFPEP  180
VTVSWNSGAL TSGVHTFPAV LQSSGLYSLS SVVTVPSSSL GTKTYTCNVD HKPSNTKVDK  240
RVESKYGPPC PSCPAPEFLG GPSVFLFPPK PKDTLMISRT PEVTCVVVDV SQEDPEVQFN  300
WYVDGVEVHN AKTKPREEQF NSTYRVVSVL TVLHQDWLNG KEYKCKVSNK GLPSSIEKTI  360
SKAKGQPREP QVYTLPPSQE EMTKNQVSLT CLVKGFYPSD IAVEWESNGQ PENNYKTTPP  420
VLDSDGSFFL YSRLTVDKSR WQEGNVFSCS VMHEALHNHY TQKSLSLSLG KRGRKRRSGS  480
GATNFSLLKQ AGDVEENPGP MVLQTQVFIS LLLWISGAYG EIVLTQSPAT LSLSPGETAI  540
ISCRTSQSGS LAWYQQRPGQ APRLVIYSGS TRAAGIPDRF SGSRWGADYN LSISNLESGD  600
FGVYYCQQYE FFGQGTKVQV DIKRTVAAPS VFIFPPSDEQ LKSGTASVVC LLNNFYPREA  660
KVQWKVDNAL QSGNSQESVT EQDSKDSTYS LSNTLTLSKA DYEKHKVYAC EVTHQGLSSP  720
VTKSFNRGEC                                                        730

SEQ ID NO: 36          moltype = DNA  length = 2214
FEATURE                Location/Qualifiers
misc_feature           1..2214
                       note = NIH45-46human IgG4 antibody
source                 1..2214
                       mol_type = other DNA
                       organism = synthetic construct
SEQUENCE: 36
ggatccgcca ccatggactg gacctggaga atcctgttcc tggtggcagc agcaaccgga  60
acacacgcac aggtgcggct gtcccagtct ggcggccaga tgaagaagcc aggagagtct  120
atgaggctga gctgcagggc atccggatac gagttcctga actgtcctat caattggatc  180
aggctggcac caggcaggag acccgagtgg atgggatggc tgaagcccag gggcggcgcc  240
gtgaactacg caaggaagtt tcagggcaga gtgaccatga cacgggacgt gtattccgat  300
accgccttcc tggagctgag aagcctgaca tccgacgata ccgccgtgta cttttgcaca  360
cgcggcaagt attgtaccgc cagggactac tataattggg atttcgagca ctggggaaga  420
ggcgcccctg tgacagtgag ctccgcctcc accaagggcc caagcgtgtt ccctctggcc  480
ccatgcagcc ggtccacatc tgagagcacc gccgccctgg gatgtctggt gaaggactac  540
ttccctgagc cagtgaccgt gtcttggaac agcggcgccc tgacatctgg cgtgcacacc  600
tttcccgccg tgctgcagtc tagcggcctg tacagcctgt cctctgtggt gacagtgcct  660
agctcctctc tgggcaccaa gacatatacc tgcaacgtgg accacaagcc atccaatacc  720
aaggtggata agcgcgtgga gtctaagtac ggccctccct gccctagctg tccagcacct  780
gagttcctgg gcggcccaag cgtgttcctg tttccaccca agcccaagga caccctgatg  840
atctctagga caccagaggt gacctgcgtg gtggtggacg tgagccagga ggaccccgag  900
gtgcagttca actggtacgt ggatggcgtg gaggtgcaca atgccaagac aaagcctcgc  960
gaggagcagt ttaacagcac atacagggtg gtgtccgtgc tgaccgtgct gcaccaggat  1020
tggctgaacg gcaaggagta taagtgcaag gtgtccaata agggcctgcc aagctccatc  1080
gagaagacaa tctctaaggc aaagggacag ccccgggagc ctcaggtgta caccctgcct  1140
ccaagccagg aggagatgac aaagaaccag gtgtccctga cctgtctggt gaagggcttc  1200
tatccctccg acatcgccgt ggagtgggag tctaatggcc agcctgagaa caattacaag  1260
accacacccc ctgtgctgga ctccgatggc tctttcttc tgtattccag actgaccgtg  1320
gataagtctc ggtggcagga gggcaacgtg ttttcctgct ctgtgatgca cgaggccctg  1380
cacaatcact acacacagaa gagcctgtcc ctgtctctgg gcaagagggg aagaaagcgg  1440
cgcagcggct ccggagcaac caacttctcc ctgctgaagc aggcaggcga cgtggaggag  1500
aatccaggac ccatggtgct gcagacacag gtgtttatct ctctgctgct gtggatcagc  1560
ggcgcctacg gcgagatcgt gctgacacag agcccagcca ccctgtctct gagccctgga  1620
gagacagcca tcatctcctg tcgcacctcc cagtctggca gcctggcatg gtaccagcag  1680
agacctggac aggccccacg gctggtcatc tactccggct ctaccagggc cgcaggcatc  1740
ccagaccgct tcagcggctc caggtggggc gccgattaca acctgtctat cagcaatctg  1800
gagagcggcg attttggcgt gtactattgc cagcagtatg agttctttgg ccagggcaca  1860
aaggtgcagg tggacatcaa gagaaccgtg gccgccccaa gcgtgttcat ctttccaccc  1920
tccgatgagc agctgaagtc tggcacagcc agcgtggtgt gcctgctgaa caatttctac  1980
ccccgggagg ccaaggtgca gtggaaggtg gacaacgccc tgcagagcgg caattcccag  2040
gagtctgtga cagagcagga cagcaaggat tccacctatt ccctgtctaa cacactgacc  2100
ctgtccaagg ccgattacga gaagcacaag gtgtatgcct gcgaggtgac acaccagggc  2160
ctgtctagcc ctgtgaccaa gagctttaat cgcggcgagt gttgataact cgag        2214
```

```
SEQ ID NO: 37          moltype = AA  length = 729
FEATURE                Location/Qualifiers
REGION                 1..729
                       note = VRC01 human IgG1
source                 1..729
                       mol_type = protein
                       organism = synthetic construct
SEQUENCE: 37
MDWTWRILFL VAAATGTHAQ VQLVQSGGQM KKPGESMRIS CRASGYEFID CTLNWIRLAP  60
GKRPEWMGWL KPRGGAVNYA RPLQGRVTMT RDVYSDTAFL ELRSLTVDDT AVYFCTRGKN  120
CDYNWDFEHW GRGTPVIVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSRDE LTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK RGRKRRSGSG  480
ATNFSLLKQA GDVEENPGPM VLQTQVFISL LLWISGAYGE IVLTQSPGTL SLSPGETAII  540
SCRTSQYGSL AWYQQRPGQA PRLVIYSGST RAAGIPDRFS GSRWGPDYNL TISNLESGDF  600
GVYYCQQYEF FGQGTKVQVD IKRTVAAPSV FIFPPSDEQL KSGTASVVCL LNNFYPREAK  660
VQWKVDNALQ SGNSQESVTE QDSKDSTYSL SNTLTLSKAD YEKHKVYACE VTHQGLSSPV  720
TKSFNRGEC                                                         729

SEQ ID NO: 38          moltype = DNA  length = 2211
FEATURE                Location/Qualifiers
misc_feature           1..2211
                       note = VRC01 human IgG1
source                 1..2211
                       mol_type = other DNA
                       organism = synthetic construct
SEQUENCE: 38
ggatccgcca ccatggattg gacatggagg attctgtttc tggtcgccgc cgccacagga  60
actcatgctc aggtgcagct ggtgcagtca ggagggcaga tgaagaaacc tggcgagagt  120
atgcgaatct catgcagggc tagcggatac gaattcatcg actgtaccct gaactggatt  180
agactggcac ctggaaagcg gccagagtgg atggggtggc tgaaaccaag aggcggagca  240
gtgaattacg ccagaccact gcagggacga gtcactatga cccgcgacgt gtatagcgat  300
accgcattcc tggaactgcg atccctgaca gtcgacgata ctgccgtgta cttctgcaca  360
aggggcaaga actgtgacta taattgggat tttgagcact ggggccgggg aacaccagtc  420
attgtgagct ccgcaagtac taagggggcc tcagtgtttc cctggctcc ttctagtaaa  480
agtacctcag ggggcacagc cgctctggga tgcctggtga aggattactt ccctgagcca  540
gtcacagtga gttggaactc aggcgccctg acatctggag tccatacttt tcccgctgtg  600
ctgcagtcaa gcggactgta cagcctgtcc tctgtggtca cagtgcctag ttcaagcctg  660
ggggacacaga cttatatctg caacgtcaat cacaagccca gcaatactaa agtggacaag  720
aaagtggaac ctaagtcctg tgataaaacc catacatgcc ctccctgtcc agctcctgag  780
ctgctgggag ggccaagcgt gttcctgttt ccacccaagc ctaaagacac cctgatgatt  840
tctcggactc ctgaagtcac ctgcgtggtc gtggacgtga gccacgagga ccccgaagtc  900
aagtttaact ggtacgtgga tggcgtcgag gtgcataatg ccaagacaaa acccagggag  960
gaacagtaca acagcaccta tagagtcgtg tccgtcctga cagtgctgca ccaggactgg  1020
ctgaacggaa aggagtataa gtgcaaagtg agcaataagg ccctgccagc tcccatcgag  1080
aaaacaattt ccaaggcaaa agggcagcca cgggaacccc aggtgtacac tctgcctcca  1140
tctcgcgacg agctgactaa gaaccaggtc agcctgacct gtctggtgaa agggttctat  1200
ccaagtgata tcgccgtgga gtgggaaagc aatggccagc ccgaaaacaa ttacaagacc  1260
acacccccctg tgctggacag cgatggctcc ttctttctgt attctaagct gaccgtggat  1320
aaaagtcgct ggcagcaggg aaacgtcttt agctgctccg tgatgcacga ggctctgcac  1380
aatcattaca cccagaagtc tctgagtctg tcacctggca agcggggacg caaaaggaga  1440
agcgggtccg gcgctacaaa cttcagcctg ctgaagcagg caggcgacgt ggaggaaaat  1500
cctggaccaa tggtcctgca gacccaggtg ttcatctccc tgctgctgtg gatttctggg  1560
gcatacggcg aaattgtgct gacccagagc cctgggacac tgtctctgag tccaggcgag  1620
acagccatca tttcctgtcg gacttctcag tacggaagtc tggcatggta tcagcagcga  1680
ccaggacagg ctcctcgact ggtcatctac tcagggagca ctagggcagc cggcattcct  1740
gaccgattct ccggatctag gtgggggcct gattacaacc tgaccatctc aaatctggaa  1800
agcggggact ttggcgtgta ctattgccag cagtatgagt tctttggaca ggggaccaag  1860
gtccaggtgg acatcaaacg cacagtcgct gcaccatccg tgttcatttt tccaccctct  1920
gatgaacagc tgaagtccgg caccgcctct gtggtgtgcc tgctgaacaa tttctacccc  1980
agggaggcaa aggtccagtg gaaagtggac aacgccctgc agtctggaaa tagtcaggag  2040
tcagtgactg aacaggacag caaggattcc acctattctc tgtccaacac tctgaccctg  2100
tccaaagctg attacgagaa gcacaaagtg tatgcatgcg aggtcactca ccaggggctg  2160
tcatcaccag tcacaaaatc cttcaacaga ggggaatgct gataactcga g           2211

SEQ ID NO: 39          moltype = AA  length = 470
FEATURE                Location/Qualifiers
REGION                 1..470
                       note = VRC01 human IgG1(heavy chain) (mod1)
source                 1..470
                       mol_type = protein
                       organism = synthetic construct
SEQUENCE: 39
MDWTWRILFL VAAATGTHAQ VQLVQSGGQM KKPGESMRIS CRASGYEFID CTLNWIRLAP  60
GKRPEWMGWL KPRGGAVNYA RPLQGRVTMT RDVYSDTAFL ELRSLTVDDT AVYFCTRGKN  120
```

```
CDYNWDFEHW GRGTPVIVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSRDE LTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 40          moltype = DNA  length = 1434
FEATURE                Location/Qualifiers
misc_feature           1..1434
                       note = VRC01 human IgG1(heavy chain) (mod1)
source                 1..1434
                       mol_type = other DNA
                       organism = synthetic construct
SEQUENCE: 40
ggatccgcca ccatggattg gacatggagg attctgtttc tggtcgccgc cgccacagga  60
actcatgctc aggtgcagct ggtgcagtca ggagggcaga tgaagaaacc tggcgagagt  120
atgcgaatct catgcagggc tagcggatac gaattcatcg actgtaccct gaactggatt  180
agactggcac ctggaaagcg gccagagtgg atggggtggc tgaaaccaag aggcggagca  240
gtgaattacg ccagaccact gcagggacga gtcactatga cccgcgacgt gtatagcgat  300
accgcattcc tggaactgcg atccctgaca gtcgacgata ctgccgtgta cttctgcaca  360
aggggcaaga actgtgacta taattgggat tttgagcact ggggccgggg aacaccagtc  420
attgtgagct ccgcaagtac taaggggccc tcagtgtttc cctggctcc ttctagtaaa  480
agtacctcag gggcacagc cgctctggga tgcctggtga aggattactt ccctgagcca  540
gtcacagtga gttggaactc aggcgccctg acatctggag tccatacttt tcccgctgtg  600
ctgcagtcaa gcggactgta cagcctgtcc tctgtggtca cagtgcctag ttcaagcctg  660
gggacacaga cttatatctg caacgtcaat cacaagccca gcaatactaa agtggacaag  720
aaagtggaac ctaagtcctg tgataaaacc catacatgcc ctccctgtcc agctcctgag  780
ctgctgggag ggccaagcgt gttcctgttt ccacccaagc ctaaagacac cctgatgatt  840
tctcggactc ctgaagtcac ctgcgtggtc gtggacgtga gccacgagga ccccgaagtc  900
aagtttaact ggtacgtgga tggcgtcgag gtgcataatg ccaagacaaa acccagggag  960
gaacagtaca acagcaccta tagagtcgtg tccgtcctga cagtgctgca ccaggactgg  1020
ctgaacggaa aggagtataa gtgcaaagtg agcaataagg ccctgccagc tcccatcgag  1080
aaaacaattt ccaaggcaaa agggcagcca cgggaacccc aggtgtacac tctgcctcca  1140
tctcgcgacg agctgactaa gaaccaggtc agcctgacct gtctggtgaa agggttctat  1200
ccaagtgata tcgccgtgga gtgggaaagc aatggccagc ccgaaaacaa ttacaagacc  1260
acacccccctg tgctggacag cgatggctcc ttctttctgt attctaagct gaccgtggat  1320
aaaagtcgct ggcagcaggg aaacgtcttt agctgctccg tgatgcacga ggctctgcac  1380
aatcattaca cccagaagtc tctgagtctg tcacctggca agtgataact cgag        1434

SEQ ID NO: 41          moltype = AA  length = 230
FEATURE                Location/Qualifiers
REGION                 1..230
                       note = VRC01 human IgG1(light chain)(mod1)
source                 1..230
                       mol_type = protein
                       organism = synthetic construct
SEQUENCE: 41
MVLQTQVFIS LLLWISGAYG EIVLTQSPGT LSLSPGETAI ISCRTSQYGS LAWYQQRPGQ  60
APRLVIYSGS TRAAGIPDRF SGSRWGPDYN LTISNLESGD FGVYYCQQYE FFGQGTKVQV  120
DIKRTVAAPS VFIFPPSDEQ LKSGTASVVC LLNNFYPREA KVQWKVDNAL QSGNSQESVT  180
EQDSKDSTYS LSNTLTLSKA DYEKHKVYAC EVTHQGLSSP VTKSFNRGEC             230

SEQ ID NO: 42          moltype = DNA  length = 714
FEATURE                Location/Qualifiers
misc_feature           1..714
                       note = VRC01 human IgG1(light chain)(mod1)
source                 1..714
                       mol_type = other DNA
                       organism = synthetic construct
SEQUENCE: 42
ggatccgcca ccatggtcct gcagacccag gtgttcatct ccctgctgct gtggatttct  60
ggggcatacg gcgaaattgt gctgacccag agccctggga cactgtctct gagtccaggc  120
gagacagcca tcatttcctg tcggacttct cagtacggaa gtctggcatg gtatcagcag  180
cgaccaggac aggctcctcg actggtcatc tactcaggga gcactagggc agccggcatt  240
cctgaccgat tctccggatc taggtggggg cctgattaca acctgaccat ctcaaatctg  300
gaaagcgggg actttggcgt gtactattgc cagcagtatg agttctttgg acaggggacc  360
aaggtccagg tggacatcaa acgcacagtc gctgcaccat ccgtgttcat ttttccaccc  420
tctgatgaac agctgaagtc cggcaccgcc tctgtggtgt gcctgctgaa caatttctac  480
cccagggagg caaaggtcca gtggaaagtg gacaacgccc tgcagtctgg aaatagtcag  540
gagtcagtga ctgaacagga cagcaaggat tccacctatt ctctgtccaa cactctgacc  600
ctgtccaaag ctgattacga gaagcacaaa gtgtatgcat gcgaggtcac tcaccagggg  660
ctgtcatcac cagtcacaaa atccttcaac agaggggaat gctgataact cgag        714

SEQ ID NO: 43          moltype = AA  length = 726
FEATURE                Location/Qualifiers
REGION                 1..726
                       note = VRC01 human IgG4 (mod 2)
source                 1..726
```

```
                        mol_type = protein
                        organism = synthetic construct
SEQUENCE: 43
MDWTWRILFL VAAATGTHAQ VQLVQSGGQM KKPGESMRIS CRASGYEFID CTLNWIRLAP  60
GKRPEWMGWL KPRGGAVNYA RPLQGRVTMT RDVYSDTAFL ELRSLTVDDT AVYFCTRGKN  120
CDYNWDFEHW GRGTPVIVSS ASTKGPSVFP LAPCSRSTSE STAALGCLVK DYFPEPVTVS  180
WNSGALTSGV HTFPAVLQSS GLYSLSSVVT VPSSSLGTKT YTCNVDHKPS NTKVDKRVES  240
KYGPPCPSCP APEFLGGPSV FLFPPKPKDT LMISRTPEVT CVVVDVSQED PEVQFNWYVD  300
GVEVHNAKTK PREEQFNSTY RVVSVLTVLH QDWLNGKEYK CKVSNKGLPS SIEKTISKAK  360
GQPREPQVYT LPPSQEEMTK NQVSLTCLVK GFYPSDIAVE WESNGQPENN YKTTPPVLDS  420
DGSFFLYSRL TVDKSRWQEG NVFSCSVMHE ALHNHYTQKS LSLSLGKRGR KRRSGSGATN  480
FSLLKQAGDV EENPGPMVLQ TQVFISLLLW ISGAYGEIVL TQSPGTLSLS PGETAIISCR  540
TSQYGSLAWY QQRPGQAPRL VIYSGSTRAA GIPDRFSGSR WGPDYNLTIS NLESGDFGVY  600
YCQQYEFFGQ GTKVQVDIKR TVAAPSVFIF PPSDEQLKSG TASVVCLLNN FYPREAKVQW  660
KVDNALQSGN SQESVTEQDS KDSTYSLSNT LTLSKADYEK HKVYACEVTH QGLSSPVTKS  720
FNRGEC                                                            726

SEQ ID NO: 44           moltype = DNA  length = 2202
FEATURE                 Location/Qualifiers
misc_feature            1..2202
                        note = VRC01 human IgG4 (mod 2)
source                  1..2202
                        mol_type = other DNA
                        organism = synthetic construct
SEQUENCE: 44
ggatccgcca ccatggattg gacttggagg attctgtttc tggtcgccgc cgctactgga  60
acccatgctc aggtgcagct ggtgcagtca ggagggcaga tgaagaaacc tggagagagc  120
atgcgaatct cctgcagggc ctctgggtac gaattcatcg actgtacact gaactggatt  180
agactggctc ctgggaagcg gccagagtgg atgggctggc tgaaaccaag aggcggagca  240
gtgaattacg ccagaccact gcagggacga gtcactatga cccgcgacgt gtattctgat  300
actgcttttc tggaactgcg aagtctgacc gtcgacgata cagcagtgta cttctgcacc  360
aggggcaaga actgtgacta taattgggat tttgagcact ggggaagagg gactcctgtc  420
attgtgagct ccgcaagcac caagggacca tccgtgttcc cactggcacc ttgcagtcgg  480
tcaactagcg agtccaccgc cgctctggga tgtctggtga aggattactt cccagaaccc  540
gtcaccgtga gctggaactc cggagccctg accagcggag tccatacatt tcctgctgtg  600
ctgcagtcta gtggactgta ctccctgtca agcgtggtca ccgtcccttc ctctagtctg  660
gggacaaaga cttatacctg caacgtggac cacaaaccat ccaatacaaa ggtcgataaa  720
cgcgtggagt caaagtacgg ccctccctgc cctagctgtc cagctcctga gttcctgggc  780
ggcccaagcg tgttcctgtt tccccctaag cctaaagaca cactgatgat ctctaggaca  840
ccagaagtca cttgcgtggt cgtggacgtg agccaggagg accccgaagt ccagttcaac  900
tggtacgtgg atggcgtcga ggtgcacaat gccaagacca aacctcggga ggaacagttt  960
aactctactt accgcgtcgt gagtgtcctg accgtgctgc atcaggactg gctgaacggc  1020
aaggagtata agtgcaaagt gtccaataag ggactgccat caagcatcga gaaaaccatt  1080
tctaaggcaa aggccagcc aagagaaccc caggtgtaca cactgccacc cagccaggag  1140
gaaatgacaa agaaccaggt ctccctgact tgtctggtga aagggtttta tccaagcgac  1200
attgccgtgg agtgggaatc caatggccag cccgagaaca attacaagac cacacctcca  1260
gtgctggact ctgatggcag tttctttctg tattcaaggc tgaccgtgga taaaagcaga  1320
tggcaggagg gaaacgtctt ctcttgcagt gtgatgcacg aagctctgca caatcattac  1380
actcagaagt cactgagcct gtccctggga aagcgaggac gaaaaaggag atctggcagt  1440
ggagctacca acttcagcct gctgaagcag gcaggagacg tggaggaaaa tcctgggcca  1500
atggtcctgc agactcaggt gttcatcagt ctgctgctgt ggatttcagg cgcctacgga  1560
gagattgtgc tgactcagtc tcccggcacc ctgtcactga gccctggaga aaccgccatc  1620
attagttgtc gaacatcaca gtacgggagc ctggcatggt atcagcagcg accaggacag  1680
gctccccgac tggtcatcta ctccggctct acacgggcag ccggaattcc cgaccgattc  1740
agtgggtcaa ggtggggccc tgattacaac ctgactatct ccaatctgga gtctggcgac  1800
tttggagtgt actattgcca gcagtatgaa ttctttggc agggcaccaa ggtccaggtg  1860
gacatcaaaa gaacagtcgc tgcaccaagc gtgttcatct ttccccttc agatgagcag  1920
ctgaagagtg gaaccgcctc agtggtgtgc ctgctgaaca atttctaccc ccgggaagca  1980
aaggtccagt ggaaagtgga caacgccctg cagtcaggca atagccagga gtccgtgaca  2040
gaacaggact ctaaggatag tacttattca ctgtccaaca cactgactct gtccaaagct  2100
gattacgaga agcacaaagt gtatgcatgc gaggtcaccc accaggggct gtcatcaccc  2160
gtcaccaagt ctttcaatag gggcgaatgt tgataactcg ag                    2202

SEQ ID NO: 45           moltype = AA  length = 726
FEATURE                 Location/Qualifiers
REGION                  1..726
                        note = VRC01 human IgG4 mut (S228P) (mod 3)
source                  1..726
                        mol_type = protein
                        organism = synthetic construct
SEQUENCE: 45
MDWTWRILFL VAAATGTHAQ VQLVQSGGQM KKPGESMRIS CRASGYEFID CTLNWIRLAP  60
GKRPEWMGWL KPRGGAVNYA RPLQGRVTMT RDVYSDTAFL ELRSLTVDDT AVYFCTRGKN  120
CDYNWDFEHW GRGTPVIVSS ASTKGPSVFP LAPCSRSTSE STAALGCLVK DYFPEPVTVS  180
WNSGALTSGV HTFPAVLQSS GLYSLSSVVT VPSSSLGTKT YTCNVDHKPS NTKVDKRVES  240
KYGPPCPPCP APEFLGGPSV FLFPPKPKDT LMISRTPEVT CVVVDVSQED PEVQFNWYVD  300
GVEVHNAKTK PREEQFNSTY RVVSVLTVLH QDWLNGKEYK CKVSNKGLPS SIEKTISKAK  360
GQPREPQVYT LPPSQEEMTK NQVSLTCLVK GFYPSDIAVE WESNGQPENN YKTTPPVLDS  420
DGSFFLYSRL TVDKSRWQEG NVFSCSVMHE ALHNHYTQKS LSLSLGKRGR KRRSGSGATN  480
```

```
FSLLKQAGDV EENPGPMVLQ TQVFISLLLW ISGAYGEIVL TQSPGTLSLS PGETAIISCR  540
TSQYGSLAWY QQRPGQAPRL VIYSGSTRAA GIPDRFSGSR WGPDYNLTIS NLESGDFGVY  600
YCQQYEFFGQ GTKVQVDIKR TVAAPSVFIF PPSDEQLKSG TASVVCLLNN FYPREAKVQW  660
KVDNALQSGN SQESVTEQDS KDSTYSLSNT LTLSKADYEK HKVYACEVTH QGLSSPVTKS  720
FNRGEC                                                             726

SEQ ID NO: 46          moltype = DNA  length = 2202
FEATURE                Location/Qualifiers
misc_feature           1..2202
                       note = VRC01 human IgG4 mut (S228P) (mod 3)
source                 1..2202
                       mol_type = other DNA
                       organism = synthetic construct
SEQUENCE: 46
ggatccgcca ccatggattg gacttggagg attctgtttc tggtcgccgc cgctactgga  60
acccatgctc aggtgcagct ggtgcagtca ggagggcaga tgaagaaacc tggagagagc  120
atgcgaatct cctgcagggc ctctgggtac gaattcatcg actgtacact gaactggatt  180
agactggctc ctgggaagcg gccagagtgg atgggctggc tgaaaccaag aggcggagca  240
gtgaattacg ccagaccact gcagggacga gtcactatga cccgcgacgt gtattctgat  300
actgcttttc tggaactgcg aagtctgacc gtcgacgata cagcagtgta cttctgcacc  360
aggggcaaga actgtgacta taattgggat tttgagcact ggggaagagg gactcctgtc  420
attgtgagct ccgcaagcac caagggacca tccgtgttcc cactggcacc ttgcagtcgg  480
tcaactagcg agtccaccgc cgctctggga tgtctggtga aggattactt cccagaaccc  540
gtcaccgtga gctggaactc cggagccctg accagcggag tccatacatt tcctgctgtg  600
ctgcagtcta gtggactgta ctccctgtca agcgtggtca ccgtcccttc ctctagtctg  660
gggacaaaga cttatacctg caacgtggac cacaaaccat ccaatacaaa ggtcgataaa  720
cgcgtggagt caaagtacgg ccctccctgc cctccctgtc cagctcctga gttcctgggc  780
ggcccaagcg tgttcctgtt tccccctaag cctaaagaca cactgatgat ctctaggaca  840
ccagaagtca cttgcgtggt cgtggacgtg agccaggagg accccgaagt ccagttcaac  900
tggtacgtgg atggcgtcga ggtgcacaat gccaagacca aacctcggga ggaacagttt  960
aactctactt accgcgtcgt gagtgtcctg accgtgctgc atcaggactg gctgaacggc  1020
aaggagtata agtgcaaagt gtccaataag ggactgccat caagcatcga gaaaaccatt  1080
tctaaggcaa aggccagcc aagagaaccc caggtgtaca cactgccacc cagccaggag  1140
gaaatgacaa agaaccaggt ctccctgact tgtctggtga aagggtttta tccaagcgac  1200
attgccgtgg agtgggaatc caatggccag cccgagaaca attacaagac cacacctcca  1260
gtgctggact ctgatggcag tttctttctg tattcaaggc tgaccgtgga taaaagcaga  1320
tggcaggagg gaaacgtctt ctcttgcagt gtgatgcacg aagctctgca caatcattac  1380
actcagaagt cactgagcct gtccctggga aagcgaggac gaaaaaggag atctggcagt  1440
ggagctacca acttcagcct gctgaagcag gcaggagacg tggaggaaaa tcctgggcca  1500
atggtcctgc agactcaggt gttcatcagt ctgctgctgt ggatttcagg cgcctacgga  1560
gagattgtgc tgactcagtc tcccggcacc ctgtcactga gccctggaga aaccgccatc  1620
attagttgtc gaacatcaca gtacgggagc ctggcatggt atcagcagcg accaggacag  1680
gctccccgac tggtcatcta ctccggctct acacgggcag ccggaattcc cgaccgattc  1740
agtgggtcaa ggtggggccc tgattacaac ctgactatct ccaatctgga gtctggcgac  1800
tttggagtgt actattgcca gcagtatgaa ttctttgggc agggcaccaa ggtccaggtg  1860
gacatcaaaa gaacagtcgc tgcaccaagc gtgttcatct ttcccccttc agatgagcag  1920
ctgaagagtg gaaccgcctc agtggtgtgc ctgctgaaca atttctaccc ccgggaagca  1980
aaggtccagt ggaaagtgga caacgccctg cagtcaggca atagccagga gtccgtgaca  2040
gaacaggact ctaaggatag tacttattca ctgtccaaca cactgactct gtccaaagct  2100
gattacgaga agcacaaagt gtatgcatgc gaggtcaccc accaggggct gtcatcaccc  2160
gtcaccaagt ctttcaatag gggcgaatgt tgataactcg ag                     2202

SEQ ID NO: 47          moltype = AA  length = 467
FEATURE                Location/Qualifiers
REGION                 1..467
                       note = VRC01 human IgG4 (heavy chain) (mod4)
source                 1..467
                       mol_type = protein
                       organism = synthetic construct
SEQUENCE: 47
MDWTWRILFL VAAATGTHAQ VQLVQSGGQM KKPGESMRIS CRASGYEFID CTLNWIRLAP  60
GKRPEWMGWL KPRGGAVNYA RPLQGRVTMT RDVYSDTAFL ELRSLTVDDT AVYFCTRGKN  120
CDYNWDFEHW GRGTPVIVSS ASTKGPSVFP LAPCSRSTSE STAALGCLVK DYFPEPVTVS  180
WNSGALTSGV HTFPAVLQSS GLYSLSSVVT VPSSSLGTKT YTCNVDHKPS NTKVDKRVES  240
KYGPPCPPCP APEFLGGPSV FLFPPKPKDT LMISRTPEVT CVVVDVSQED PEVQFNWYVD  300
GVEVHNAKTK PREEQFNSTY RVVSVLTVLH QDWLNGKEYK CKVSNKGLPS SIEKTISKAK  360
GQPREPQVYT LPPSQEEMTK NQVSLTCLVK GFYPSDIAVE WESNGQPENN YKTTPPVLDS  420
DGSFFLYSRL TVDKSRWQEG NVFSCSVMHE ALHNHYTQKS LSLSLGK                467

SEQ ID NO: 48          moltype = DNA  length = 1425
FEATURE                Location/Qualifiers
misc_feature           1..1425
                       note = VRC01 human IgG4 (heavy chain) (mod4)
source                 1..1425
                       mol_type = other DNA
                       organism = synthetic construct
SEQUENCE: 48
ggatccgcca ccatggattg gacttggagg attctgtttc tggtcgccgc cgctactgga  60
acccatgctc aggtgcagct ggtgcagtca ggagggcaga tgaagaaacc tggagagagc  120
```

-continued

```
atgcgaatct cctgcagggc ctctgggtac gaattcatcg actgtacact gaactggatt  180
agactggctc ctgggaagcg gccagagtgg atgggctggc tgaaaccaag aggcggagca  240
gtgaattacg ccagaccact gcagggacga gtcactatga cccgcgacgt gtattctgat  300
actgcttttc tggaactgcg aagtctgacc gtcgacgata cagcagtgta cttctgcacc  360
aggggcaaga actgtgacta taattgggat tttgagcact ggggaagagg gactcctgtc  420
attgtgagct ccgcaagcac caagggacca tccgtgttcc cactggcacc ttgcagtcgg  480
tcaactagcg agtccaccgc cgctctggga tgtctggtga aggattactt cccagaaccc  540
gtcaccgtga gctggaactc cggagccctg accagcggag tccatacatt tcctgctgtg  600
ctgcagtcta gtggactgta ctccctgtca agcgtggtca ccgtcccttc ctctagtctg  660
gggacaaaga cttatacctg caacgtggac cacaaaccat ccaatacaaa ggtcgataaa  720
cgcgtggagt caaagtacgg ccctccctgc cctccctgtc cagctcctga gttcctgggc  780
ggcccaagcg tgttcctgtt tccccctaag cctaaagaca cactgatgat ctctaggaca  840
ccagaagtca cttgcgtggt cgtggacgtg agccaggagg accccgaagt ccagttcaac  900
tggtacgtgg atggcgtcga ggtgcacaat gccaagacca aacctcggga ggaacagttt  960
aactctactt accgcgtcgt gagtgtcctg accgtgctgc atcaggactg gctgaacggc  1020
aaggagtata agtgcaaagt gtccaataag ggactgccat caagcatcga gaaaaccatt  1080
tctaaggcaa aaggccagcc aagagaaccc caggtgtaca cactgccacc cagccaggag  1140
gaaatgacaa agaaccaggt ctccctgact tgtctggtga aagggtttta tccaagcgac  1200
attgccgtgg agtgggaatc caatggccag cccgagaaca attacaagac cacacctcca  1260
gtgctggact ctgatggcag tttctttctg tattcaaggc tgaccgtgga taaaagcaga  1320
tggcaggagg gaaacgtctt ctcttgcagt gtgatgcacg aagctctgca caatcattac  1380
actcagaagt cactgagcct gtccctggga aagtgataac tcgag                 1425

SEQ ID NO: 49          moltype = AA  length = 230
FEATURE                Location/Qualifiers
REGION                 1..230
                       note = VRC01 human IgG4 (light chain)(mod4)
source                 1..230
                       mol_type = protein
                       organism = synthetic construct
SEQUENCE: 49
MVLQTQVFIS LLLWISGAYG EIVLTQSPGT LSLSPGETAI ISCRTSQYGS LAWYQQRPGQ  60
APRLVIYSGS TRAAGIPDRF SGSRWGPDYN LTISNLESGD FGVYYCQQYE FFGQGTKVQV  120
DIKRTVAAPS VFIFPPSDEQ LKSGTASVVC LLNNFYPREA KVQWKVDNAL QSGNSQESVT  180
EQDSKDSTYS LSNTLTLSKA DYEKHKVYAC EVTHQGLSSP VTKSFNRGEC             230

SEQ ID NO: 50          moltype = DNA  length = 714
FEATURE                Location/Qualifiers
misc_feature           1..714
                       note = VRC01 human IgG4 (light chain)(mod4)
source                 1..714
                       mol_type = other DNA
                       organism = synthetic construct
SEQUENCE: 50
ggatccgcca ccatggtcct gcagactcag gtgttcatca gtctgctgct gtggatttca  60
ggcgcctacg gagagattgt gctgactcag tctcccggca ccctgtcact gagccctgga  120
gaaaccgcca tcattagttg tcgaacatca cagtacggga gcctggcatg gtatcagcag  180
cgaccaggac aggctccccg actggtcatc tactccggct ctacacgggc agccggaatt  240
cccgaccgat tcagtgggtc aaggtggggc cctgattaca acctgactat ctccaatctg  300
gagtctggcg actttggagt gtactattgc cagcagtatg aattctttgg gcagggcacc  360
aaggtccagg tggacatcaa aagaacagtc gctgcaccaa gcgtgttcat ctttcccccct  420
tcagatgagc agctgaagag tggaaccgcc tcagtggtgt gcctgctgaa caatttctac  480
ccccgggaag caaaggtcca gtggaaagtg gacaacgccc tgcagtcagg caatagccag  540
gagtccgtga cagaacagga ctctaaggat agtacttatt cactgtccaa cacactgact  600
ctgtccaaag ctgattacga gaagcacaaa gtgtatgcat gcgaggtcac ccaccagggg  660
ctgtcatcac ccgtcaccaa gtctttcaat aggggcgaat gttgataact cgag       714

SEQ ID NO: 51          moltype = AA  length = 725
FEATURE                Location/Qualifiers
REGION                 1..725
                       note = VRC01 human IgG2_New
source                 1..725
                       mol_type = protein
                       organism = synthetic construct
SEQUENCE: 51
MDWTWRILFL VAAATGTHAQ VQLVQSGGQM KKPGESMRIS CRASGYEFID CTLNWIRLAP  60
GKRPEWMGWL KPRGGAVNYA RPLQGRVTMT RDVYSDTAFL ELRSLTVDDT AVYFCTRGKN  120
CDYNWDFEHW GRGTPVIVSS ASTKGPSVFP LAPCSRSTSE STAALGCLVK DYFPEPVTVS  180
WNSGALTSGV HTFPAVLQSS GLYSLSSVVT VPSSNFGTQT YTCNVDHKPS NTKVDKTVER  240
KCCVECPPCP APPVAGPSVF LFPPKPKDTL MISRTPEVTC VVVDVSHEDP EVQFNWYVDG  300
VEVHNAKTKP REEQFNSTFR VVSVLTVVHQ DWLNGKEYKC KVSNKGLPAP IEKTISKTKG  360
QPREPQVYTL PPSREEMTKN QVSLTCLVKG FYPSDIAVEW ESNGQPENNY KTTPPMLDSD  420
GSFFLYSKLT VDKSRWQQGN VFSCSVMHEA LHNHYTQKSL SLSPGKRGRK RRSGSGATNF  480
SLLKQAGDVE ENPGPMVLQT QVFISLLLWI SGAYGEIVLT QSPGTLSLSP GETAIISCRT  540
SQYGSLAWYQ QRPGQAPRLV IYSGSTRAAG IPDRFSGSRW GPDYNLTISN LESGDFGVYY  600
CQQYEFFGQG TKVQVDIKRT VAAPSVFIFP PSDEQLKSGT ASVVCLLNNF YPREAKVQWK  660
VDNALQSGNS QESVTEQDSK DSTYSLSNTL TLSKADYEKH KVYACEVTHQ GLSSPVTKSF  720
NRGEC                                                            725
```

```
SEQ ID NO: 52          moltype = DNA  length = 2199
FEATURE                Location/Qualifiers
misc_feature           1..2199
                       note = VRC01 human IgG2_New
source                 1..2199
                       mol_type = other DNA
                       organism = synthetic construct
SEQUENCE: 52
ggatccgcca ccatggattg gacatggagg attctgtttc tggtcgccgc cgccactgga  60
actcatgctc aggtgcagct ggtgcagtct ggagggcaga tgaagaaacc aggggagtct  120
atgcgaatca gttgcagggc ttcaggctac gaattcatcg actgtaccct gaactggatt  180
agactggcac ctggcaagcg accagagtgg atgggatggc tgaaacccag aggcggagcc  240
gtgaattacg ctagacctct gcagggacgg gtcactatga cccgcgacgt gtatagcgat  300
acagcttttc tggagctgcg aagcctgacc gtcgacgata cagcagtgta cttctgcact  360
aggggcaaga actgtgacta taattgggat tttgaacact gggggagagg caccccagtc  420
attgtgagct ccgcatctac aaaaggacct agcgtgttcc cactggcacc ttgcagccgg  480
tccacttctg agagtaccgc cgctctggga tgtctggtga aggattactt ccccgaacct  540
gtcacagtgt cttggaacag tggggccctg actagcggcg tccacacctt tcccgctgtg  600
ctgcagtcta gtgggctgta cagcctgtca agcgtggtca ctgtgccatc ctctaatttt  660
ggcacacaga cttatacctg caacgtggac cataagccct ccaatacaaa ggtcgataaa  720
actgtggaga gaaaatgctg cgtggaatgc cctccctgtc cagcaccacc cgtcgcagga  780
ccaagcgtgt tcctgtttcc tccaaagcca aaagacacac tgatgatcag ccggacaccc  840
gaggtcactt gcgtggtcgt ggacgtgagc cacgaggacc ccgaagtcca gttcaactgg  900
tacgtggatg gcgtcgaagt gcataatgct aagaccaaac caagggagga acagttcaac  960
tcaaccttta gagtcgtgag cgtgctgaca gtcgtgcatc aggactggct gaacggaaag  1020
gagtataagt gcaaagtgtc caataagggg ctgccagccc ccatcgagaa aaccatttct  1080
aagacaaaag gccagccacg ggaaccccag gtgtacacac tgccccccttc ccgcgaggaa  1140
atgactaaga accaggtctc tctgacctgt ctggtgaaag gcttttatcc ctctgacatt  1200
gccgtggagt gggaaagtaa tggacagcct gagaacaatt acaagaccac accacccatg  1260
ctggactcag atggaagctt ctttctgtat tccaagctga ccgtggataa atctagatgg  1320
cagcagggga acgtcttctc atgcagcgtg atgcacgagg ccctgcacaa tcattacact  1380
cagaagtccc tgtctctgag tcctgggaag cggggccgca aaaggagatc aggaagcggg  1440
gctaccaact tcagcctgct gaagcaggca ggggacgtgg aggaaaatcc tggcccaatg  1500
gtcctgcaga ctcaggtgtt catcagcctg ctgctgtgga tttccggagc atacggggag  1560
attgtgctga cccagtcacc tggaacactg tccctgtctc caggggaaac agccatcatt  1620
agctgtcgaa cttcccagta cggctctctg gcatggtatc agcagcgacc aggacaggct  1680
cctcgactgg tcatctacag tggatcaacc cgggcagccg ggattcctga ccgattcagc  1740
ggctccaggt ggggacctga ttacaacctg acaatcagta atctggagtc aggagacttt  1800
ggggtgtact attgccagca gtatgaattc tttggccagg gaacaaaggt ccaggtggac  1860
atcaaacgca ctgtcgctgc acccagcgtg ttcatttttc ctccatccga tgagcagctg  1920
aagagcggaa ccgcatccgt ggtgtgcctg ctgaacaatt tctaccctag ggaagcaaag  1980
gtccagtgga aagtggacaa cgccctgcag tccggcaatt ctcaggagag tgtgactgaa  2040
caggactcaa aggatagcac ctattccctg agtaacacac tgactctgag caaagctgat  2100
tacgagaagc acaaagtgta tgcatgcgaa gtcacccacc aggggctgag ctctccagtc  2160
actaagtctt ttaatcgggg cgaatgctga taactcgag                       2199

SEQ ID NO: 53          moltype = AA  length = 776
FEATURE                Location/Qualifiers
REGION                 1..776
                       note = VRC01 human IgG3_new
source                 1..776
                       mol_type = protein
                       organism = synthetic construct
SEQUENCE: 53
MDWTWRILFL VAAATGTHAQ VQLVQSGGQM KKPGESMRIS CRASGYEFID CTLNWIRLAP  60
GKRPEWMGWL KPRGGAVNYA RPLQGRVTMT RDVYSDTAFL ELRSLTVDDT AVYFCTRGKN  120
CDYNWDFEHW GRGTPVIVSS ASTKGPSVFP LAPCSRSTSG GTAALGCLVK DYFPEPVTVS  180
WNSGALTSGV HTFPAVLQSS GLYSLSSVVT VPSSSLGTQT YTCNVNHKPS NTKVDKRVEL  240
KTPLGDTTHT CPRCPEPKSC DTPPPCPRCP EPKSCDTPPP CPRCPEPKSC DTPPPCPRCP  300
APELLGGPSV FLFPPKPKDT LMISRTPEVT CVVVDVSHED PEVQFKWYVD GVEVHNAKTK  360
PREEQYNSTF RVVSVLTVLH QDWLNGKEYK CKVSNKALPA PIEKTISKTK GQPREPQVYT  420
LPPSREEMTK NQVSLTCLVK GFYPSDIAVE WESSGQPENN YNTTPPMLDS DGSFFLYSKL  480
TVDKSRWQQG NIFSCSVMHE ALHNRFTQKS LSLSPGKRGR KRRSGSGATN FSLLKQAGDV  540
EENPGPMVLQ TQVFISLLLW ISGAYGEIVL TQSPGTLSLS PGETAIISCR TSQYGSLAWY  600
QQRPGQAPRL VIYSGSTRAA GIPDRFSGSR WGPDYNLTIS NLESGDFGVY YCQQYEFFGQ  660
GTKVQVDIKR TVAAPSVFIF PPSDEQLKSG TASVVCLLNN FYPREAKVQW KVDNALQSGN  720
SQESVTEQDS KDSTYSLSNT LTLSKADYEK HKVYACEVTH QGLSSPVTKS FNRGEC      776

SEQ ID NO: 54          moltype = DNA  length = 2352
FEATURE                Location/Qualifiers
misc_feature           1..2352
                       note = VRC01 human IgG3_new
source                 1..2352
                       mol_type = other DNA
                       organism = synthetic construct
SEQUENCE: 54
ggatccgcca ccatggattg gacatggagg attctgttcc tggtcgccgc cgccacagga  60
acccatgctc aggtgcagct ggtgcagtct ggagggcaga tgaagaaacc cggcgagtca  120
atgcgaatca gctgcagggc ttccggatac gaattcatcg attgtaccct gaactggatt  180
```

```
agactggcac caggaaagcg gcccgagtgg atggggtggc tgaaaccacg cggcggagca  240
gtgaattacg ccagacccct gcagggccgg gtcacaatga ctcgcgacgt gtattcagat  300
accgcattcc tggagctgcg aagcctgact gtcgacgata ccgccgtgta cttctgcaca  360
aggggcaaaa actgtgacta caactgggat ttcgaacact ggggccgcgg aaccccagtc  420
attgtgagct ccgcatcaac aaaggggcct agcgtgtttc ctctggcccc atgcagtagg  480
tcaacaagcg gggcactgc cgctctggga tgtctggtga aggactattt cccagagccc  540
gtcaccgtgt catggaacag cggcgccctg acatccggag tccatacttt tcccgctgtg  600
ctgcagtcta gtggactgta ctctctgtca agcgtggtca cagtcccttc ctctagtctg  660
gggacccaga catatacttg taacgtgaat cacaagccaa gcaacactaa ggtcgacaaa  720
agagtggagc tgaaaacccc tctgggcgat accacacata catgcccaag atgtcctgag  780
ccaaagtcct gcgacacgcc tccaccatgc cctcggtgtc ccgaacctaa atcttgtgat  840
acacccccctc catgcccacg atgtccagag ccaaagagct gcgacactcc ccctccatgt  900
cctcgatgtc ctgctccaga actgctggga gggccctccg tgttcctgtt tccccctaag  960
cctaaagata ccctgatgat cagtcggacc ccagaggtca catgcgtggt cgtggacgtg  1020
tcccacgagg accccgaagt ccagttcaag tggtacgtgg acggcgtcga agtgcataac  1080
gccaagacaa aacctaggga ggaacagtat aattccactt ttagagtcgt gtctgtcctg  1140
accgtgctgc accaggactg gctgaacgga aaggagtaca agtgtaaagt gtctaataag  1200
gccctgcccg ctcctatcga gaaaactatt agcaagacca aagggcagcc ccgggaacct  1260
caggtgtaca ccctgccacc ctcccgcgag gaaatgacta agaaccaggt ctctctgacc  1320
tgcctggtga aagggttcta tcccagcgat atcgctgtgg agtgggaatc aagcggccag  1380
cctgagaaca attacaatac taccccctcca atgctggact ccgatggctc tttctttctg  1440
tatagtaagc tgacagtgga caaatcaaga tggcagcagg gaaacatttt ctcctgttct  1500
gtgatgcacg aagccctgca taatcggttt acccagaaga gtctgtcact gagcccaggc  1560
aagcggggac gcaaaaggag atccgggtct ggcgctacaa acttctccct gctgaagcag  1620
gcaggcgacg tggaggaaaa tccaggacct atggtcctgc agacccaggt gttcatctct  1680
ctgctgctgt ggattagtgg ggcatacggc gaaattgtgc tgacccagtc cccagggaca  1740
ctgagtctgt cacccggcga gacagccatc atttcttgcc ggactagtca gtacggatca  1800
ctggcatggt atcagcagcg acctggacag gctccacgac tggtcatcta cagcgggtcc  1860
actagggcag ccggcattcc tgaccgattc tctggaagta ggtgggggcc tgattacaac  1920
ctgaccatca gcaatctgga gtccggggac tttggcgtgt actattgtca gcagtatgaa  1980
ttctttggac aggggactaa ggtccaggtg gatatcaaac gcaccgtcgc tgcacccagc  2040
gtgttcatct ttcccccctag tgacgaacag ctgaagtctg gcaccgccag tgtcgtgtgc  2100
ctgctgaaca acttctaccc tagggaggca aaggtccagt ggaaagtgga taacgccctg  2160
cagagtggaa attcacagga gagcgtgaca gaacaggact ccaaggattc tacttatagt  2220
ctgtccaaca ccctgacact gagcaaagct gactacgaga agcacaaagt gtatgcatgt  2280
gaggtcaccc accaggggct gagctcacca gtcacaaaat ccttcaatag gggagaatgt  2340
tgataactcg ag                                                    2352
```

```
SEQ ID NO: 55          moltype = AA  length = 489
FEATURE                Location/Qualifiers
REGION                 1..489
                       note = PGT145 Heavy Chain
source                 1..489
                       mol_type = protein
                       organism = synthetic construct
SEQUENCE: 55
MDWTWRILFL VAAATGTHAQ VQLVQSGAEV KKPGSSVKVS CKASGNSFSN HDVHWVRQAT  60
GQGLEWMGWM SHEGDKTGLA QKFQGRVTIT RDSGASTVYM ELRGLTADDT AIYYCLTGSK  120
HRLRDYFLYN EYGPNYEEWG DYLATLDVWG HGTAVTVSSA STKGPSVFPL APSSKSTSGG  180
TAALGCLVKD YFPEPVTVSW NSGALTSGVH TFPAVLQSSG LYSLSSVVTV PSSSLGTQTY  240
ICNVNHKPSN TKVDKKVEPK SCDKTHTCPP CPAPELLGGP SVFLFPPKPK DTLMISRTPE  300
VTCVVVDVSH EDPEVKFNWY VDGVEVHNAK TKPREEQYNS TYRVVSVLTV LHQDWLNGKE  360
YKCKVSNKAL PAPIEKTISK AKGQPREPQV YTLPPSRDEL TKNQVSLTCL VKGFYPSDIA  420
VEWESNGQPE NNYKTTPPVL DSDGSFFLYS KLTVDKSRWQ QGNVFSCSVM HEALHNHYTQ  480
KSLSLSPGK                                                        489
```

```
SEQ ID NO: 56          moltype = DNA  length = 1467
FEATURE                Location/Qualifiers
misc_feature           1..1467
                       note = PGT145 Heavy Chain
source                 1..1467
                       mol_type = other DNA
                       organism = synthetic construct
SEQUENCE: 56
atggattgga catggaggat tctgtttctg gtcgccgccg ccactggaac tcacgctcag  60
gtgcagctgg tgcagtcagg ggccgaagtg aagaagcccg gcagctccgt gaaggtgtcc  120
tgcaaggcct ctggcaactc cttctctaat cacgacgtgc actgggtgag gcaggcaacc  180
ggacagggcc tggagtggat gggctggatg tcccacgagg gcgacaagac aggcctggca  240
cagaagtttc agggccgggt gaccatcaca cgcgattccg gcgcctctac cgtgtatatg  300
gagctgagag gcctgaccgc cgacgataca gccatctact attgcctgac aggcagcaag  360
cacaggctga gagactactt cctgtataac gagtacggcc ctaattatga ggagtggggc  420
gactacctgg ccaccctgga cgtgtgggga cacggaaccg cagtgacagt gtctagcgcc  480
agcacaaagg gcccatccgt gtttccactg gcaccctcct ctaagagcac ctccggcggc  540
acagccgccc tgggctgtct ggtgaaggat tacttcccag agccagtgac cgtgagctgg  600
aactccggcg ccctgacctc cggagtgcac acatttccag ccgtgctgca gagctccggc  660
ctgtatagcc tgtctagcgt ggtgaccgtg ccctcctcta gcctgggcac ccagacatac  720
atctgcaacg tgaatcacaa gccatccaat acaaaggtgg acaagaaggt ggagcccaag  780
tcttgtgata agacccacac atgccctccc tgtcctgcac cagagctgct gggcggccca  840
tccgtgttcc tgtttccacc caagcctaag gacaccctga tgatcagccg gaccccagag  900
```

```
gtgacatgcg tggtggtgga cgtgtcccac gaggaccccg aggtgaagtt caactggtac  960
gtggatggcg tggaggtgca caatgccaag accaagccta gggaggagca gtataactct  1020
acctacagag tggtgagcgt gctgacagtg ctgcaccagg actggctgaa cggcaaggag  1080
tacaagtgca aggtgtctaa taaggccctg cccgccccta tcgagaagac catcagcaag  1140
gcaaagggac agcctcggga gccacaggtg tatacactgc ctccatctcg cgacgagctg  1200
accaagaacc aggtgagcct gacatgtctg gtgaagggct tctaccctag cgatatcgcc  1260
gtggagtggg agtccaatgg ccagccagag aacaattata agaccacacc ccctgtgctg  1320
gactctgatg gcagcttctt tctgtactcc aagctgaccg tggataagtc tcgctggcag  1380
cagggcaacg tgttcagctg tagcgtgatg cacgaagccc tgcacaacca ctacacccag  1440
aaaagcctgt cactgagccc cggaaaa                                     1467

SEQ ID NO: 57           moltype = AA  length = 239
FEATURE                 Location/Qualifiers
REGION                  1..239
                        note = PGT145 Kappa Light Chain
source                  1..239
                        mol_type = protein
                        organism = synthetic construct
SEQUENCE: 57
MVLQTQVFIS LLLWISGAYG EVVITQSPLF LPVTPGEAAS LSCKCSHSLQ HSTGANYLAW  60
YLQRPGQTPR LLIHLATHRA SGVPDRFSGS GSGTDFTLKI SRVESDDVGT YYCMQGLHSP  120
WTFGQGTKVE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 58           moltype = DNA  length = 717
FEATURE                 Location/Qualifiers
misc_feature            1..717
                        note = PGT145 Kappa Light Chain
source                  1..717
                        mol_type = other DNA
                        organism = synthetic construct
SEQUENCE: 58
atggtgctgc agacccaggt gttcatttca ctgctgctgt ggatttcagg agcctacgga  60
gaagtcgtca ttacccagtc ccctctgttc ctgccagtga ccccaggaga ggcagcatct  120
ctgagctgca agtgttccca ctctctgcag cacagcacag gcgccaacta cctggcctgg  180
tatctgcaga ggcctggcca gaccccaaga ctgctgatcc acctggcaac acacagggca  240
tccggagtgc cagaccgctt cagcggctcc ggctctggaa ccgacttcac cctgaagatc  300
agcagggtgg agtccgacga tgtgggcacc tactattgca tgcagggcct gcactctccc  360
tggaccttcg gccagggcac aaaggtggag atcaagagga ccgtggcagc accttccgtg  420
ttcatctttc ccccttctga cgagcagctg aagtctggca cagccagcgt ggtgtgcctg  480
ctgaacaact tctaccccag ggaggccaag gtgcagtgga aggtggataa cgccctgcag  540
agcggcaatt cccaggagtc tgtgaccgag caggacagca aggattccac atattctctg  600
agctccaccc tgacactgag caaggccgac tacgagaagc acaaggtgta tgcctgcgag  660
gtcacccatc aggggctgtc aagtccagtc acaaagtcct tcaatagggg cgaatgc    717

SEQ ID NO: 59           moltype = AA  length = 484
FEATURE                 Location/Qualifiers
REGION                  1..484
                        note = PGT151 Heavy Chain
source                  1..484
                        mol_type = protein
                        organism = synthetic construct
SEQUENCE: 59
MDWTWRILFL VAAATGTHAR VQLVESGGGV VQPGKSVRLS CVVSDFPFSK YPMYWVRQAP  60
GKGLEWVAAI SGDAWHVVYS NSVQGRFLVS RDNVKNTLYL EMNSLKIEDT AVYRCARMFQ  120
ESGPPRLDRW SGRNYYYYSG MDVWGQGTTV TVSSASTKGP SVFPLAPSSK STSGGTAALG  180
CLVKDYFPEP VTVSWNSGAL TSGVHTFPAV LQSSGLYSLS SVVTVPSSSL GTQTYICNVN  240
HKPSNTKVDK KVEPKSCDKT HTCPPCPAPE LLGGPSVFLF PPKPKDTLMI SRTPEVTCVV  300
VDVSHEDPEV KFNWYVDGVE VHNAKTKPRE EQYNSTYRVV SVLTVLHQDW LNGKEYKCKV  360
SNKALPAPIE KTISKAKGQP REPQVYTLPP SRDELTKNQV SLTCLVKGFY PSDIAVEWES  420
NGQPENNYKT TPPVLDSDGS FFLYSKLTVD KSRWQQGNVF SCSVMHEALH NHYTQKSLSL  480
SPGK                                                              484

SEQ ID NO: 60           moltype = DNA  length = 1452
FEATURE                 Location/Qualifiers
misc_feature            1..1452
                        note = PGT151 Heavy Chain
source                  1..1452
                        mol_type = other DNA
                        organism = synthetic construct
SEQUENCE: 60
atggactgga cttggcgcat tctgtttctg gtcgcagccg caaccgggac tcacgctcgg  60
gtgcagctgg tcgaatcagg aggaggagtg gtgcagccag gcaagagcgt gcggctgtcc  120
tgcgtggtgt ctgacttccc cttcagcaag tacccaatgt attgggtgcg ccaggcacca  180
ggcaagggcc tggagtgggt ggcagcaatc tccggcgatg catggcacgt ggtgtactct  240
aacagcgtgc agggcaggtt cctggtgagc agagacaacg tgaagaatac cctgtacctg  300
gagatgaatt ccctgaagat cgaggataca gccgtgtata ggtgcgccag aatgtttcag  360
gagagcggcc ctcccaggct ggacaggtgg agcggaagga actactatta ctattccgga  420
atggacgtgt ggggacaggg aaccacagtg accgtgagct ccgccagcac aaagggccct  480
```

```
tccgtgttcc ctctggcccc atctagcaag tccacctctg gcggcacagc cgccctgggc  540
tgtctggtga aggactactt ccctgagcca gtgaccgtgt cttggaacag cggcgccctg  600
acctctggag tgcacacatt tcccgccgtg ctgcagtcct ctggcctgta ctccctgagc  660
tccgtggtga ccgtgccttc tagctccctg ggcacccaga catatatctg caacgtgaat  720
cacaagccca gcaatacaaa ggtggacaag aaggtggagc ctaagtcctg tgataagacc  780
cacacatgcc caccctgtcc agcacctgag ctgctgggcg gccctagcgt gttcctgttt  840
cctccaaagc caaaggacac cctgatgatc tctagaaccc ctgaggtgac atgcgtggtg  900
gtggacgtga gccacgagga ccccgaggtg aagtttaact ggtacgtgga tggcgtggag  960
gtgcacaatg ccaagacaaa gccccgggag gagcagtaca actctaccta tcgcgtggtg  1020
agcgtgctga cagtgctgca ccaggactgg ctgaacggca aggagtataa gtgcaaggtg  1080
tccaataagg ccctgccagc ccccatcgag aagaccatct ctaaggcaaa gggacagccc  1140
agggagcctc aggtgtacac actgccccct tccagagacg agctgaccaa gaaccaggtg  1200
tctctgacat gtctggtgaa gggcttctat ccatctgata tcgccgtgga gtgggagagc  1260
aatggccagc ccgagaacaa ttacaagacc acaccacccg tgctggactc cgatggctct  1320
ttctttctgt attccaagct gaccgtggat aagtctaggt ggcagcaggg caacgtgttc  1380
agctgttccg tgatgcacga agcactgcac aaccattaca cccagaagag cctgagcctg  1440
agccccggca ag                                                     1452
```

```
SEQ ID NO: 61          moltype = AA  length = 239
FEATURE                Location/Qualifiers
REGION                 1..239
                       note = PGT151 Kappa Light Chain
source                 1..239
                       mol_type = protein
                       organism = synthetic construct
SEQUENCE: 61
MVLQTQVFIS LLLWISGAYG DIVMTQTPLS LSVTPGQPAS ISCKSSESLR QSNGKTSLYW  60
YRQKPGQSPQ LLVFEVSNRF SGVSDRFVGS GSGTDFTLRI SRVEAEDVGF YYCMQSKDFP  120
LTFGGGTKVD LKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239
```

```
SEQ ID NO: 62          moltype = DNA  length = 717
FEATURE                Location/Qualifiers
misc_feature           1..717
                       note = PGT151 Kappa Light Chain
source                 1..717
                       mol_type = other DNA
                       organism = synthetic construct
SEQUENCE: 62
atggtgctgc agactcaggt gtttattagc ctgctgctgt ggatttccgg ggcctacggg  60
gacattgtga tgacccagac tcctctgtcc ctgtctgtga ccccaggaca gccagcaagc  120
atctcctgca agagctccga gagcctgagg cagtccaacg gcaagacaag cctgtactgg  180
tatagacaga agcctggcca gagcccacag ctgctggtgt tcgaggtgtc caatcggttt  240
tccggcgtgt ctgacaggtt cgtgggctct ggcagcggaa ccgacttcac cctgaggatc  300
tctagagtgg aggccgagga cgtgggcttc tactattgca tgcagtccaa ggatttcccc  360
ctgaccttcg gcggcggcac aaaggtggac ctgaagagga ccgtggcagc accttccgtg  420
ttcatctttc ccccttctga tgagcagctg aagtctggca cagccagcgt ggtgtgcctg  480
ctgaacaact tctacccccg cgaggccaag gtgcagtgga aggtggacaa cgccctgcag  540
agcggcaatt cccaggagtc tgtgaccgag caggacagca aggattccac atattctctg  600
tctagcaccc tgacactgtc caaggccgat tacgagaagc acaaggtgta tgcctgtgag  660
gtcacccacc aggggctgtc cagtccagtc acaaaatcct tcaatcgggg agaatgt     717
```

```
SEQ ID NO: 63          moltype = AA  length = 490
FEATURE                Location/Qualifiers
REGION                 1..490
                       note = PGDM1400 Heavy Chain
source                 1..490
                       mol_type = protein
                       organism = synthetic construct
SEQUENCE: 63
MDWTWRILFL VAAATGTHAQ AQLVQSGPEV RKPGTSVKVS CKAPGNTLKT YDLHWVRSVP  60
GQGLQWMGWI SHEGDKKVIV ERFKAKVTID WDRSTNTAYL QLSGLTSGDT AVYYCAKGSK  120
HRLRDYALYD DDGALNWAVD VDYLSNLEFW GQGTAVTVSS ASTKGPSVFP LAPSSKSTSG  180
GTAALGCLVK DYFPEPVTVS WNSGALTSGV HTFPAVLQSS GLYSLSSVVT VPSSSLGTQT  240
YICNVNHKPS NTKVDKKVEP KSCDKTHTCP PCPAPELLGG PSVFLFPPKP KDTLMISRTP  300
EVTCVVVDVS HEDPEVKFNW YVDGVEVHNA KTKPREEQYN STYRVVSVLT VLHQDWLNGK  360
EYKCKVSNKA LPAPIEKTIS KAKGQPREPQ VYTLPPSRDE LTKNQVSLTC LVKGFYPSDI  420
AVEWESNGQP ENNYKTTPPV LDSDGSFFLY SKLTVDKSRW QQGNVFSCSV MHEALHNHYT  480
QKSLSLSPGK                                                        490
```

```
SEQ ID NO: 64          moltype = DNA  length = 1470
FEATURE                Location/Qualifiers
misc_feature           1..1470
                       note = PGDM1400 Heavy Chain
source                 1..1470
                       mol_type = other DNA
                       organism = synthetic construct
SEQUENCE: 64
atggattgga catggaggat tctgtttctg gtcgccgccg caaccggaac tcacgctcag  60
```

```
gctcagctgg tgcagtctgg acctgaagtg aggaagccag gcacctccgt gaaggtgtct  120
tgcaaggccc ccggcaacac cctgaagaca tacgatctgc actgggtgag atctgtgcca  180
ggacagggcc tgcagtggat gggatggatc agccacgagg gcgacaagaa agtgatcgtg  240
gagaggttca aggccaaggt gaccatcgat tgggacagat ccaccaatac agcctacctg  300
cagctgagcg gcctgacctc cggcgataca gccgtgtact attgcgccaa gggcagcaag  360
cacaggctga gagactacgc cctgtatgac gatgacggcg ccctgaactg ggccgtggat  420
gtggactatc tgtccaatct ggagttctgg ggacagggaa ccgcagtgac agtgagctcc  480
gcctctacca agggccctag cgtgtttcca ctggccccct ctagcaagtc taccagcggc  540
ggcacagccg ccctgggatg tctggtgaag gactacttcc cagagcccgt gacagtgagc  600
tggaactccg gcgccctgac ctctggagtg cacacatttc ctgccgtgct gcagtcctct  660
ggcctgtaca gcctgagctc cgtggtgacc gtgccatcta gctccctggg cacccagaca  720
tatatctgca acgtgaatca caagcctagc aatacaaagg tggataagaa ggtggagcca  780
aagtcctgtg acaagaccca cacatgccct ccctgtcctg caccagagct gctgggcggc  840
ccaagcgtgt tcctgtttcc acccaagcct aaggataccc tgatgatctc ccggacccca  900
gaggtgacat gcgtggtggt ggacgtgagc cacgaggacc ccgaggtgaa gtttaactgg  960
tacgtggacg gcgtggaggt gcacaatgcc aagacaaagc cccgggagga gcagtacaac  1020
tccacctatc gcgtggtgtc tgtgctgaca gtgctgcacc aggattggct gaacggcaag  1080
gagtataagt gcaaggtgag caataaggcc ctgcccgccc ctatcgagaa gaccatctcc  1140
aaggcaaagg gacagcctcg ggagccacag gtgtacacac tgcctccatc ccgcgatgag  1200
ctgaccaaga accaggtgtc tctgacatgt ctggtgaagg gcttctatcc ctctgacatc  1260
gccgtggagt gggagagcaa tggccagcct gagaacaatt acaagaccac accccctgtg  1320
ctggattctg acggcagctt ctttctgtat agcaagctga ccgtggacaa gtcccgctgg  1380
cagcagggca acgtgttcag ctgttctgtg atgcacgaag cactgcacaa ccactacacc  1440
cagaagtcac tgtcactgtc accaggaaaa                                   1470

SEQ ID NO: 65           moltype = AA  length = 239
FEATURE                 Location/Qualifiers
REGION                  1..239
                        note = PGDM1400 Kappa Light Chain
source                  1..239
                        mol_type = protein
                        organism = synthetic construct
SEQUENCE: 65
MVLQTQVFIS LLLWISGAYG DFVLTQSPHS LSVTPGESAS ISCKSSHSLI HGDRNNYLAW  60
YVQKPGRSPQ LLIYLASSRA SGVPDRFSGS GSDKDFTLKI SRVETEDVGT YYCMQGRESP  120
WTFGQGTKVD IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 66           moltype = DNA  length = 717
FEATURE                 Location/Qualifiers
misc_feature            1..717
                        note = PGDM1400 Kappa Light Chain
source                  1..717
                        mol_type = other DNA
                        organism = synthetic construct
SEQUENCE: 66
atggtgctgc agacccaggt gttcatttca ctgctgctgt ggatttccgg ggcatacggg  60
gacttcgtgc tgactcagag ccctcatagc ctgtccgtga ccccaggaga gtctgccagc  120
atctcctgca agagctccca cagcctgatc cacggcgacc ggaacaatta cctggcctgg  180
tacgtgcaga agccaggccg cagcccccag ctgctgatct acctggcctc tagcagggcc  240
tccggagtgc ctgacagatt ctctggcagc ggctccgaca aggacttcac cctgaagatc  300
tctagggtgg agacagagga tgtgggcaca tactattgca tgcagggcag agagtcccct  360
tggaccttcg gccagggcac aaaggtggac atcaagagga ccgtggcagc accatccgtg  420
ttcatctttc ccccttctga tgagcagctg aagtctggca cagccagcgt ggtgtgcctg  480
ctgaacaact tctacccccg cgaggccaag gtgcagtgga aggtggacaa cgccctgcag  540
tctggcaata gccaggagtc cgtgaccgag caggactcta aggatagcac atattccctg  600
tcctctaccc tgacactgtc caaggccgat tacgagaagc acaaggtgta tgcctgtgag  660
gtcacccacc aggggctgtc cagtcccgtc acaaagtcct tcaatagggg cgaatgc     717

SEQ ID NO: 67           moltype = AA  length = 471
FEATURE                 Location/Qualifiers
REGION                  1..471
                        note = 12A21 Heavy Chain
source                  1..471
                        mol_type = protein
                        organism = synthetic construct
SEQUENCE: 67
MDWTWRILFL VAAATGTHAS QHLVQSGTQV KKPGASVRVS CQASGYTFTN YILHWWRQAP  60
GQGLEWMGLI KPVFGAVNYA RQFQGRIQLT RDIYREIAFL DLSGLRSDDT AVYYCARDES  120
GDDLKWHLHP WGQGTQVIVS PASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKKVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRD ELTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471

SEQ ID NO: 68           moltype = DNA  length = 1413
FEATURE                 Location/Qualifiers
misc_feature            1..1413
```

```
                         note = 12A21 Heavy Chain
source                   1..1413
                         mol_type = other DNA
                         organism = synthetic construct
SEQUENCE: 68
atggattgga catggcgcat tctgtttctg gtcgcagccg ctactggaac ccacgcatca  60
cagcatctgg tgcagtctgg aactcaggtg aagaagccag gagcatccgt gcgggtgtct  120
tgccaggcaa gcggctacac cttcacaaac tatatcctgc actggtggag gcaggcacca  180
ggacagggcc tggagtggat gggcctgatc aagcccgtgt tcggcgccgt gaattacgcc  240
cggcagtttc agggccgcat ccagctgacc agggacatct atagagagat cgcctttctg  300
gatctgtccg gcctgcggtc tgacgataca gccgtgtact attgcgcccg cgacgagagc  360
ggcgacgatc tgaagtggca cctgcaccct tggggacagg gaacccaggt catcgtgagc  420
ccagcatcta caaagggacc ttccgtgttc ccactggcac ccagctccaa gagcacctcc  480
ggcggcacag ccgccctggg ctgtctggtg aaggattact tcccagagcc agtgaccgtg  540
agctggaact ccggcgccct gacctctgga gtgcacacat tcccgccgt gctgcagtct  600
agcggcctgt actccctgtc ctctgtggtg accgtgccta gctcctctct gggcacccag  660
acatatatct gcaacgtgaa tcacaagcct tctaatacaa aggtggacaa gaaggtggag  720
ccaaagagct gtgataagac ccacacatgc cctccctgtc ctgcaccaga gctgctgggc  780
ggcccaagcg tgttcctgtt tccacccaag cccaaggaca ccctgatgat ctccaggacc  840
cctgaggtga catgcgtggt ggtggacgtg tctcacgagg accccgaggt gaagtttaac  900
tggtacgtgg atggcgtgga ggtgcacaat gccaagacaa agcccaggga ggagcagtac  960
aacagcacct atagagtggt gtccgtgctg acagtgctgc accaggactg gctgaacggc  1020
aaggagtata agtgcaaggt gagcaataag gccctgcccg cccctatcga gaagaccatc  1080
tccaaggcca agggccagcc tagggagcca caggtgtaca cactgcctcc aagcagagac  1140
gagctgacca agaaccaggt gtccctgaca tgtctggtga agggctttta tccatccgat  1200
atcgccgtgg agtgggagtc taatggccag cccgagaaca attacaagac cacacccct  1260
gtgctggact ctgatggcag cttctttctg tattctaagc tgaccgtgga taagagcaga  1320
tggcagcagg gcaacgtgtt cagctgtagc gtgatgcacg aagcactgca caaccactac  1380
acccagaagt cactgtcact gagcccagga aaa                              1413

SEQ ID NO: 69            moltype = AA  length = 230
FEATURE                  Location/Qualifiers
REGION                   1..230
                         note = 12A21 Kappa Light Chain
source                   1..230
                         mol_type = protein
                         organism = synthetic construct
SEQUENCE: 69
MVLQTQVFIS LLLWISGAYG DIQMTQSPSS LSASVGDRVT INCQAGQGIG SSLNWYQKKP  60
GRAPKLLVHG ASNLQRGVPS RFSGSGFHTT FTLTISSLQP DDVATYFCAV FQWFGPGTKV  120
DIKRTVAAPS VFIFPPSDEQ LKSGTASVVC LLNNFYPREA KVQWKVDNAL QSGNSQESVT  180
EQDSKDSTYS LSSTLTLSKA DYEKHKVYAC EVTHQGLSSP VTKSFNRGEC            230

SEQ ID NO: 70            moltype = DNA  length = 690
FEATURE                  Location/Qualifiers
misc_feature             1..690
                         note = 12A21 Kappa Light Chain
source                   1..690
                         mol_type = other DNA
                         organism = synthetic construct
SEQUENCE: 70
atggtgctgc agactcaggt gtttatttca ctgctgctgt ggatttcagg agcctacggc  60
gacattcaga tgactcagag cccctcaagc ctgtccgcct ctgtgggcga ccgggtgacc  120
atcaactgcc aggcaggaca gggaatcggc agctccctga attggtacca gaagaagcca  180
ggaagggcac caaagctgct ggtgcacgga gcatccaacc tgcagagggg cgtgcccagc  240
agattcagcg gctccggctt ccacaccacc ttcaccctga caatctctag cctgcagcct  300
gacgatgtgg ccacctattt ttgcgccgtg ttccagtggt ttggccctgg caccaaggtg  360
gacatcaaga ggacagtggc cgccccatcc gtgttcatct ttccccttc tgatgagcag  420
ctgaagtctg gcacagccag cgtggtgtgc ctgctgaaca atttctaccc ccgggaggcc  480
aaggtgcagt ggaaggtgga caacgccctg cagtctggca atagccagga gtccgtgacc  540
gagcaggact ctaaggatag cacatattcc ctgtcctcta ccctgacact gtccaaggcc  600
gattacgaga agcacaaggt gtatgcctgt gaggtcaccc accaggggct gtcaagtcca  660
gtcacaaaat ccttcaatcg gggagaatgc                                  690

SEQ ID NO: 71            moltype = AA  length = 471
FEATURE                  Location/Qualifiers
REGION                   1..471
                         note = VRC3401 Heavy Chain
source                   1..471
                         mol_type = protein
                         organism = synthetic construct
SEQUENCE: 71
MDWTWRILFL VAAATGTHAQ EVLVQSGAEV KKPGASVKVS CRAFGYTFTG NALHWVRQAP  60
GQGLEWLGWI NPHSGDTTTS QKFQGRVYMT RDKSINTAFL DVTRLTSDDT GIYYCARDKY  120
YGNEAVGMDV WGQGTSVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKKVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRD ELTKNQVSLT CLVKGFYPSD IAVEWESNGQ PENNYKTTPP  420
```

```
VLDSDGSFFL YSKLTVDKSR WQQGNVFSCS VMHEALHNHY TQKSLSLSPG K          471

SEQ ID NO: 72          moltype = DNA  length = 1413
FEATURE                Location/Qualifiers
misc_feature           1..1413
                       note = VRC3401 Heavy Chain
source                 1..1413
                       mol_type = other DNA
                       organism = synthetic construct
SEQUENCE: 72
atggattgga catggcgcat tctgtttctg gtcgcagccg ctaccggaac ccacgctcag  60
gaagtgctgg tgcagtcagg ggccgaagtg aagaagcccg gcgcctccgt gaaggtgtct  120
tgcagggcct tcggctacac cttcaccggc aacgcactgc actgggtgag acaggcacct  180
ggacagggcc tggagtggct gggatggatc aatccacact ctggcgacac cacaaccagc  240
cagaagttcc agggcagggt gtatatgaca agagacaagt ctatcaacac cgcctttctg  300
gatgtgacac ggctgaccag cgacgataca ggcatctact attgcgcccg cgacaagtac  360
tatggcaatg aggcagtggg aatggacgtg tggggacagg gcacatccgt gaccgtgagc  420
tccgccagca ccaagggacc ttccgtgttc ccactggcac cctctagcaa gtctacaagc  480
ggcggcaccg ccgccctggg atgtctggtg aaggattact tcccagagcc agtgaccgtg  540
agctggaact ccggcgccct gacatctggc gtgcacacct ttcctgccgt gctgcagtcc  600
tctggcctgt acagcctgag ctccgtggtg acagtgccat ctagctccct gggcacacag  660
acctatatct gcaacgtgaa tcacaagcca agcaatacca aggtggacaa gaaggtggag  720
cccaagtcct gtgataagac acacacctgc cctccctgtc ctgcaccaga gctgctgggc  780
ggcccaagcg tgttcctgtt tccacccaag cctaaggaca cactgatgat ctcccggaca  840
ccagaggtga cctgcgtggt ggtggacgtg tctcacgagg accccgaggt gaagtttaac  900
tggtacgtgg atggcgtgga ggtgcacaat gccaagacca agccccggga ggagcagtac  960
aactccacat atcgcgtggt gtctgtgctg accgtgctgc accaggactg gctgaacggc  1020
aaggagtata agtgcaaggt gagcaataag gccctgcccg cccctatcga gaagacaatc  1080
tccaaggcca agggccagcc tagggagcca caggtgtaca ccctgcctcc atccagagac  1140
gagctgacaa agaaccaggt gtctctgacc tgtctggtga agggcttcta tccctctgat  1200
atcgccgtgg agtgggagag caatggccag cctgagaaca attacaagac aacccctccc  1260
gtgctggact ctgatggcag cttctttctg tatagcaagc tgaccgtgga taagtcccgc  1320
tggcagcagg gcaacgtgtt cagctgttct gtgatgcacg aagcactgca caaccactac  1380
acccagaagt cactgtcact gagcccagga aag                               1413

SEQ ID NO: 73          moltype = AA  length = 232
FEATURE                Location/Qualifiers
REGION                 1..232
                       note = VRC3401 Kappa Light Chain
source                 1..232
                       mol_type = protein
                       organism = synthetic construct
SEQUENCE: 73
MVLQTQVFIS LLLWISGAYG QLTQSPSFLS ASVGDKVTIT CRASQGVRNE LAWYQQKPGK  60
APNLLIYYAS TLQSGVPSRF SATGSGTHFT LTVSSLQPED FATYFCQHMS SYPLTFGGGT  120
KVEIKRTVAA PSVFIFPPSD EQLKSGTASV VCLLNNFYPR EAKVQWKVDN ALQSGNSQES  180
VTEQDSKDST YSLSSTLTLS KADYEKHKVY ACEVTHQGLS SPVTKSFNRG EC          232

SEQ ID NO: 74          moltype = DNA  length = 696
FEATURE                Location/Qualifiers
misc_feature           1..696
                       note = VRC3401 Kappa Light Chain
source                 1..696
                       mol_type = other DNA
                       organism = synthetic construct
SEQUENCE: 74
atggtgctgc agacccaggt gtttatttca ctgctgctgt ggattagcgg agcctacggc  60
cagctgaccc agagcccaag tttcctgagc gcctccgtgg gcgacaaggt gaccatcaca  120
tgcagggcct cccagggcgt gagaaacgag ctggcctggt accagcagaa gccaggcaag  180
gcccccaatc tgctgatcta ctatgcctcc accctgcagt ctggagtgcc ctctaggttc  240
agcgccaccg gctctggcac acactttacc ctgacagtga gctccctgca gcctgaggat  300
ttcgccacat actttttgcca gcacatgtct agctatccac tgaccttcgg cggcggcaca  360
aaggtggaga tcaagaggac cgtggcagca cccaagcgtgt tcatctttcc ccctagcgac  420
gagcagctga agagcggcac agcctccgtg gtgtgcctgc tgaacaactt ctaccctcgc  480
gaggccaagg tgcagtggaa ggtggataac gccctgcagt ccggcaattc tcaggagagc  540
gtgaccgagc aggactccaa ggattctaca tatagcctgt cctctaccct gacactgagc  600
aaggccgact acgagaagca caaggtgtat gcctgtgagg tcacccacca ggggctgagc  660
agtccagtca ccaagtcctt caatcggggc gaatgt                            696

SEQ ID NO: 75          moltype = AA  length = 475
FEATURE                Location/Qualifiers
REGION                 1..475
                       note = IOMA Heavy Chain
source                 1..475
                       mol_type = protein
                       organism = synthetic construct
SEQUENCE: 75
MDWTWRILFL VAAATGTHAE VQLVESGAQV KKPGASVTVS CTASGYKFTG YHMHWVRQAP  60
GRGLEWMGWI NPFRGAVKYP QNFRGRVSMT RDTSMEIFYM ELSRLTSDDT AVYYCAREMF  120
```

```
DSSADWSPWR GMVAWGQGTL VTVSSASTKG PSVFPLAPSS KSTSGGTAAL GCLVKDYFPE  180
PVTVSWNSGA LTSGVHTFPA VLQSSGLYSL SSVVTVPSSS LGTQTYICNV NHKPSNTKVD  240
KKVEPKSCDK THTCPPCPAP ELLGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPQVYTLP PSRDELTKNQ VSLTCLVKGF YPSDIAVEWE SNGQPENNYK  420
TTPPVLDSDG SFFLYSKLTV DKSRWQQGNV FSCSVMHEAL HNHYTQKSLS LSPGK       475

SEQ ID NO: 76          moltype = DNA  length = 1425
FEATURE                Location/Qualifiers
misc_feature           1..1425
                       note = IOMA Heavy Chain
source                 1..1425
                       mol_type = other DNA
                       organism = synthetic construct
SEQUENCE: 76
atggactgga catggagaat cctgttcctg gtcgcagcag caaccggcac ccacgcagaa  60
gtgcagctgg tcgaaagcgg ggctcaggtg aagaagccag gagcaagcgt gaccgtgtcc  120
tgcacagcat ctggctacaa gttcaccggc tatcacatgc actgggtgcg gcaggcacct  180
ggaaggggcc tggagtggat gggatggatc aaccccttca ggggcgccgt gaagtaccct  240
cagaacttca ggggcagagt gtccatgacc agggacacat ctatggagat cttctatatg  300
gagctgagca gactgacctc cgacgataca gccgtgtact attgcgcccg ggagatgttt  360
gacagctccg ccgattggag cccctggagg ggaatggtgg catggggaca gggcaccctg  420
gtgacagtgt ctagcgcctc taccaagggc cctagcgtgt ttccactggc cccctcctct  480
aagtccacct ctggcggcac agccgccctg ggctgtctgg tgaaggatta cttcccagag  540
cccgtgacag tgtcttggaa cagcggcgcc ctgaccagcg gagtgcacac atttcctgcc  600
gtgctgcaga gctccggcct gtactccctg tctagcgtgg tgaccgtgcc atcctctagc  660
ctgggcaccc agacatatat ctgcaacgtg aatcacaagc cttctaatac aaaggtggac  720
aagaaggtgg agccaaagag ctgtgataag acccacacat gccctccctg tcctgcacca  780
gagctgctgg gcggcccatc cgtgttcctg tttccaccca agcccaagga caccctgatg  840
atctccagga ccccagaggt gacatgcgtg gtggtggacg tgtctcacga ggaccccgag  900
gtgaagttca actggtacgt ggatggcgtg gaggtgcaca atgccaagac aaagcccagg  960
gaggagcagt acaacagcac ctatagagtg gtgtccgtgc tgacagtgct gcaccaggac  1020
tggctgaacg gcaaggagta taagtgcaag gtgagcaata aggccctgcc cgcccctatc  1080
gagaagacca tctccaaggc aaagggacag cctcgggagc cacaggtgta cacactgcct  1140
ccaagccgcg acgagctgac caagaaccag gtgtccctga catgtctggt gaagggcttc  1200
tatccctccg atatcgccgt ggagtgggag tctaatggcc agcctgagaa caattacaag  1260
accacacccc ctgtgctgga ctccgatggc tctttctttc tgtattctaa gctgaccgtg  1320
gataagagca gatggcagca gggcaacgtg ttcagctgtt ccgtgatgca cgaagcactg  1380
cacaaccatt acactcagaa gtcactgtca ctgtcaccag ggaag                 1425

SEQ ID NO: 77          moltype = AA  length = 234
FEATURE                Location/Qualifiers
REGION                 1..234
                       note = IOMA Lambda Light Chain
source                 1..234
                       mol_type = protein
                       organism = synthetic construct
SEQUENCE: 77
MAWTPLFLFL LTCCPGGSNS QSALTQPASV SGSPGQSITI SCAGSSRDVG GFDLVSWYQQ  60
HPGKAPKLII YEVNKRPSGI SSRFSASKSG NTASLTISGL QEEDEAHYYC YSYADGVAFG  120
GGTKLTVLGQ PKAAPSVTLF PPSSEELQAN KATLVCLISD FYPGAVTVAW KADSSPVKAG  180
VETTTPSKQS NNKYAASSYL SLTPEQWKSH KSYSCQVTHE GSTVEKTVAP TECS        234

SEQ ID NO: 78          moltype = DNA  length = 702
FEATURE                Location/Qualifiers
misc_feature           1..702
                       note = IOMA Lambda Light Chain
source                 1..702
                       mol_type = other DNA
                       organism = synthetic construct
SEQUENCE: 78
atggcttgga cccctctgtt tctgtttctg ctgacctgtt gccccggagg aagtaattcc  60
cagtctgccc tgacccagcc tgcatcagtg tccggctctc ctggccagtc catcacaatc  120
tcttgcgcag gcagctccag ggacgtgggc ggctttgatc tggtgtcctg gtaccagcag  180
cacccaggca aggcccccaa gctgatcatc tatgaggtga acaagaggcc ctctggcatc  240
tctagcagat tcagcgcctc caagtctggc aatacagcca gcctgaccat ctccggcctg  300
caggaggagg acgaggcaca ctactattgc tactcctatg cagatggagt ggccttcggc  360
ggcggcacaa agctgaccgt gctgggacag cctaaggcag caccatccgt gacactgttt  420
cccccttcct ctgaggagct gcaggccaac aaggccaccc tggtgtgcct gatcagcgac  480
ttctacccag gagcagtgac cgtggcatgg aaggcagata gctccccagt gaaggcagga  540
gtggagacaa caaccccttc taagcagagc aacaataagt acgccgcctc tagctatctg  600
tctctgaccc ccgagcagtg gaagagccac aagagctatt cctgccaggt cacccatgaa  660
ggctcaaccg tggagaaaac agtcgcccct accgaatgct ca                    702

SEQ ID NO: 79          moltype = AA  length = 478
FEATURE                Location/Qualifiers
REGION                 1..478
                       note = PGT130 Heavy Chain
source                 1..478
```

```
                         mol_type = protein
                         organism = synthetic construct
SEQUENCE: 79
MDWTWRILFL VAAATGTHAQ VQLQESGPGL VKPAETLSLT CSVSGESINT GHYYWGWVRQ  60
VPGKGLEWIG HIHYTTAVLH NPSLKSRLTI KIYTLRNQIT LRLSNVTAAD TAVYHCVRSG  120
GDILYYYEWQ KPHWFSPWGP GIHVTVSSAS TKGPSVFPLA PSSKSTSGGT AALGCLVKDY  180
FPEPVTVSWN SGALTSGVHT FPAVLQSSGL YSLSSVVTVP SSSLGTQTYI CNVNHKPSNT  240
KVDKKVEPKS CDKTHTCPPC PAPELLGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVY TLPPSRDELT KNQVSLTCLV KGFYPSDIAV EWESNGQPEN  420
NYKTTPPVLD SDGSFFLYSK LTVDKSRWQQ GNVFSCSVMH EALHNHYTQK SLSLSPGK    478

SEQ ID NO: 80            moltype = DNA  length = 1434
FEATURE                  Location/Qualifiers
misc_feature             1..1434
                         note = PGT130 Heavy Chain
source                   1..1434
                         mol_type = other DNA
                         organism = synthetic construct
SEQUENCE: 80
atggactgga cttggaggat tctgtttctg gtcgccgccg ctactggaac tcacgctcag  60
gtgcagctgc aggaatctgg ccccggactg gtgaagcctg ccgagacact gtccctgaca  120
tgctctgtga gcggcgagtc tatcaacacc ggccactact attggggatg ggtgcggcag  180
gtgccaggca agggcctgga gtggatcggc cacatccact ataccacagc cgtgctgcac  240
aatccttctc tgaagagccg cctgaccatc aagatctaca cactgaggaa ccagatcacc  300
ctgagactgt ctaatgtgac cgccgccgac acagccgtgt atcactgcgt gagaagcggc  360
ggcgatatcc tgtactatta cgagtggcag aagccacact ggttctcccc atggggacca  420
ggcatccacg tgaccgtgag ctccgcctct acaaagggcc ccagcgtgtt tcctctggcc  480
ccatctagca agtccacctc tggcggcaca gccgccctgg gctgtctggt gaaggactac  540
ttcccagagc ccgtgaccgt gtcctggaac tctggcgccc tgacctccgg agtgcacaca  600
tttcctgccg tgctgcagtc ctctggcctg tatagcctga gctccgtggt gaccgtgcca  660
tctagctccc tgggcaccca gacatacatc tgcaacgtga atcacaagcc ttctaataca  720
aaggtggaca agaaggtgga gccaaagagc tgtgataaga cccacacatg ccctccctgt  780
cctgcaccag agctgctggg cggcccaagc gtgttcctgt ttccacccaa gcccaaggac  840
accctgatga tctccaggac cccagaggtg acatgcgtgg tggtggacgt gtctcacgag  900
gaccccgagg tgaagttcaa ctggtacgtg gatggcgtgg aggtgcacaa tgccaagaca  960
aagccccggg aggagcagta taactccacc taccgcgtgg tgtctgtgct gacagtgctg  1020
caccaggact ggctgaacgg caaggagtac aagtgcaagg tgagcaataa ggccctgccc  1080
gcccctatcg agaagaccat ctccaaggca aagggacagc ccagggagcc tcaggtgtat  1140
acactgcctc caagcagaga cgagctgacc aagaaccagg tgtccctgac atgtctggtg  1200
aagggcttct accccctctga tatcgccgtg gagtgggaga gcaatggcca gcctgagaac  1260
aattataaga ccacaccccc tgtgctggac agcgatggct ccttctttct gtacagcaag  1320
ctgaccgtgg ataagtccag gtggcagcag ggcaacgtgt tcagctgttc cgtgatgcac  1380
gaagcactgc acaaccatta cacccagaag tccctgtcac tgtcacccgg caaa        1434

SEQ ID NO: 81            moltype = AA  length = 236
FEATURE                  Location/Qualifiers
REGION                   1..236
                         note = PGT130 Lambda Light Chain
source                   1..236
                         mol_type = protein
                         organism = synthetic construct
SEQUENCE: 81
MAWTPLFLFL LTCCPGGSNS QSALTQPPSA SGSLGQSVTI SCNGTSSDIG GWNFVSWYQQ  60
FPGRAPRLII FEVNKRPSGV PGRFSGSKSG NSASLTVSGL QSDDEGQYFC SSLFGRWDVV  120
FGGGTKLTVL GQPKAAPSVT LFPPSSEELQ ANKATLVCLI SDFYPGAVTV AWKADSSPVK  180
AGVETTTPSK QSNNKYAASS YLSLTPEQWK SHKSYSCQVT HEGSTVEKTV APTECS      236

SEQ ID NO: 82            moltype = DNA  length = 708
FEATURE                  Location/Qualifiers
misc_feature             1..708
                         note = PGT130 Lambda Light Chain
source                   1..708
                         mol_type = other DNA
                         organism = synthetic construct
SEQUENCE: 82
atggcatgga cacccctgtt tctgttcctg ctgacctgtt gccccggagg ctcaaatagc  60
cagtctgccc tgacccagcc cccaagcgcc tccggctctc tgggccagag cgtgacaatc  120
tcctgcaacg gcaccagctc cgacatcggc ggatggaatt tcgtgagctg gtaccagcag  180
tttccaggca gggcccccag actgatcatc ttcgaggtga acaagcggcc ttccggagtg  240
ccaggccgct ttagcggctc caagtctggc aatagcgcct ccctgacagt gtctggcctg  300
cagagcgacg atgagggcca gtatttctgc tctagcctgt ttggcaggtg ggatgtggtg  360
ttcggcggcg gaacaaagct gaccgtgctg ggacagccaa aggcagcacc ttctgtgacc  420
ctgtttcccc cttcctctga ggagctgcag gccaacaagg ccaccctggt gtgcctgatc  480
agcgacttct accctggagc agtgaccgtg gcatggaagg ccgatagctc cccagtgaag  540
gccggcgtgg agacaacaac cccctccaag cagtctaaca ataagtacgc cgcctctagc  600
tatctgtccc tgacacccga gcagtggaag tctcacaagt cttatagctg ccaggtcacc  660
catgaaggaa gcacagtgga aaaaaccgtc gcaccaaccg aatgtagc                708
```

-continued

```
SEQ ID NO: 83           moltype = AA  length = 481
FEATURE                 Location/Qualifiers
REGION                  1..481
                        note = PGT121 Heavy Chain
source                  1..481
                        mol_type = protein
                        organism = synthetic construct
SEQUENCE: 83
MDWTWRILFL VAAATGTHAQ MQLQESGPGL VKPSETLSLT CSVSGASISD SYWSWIRRSP  60
GKGLEWIGYV HKSGDTNYSP SLKSRVNLSL DTSKNQVSLS LVAATAADSG KYYCARTLHG  120
RRIYGIVAFN EWFTYFYMDV WGNGTQVTVS SASTKGPSVF PLAPSSKSTS GGTAALGCLV  180
KDYFPEPVTV SWNSGALTSG VHTFPAVLQS SGLYSLSSVV TVPSSSLGTQ TYICNVNHKP  240
SNTKVDKKVE PKSCDKTHTC PPCPAPELLG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
ALPAPIEKTI SKAKGQPREP QVYTLPPSRD ELTKNQVSLT CLVKGFYPSD IAVEWESNGQ  420
PENNYKTTPP VLDSDGSFFL YSKLTVDKSR WQQGNVFSCS VMHEALHNHY TQKSLSLSPG  480
K                                                                 481

SEQ ID NO: 84           moltype = DNA  length = 1443
FEATURE                 Location/Qualifiers
misc_feature            1..1443
                        note = PGT121 Heavy Chain
source                  1..1443
                        mol_type = other DNA
                        organism = synthetic construct
SEQUENCE: 84
atggattgga catggaggat tctgtttctg gtcgccgccg ctactggaac ccacgctcag  60
atgcagctgc aggagtcagg ccccggactg gtgaagccct ccgagacact gtctctgaca  120
tgctctgtga gcggcgcctc catctctgac agctactggt cttggatcag gagaagccct  180
ggcaagggcc tggagtggat cggctacgtg cacaagtctg gcgacaccaa ctattcccca  240
tctctgaaga gcagggtgaa cctgagcctg gatacatcca agaatcaggt gagcctgtcc  300
ctggtggcag caaccgcagc agacagcggc aagtactatt gcgccagaac actgcacggc  360
aggaggatct acggcatcgt ggccttcaac gagtggttca cctactttta tatggacgtg  420
tggggcaatg gcacccaggt gacagtgagc tccgcctcca caaagggacc tagcgtgttc  480
ccactggcac cctctagcaa gtctaccagc ggcggcacag ccgccctggg atgtctggtg  540
aaggattatt tcccagagcc agtgaccgtg agctggaact ccggcgccct gaccagcgga  600
gtgcacacat ttccagccgt gctgcagtcc tctggcctgt actccctgag ctccgtggtg  660
accgtgccct ctagctccct gggcacccag acatatatct gcaacgtgaa tcacaagcca  720
tccaatacaa aggtggacaa gaaggtggag cccaagtctt gtgataagac ccacacatgc  780
cctccctgtc ctgcaccaga gctgctgggc ggcccaagcg tgttcctgtt tccacccaag  840
cctaaggaca ccctgatgat cagccggacc ccagaggtga catgcgtggt ggtggacgtg  900
tcccacgagg accccgaggt gaagttcaac tggtacgtgg atggcgtgga ggtgcacaat  960
gccaagacaa agcccaggga ggagcagtac aacagcacct atagagtggt gtccgtgctg  1020
acagtgctgc accaggactg gctgaacggc aaggagtata agtgcaaggt gtctaataag  1080
gccctgcccg cccctatcga gaagaccatc tccaaggcaa agggacagcc tcgggagcca  1140
caggtgtaca cactgcctcc aagccgcgac gagctgacca agaaccaggt gtccctgaca  1200
tgtctggtga agggcttcta tccttccgat atcgccgtgg agtgggagtc taatggccag  1260
ccagagaaca attacaagac cacaccccct gtgctggact ctgatggcag cttctttctg  1320
tattctaagc tgaccgtgga taagagccgc tggcagcagg gcaacgtgtt cagctgttct  1380
gtgatgcacg aagcactgca caaccactac actcagaagt ccctgtccct gtcccctggc  1440
aag                                                               1443

SEQ ID NO: 85           moltype = AA  length = 230
FEATURE                 Location/Qualifiers
REGION                  1..230
                        note = PGT121 Lambda Light Chain
source                  1..230
                        mol_type = protein
                        organism = synthetic construct
SEQUENCE: 85
MAWTPLFLFL LTCCPGGSNS DISVAPGETA RISCGEKSLG SRAVQWYQHR AGQAPSLIIY  60
NNQDRPSGIP ERFSGSPDSP FGTTATLTIT SVEAGDEADY YCHIWDSRVP TKWVFGGGTT  120
LTVLGQPKAA PSVTLFPPSS EELQANKATL VCLISDFYPG AVTVAWKADS SPVKAGVETT  180
TPSKQSNNKY AASSYLSLTP EQWKSHKSYS CQVTHEGSTV EKTVAPTECS            230

SEQ ID NO: 86           moltype = DNA  length = 690
FEATURE                 Location/Qualifiers
misc_feature            1..690
                        note = PGT121 Lambda Light Chain
source                  1..690
                        mol_type = other DNA
                        organism = synthetic construct
SEQUENCE: 86
atggcttgga ctcccctgtt cctgttcctg ctgacttgtt gccctggcgg ctctaactct  60
gacatttccg tcgctcctgg cgagactgcc aggatcagct gcggagagaa gtccctgggc  120
tctcgggccg tgcagtggta ccagcacagg gcaggacagg caccatccct gatcatctat  180
aacaatcagg acaggccttc tggcatccca gagagattca gcggctcccc agatagcccc  240
tttggcacca cagccacact gaccatcaca tccgtggagg caggcgacga ggcagattac  300
tattgccaca tctgggactc ccgggtgcct accaagtggg tgttcggcgg cggaaccaca  360
```

```
ctgacagtgc tgggacagcc aaaggcagca ccttctgtga ccctgtttcc ccctagctcc  420
gaggagctgc aggccaacaa ggccaccctg gtgtgcctga tctccgactt ctaccctgga  480
gcagtgacag tggcatggaa ggccgattct agcccagtga aggccggcgt ggagacaaca  540
acccccagca agcagtccaa caataagtac gccgcctcct cttatctgtc tctgacacca  600
gagcagtgga agagccacaa gtcttatagc tgccaggtca cccatgaagg aagcaccgtg  660
gagaaaacag tcgccccaac agaatgtagc                                    690

SEQ ID NO: 87           moltype = AA  length = 473
FEATURE                 Location/Qualifiers
REGION                  1..473
                        note = 2219 Heavy Chain
source                  1..473
                        mol_type = protein
                        organism = synthetic construct
SEQUENCE: 87
MDWTWRILFL VAAATGTHAE IQLEQSGAEV KKSGESLKIS CQTSGYSFSD YWIGWVRQMP  60
GKGLEWMGIF YPGDSDSRYS PSFEGQVTMS ADRSTNTAHL QWSSLKPSDT ALYYCARLGG  120
DYEDSGADAF DFWGQGTLVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS RDELTKNQVS LTCLVKGFYP SDIAVEWESN GQPENNYKTT  420
PPVLDSDGSF FLYSKLTVDK SRWQQGNVFS CSVMHEALHN HYTQKSLSLS PGK          473

SEQ ID NO: 88           moltype = DNA  length = 1419
FEATURE                 Location/Qualifiers
misc_feature            1..1419
                        note = 2219 Heavy Chain
source                  1..1419
                        mol_type = other DNA
                        organism = synthetic construct
SEQUENCE: 88
atggattgga catggaggat tctgtttctg gtcgccgccg ccactggaac tcacgctgag  60
attcagctgg agcagagtgg agcagaagtc aagaagagcg gggagagcct gaagattagt  120
tgccagacaa gcggatacag tttctctgac tactggatcg gatgggtgcg gcagatgcca  180
ggcaagggcc tggagtggat gggcatcttc taccccggcg actctgatag caggtattcc  240
ccttctttg agggccaggt gaccatgagc gccgatagat ccaccaacac agcccacctg  300
cagtggagct ccctgaagcc ctccgacaca gccctgtact attgcgcaag gctgggcggc  360
gattatgagg acagcggagc cgacgccttt gatttttggg ggcaggggac tctggtgacc  420
gtgagcagcg ccagcacaaa gggcccatcc gtgtttccac tggcaccctc ctctaagagc  480
acctccggcg gcacagccgc cctgggctgt ctggtgaagg attacttccc agagccagtg  540
accgtgagct ggaactccgg cgccctgacc tccggagtgc acacatttcc agccgtgctg  600
cagagctccg gcctgtatag cctgtctagc gtggtgaccg tgccctcctc tagcctgggc  660
acccagacat acatctgcaa cgtgaatcac aagccatcca atacaaaggt ggacaagaag  720
gtggagccca agtcttgtga taagacccac acatgccctc cctgtcctgc accagagctg  780
ctgggcggcc catccgtgtt cctgtttcca cccaagccta aggacaccct gatgatcagc  840
cggaccccag aggtgacatg cgtggtggtg gacgtgtccc acgaggaccc cgaggtgaag  900
ttcaactggt acgtggatgg cgtggaggtg cacaatgcca agaccaagcc tagggaggag  960
cagtataact ctacctacag agtggtgagc gtgctgacag tgctgcacca ggactggctg  1020
aacggcaagg agtacaagtg caaggtgtct aataaggccc tgcccgcccc tatcgagaag  1080
accatcagca aggcaaaggg acagcctcgg gagccacagg tgtatacact gcctccatct  1140
cgcgacgagc tgaccaagaa ccaggtgagc ctgacatgtc tggtgaaggg cttctaccct  1200
agcgatatcg ccgtggagtg ggagtccaat ggccagccag agaacaatta taagaccaca  1260
ccccctgtgc tggactctga tggcagcttc tttctgtact ccaagctgac cgtggataag  1320
tctcgctggc agcagggcaa cgtgttcagc tgtagcgtga tgcacgaagc cctgcacaac  1380
cactacaccc agaaaagcct gtcactgagc cccggaaaa                          1419

SEQ ID NO: 89           moltype = AA  length = 238
FEATURE                 Location/Qualifiers
REGION                  1..238
                        note = 2219 Lambda Light Chain
source                  1..238
                        mol_type = protein
                        organism = synthetic construct
SEQUENCE: 89
MAWTPLFLFL LTCCPGGSNS QSVLTQPPSA SGTPGQRISI SCSGTSSNVE NNYVYWYQHL  60
PGTAPKLLIY RNDHRSSGIP DRFSASKSGT SASLAISGLR PEDEGDYYCA AWDDSRGGPD  120
WVFGGGTKLT VLGQPKAAPS VTLFPPSSEE LQANKATLVC LISDFYPGAV TVAWKADSSP  180
VKAGVETTTP SKQSNNKYAA SSYLSLTPEQ WKSHKSYSCQ VTHEGSTVEK TVAPTECS    238

SEQ ID NO: 90           moltype = DNA  length = 714
FEATURE                 Location/Qualifiers
misc_feature            1..714
                        note = 2219 Lambda Light Chain
source                  1..714
                        mol_type = other DNA
                        organism = synthetic construct
SEQUENCE: 90
atggcttgga cccctctgtt tctgtttctg ctgacctgtt gccccggagg aagtaattcc  60
```

```
cagtccgtcc tgacccagcc tccctctgcc agtggaacac ccggccagcg aatctctatc  120
tcctgtagtg gaacttcatc taatgtcgag aacaattacg tgtattggta ccagcacctg  180
ccaggaaccg cacctaagct gctgatctat aggaacgacc acagaagctc cggcatccca  240
gatcggttct ctgccagcaa gtccggcaca tctgccagcc tggcaatctc cggcctgcgc  300
cccgaggacg agggcgatta ctattgcgcc gcctgggatg attccagagg aggaccagat  360
tgggtgttcg gcggcgggac taaactgacc gtgctgggac agcctaaggc agcaccatcc  420
gtgacactgt ttccccttc ctctgaggag ctgcaggcca acaaggccac cctggtgtgc  480
ctgatcagcg acttctaccc aggagcagtg accgtggcat ggaaggcaga tagctcccca  540
gtgaaggcag gagtggagac aacaacccct tctaagcaga gcaacaataa gtacgccgcc  600
tctagctatc tgtctctgac cccgagcag tggaagagcc acaagagcta ttcctgccag  660
gtcacccatg aaggctcaac cgtggagaaa acagtcgccc ctaccgaatg ctca        714

SEQ ID NO: 91          moltype = AA  length = 476
FEATURE                Location/Qualifiers
REGION                 1..476
                       note = 3074 Heavy Chain
source                 1..476
                       mol_type = protein
                       organism = synthetic construct
SEQUENCE: 91
MDWTWRILFL VAAATGTHAQ VQLQESGPGL VKPSETLSLT CTVSGGSISG FHWSWIRQPP  60
GKGLEYIGYI YYSGSTSYNP SLKSRVSMSV DTSRNQFSLE LSSVTAADTA VYYCARDFGE  120
YHYDGRGFQC EGFDLWGQGT LVTVSSASTK GPSVFPLAPS SKSTSGGTAA LGCLVKDYFP  180
EPVTVSWNSG ALTSGVHTFP AVLQSSGLYS LSSVVTVPSS SLGTQTYICN VNHKPSNTKV  240
DKKVEPKSCD KTHTCPPCPA PELLGGPSVF LFPPKPKDTL MISRTPEVTC VVVDVSHEDP  300
EVKFNWYVDG VEVHNAKTKP REEQYNSTYR VVSVLTVLHQ DWLNGKEYKC KVSNKALPAP  360
IEKTISKAKG QPREPQVYTL PPSRDELTKN QVSLTCLVKG FYPSDIAVEW ESNGQPENNY  420
KTTPPVLDSD GSFFLYSKLT VDKSRWQQGN VFSCSVMHEA LHNHYTQKSL SLSPGK      476

SEQ ID NO: 92          moltype = DNA  length = 1428
FEATURE                Location/Qualifiers
misc_feature           1..1428
                       note = 3074 Heavy Chain
source                 1..1428
                       mol_type = other DNA
                       organism = synthetic construct
SEQUENCE: 92
atggattgga catggaggat tctgtttctg gtcgccgccg ccactggaac tcacgctcag  60
gtgcagctgc aggaaagcgg gcctggactg gtgaagccta gtgaaactct gagcctgact  120
tgtaccgtga gcggaggaag cattagcggc ttccactggt cctggatcag gcagccccct  180
ggcaagggcc tggagtacat cggctatatc tactattctg gcagcacctc ctacaacccc  240
tccctgaagt ctagggtgtc tatgagcgtg gacacatcta gaaatcagtt cagcctggag  300
ctgagctccg tgaccgcagc agatacagcc gtgtactatt gcgcccggga ctttggcgag  360
taccactatg atggccgcgg ctttcagtgc gagggctttg atctgtgggg gcagggaact  420
ctggtgaccg tgagcagcgc cagcacaaag ggcccatccg tgtttccact ggcaccctcc  480
tctaagagca cctccggcgg cacagccgcc ctgggctgtc tggtgaagga ttacttccca  540
gagccagtga ccgtgagctg gaactccggc gccctgacct ccggagtgca cacatttcca  600
gccgtgctgc agagctccgg cctgtatagc ctgtctagcg tggtgaccgt gccctcctct  660
agcctgggca cccagacata catctgcaac gtgaatcaca agccatccaa tacaaaggtg  720
gacaagaagg tggagcccaa gtcttgtgat aagacccaca catgccctcc ctgtcctgca  780
ccagagctgc tgggcggccc atccgtgttc ctgtttccac ccaagcctaa ggacaccctg  840
atgatcagcc ggaccccaga ggtgacatgc gtggtggtgg acgtgtccca cgaggacccc  900
gaggtgaagt tcaactggta cgtggatggc gtggaggtgc acaatgccaa gaccaagcct  960
agggaggagc agtataactc tacctacaga gtggtgagcg tgctgacagt gctgcaccag  1020
gactggctga acggcaagga gtacaagtgc aaggtgtcta ataaggccct gcccgcccct  1080
atcgagaaga ccatcagcaa ggcaaaggga cagcctcggg agccacaggt gtatacactg  1140
cctccatctc gcgacgagct gaccaagaac caggtgagcc tgacatgtct ggtgaagggc  1200
ttctacccta gcgatatcgc cgtggagtgg gagtccaatg gccagccaga gaacaattat  1260
aagaccacac cccctgtgct ggactctgat ggcagcttct ttctgtactc caagctgacc  1320
gtggataagt ctcgctggca gcagggcaac gtgttcagct gtagcgtgat gcacgaagcc  1380
ctgcacaacc actacaccca gaaaagcctg tcactgagcc ccggaaaa               1428

SEQ ID NO: 93          moltype = AA  length = 235
FEATURE                Location/Qualifiers
REGION                 1..235
                       note = 3074 Lambda Light Chain
source                 1..235
                       mol_type = protein
                       organism = synthetic construct
SEQUENCE: 93
MAWTPLFLFL LTCCPGGSNS QSVLTQPPSV SAAPGQKVTI SCSGSSSNIG NNMVSWYQQH  60
PGTAPKLLIY ENSKRPSGIP DRFSGSRSGT SATLGIIGLQ TGDEAEYYCA TWDGSLRTVF  120
GGGTKLTVLG QPKAAPSVTL FPPSSEELQA NKATLVCLIS DFYPGAVTVA WKADSSPVKA  180
GVETTTPSKQ SNNKYAASSY LSLTPEQWKS HKSYSCQVTH EGSTVEKTVA PTECS        235

SEQ ID NO: 94          moltype = DNA  length = 705
FEATURE                Location/Qualifiers
misc_feature           1..705
                       note = 3074 Lambda Light Chain
```

-continued

```
source                  1..705
                        mol_type = other DNA
                        organism = synthetic construct
SEQUENCE: 94
atggcttgga cccctctgtt tctgtttctg ctgacctgtt gccccggagg aagtaattcc  60
cagagcgtcc tgactcagcc tccaagcgtg tccgcagccc ctgggcagaa ggtgaccatt  120
agttgtagcg gcagcagcag caatatcggc aacaatatgg tgtcttggta ccagcagcac  180
ccaggaaccg cacctaagct gctgatctat gagaacagca agaggccatc cggcatcccc  240
gacaggttca gcggctccag atctggcacc agcgccacac tgggcatcat cggcctgcag  300
acaggcgatg aggccgagta ctattgcgct acttgggatg ggagcctgcg gaccgtcttt  360
gggggaggaa ctaaactgac tgtgctggga cagcctaagg cagcaccatc cgtgacactg  420
tttccccctt cctctgagga gctgcaggcc aacaaggcca ccctggtgtg cctgatcagc  480
gacttctacc caggagcagt gaccgtggca tggaaggcag atagctcccc agtgaaggca  540
ggagtggaga caacaacccc ttctaagcag agcaacaata agtacgccgc ctctagctat  600
ctgtctctga cccccgagca gtggaagagc cacaagagct attcctgcca ggtcacccat  660
gaaggctcaa ccgtggagaa aacagtcgcc cctaccgaat gctca                 705

SEQ ID NO: 95           moltype = AA  length = 473
FEATURE                 Location/Qualifiers
REGION                  1..473
                        note = 4028 Heavy Chain
source                  1..473
                        mol_type = protein
                        organism = synthetic construct
SEQUENCE: 95
MDWTWRILFL VAAATGTHAE VQLVQSGAEV KKPGESLKIS CKASGYSFSS YWIAWVRQMP  60
GKGLEWMGFI YPADSDTRYS PSFQGQGTIS ADKSISTAYL QWSSLKASDT AMYYCAILGF  120
WGANRGGGGM DVWGQGTTVI VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS RDELTKNQVS LTCLVKGFYP SDIAVEWESN GQPENNYKTT  420
PPVLDSDGSF FLYSKLTVDK SRWQQGNVFS CSVMHEALHN HYTQKSLSLS PGK         473

SEQ ID NO: 96           moltype = DNA  length = 1419
FEATURE                 Location/Qualifiers
misc_feature            1..1419
                        note = 4028 Heavy Chain
source                  1..1419
                        mol_type = other DNA
                        organism = synthetic construct
SEQUENCE: 96
atggattgga catggaggat tctgtttctg gtcgccgccg ccactggaac tcacgctgaa  60
gtgcagctgg tgcagagcgg agccgaggtc aagaagcctg gcgaaagcct gaaaatctca  120
tgtaaagcaa gcggatactc attcagctcc tactggatcg catgggtgag gcagatgcca  180
ggcaagggcc tggagtggat gggcttcatc taccccgccg actctgatac cagatattcc  240
ccttctttcc agggccaggg caccatcagc gccgacaaga gcatctccac agcctatctg  300
cagtggtcta gcctgaaggc ctccgataca gccatgtact attgcgccat cctgggcttc  360
tggggcgcca atcggggcgg aggcgggatg gatgtctggg ggcagggaac caccgtcatt  420
gtcagcagtg ccagcacaaa gggcccatcc gtgtttccac tggcaccctc ctctaagagc  480
acctccggcg gcacagccgc cctgggctgt ctggtgaagg attacttccc agagccagtg  540
accgtgagct ggaactccgg cgccctgacc tccggagtgc acacatttcc agccgtgctg  600
cagagctccg gcctgtatag cctgtctagc gtggtgaccg tgccctcctc tagcctgggc  660
acccagacat acatctgcaa cgtgaatcac aagccatcca atacaaaggt ggacaagaag  720
gtggagccca agtcttgtga taagacccac acatgccctc cctgtcctgc accagagctg  780
ctgggcggcc catccgtgtt cctgtttcca cccaagccta aggacaccct gatgatcagc  840
cggaccccag aggtgacatg cgtggtggtg gacgtgtccc acgaggaccc cgaggtgaag  900
ttcaactggt acgtggatgg cgtggaggtg cacaatgcca agaccaagcc tagggaggag  960
cagtataact ctacctacag agtggtgagc gtgctgacag tgctgcacca ggactggctg  1020
aacggcaagg agtacaagtg caaggtgtct aataaggccc tgcccgcccc tatcgagaag  1080
accatcagca aggcaaaggg acagcctcgg gagccacagg tgtatacact gcctccatct  1140
cgcgacgagc tgaccaagaa ccaggtgagc ctgacatgtc tggtgaaggg cttctaccct  1200
agcgatatcg ccgtggagtg ggagtccaat ggccagccag agaacaatta taagaccaca  1260
ccccctgtgc tggactctga tggcagcttc tttctgtact ccaagctgac cgtggataag  1320
tctcgctggc agcagggcaa cgtgttcagc tgtagcgtga tgcacgaagc cctgcacaac  1380
cactacaccc agaaaagcct gtcactgagc cccggaaaa                       1419

SEQ ID NO: 97           moltype = AA  length = 235
FEATURE                 Location/Qualifiers
REGION                  1..235
                        note = 4028 Lambda Light Chain
source                  1..235
                        mol_type = protein
                        organism = synthetic construct
SEQUENCE: 97
MAWTPLFLFL LTCCPGGSNS QSYELTQPPS VSVSPGQTAR ITCSGDALPE KYAYWYQQKS  60
GQAPVLIIYE DSKRPSGIPE RFSGSRSGTM ATLTISGAQV DDEADYYCYS TNSGGTFFVF  120
GTGTKVTVLG QPKAAPSVTL FPPSSEELQA NKATLVCLIS DFYPGAVTVA WKADSSPVKA  180
GVETTTPSKQ SNNKYAASSY LSLTPEQWKS HKSYSCQVTH EGSTVEKTVA PTECS       235
```

```
SEQ ID NO: 98          moltype = DNA  length = 705
FEATURE                Location/Qualifiers
misc_feature           1..705
                       note = 4028 Lambda Light Chain
source                 1..705
                       mol_type = other DNA
                       organism = synthetic construct
SEQUENCE: 98
atggcttgga cccctctgtt tctgtttctg ctgacctgtt gccccggagg aagtaattcc  60
cagagctacg aactgactca gcctcccagc gtgtccgtgt cccccggcca gactgccaga  120
atcacttgca gcggcgatgc cctgccagag aagtacgcct attggtacca gcagaagtct  180
ggccaggccc ccgtgctgat catctatgag gacagcaaga ggccctccgg catccctgag  240
aggttcagcg gctccagatc tggcaccatg gccaccctga caatcagcgg agcacaggtg  300
gacgatgagg cagattacta ttgctactcc actaactcag gcgggacatt tttcgtgttt  360
gggacaggga ctaaggtcac cgtgctggga cagcctaagg cagcaccatc cgtgacactg  420
tttccccctt cctctgagga gctgcaggcc aacaaggcca ccctggtgtg cctgatcagc  480
gacttctacc caggagcagt gaccgtggca tggaaggcag atagctcccc agtgaaggca  540
ggagtggaga caacaacccc ttctaagcag agcaacaata agtacgccgc ctctagctat  600
ctgtctctga cccccgagca gtggaagagc cacaagagct attcctgcca ggtcacccat  660
gaaggctcaa ccgtggagaa aacagtcgcc cctaccgaat gctca                  705

SEQ ID NO: 99          moltype = AA  length = 473
FEATURE                Location/Qualifiers
REGION                 1..473
                       note = 2557 Heavy Chain
source                 1..473
                       mol_type = protein
                       organism = synthetic construct
SEQUENCE: 99
MDWTWRILFL VAAATGTHAE VQLVESGGEV KQPGQSLKIS CKSSGYNFLD SWIGWVRQIP  60
GKGLEWIGII YPDDSDAHYS PSFEGQVTMS VDKSISTAYL QWTTLQASDT GKYFCTRLYL  120
FEGAQSSNAF DLWGQGTMIL VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS RDELTKNQVS LTCLVKGFYP SDIAVEWESN GQPENNYKTT  420
PPVLDSDGSF FLYSKLTVDK SRWQQGNVFS CSVMHEALHN HYTQKSLSLS PGK         473

SEQ ID NO: 100         moltype = DNA  length = 1419
FEATURE                Location/Qualifiers
misc_feature           1..1419
                       note = 2557 Heavy Chain
source                 1..1419
                       mol_type = other DNA
                       organism = synthetic construct
SEQUENCE: 100
atggattgga catggaggat tctgtttctg gtcgccgccg ccactggaac tcacgctgaa  60
gtgcagctgg tggaatccgg gggcgaggtc aaacagcctg ggcagagcct gaagatcagt  120
tgtaaaagta gtgggtataa tttcctggac agctggatcg gatgggtgag gcagatccca  180
ggcaagggcc tggagtggat cggcatcatc taccccgacg attccgacgc ccactatagc  240
ccttccttcg agggccaggt gaccatgtct gtggataagt ctatcagcac agcctacctg  300
cagtggacca cactgcaggc ctccgatacc ggcaagtact tctgcacaag actgtatctg  360
tttgagggcg ctcagtcaag caacgcattc gatctgtggg gcagggaac tatgattctg  420
gtgtcaagcg ccagcacaaa gggcccatcc gtgtttccac tggcaccctc ctctaagagc  480
acctccggcg gcacagccgc cctgggctgt ctggtgaagg attacttccc agagccagtg  540
accgtgagct ggaactccgg cgccctgacc tccggagtgc acacatttcc agccgtgctg  600
cagagctccg gcctgtatag cctgtctagc gtggtgaccg tgccctcctc tagcctgggc  660
acccagacat acatctgcaa cgtgaatcac aagccatcca atacaaaggt ggacaagaag  720
gtggagccca agtcttgtga taagacccac acatgccctc cctgtcctgc accagagctg  780
ctgggcggcc catccgtgtt cctgtttcca cccaagccta aggacaccct gatgatcagc  840
cggaccccag aggtgacatg cgtggtggtg gacgtgtccc acgaggaccc cgaggtgaag  900
ttcaactggt acgtggatgg cgtggaggtg cacaatgcca agaccaagcc tagggaggag  960
cagtataact ctacctacag agtggtgagc gtgctgacag tgctgcacca ggactggctg  1020
aacggcaagg agtacaagtg caaggtgtct aataaggccc tgcccgcccc tatcgagaag  1080
accatcagca aggcaaaggg acagcctcgg gagccacagg tgtatacact gcctccatct  1140
cgcgacgagc tgaccaagaa ccaggtgagc ctgacatgtc tggtgaaggg cttctaccct  1200
agcgatatcg ccgtggagtg ggagtccaat ggccagccag agaacaatta taagaccaca  1260
ccccctgtgc tggactctga tggcagcttc tttctgtact ccaagctgac cgtggataag  1320
tctcgctggc agcagggcaa cgtgttcagc tgtagcgtga tgcacgaagc cctgcacaac  1380
cactacaccc agaaaagcct gtcactgagc cccggaaaa                         1419

SEQ ID NO: 101         moltype = AA  length = 233
FEATURE                Location/Qualifiers
REGION                 1..233
                       note = 2557 Lambda Light Chain
source                 1..233
                       mol_type = protein
                       organism = synthetic construct
```

```
SEQUENCE: 101
MAWTPLFLFL LTCCPGGSNS QSYLLTQPPS VSVSPGQTAS ISCSGDKLDD KYVSWYYQRP  60
GQSPVLLMYQ DFKRPSGIPE RLSGSKSGKT ATLTISGTQS LDEGDYYCQA WDASTGVSGG  120
GTKLTVLGQP KAAPSVTLFP PSSEELQANK ATLVCLISDF YPGAVTVAWK ADSSPVKAGV  180
ETTTPSKQSN NKYAASSYLS LTPEQWKSHK SYSCQVTHEG STVEKTVAPT ECS         233

SEQ ID NO: 102          moltype = DNA  length = 699
FEATURE                 Location/Qualifiers
misc_feature            1..699
                        note = 2557 Lambda Light Chain
source                  1..699
                        mol_type = other DNA
                        organism = synthetic construct
SEQUENCE: 102
atggcttgga cccctctgtt tctgtttctg ctgacctgtt gccccggagg aagtaattcc  60
cagagctacc tgctgaccca gcctccttcc gtgagcgtga gccctggaca gaccgcatca  120
atttcttgtt ccggcgataa actggatgac aagtacgtgt cttggtacta tcagaggccc  180
ggacagagcc ctgtgctgct gatgtatcag gatttcaaga ggccatccgg catccccgag  240
agactgagcg gctccaagtc tggcaagacc gccacactga ccatcagcgg cacacagtcc  300
ctggacgagg gcgattacta ttgccaggct tgggatgctt caacaggcgt ctctggggga  360
ggaacaaaac tgaccgtgct gggacagcct aaggcagcac catccgtgac actgtttccc  420
ccttcctctg aggagctgca ggccaacaag gccaccctgg tgtgcctgat cagcgacttc  480
tacccaggag cagtgaccgt ggcatggaag gcagatagct ccccagtgaa ggcaggagtg  540
gagacaacaa ccccttctaa gcagagcaac aataagtacg ccgcctctag ctatctgtct  600
ctgaccccccg agcagtggaa gagccacaag agctattcct gccaggtcac ccatgaaggc  660
tcaaccgtgg agaaaacagt cgcccctacc gaatgctca                         699

SEQ ID NO: 103          moltype = AA  length = 472
FEATURE                 Location/Qualifiers
REGION                  1..472
                        note = F425-B4e8 Heavy Chain
source                  1..472
                        mol_type = protein
                        organism = synthetic construct
SEQUENCE: 103
MDWTWRILFL VAAATGTHAQ VQLVQSGGGL VQPGGSLRLS CAAFGFNFSS YVMHWVRQAP  60
GQGLEYLSAI SSDGETTYHA NSVKGRFTSS RDNSKNTLFL QMGSLRTEDV AVYYCARDRY  120
YETSGSNAFD VWGQGTMVVV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSCDKTHT CPPCPAPELL GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 104          moltype = DNA  length = 1416
FEATURE                 Location/Qualifiers
misc_feature            1..1416
                        note = F425-B4e8 Heavy Chain
source                  1..1416
                        mol_type = other DNA
                        organism = synthetic construct
SEQUENCE: 104
atggattgga catggaggat tctgtttctg gtcgccgccg ccactggaac tcacgctcag  60
gtgcagctgg tgcagagcgg gggcggcctg gtgcagcctg gagggtcact gagactgtcc  120
tgtgccgcat tcgggttcaa tttcagctcc tacgtgatgc actgggtgag gcaggcacca  180
ggacagggcc tggagtacct gtctgccatc tctagcgacg gcgagacaac atatcacgcc  240
aactccgtga agggccggtt cacctcctct cgcgataaca gcaagaatac actgtttctg  300
cagatgggct ccctgaggac cgaggacgtg gccgtgtact attgcgccag ggatagatac  360
tatgagacaa gcggaagcaa cgcctttgac gtgtgggggc agggaacaat ggtggtggtc  420
tcctcagcca gcacaaaggg cccatccgtg tttccactgg caccctcctc taagagcacc  480
tccggcggca cagccgccct gggctgtctg gtgaaggatt acttcccaga gccagtgacc  540
gtgagctgga actccggcgc cctgacctcc ggagtgcaca catttccagc cgtgctgcag  600
agctccggcc tgtatagcct gtctagcgtg gtgaccgtgc cctcctctag cctgggcacc  660
cagacataca tctgcaacgt gaatcacaag ccatccaata caaaggtgga caagaaggtg  720
gagcccaagt cttgtgataa gacccacaca tgccctccct gtcctgcacc agagctgctg  780
ggcggcccat ccgtgttcct gtttccaccc aagcctaagg acaccctgat gatcagccgg  840
accccagagg tgacatgcgt ggtggtggac gtgtcccacg aggaccccga ggtgaagttc  900
aactggtacg tggatggcgt ggaggtgcac aatgccaaga ccaagcctag ggaggagcag  960
tataactcta cctacagagt ggtgagcgtg ctgacagtgc tgcaccagga ctggctgaac  1020
ggcaaggagt acaagtgcaa ggtgtctaat aaggccctgc ccgcccctat cgagaagacc  1080
atcagcaagg caaagggaca gcctcgggag ccacaggtgt atacactgcc tccatctcgc  1140
gacgagctga ccaagaacca ggtgagcctg acatgtctgg tgaagggctt ctaccctagc  1200
gatatcgccg tggagtggga gtccaatggc cagccagaga acaattataa gaccacaccc  1260
cctgtgctgg actctgatgg cagcttcttt ctgtactcca agctgaccgt ggataagtct  1320
cgctggcagc agggcaacgt gttcagctgt agcgtgatgc acgaagccct gcacaaccac  1380
tacacccaga aaagcctgtc actgagcccc ggaaaa                           1416

SEQ ID NO: 105          moltype = AA  length = 235
FEATURE                 Location/Qualifiers
```

```
REGION                  1..235
                        note = F425 Kappa Light Chain
source                  1..235
                        mol_type = protein
                        organism = synthetic construct
SEQUENCE: 105
MVLQTQVFIS LLLWISGAYG NSVLTQSPSS LSASVGDRVT ITCQASQDIS NYLNWYQHKP  60
GKAPKLLIYT ASNLETGVPS RFSGGGSGTH FSFTITSLQP EDAATYFCQQ YDNLGDLSFG  120
GGTKVEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 106          moltype = DNA  length = 705
FEATURE                 Location/Qualifiers
misc_feature            1..705
                        note = F425 Kappa Light Chain
source                  1..705
                        mol_type = other DNA
                        organism = synthetic construct
SEQUENCE: 106
atggtgctgc agacccaggt gttcatttca ctgctgctgt ggatttcagg agcctacgga  60
aactctgtgc tgacccagtc tccatcttct ctgagcgcat ccgtcggcga ccgcgtgacc  120
atcacttgcc aggcttccca ggacatttct aactacctga attggtatca gcacaagccc  180
ggcaaggccc ctaagctgct gatctacacc gccagcaacc tggagacagg agtgcccagc  240
aggttcagcg gcggcggcag cggcacccac ttcagcttta ccatcacatc cctgcagcca  300
gaggacgcag caacatattt ttgccagcag tacgataatc tgggggacct gtcattcggc  360
ggcgggacca aagtggaaat caagcggacc gtggcagcac cttccgtgtt catctttccc  420
ccttctgacg agcagctgaa gtctggcaca gccagcgtgg tgtgcctgct gaacaacttc  480
taccccaggg aggccaaggt gcagtggaag gtggataacg ccctgcagag cggcaattcc  540
caggagtctg tgaccgagca ggacagcaag gattccacat attctctgag ctccaccctg  600
acactgagca aggccgacta cgagaagcac aaggtgtatg cctgcgaggt cacccatcag  660
gggctgtcaa gtccagtcac aaagtccttc aataggggcg aatgc                  705

SEQ ID NO: 107          moltype = AA  length = 477
FEATURE                 Location/Qualifiers
REGION                  1..477
                        note = 17B Heavy Chain
source                  1..477
                        mol_type = protein
                        organism = synthetic construct
SEQUENCE: 107
MDWTWRILFL VAAATGTHAE VQLVESGAEV KKPGSSVKVS CKASGDTFIR YSFTWVRQAP  60
GQGLEWMGRI ITILDVAHYA PHLQGRVTIT ADKSTSTVYL ELRNLRSDDT AVYFCAGVYE  120
GEADEGEYDN NGFLKHWGQG TLVTVSSAST KGPSVFPLAP SSKSTSGGTA ALGCLVKDYF  180
PEPVTVSWNS GALTSGVHTF PAVLQSSGLY SLSSVVTVPS SSLGTQTYIC NVNHKPSNTK  240
VDKKVEPKSC DKTHTCPPCP APELLGGPSV FLFPPKPKDT LMISRTPEVT CVVVDVSHED  300
PEVKFNWYVD GVEVHNAKTK PREEQYNSTY RVVSVLTVLH QDWLNGKEYK CKVSNKALPA  360
PIEKTISKAK GQPREPQVYT LPPSRDELTK NQVSLTCLVK GFYPSDIAVE WESNGQPENN  420
YKTTPPVLDS DGSFFLYSKL TVDKSRWQQG NVFSCSVMHE ALHNHYTQKS LSLSPGK     477

SEQ ID NO: 108          moltype = DNA  length = 1431
FEATURE                 Location/Qualifiers
misc_feature            1..1431
                        note = 17B Heavy Chain
source                  1..1431
                        mol_type = other DNA
                        organism = synthetic construct
SEQUENCE: 108
atggattgga catggaggat tctgtttctg gtcgccgccg ccactggaac tcacgctgaa  60
gtgcagctgg tggaaagcgg agccgaagtc aaaaaacctg ggtcaagcgt caaagtcagt  120
tgtaaggcaa gcggggatac attcatccgg tactctttca cctgggtgcg ccaggcacca  180
ggacagggcc tggagtggat gggcaggatc atcacaatcc tggacgtggc acactacgcc  240
cctcacctgc agggaagggt gaccatcaca gccgataaga gcacctccac agtgtatctg  300
gagctgagga acctgagaag cgacgatacc gccgtgtact tttgcgcagg cgtgtatgag  360
ggagaggcag acgagggcga gtacgacaac aacggatttc tgaagcattg gggacagggg  420
actctggtga cagtgagcag cgccagcaca aagggcccat ccgtgtttcc actggcaccc  480
tcctctaaga gcacctccgg cggcacagcc gccctgggct gtctggtgaa ggattacttc  540
ccagagccag tgaccgtgag ctggaactcc ggcgccctga cctccggagt gcacacattt  600
ccagccgtgc tgcagagctc cggcctgtat agcctgtcta gcgtggtgac cgtgccctcc  660
tctagcctgg gcacccagac atacatctgc aacgtgaatc acaagcccatc caatacaaag  720
gtggacaaga aggtggagcc caagtcttgt gataagaccc acacatgccc tccctgtcct  780
gcaccagagc tgctgggcgg cccatccgtg ttcctgtttc cacccaagcc taaggacacc  840
ctgatgatca gccggacccc agaggtgaca tgcgtggtgg tggacgtgtc ccacgaggac  900
cccgaggtga agttcaactg gtacgtggat ggcgtggagg tgcacaatgc caagaccaag  960
cctagggagg agcagtataa ctctacctac agagtggtga gcgtgctgac agtgctgcac  1020
caggactggc tgaacggcaa ggagtacaag tgcaaggtgt ctaataaggc cctgcccgcc  1080
cctatcgaga agaccatcag caaggcaaag ggacagcctc gggagccaca ggtgtataca  1140
ctgcctccat ctcgcgacga gctgaccaag aaccaggtga gcctgacatg tctggtgaag  1200
ggcttctacc ctagcgatat cgccgtggag tgggagtcca atggccagcc agagaacaat  1260
tataagacca cacccccctgt gctggactct gatggcagct tctttctgta ctccaagctg  1320
```

```
accgtggata agtctcgctg gcagcagggc aacgtgttca gctgtagcgt gatgcacgaa  1380
gccctgcaca accactacac ccagaaaagc ctgtcactga gccccggaaa a           1431

SEQ ID NO: 109          moltype = AA  length = 236
FEATURE                 Location/Qualifiers
REGION                  1..236
                        note = 17B Kappa Light Chain
source                  1..236
                        mol_type = protein
                        organism = synthetic construct
SEQUENCE: 109
MVLQTQVFIS LLLWISGAYG DIVMTQSPAT LSVSPGERAT LSCRASESVS SDLAWYQQKP  60
GQAPRLLIYG ASTRATGVPA RFSGSGSGAE FTLTISSLQS EDFAVYYCQQ YNNWPPRYTF  120
GQGTRLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 110          moltype = DNA  length = 708
FEATURE                 Location/Qualifiers
misc_feature            1..708
                        note = 17B Kappa Light Chain
source                  1..708
                        mol_type = other DNA
                        organism = synthetic construct
SEQUENCE: 110
atggtgctgc agacccaggt gttcatttca ctgctgctgt ggatttcagg agcctacgga  60
gatattgtga tgacccagag cccagccacc ctgtccgtga gccccggcga gagagccacc  120
ctgtcctgta gagcctccga gagcgtgagc tccgacctgg catggtacca gcagaagcca  180
ggacaggccc ctaggctgct gatctatgga gcatccacca gggccacagg agtgccagca  240
agattctccg gctctggcag cggagcagag tttaccctga caatctctag cctgcagtct  300
gaggatttcg ccgtgtacta ttgccagcag tacaataact ggcctcctcg ctacaccttc  360
gggcagggca cacggctgga aatcaaaaga accgtggcag caccttccgt gttcatcttt  420
ccccccttctg acgagcagct gaagtctggc acagccagcg tggtgtgcct gctgaacaac  480
ttctacccca gggaggccaa ggtgcagtgg aaggtggata acgccctgca gagcggcaat  540
tcccaggagt ctgtgaccga gcaggacagc aaggattcca catattctct gagctccacc  600
ctgacactga gcaaggccga ctacgagaag cacaaggtgt atgcctgcga ggtcacccat  660
caggggctgt caagtccagt cacaaagtcc ttcaataggg gcgaatgc              708

SEQ ID NO: 111          moltype = AA  length = 472
FEATURE                 Location/Qualifiers
REGION                  1..472
                        note = F105 Heavy Chain
source                  1..472
                        mol_type = protein
                        organism = synthetic construct
SEQUENCE: 111
MDWTWRILFL VAAATGTHAQ VQLQESGPGL VKPSETLSLT CTVSGGSISS HYWSWIRQSP  60
GKGLQWIGYI YYSGSTNYSP SLKSRVTISV ETAKNQFSLK LTSMTAADTA VYYCARGPVP  120
AVFYGDYRLD PWGQGTLVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSCDKTHT CPPCPAPELL GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 112          moltype = DNA  length = 1416
FEATURE                 Location/Qualifiers
misc_feature            1..1416
                        note = F105 Heavy Chain
source                  1..1416
                        mol_type = other DNA
                        organism = synthetic construct
SEQUENCE: 112
atggattgga catggaggat tctgtttctg gtcgccgccg ccactggaac tcacgctcag  60
gtgcagctgc aggaaagcgg acccggcctg gtgaagccct ctgaaactct gtcactgact  120
tgtaccgtct ctgggggaag catcagctcc cactactgga gctggatcag gcagtcccca  180
ggcaagggcc tgcagtggat cggctacatc tactattctg gcagcaccaa ctattccccc  240
tctctgaagt ctagagtgac catcagcgtg gagacagcca agaatcagtt ctccctgaag  300
ctgacctcta tgacagccgc cgacacagcc gtgtactatt gcgccagggg ccccgtgcct  360
gccgtgtttt acggagatta tcggctggac ccttgggggc agggaacact ggtgactgtg  420
agtagcgcca gcacaaaggg cccatccgtg tttccactgg caccctcctc taagagcacc  480
tccggcggca cagccgccct gggctgtctg gtgaaggatt acttcccaga gccagtgacc  540
gtgagctgga actccggcgc cctgacctcc ggagtgcaca catttccagc cgtgctgcag  600
agctccggcc tgtatagcct gtctagcgtg gtgaccgtgc cctcctctag cctgggcacc  660
cagacataca tctgcaacgt gaatcacaag ccatccaata caaaggtgga caagaaggtg  720
gagcccaagt cttgtgataa gacccacaca tgccctccct gtcctgcacc agagctgctg  780
ggcggcccat ccgtgttcct gtttccaccc aagcctaagg acaccctgat gatcagccgg  840
accccagagg tgacatgcgt ggtggtggac gtgtcccacg aggaccccga ggtgaagttc  900
aactggtacg tggatggcgt ggaggtgcac aatgccaaga ccaagcctag ggaggagcag  960
tataactcta cctacagagt ggtgagcgtg ctgacagtgc tgcaccagga ctggctgaac  1020
```

```
ggcaaggagt acaagtgcaa ggtgtctaat aaggccctgc ccgcccctat cgagaagacc  1080
atcagcaagg caaagggaca gcctcgggag ccacaggtgt atacactgcc tccatctcgc  1140
gacgagctga ccaagaacca ggtgagcctg acatgtctgg tgaagggctt ctaccctagc  1200
gatatcgccg tggagtggga gtccaatggc cagccagaga acaattataa gaccacaccc  1260
cctgtgctgg actctgatgg cagcttcttt ctgtactcca agctgaccgt ggataagtct  1320
cgctggcagc agggcaacgt gttcagctgt agcgtgatgc acgaagccct gcacaaccac  1380
tacacccaga aaagcctgtc actgagcccc ggaaaa                            1416

SEQ ID NO: 113          moltype = AA  length = 235
FEATURE                 Location/Qualifiers
REGION                  1..235
                        note = F105 Kappa Light Chain
source                  1..235
                        mol_type = protein
                        organism = synthetic construct
SEQUENCE: 113
MVLQTQVFIS LLLWISGAYG EIVLTQSPGT LSLSAGERAT LSCRASQSVS SRYLAWYQQK  60
PGQAPRLLIY GASSRATGIP DRFSGSGSGT DFTLTISRVE PEDFAVYYCQ QYDNSVCTFG  120
QGTKLEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 114          moltype = DNA  length = 705
FEATURE                 Location/Qualifiers
misc_feature            1..705
                        note = F105 Kappa Light Chain
source                  1..705
                        mol_type = other DNA
                        organism = synthetic construct
SEQUENCE: 114
atggtgctgc agacccaggt gttcatttca ctgctgctgt ggatttcagg agcctacgga  60
gaaatcgtcc tgacccagtc ccccggaacc ctgagtctga gcgccggaga gcgagccacc  120
ctgagttgta gagcatcaca gagtgtcagc tcccggtacc tggcctggta tcagcagaag  180
ccaggacagg cccctcgcct gctgatctac ggagcctcta gcagggccac cggcatccca  240
gacagattct ccggctctgg cagcggcaca gacttcaccc tgacaatctc cagggtggag  300
cccgaggact tcgccgtgta ctattgccag cagtatgaca atagcgtctg taccttcggg  360
cagggcacca aactggaaat caagaggacc gtggcagcac cttccgtgtt catctttccc  420
ccttctgacg agcagctgaa gtctggcaca gccagcgtgg tgtgcctgct gaacaacttc  480
taccccaggg aggccaaggt gcagtggaag gtggataacg ccctgcagag cggcaattcc  540
caggagtctg tgaccgagca ggacagcaag gattccacat attctctgag ctccaccctg  600
acactgagca aggccgacta cgagaagcac aaggtgtatg cctgcgaggt cacccatcag  660
ggctgtcaa gtccagtcac aaagtccttc aatagggggcg aatgc                 705

SEQ ID NO: 115          moltype = AA  length = 476
FEATURE                 Location/Qualifiers
REGION                  1..476
                        note = b12 Heavy Chain
source                  1..476
                        mol_type = protein
                        organism = synthetic construct
SEQUENCE: 115
MDWTWRILFL VAAATGTHAQ VQLVQSGAEV KKPGASVKVS CQASGYRFSN FVIHWVRQAP  60
GQRFEWMGWI NPYNGNKEFS AKFQDRVTFT ADTSANTAYM ELRSLRSADT AVYYCARVGP  120
YSWDDSPQDN YYMDVWGKGT TVIVSSASTK GPSVFPLAPS SKSTSGGTAA LGCLVKDYFP  180
EPVTVSWNSG ALTSGVHTFP AVLQSSGLYS LSSVVTVPSS SLGTQTYICN VNHKPSNTKV  240
DKKVEPKSCD KTHTCPPCPA PELLGGPSVF LFPPKPKDTL MISRTPEVTC VVVDVSHEDP  300
EVKFNWYVDG VEVHNAKTKP REEQYNSTYR VVSVLTVLHQ DWLNGKEYKC KVSNKALPAP  360
IEKTISKAKG QPREPQVYTL PPSRDELTKN QVSLTCLVKG FYPSDIAVEW ESNGQPENNY  420
KTTPPVLDSD GSFFLYSKLT VDKSRWQQGN VFSCSVMHEA LHNHYTQKSL SLSPGK      476

SEQ ID NO: 116          moltype = DNA  length = 1428
FEATURE                 Location/Qualifiers
misc_feature            1..1428
                        note = b12 Heavy Chain
source                  1..1428
                        mol_type = other DNA
                        organism = synthetic construct
SEQUENCE: 116
atggattgga catggaggat tctgtttctg gtcgccgccg ccactggaac tcacgctcag  60
gtgcagctgg tccagtcagg agcagaagtg aagaaacccg gagcatcagt gaaagtcagt  120
tgtcaggcaa gcggatacag atttagcaac ttcgtgatcc actgggtgcg gcaggcacca  180
ggacagaggt tcgagtggat gggctggatc aatccttaca acggcaataa ggagttctcc  240
gccaagtttc aggacagggt gaccttcaca gccgatacct ctgccaacac agcctacatg  300
gagctgagga gcctgagatc cgccgacacc gccgtgtact attgcgcccg ggtgggacca  360
tattcttggg acgatagccc tcaggataac tattacatgg acgtgtgggg gaagggaaca  420
acagtcatcg tgtcatcagc cagcacaaag ggcccatccg tgtttccact ggcaccctcc  480
tctaagagca cctccggcgg cacagccgcc ctgggctgtc tggtgaagga ttacttccca  540
gagccagtga ccgtgagctg gaactccggc gccctgacct ccggagtgca cacatttcca  600
gccgtgctgc agagctccgg cctgtatagc ctgtctagcg tggtgaccgt gccctcctct  660
agcctgggca cccagacata catctgcaac gtgaatcaca agccatccaa tacaaaggtg  720
```

```
gacaagaagg tggagcccaa gtcttgtgat aagacccaca catgccctcc ctgtcctgca  780
ccagagctgc tgggcggccc atccgtgttc ctgtttccac ccaagcctaa ggacaccctg  840
atgatcagcc ggaccccaga ggtgacatgc gtggtggtgg acgtgtccca cgaggacccc  900
gaggtgaagt tcaactggta cgtggatggc gtggaggtgc acaatgccaa gaccaagcct  960
agggaggagc agtataactc tacctacaga gtggtgagcg tgctgacagt gctgcaccag  1020
gactggctga acggcaagga gtacaagtgc aaggtgtcta ataaggccct gcccgcccct  1080
atcgagaaga ccatcagcaa ggcaaaggga cagcctcggg agccacaggt gtatacactg  1140
cctccatctc gcgacgagct gaccaagaac caggtgagcc tgacatgtct ggtgaagggc  1200
ttctacccta gcgatatcgc cgtggagtgg gagtccaatg gccagccaga gaacaattat  1260
aagaccacac cccctgtgct ggactctgat ggcagcttct ttctgtactc caagctgacc  1320
gtggataagt ctcgctggca gcagggcaac gtgttcagct gtagcgtgat gcacgaagcc  1380
ctgcacaacc actacaccca gaaaagcctg tcactgagcc ccggaaaa              1428

SEQ ID NO: 117         moltype = AA  length = 235
FEATURE                Location/Qualifiers
REGION                 1..235
                       note = b12 Kappa Light Chain
source                 1..235
                       mol_type = protein
                       organism = synthetic construct
SEQUENCE: 117
MVLQTQVFIS LLLWISGAYG EIVLTQSPGT LSLSPGERAT FSCRSSHSIR SRRVAWYQHK  60
PGQAPRLVIH GVSNRASGIS DRFSGSGSGT DFTLTITRVE PEDFALYYCQ VYGASSYTFG  120
QGTKLERKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 118         moltype = DNA  length = 705
FEATURE                Location/Qualifiers
misc_feature           1..705
                       note = b12 Kappa Light Chain
source                 1..705
                       mol_type = other DNA
                       organism = synthetic construct
SEQUENCE: 118
atggtgctgc agacccaggt gttcatttca ctgctgctgt ggatttcagg agcctacgga  60
gagattgtgc tgacccagag tcctggaacc ctgtccctga gtcctggaga acgggccacc  120
ttttcatgcc gatcatccca tagtatcagg tctaggagag tggcatggta ccagcacaag  180
ccaggacagg cccctcggct ggtcatccac ggcgtgagca acagggcaag cggaatctcc  240
gaccgcttca gcggctccgg ctctggcaca gacttcaccc tgacaatcac cagggtggag  300
cccgaggact tcgccctgta ctattgccag gtctacgggg catcctccta tacattcgga  360
cagggcacaa aactggaacg gaaaagaacc gtggcagcac cttccgtgtt catctttccc  420
ccttctgacg agcagctgaa gtctggcaca gccagcgtgg tgtgcctgct gaacaacttc  480
taccccaggg aggccaaggt gcagtggaag gtggataacg ccctgcagag cggcaattcc  540
caggagtctg tgaccgagca ggacagcaag gattccacat attctctgag ctccaccctg  600
acactgagca aggccgacta cgagaagcac aaggtgtatg cctgcgaggt cacccatcag  660
gggctgtcaa gtccagtcac aaagtccttc aataggggcg aatgc                 705

SEQ ID NO: 119         moltype = AA  length = 482
FEATURE                Location/Qualifiers
REGION                 1..482
                       note = b6 Heavy Chain
source                 1..482
                       mol_type = protein
                       organism = synthetic construct
SEQUENCE: 119
MDWTWRILFL VAAATGTHAN SQLEESGGGL VKPGGSLRLS CVGSGFTFSS AWMAWVRQAP  60
GRGLEWVGLI KSKADGETTD YATPVKGRFS ISRNNLKDTV YLQMDSLRAD DTAVYYCATQ  120
KPRYFDLLSG QYRRVAGAFD VWGHGTTVTV SPASTKGPSV FPLAPSSKST SGGTAALGCL  180
VKDYFPEPVT VSWNSGALTS GVHTFPAVLQ SSGLYSLSSV VTVPSSSLGT QTYICNVNHK  240
PSNTKVDKKV EPKSCDKTHT CPPCPAPELL GGPSVFLFPP KPKDTLMISR TPEVTCVVVD  300
VSHEDPEVKF NWYVDGVEVH NAKTKPREEQ YNSTYRVVSV LTVLHQDWLN GKEYKCKVSN  360
KALPAPIEKT ISKAKGQPRE PQVYTLPPSR DELTKNQVSL TCLVKGFYPS DIAVEWESNG  420
QPENNYKTTP PVLDSDGSFF LYSKLTVDKS RWQQGNVFSC SVMHEALHNH YTQKSLSLSP  480
GK                                                                482

SEQ ID NO: 120         moltype = DNA  length = 1446
FEATURE                Location/Qualifiers
misc_feature           1..1446
                       note = b6 Heavy Chain
source                 1..1446
                       mol_type = other DNA
                       organism = synthetic construct
SEQUENCE: 120
atggattgga catggaggat tctgtttctg gtcgccgccg ccactggaac tcacgctaac  60
tcacagctgg aggagagcgg cggcggcctg gtcaaacctg gcgggtccct gcgactgtct  120
tgcgtggggt ctggctttac tttcagctcc gcctggatgg catgggtgag gcaggcacca  180
ggaagaggcc tggagtgggt gggcctgatc aagagcaagg ccgacggcga gacaacagat  240
tacgccaccc ctgtgaaggg ccggttctct atcagccgca acaatctgaa ggacacagtg  300
tatctgcaga tggattccct gagggccgac gataccgccg tgtactattg cgccacacag  360
```

```
aagccccggt actttgacct gctgtctggc cagtatcgga gagtcgcagg ggcttttgat  420
gtctgggggc acggcacaac agtcacagtg tcaccagcca gcacaaaggg cccatccgtg  480
tttccactgg caccctcctc taagagcacc tccggcggca cagccgccct gggctgtctg  540
gtgaaggatt acttcccaga gccagtgacc gtgagctgga actccggcgc cctgacctcc  600
ggagtgcaca catttccagc cgtgctgcag agctccggcc tgtatagcct gtctagcgtg  660
gtgaccgtgc cctcctctag cctgggcacc cagacataca tctgcaacgt gaatcacaag  720
ccatccaata caaaggtgga caagaaggtg gagcccaagt cttgtgataa gacccacaca  780
tgccctccct gtcctgcacc agagctgctg ggcggcccat ccgtgttcct gtttccaccc  840
aagcctaagg acaccctgat gatcagccgg accccagagg tgacatgcgt ggtggtggac  900
gtgtcccacg aggaccccga ggtgaagttc aactggtacg tggatggcgt ggaggtgcac  960
aatgccaaga ccaagcctag ggaggagcag tataactcta cctacagagt ggtgagcgtg  1020
ctgacagtgc tgcaccagga ctggctgaac ggcaaggagt acaagtgcaa ggtgtctaat  1080
aaggccctgc ccgcccctat cgagaagacc atcagcaagg caaagggaca gcctcgggag  1140
ccacaggtgt atacactgcc tccatctcgc gacgagctga ccaagaacca ggtgagcctg  1200
acatgtctgg tgaagggctt ctaccctagc gatatcgccg tggagtggga gtccaatggc  1260
cagccagaga acaattataa gaccacaccc cctgtgctgg actctgatgg cagcttcttt  1320
ctgtactcca agctgaccgt ggataagtct cgctggcagc agggcaacgt gttcagctgt  1380
agcgtgatgc acgaagccct gcacaaccac tacacccaga aaagcctgtc actgagcccc  1440
ggaaaa                                                             1446

SEQ ID NO: 121         moltype = AA  length = 235
FEATURE                Location/Qualifiers
REGION                 1..235
                       note = b6 Kappa Light Chain
source                 1..235
                       mol_type = protein
                       organism = synthetic construct
SEQUENCE: 121
MVLQTQVFIS LLLWISGAYG EIVLTQSPGT LSLSPGERAT LSCRAGQSIS SNYLAWYQQK  60
PGQAPRLLIY GASNRATGIP DRFSGSGSGT DFTLSISRLE PEDFAVYYCQ QYGTSPYTFG  120
QGTQLDIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 122         moltype = DNA  length = 705
FEATURE                Location/Qualifiers
misc_feature           1..705
                       note = b6 Kappa Light Chain
source                 1..705
                       mol_type = other DNA
                       organism = synthetic construct
SEQUENCE: 122
atggtgctgc agacccaggt gttcatttca ctgctgctgt ggatttcagg agcctacgga  60
gaaatcgtcc tgacccagtc ccctggcacc ctgtccctgt cccctggaga aagagccacc  120
ctgagttgta gagccgggca gagcattagc tccaactacc tggcctggta tcagcagaag  180
ccaggacagg cccctcggct gctgatctac ggagcatcca atagggcaac cggcatccca  240
gacagattct ctggcagcgg ctccggaacc gacttcaccc tgtctatcag ccgcctggag  300
ccagaggact tcgccgtgta ctattgccag cagtatggca cttcacctta cacttttgga  360
cagggaactc agctggacat caagcgaacc gtggcagcac cttccgtgtt catctttccc  420
ccttctgacg agcagctgaa gtctggcaca gccagcgtgg tgtgcctgct gaacaacttc  480
taccccaggg aggccaaggt gcagtggaag gtggataacg ccctgcagag cggcaattcc  540
caggagtctg tgaccgagca ggacagcaag gattccacat attctctgag ctccaccctg  600
acactgagca aggccgacta cgagaagcac aaggtgtatg cctgcgaggt cacccatcag  660
ggctgtcaa gtccagtcac aaagtccttc aataggggcg aatgc                  705

SEQ ID NO: 123         moltype = AA  length = 471
FEATURE                Location/Qualifiers
REGION                 1..471
                       note = 11A Heavy Chain
source                 1..471
                       mol_type = protein
                       organism = synthetic construct
SEQUENCE: 123
MDWTWRILFL VAAATGTHAN SQLVESGGGL VKPGTSLSLT CKASGFDFSD NYYICWVRQA  60
PGKGLEWIGC IFTQNVRTYY ANWAKGRFTI SKTSSTTVTL QMTSLTVADT ATYFCARFSD  120
TGPDYGLGNL WGPGSLVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKKVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRD ELTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K          471

SEQ ID NO: 124         moltype = DNA  length = 1413
FEATURE                Location/Qualifiers
misc_feature           1..1413
                       note = 11A Heavy Chain
source                 1..1413
                       mol_type = other DNA
                       organism = synthetic construct
SEQUENCE: 124
```

```
atggattgga catggaggat tctgtttctg gtcgccgccg ccactggaac tcacgctaat  60
agccagctgg tggagagcgg cggcggcctg gtgaaacctg gaacctcact gtccctgacc  120
tgtaaggcaa gcggatttga cttctccgac aactactata tctgctgggt gcggcaggca  180
ccaggcaagg gcctggagtg gatcggctgt atcttcaccc agaacgtgag gacatactat  240
gccaattggg ccaagggcag gttcaccatc tctaagacaa gctccaccac agtgaccctg  300
cagatgacca gcctgacagt ggccgacacc gccacatact tctgcgcccg cttttctgat  360
acaggacctg actacggact gggaaatctg tggggacctg ggagcctggt gactgtctca  420
tcagccagca caaagggccc atccgtgttt ccactggcac cctcctctaa gagcacctcc  480
ggcggcacag ccgccctggg ctgtctggtg aaggattact tcccagagcc agtgaccgtg  540
agctggaact ccggcgccct gacctccgga gtgcacacat ttccagccgt gctgcagagc  600
tccggcctgt atagcctgtc tagcgtggtg accgtgccct cctctagcct gggcacccag  660
acatacatct gcaacgtgaa tcacaagcca tccaatacaa aggtggacaa gaaggtggag  720
cccaagtctt gtgataagac ccacacatgc cctccctgtc ctgcaccaga gctgctgggc  780
ggcccatccg tgttcctgtt tccacccaag cctaaggaca ccctgatgat cagccggacc  840
ccagaggtga catgcgtggt ggtggacgtg tcccacgagg accccgaggt gaagttcaac  900
tggtacgtgg atggcgtgga ggtgcacaat gccaagacca agcctaggga ggagcagtat  960
aactctacct acagagtggt gagcgtgctg acagtgctgc accaggactg gctgaacggc  1020
aaggagtaca agtgcaaggt gtctaataag gccctgcccg cccctatcga gaagaccatc  1080
agcaaggcaa agggacagcc tcgggagcca caggtgtata cactgcctcc atctcgcgac  1140
gagctgacca agaaccaggt gagcctgaca tgtctggtga agggcttcta ccctagcgat  1200
atcgccgtgg agtgggagtc caatggccag ccagagaaca attataagac cacacccccct  1260
gtgctggact ctgatggcag cttctttctg tactccaagc tgaccgtgga taagtctcgc  1320
tggcagcagg gcaacgtgtt cagctgtagc gtgatgcacg aagccctgca caaccactac  1380
acccagaaaa gcctgtcact gagccccgga aaa                              1413
```

```
SEQ ID NO: 125         moltype = AA  length = 240
FEATURE                Location/Qualifiers
REGION                 1..240
                       note = 11A Kappa Light Chain
source                 1..240
                       mol_type = protein
                       organism = synthetic construct
SEQUENCE: 125
MVLQTQVFIS LLLWISGAYG DIGMTQTPAS GEAAVGGTVT IKCQASQRIG SHVSWYQQKP  60
GQRPKLLIYG ASNLESGVPS RFSGRGSGTQ FTLTISDLEC ADAATYYCQA TYDPYTGGSY  120
GAGFGGGTAV VVKRTVAAPS VFIFPPSDEQ LKSGTASVVC LLNNFYPREA KVQWKVDNAL  180
QSGNSQESVT EQDSKDSTYS LSSTLTLSKA DYEKHKVYAC EVTHQGLSSP VTKSFNRGEC  240
```

```
SEQ ID NO: 126         moltype = DNA  length = 720
FEATURE                Location/Qualifiers
misc_feature           1..720
                       note = 11A Kappa Light Chain
source                 1..720
                       mol_type = other DNA
                       organism = synthetic construct
SEQUENCE: 126
atggtgctgc agacccaggt gttcatttca ctgctgctgt ggatttcagg agcctacgga  60
gacatcggaa tgacccagac accagccagc ggggaagcag ccgtcggggg aacagtgaca  120
atcaagtgcc aggccagcca gagaatcggc agccacgtgt cctggtacca gcagaagccc  180
ggccagaggc ctaagctgct gatctatggc gcctccaacc tggagtctgg cgtgccatct  240
aggttcagcg gcagaggcag cggcacccag tttaccctga caatctccga cctggagtgc  300
gcagatgcag caacctacta ttgtcaggcc acatacgacc cctacactgg gggcagctat  360
ggagcaggat ttgggggagg aacagccgtc gtcgtgaaaa ggaccgtggc agcaccttcc  420
gtgttcatct ttccccctc tgacgagcag ctgaagtctg gcacagccag cgtggtgtgc  480
ctgctgaaca acttctaccc cagggaggcc aaggtgcagt ggaaggtgga taacgccctg  540
cagagcggca attcccagga gtctgtgacc gagcaggaca gcaaggattc cacatattct  600
ctgagctcca ccctgacact gagcaaggcc gactacgaga agcacaaggt gtatgcctgc  660
gaggtcaccc atcaggggct gtcaagtcca gtcacaaagt ccttcaatag gggcgaatgc  720
```

```
SEQ ID NO: 127         moltype = AA  length = 473
FEATURE                Location/Qualifiers
REGION                 1..473
                       note = 12N Heavy Chain
source                 1..473
                       mol_type = protein
                       organism = synthetic construct
SEQUENCE: 127
MDWTWRILFL VAAATGTHAN SQLVESGGDL VKPEGSLTLT CTASGFSFSS GYYVCWVRQA  60
PGKGLDWVAC IYVGSSGITD YATWAKGRFT ISRTSSTTVT LQMTSLTAAD TATYFCARGG  120
VGDYGVISDF RLWGPGTLVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS RDELTKNQVS LTCLVKGFYP SDIAVEWESN GQPENNYKTT  420
PPVLDSDGSF FLYSKLTVDK SRWQQGNVFS CSVMHEALHN HYTQKSLSLS PGK         473
```

```
SEQ ID NO: 128         moltype = DNA  length = 1419
FEATURE                Location/Qualifiers
misc_feature           1..1419
```

```
                        note = 12N Heavy Chain
source                  1..1419
                        mol_type = other DNA
                        organism = synthetic construct
SEQUENCE: 128
atggattgga catggaggat tctgtttctg gtcgccgccg ccactggaac tcacgctaac  60
tcacagctgg tggaaagtgg aggcgacctg gtgaaacccg aaggcagtct gaccctgacc  120
tgtaccgcaa gtggattctc attcagctcc ggctactacg tgtgctgggt gcggcaggca  180
ccaggcaagg gcctggactg ggtggcctgt atctacgtgg gctctagcgg catcaccgat  240
tatgccacat gggccaaggg caggttcacc atcagcagaa catcctctac cacagtgacc  300
ctgcagatga cctccctgac agcagcagac accgcaacat acttttgcgc ccgcggcggc  360
gtgggcgatt atggggtcat ttctgatttt cggctgtggg ggcctgggac actggtcacc  420
gtctcatctg ccagcacaaa gggcccatcc gtgtttccac tggcaccctc ctctaagagc  480
acctccggcg gcacagccgc cctgggctgt ctggtgaagg attacttccc agagccagtg  540
accgtgagct ggaactccgg cgccctgacc tccggagtgc acacatttcc agccgtgctg  600
cagagctccg gcctgtatag cctgtctagc gtggtgaccg tgccctcctc tagcctgggc  660
acccagacat acatctgcaa cgtgaatcac aagccatcca atacaaaggt ggacaagaag  720
gtggagccca agtcttgtga taagacccac acatgccctc cctgtcctgc accagagctg  780
ctgggcggcc catccgtgtt cctgtttcca cccaagccta aggacaccct gatgatcagc  840
cggaccccag aggtgacatg cgtggtggtg gacgtgtccc acgaggaccc cgaggtgaag  900
ttcaactggt acgtggatgg cgtggaggtg cacaatgcca agaccaagcc tagggaggag  960
cagtataact ctacctacag agtggtgagc gtgctgacag tgctgcacca ggactggctg  1020
aacggcaagg agtacaagtg caaggtgtct aataaggccc tgcccgcccc tatcgagaag  1080
accatcagca aggcaaaggg acagcctcgg gagccacagg tgtatacact gcctccatct  1140
cgcgacgagc tgaccaagaa ccaggtgagc ctgacatgtc tggtgaaggg cttctaccct  1200
agcgatatcg ccgtggagtg ggagtccaat ggccagccag agaacaatta taagaccaca  1260
ccccctgtgc tggactctga tggcagcttc tttctgtact ccaagctgac cgtggataag  1320
tctcgctggc agcagggcaa cgtgttcagc tgtagcgtga tgcacgaagc cctgcacaac  1380
cactacaccc agaaaagcct gtcactgagc cccggaaaa                         1419

SEQ ID NO: 129          moltype = AA  length = 241
FEATURE                 Location/Qualifiers
REGION                  1..241
                        note = 12N Kappa Light Chain
source                  1..241
                        mol_type = protein
                        organism = synthetic construct
SEQUENCE: 129
MVLQTQVFIS LLLWISGAYG DIVMTQTPAS VEVPVGGTVT IKCQASQNIY SHNYLSWYQL  60
KLGQPPKLLI YKASTLESGV PSRFKGSGSG TEFTLTISDL ECADAATYYC QFTYGSASTG  120
TYVAFGGGTE VVVKRTVAAP SVFIFPPSDE QLKSGTASVV CLLNNFYPRE AKVQWKVDNA  180
LQSGNSQESV TEQDSKDSTY SLSSTLTLSK ADYEKHKVYA CEVTHQGLSS PVTKSFNRGE  240
C                                                                  241

SEQ ID NO: 130          moltype = DNA  length = 723
FEATURE                 Location/Qualifiers
misc_feature            1..723
                        note = 12N Kappa Light Chain
source                  1..723
                        mol_type = other DNA
                        organism = synthetic construct
SEQUENCE: 130
atggtgctgc agacccaggt gttcatttca ctgctgctgt ggatttcagg agcctacgga  60
gacattgtga tgactcagac accagccagc gtggaagtgc cagtgggagg aacagtgacc  120
attaagtgcc aggccagcca gaacatttac tctcacaact atctgagctg gtaccagctg  180
aagctgggcc agcccccctaa gctgctgatc tataaggcat ctaccctgga gagcggagtg  240
ccctccaggt tcaagggcag cggctccggc acagagttta ccctgacaat ctccgacctg  300
gagtgcgcag atgcagcaac ctactattgt cagttcacat acggctcagc atcaacagga  360
acctatgtgg cattcggcgg agggacagaa gtggtggtga agcggaccgt ggcagcacct  420
tccgtgttca tctttccccc ttctgacgag cagctgaagt ctggcacagc cagcgtggtg  480
tgcctgctga acaacttcta ccccagggag gccaaggtgc agtggaaggt ggataacgcc  540
ctgcagagcg gcaattccca ggagtctgtg accgagcagg acagcaagga ttccacatat  600
tctctgagct ccaccctgac actgagcaag gccgactacg agaagcacaa ggtgtatgcc  660
tgcgaggtca cccatcaggg gctgtcaagt ccagtcacaa agtccttcaa taggggcgaa  720
tgc                                                                723

SEQ ID NO: 131          moltype = AA  length = 476
FEATURE                 Location/Qualifiers
REGION                  1..476
                        note = 39F Heavy Chain
source                  1..476
                        mol_type = protein
                        organism = synthetic construct
SEQUENCE: 131
MDWTWRILFL VAAATGTHAE VQLVQSGAEV KKPGSTVKIS CKASGYTFTD FYIQWLRQAP  60
VKGLEWMGLV DPEDGQTRYP QRFQGRVTMT ADPSTDTAYM EVSGLDFEDT ADYYCATSTL  120
LGGPYDNSGH DAFDIWGQGT KVIVSSASTK GPSVFPLAPS SKSTSGGTAA LGCLVKDYFP  180
EPVTVSWNSG ALTSGVHTFP AVLQSSGLYS LSSVVTVPSS SLGTQTYICN VNHKPSNTKV  240
DKKVEPKSCD KTHTCPPCPA PELLGGPSVF LFPPKPKDTL MISRTPEVTC VVVDVSHEDP  300
```

```
EVKFNWYVDG VEVHNAKTKP REEQYNSTYR VVSVLTVLHQ DWLNGKEYKC KVSNKALPAP  360
IEKTISKAKG QPREPQVYTL PPSRDELTKN QVSLTCLVKG FYPSDIAVEW ESNGQPENNY  420
KTTPPVLDSD GSFFLYSKLT VDKSRWQQGN VFSCSVMHEA LHNHYTQKSL SLSPGK      476

SEQ ID NO: 132         moltype = DNA  length = 1428
FEATURE                Location/Qualifiers
misc_feature           1..1428
                       note = 39F Heavy Chain
source                 1..1428
                       mol_type = other DNA
                       organism = synthetic construct
SEQUENCE: 132
atggattgga catggaggat tctgtttctg gtcgccgccg ccactggaac tcacgctgaa  60
gtgcagctgg tccagtcagg ggcagaggtc aaaaaacccg gctccaccgt gaagattagt  120
tgtaaagcaa gcggctatac atttaccgat ttctacatcc agtggctgag gcaggcacca  180
gtgaagggcc tggagtggat gggcctggtg gaccccgagg atggacagac aaggtaccct  240
cagagattcc agggccgggt gaccatgaca gccgatccaa gcaccgacac agcctatatg  300
gaggtgtccg gcctggactt tgaggatacc gccgactact attgcgccac ctctacactg  360
ctgggcggcc catatgacaa tagcggacac gacgccttcg acatctgggg gcaggggact  420
aaagtgattg tgagtagcgc cagcacaaag ggcccatccg tgtttccact ggcaccctcc  480
tctaagagca cctccggcgg cacagccgcc ctgggctgtc tggtgaagga ttacttccca  540
gagccagtga ccgtgagctg gaactccggc gccctgacct ccggagtgca cacatttcca  600
gccgtgctgc agagctccgg cctgtatagc ctgtctagcg tggtgaccgt gccctcctct  660
agcctgggca cccagacata catctgcaac gtgaatcaca agccatccaa tacaaaggtg  720
gacaagaagg tggagcccaa gtcttgtgat aagacccaca catgccctcc ctgtcctgca  780
ccagagctgc tgggcggccc atccgtgttc ctgtttccac ccaagcctaa ggacaccctg  840
atgatcagcc ggaccccaga ggtgacatgc gtggtggtgg acgtgtccca cgaggacccc  900
gaggtgaagt tcaactggta cgtggatggc gtggaggtgc acaatgccaa gaccaagcct  960
agggaggagc agtataactc tacctacaga gtggtgagcg tgctgacagt gctgcaccag  1020
gactggctga acggcaagga gtacaagtgc aaggtgtcta ataaggccct gcccgcccct  1080
atcgagaaga ccatcagcaa ggcaaaggga cagcctcggg agccacaggt gtatacactg  1140
cctccatctc gcgacgagct gaccaagaac caggtgagcc tgacatgtct ggtgaagggc  1200
ttctacccta gcgatatcgc cgtggagtgg gagtccaatg gccagccaga gaacaattat  1260
aagaccacac cccctgtgct ggactctgat ggcagcttct ttctgtactc caagctgacc  1320
gtggataagt ctcgctggca gcagggcaac gtgttcagct gtagcgtgat gcacgaagcc  1380
ctgcacaacc actacaccca gaaaagcctg tcactgagcc ccggaaaa               1428

SEQ ID NO: 133         moltype = AA  length = 236
FEATURE                Location/Qualifiers
REGION                 1..236
                       note = 39F Lambda Light Chain
source                 1..236
                       mol_type = protein
                       organism = synthetic construct
SEQUENCE: 133
MAWTPLFLFL LTCCPGGSNS QLPVLTQPPS ASGTPGQRVT ISCSGSGSSF ERNYVYWYQQ  60
LPGMAPKLLI YRSDQRLSGV PDRFSGSKSD TSASLAISGL RSEDEATYYC AAWDDSLTLL  120
FGGGTKLTVL GQPKAAPSVT LFPPSSEELQ ANKATLVCLI SDFYPGAVTV AWKADSSPVK  180
AGVETTTPSK QSNNKYAASS YLSLTPEQWK SHKSYSCQVT HEGSTVEKTV APTECS      236

SEQ ID NO: 134         moltype = DNA  length = 708
FEATURE                Location/Qualifiers
misc_feature           1..708
                       note = 39F Lambda Light Chain
source                 1..708
                       mol_type = other DNA
                       organism = synthetic construct
SEQUENCE: 134
atggcttgga cccctctgtt tctgtttctg ctgacctgtt gccccggagg aagtaattcc  60
cagctgcccg tcctgactca gcctcctagc gcaagcggca ctcctggaca gagggtgacc  120
attagttgta gcggaagcgg aagtagtttc gagaggaact acgtgtattg gtaccagcag  180
ctgcccggca tggcccctaa gctgctgatc tataggtccg accagagact gtctggcgtg  240
cccgatcggt ttagcggctc caagtctgac accagcgcct ccctggcaat ctctggcctg  300
cgcagcgagg atgaggccac atactattgc gctgcttggg atgactctct gacactgctg  360
ttcgggggag ggacaaaact gactgtgctg ggacagccta aggcagcacc atccgtgaca  420
ctgtttcccc cttcctctga ggagctgcag gccaacaagg ccaccctggt gtgcctgatc  480
agcgacttct acccaggagc agtgaccgtg gcatggaagg cagatagctc cccagtgaag  540
gcaggagtgg agacaacaac cccttctaag cagagcaaca ataagtacgc cgcctctagc  600
tatctgtctc tgacccccga gcagtggaag agccacaaga gctattcctg ccaggtcacc  660
catgaaggct caaccgtgga gaaaacagtc gcccctaccg aatgctca               708

SEQ ID NO: 135         moltype = DNA  length = 2142
FEATURE                Location/Qualifiers
misc_feature           1..2142
                       note = Subtype A consensus Envelope DNA sequence construct
source                 1..2142
                       mol_type = other DNA
                       organism = synthetic construct
SEQUENCE: 135
```

```
ggatccatgg actggacctg gattctgttc ctggtggccg ccgccaccag agtgcacagc  60
agagtgatgg gcatccagcg gaattgccag cacctgtgga gatggggcac catgatcctg  120
ggcatgatca tcatctgctc tgccgccgag aacctgtggg tgaccgtgta ctacggcgtg  180
cctgtgtgga aggacgccga gaccaccctg ttctgcgcca gcgacgccaa ggcctacgat  240
accgaagtgc acaatgtgtg ggccacccac gcctgcgtgc ctaccgatcc caacccccag  300
gagatcaacc tggagaacgt gaccgaggag ttcaacatgt ggaagaacaa catggtggag  360
cagatgcaca ccgacatcat cagcctgtgg gaccagagcc tgaagccttg cgtgaagctg  420
acccctctgt gcgtgaccct gaactgcagc aacgtgaacg tgaccaccaa catcatgaag  480
ggcgagatca agaactgcag cttcaacatg accaccgagc tgcgggacaa gaagcagaaa  540
gtgtacagcc tgttctacaa gctggacgtg gtgcagatca acaagagcaa cagcagcagc  600
cagtaccggc tgatcaactg caacaccagc gccatcaccc aggcctgccc caaagtgagc  660
ttcgagccca tccccatcca ctactgcgcc cctgccggct tcgccatcct gaagtgcaag  720
gacaaggagt ttaacggcac cggcccctgc aagaatgtga gcaccgtgca gtgcacccac  780
ggcatcaagc ccgtggtgtc cacccagctg ctgctgaacg gcagcctggc cgaggaggaa  840
gtgatgatcc ggagcgagaa catcaccaac aacgccaaga acatcatcgt gcagctgacc  900
aagcccgtga agatcaattg cacccggccc aacaacaaca cccggaagag catcagaatc  960
ggccctggcc aggccttcta cgccaccggc gacatcatcg gcgatatcag gcaggcccac  1020
tgcaatgtga gccggaccga gtggaacgag accctgcaga aagtggccaa gcagctgcgg  1080
aagtacttca acaacaagac catcatcttc accaacagca gcggcggcag actgagaatc  1140
accacccaca gcttcaattg tggcggcgag ttcttctact gcaatacctc cggcctgttc  1200
aacagcacct ggaacggcaa cggcaccaag aagaagaaca gcaccgagag caacgacacc  1260
atcaccctgc cctgccggat caagcagatc atcaatatgt ggcagagggt gggccaggcc  1320
atgtacgccc ctcccatcca gggcgtgatc agatgcgaga gcaacatcac cggcctgctg  1380
ctgaccagag atggcggcga caacaacagc aagaacgaga ccttcagacc tggcggcgga  1440
gacatgaggg acaactggcg gagcgagctg tacaagtaca aagtggtgaa gatcgagccc  1500
ctgggcgtgg cccccaccaa ggccaagaga agagtggtgg agcgggagaa gagagctgtg  1560
ggcatcggcg ccgtgttcct gggcttcctg ggagccgccg gaagcaccat gggagccgcc  1620
agcatcaccc tgaccgtgca ggccagacag ctgctgagcg gcattgtgca gcagcagagc  1680
aacctgctga gagccatcga ggcccagcag cacctgctga agctgacagt gtggggcatc  1740
aaacagctgc aggcccgcgt gctggccgtg gagagatacc tgaaggacca gcagctgctg  1800
ggcatctggg gctgcagcgg caagctgatc tgcaccacca acgtgccctg gaatagcagc  1860
tggagcaaca agagccagag cgagatctgg gacaacatga cctggctgca gtgggacaag  1920
gagatcagca actacaccga tatcatctac aacctgatcg aggagagcca gaaccagcag  1980
gagaagaacg agcaggatct gctggccctg gacaagtggg ccaacctgtg gaactggttc  2040
gacatcagca actggctgtg gtacatcaag atcttcatca tgattgtggg cggcctgatc  2100
ggcctgagaa tcgtgttcgc cgtgctgtct gtgtgactcg ag                    2142
```

```
SEQ ID NO: 136          moltype = AA  length = 709
FEATURE                 Location/Qualifiers
REGION                  1..709
                        note = Subtype A consensus Envelope protein sequence
                         construct
source                  1..709
                        mol_type = protein
                        organism = synthetic construct
SEQUENCE: 136
MDWTWILFLV AAATRVHSRV MGIQRNCQHL WRWGTMILGM IIICSAAENL WVTVYYGVPV  60
WKDAETTLFC ASDAKAYDTE VHNVWATHAC VPTDPNPQEI NLENVTEEFN MWKNNMVEQM  120
HTDIISLWDQ SLKPCVKLTP LCVTLNCSNV NVTTNIMKGE IKNCSFNMTT ELRDKKQKVY  180
SLFYKLDVVQ INKSNSSSQY RLINCNTSAI TQACPKVSFE PIPIHYCAPA GFAILKCKDK  240
EFNGTGPCKN VSTVQCTHGI KPVVSTQLLL NGSLAEEEVM IRSENITNNA KNIIVQLTKP  300
VKINCTRPNN NTRKSIRIGP GQAFYATGDI IGDIRQAHCN VSRTEWNETL QKVAKQLRKY  360
FNNKTIIFTN SSGGRLRITT HSFNCGGEFF YCNTSGLFNS TWNGNGTKKK NSTESNDTIT  420
LPCRIKQIIN MWQRVGQAMY APPIQGVIRC ESNITGLLLT RDGGDNNSKN ETFRPGGGDM  480
RDNWRSELYK YKVVKIEPLG VAPTKAKRRV VEREKRAVGI GAVFLGFLGA AGSTMGAASI  540
TLTVQARQLL SGIVQQQSNL LRAIEAQQHL LKLTVWGIKQ LQARVLAVER YLKDQQLLGI  600
WGCSGKLICT TNVPWNSSWS NKSQSEIWDN MTWLQWDKEI SNYTDIIYNL IEESQNQQEK  660
NEQDLLALDK WANLWNWFDI SNWLWYIKIF IMIVGGLIGL RIVFAVLSV             709
```

```
SEQ ID NO: 137          moltype = DNA  length = 2734
FEATURE                 Location/Qualifiers
misc_feature            1..2734
                        note = Subtype B consensus Envelope DNA sequence construct
source                  1..2734
                        mol_type = other DNA
                        organism = synthetic construct
SEQUENCE: 137
ggatccgcca ccatggactg gacctggatt ctgttcctgg tggccgccgc caccagagtg  60
cacagcagag tgaagggcat ccggaagaac taccagcacc tgtggagatg gggcaccatg  120
ctgctgggca tgctgatgat ctgttctgcc gccgagaagc tgtgggtgac cgtgtactac  180
ggcgtgcctg tgtggaagga ggccaccacc accctgttct gcgccagcga cgccaaggcc  240
tacgataccg aagtgcacaa tgtgtgggcc acccacgcct gcgtgcctac cgatcccaac  300
cctcaggaag tggtgctgga gaacgtgacc gagaacttca acatgtggaa gaacaacatg  360
gtggagcaga tgcacgagga catcatcagc ctgtgggacc agagcctgaa gccttgcgtg  420
aagctgaccc ctctgtgcgt gaccctgaac tgcaccgacc tgagcggcga gaagatggag  480
aagggcgaga tcaagaactg cagcttcaac atcaccacct ccatccggga caaagtgcag  540
aaggagtacg ccctgttcta caagctggac gtggtgccca tcgacaacga caacaccagc  600
taccggctga tcagctgcaa caccagcgtg atcacccagg cctgccccaa agtgagcttc  660
gagcccatcc ccatccacta ctgcgcccct gccggcttcg ccatcctgaa gtgcaacgac  720
```

```
aagaagttca acggcaccgg cccttgcacc aatgtgagca ccgtgcagtg cacccacggc  780
atcagacccg tggtgtccac ccagctgctg ctgaacggca gcctggccga ggaagaagtg  840
gtgatccgga gcgagaattt caccaacaac gccaagacca tcatcgtgca gctgaacgag  900
agcgtggaga tcaactgcac ccggcccaac aacaataccc ggaagagcat ccacatcggc  960
cctggccagg ccttctacac caccggcgag atcatcggcg atatcaggca ggcccactgc  1020
aatatcagcc gggccaagtg gaacaacacc ctgaagcaga tcgtgaagaa gctgcgggag  1080
cagttcggca acaagaccat cgtgttcaac cagagcagcg gcggcagacc tagaatcgtg  1140
atgcacagct tcaactgtgg cggcgagttc ttctactgca acacaaccca gctgttcaac  1200
agcacctgga acgtgaacgg gacctggaac aacaacaccg agggcaacga caccatcacc  1260
ctgccctgcc ggatcaagca gatcatcaat atgtggcagg aggtgggcaa ggccatgtac  1320
gcccctccca tcagaggcca gatccggtgc agcagcaata tcaccggcct gctgctgacc  1380
agagatggcg gcaacaataa caccaacgag accgagatct ttagacctgg cggcggagac  1440
atgagggaca actggcggag cgagctgtac aagtacaaag tggtgaagat cgagcccctg  1500
ggcgtggccc ccaccaaggc caagagaaga gtggtgcagc gggagaagag agctgtgggc  1560
atcggcgcca tgtttctggg ctttctggga gccgccggaa gcaccatggg agccgccagc  1620
atgaccctga ccgtgcaggc cagacagctg ctgagcggca tcgtgcagca gcagaacaac  1680
ctgctgagag ccatcgaggc ccagcagcac ctgctgcagc tgacagtgtg gggcatcaag  1740
cagctgcagg cccgcgtgct ggccgtggag agatacctga aggaccagca gctgctggga  1800
atctggggct gcagcggcaa gctgatctgc accaccaccg tgccctggaa cgccagctgg  1860
agcaacaaga gcctggacga gatctgggac aacatgacct ggatggagtg ggagcgggag  1920
atcgacaact acaccagcct gatctacacc ctgatcgagg agagccagaa ccagcaggag  1980
aagaacgagc aggagctgct ggagctggac aagtgggcca gcctgtggaa ctggttcgac  2040
atcaccaact ggctgtggta catcaagatc ttcatcatga ttgtgggcgg cctgatcggc  2100
ctgagaatcg tgttcgccgt gctgagcatc taccccctacg acgtgcccga ttacgcctga  2160
gaattcgtaa gtaagtgtca tatgggagag ctcgactaga ctggacagcc aatgacgggt  2220
aagagagtga catttctcac taacctaaga caggagggcc gtcaaagcta ctgcctaatc  2280
caatgacggg taatagtgac aagaaatgta tcactccaac ctaagacagg cgcagcctcc  2340
gagggatgtg tcttttgttt tttataatta aaaagggtga catgtccgga gccgtgctgc  2400
ccggatgatg tcttggcctc tgtttgctac cggtatcgat gttaacgtcg accccgggct  2460
cgaggtaagt aagtgtcata tgggagagct cgactagact ggacagccaa tgacgggtaa  2520
gagagtgaca tttctcacta acctaagaca ggagggccgt caaagctact gcctaatcca  2580
atgacgggta atagtgacaa gaaatgtatc actccaacct aagacaggcg cagcctccga  2640
gggatgtgtc ttttgttttt tataattaaa aagggtgaca tgtccggagc cgtgctgccc  2700
ggatgatgtc ttggcctctg tttgctgcgg ccgc                              2734

SEQ ID NO: 138          moltype = AA  length = 715
FEATURE                 Location/Qualifiers
REGION                  1..715
                        note = Subtype B consensus Envelope protein sequence
                         construct
source                  1..715
                        mol_type = protein
                        organism = synthetic construct
SEQUENCE: 138
MDWTWILFLV AAATRVHSRV KGIRKNYQHL WRWGTMLLGM LMICSAAEKL WVTVYYGVPV  60
WKEATTTLFC ASDAKAYDTE VHNVWATHAC VPTDPNPQEV VLENVTENFN MWKNNMVEQM  120
HEDIISLWDQ SLKPCVKLTP LCVTLNCTDL SGEKMEKGEI KNCSFNITTS IRDKVQKEYA  180
LFYKLDVVPI DNDNTSYRLI SCNTSVITQA CPKVSFEPIP IHYCAPAGFA ILKCNDKKFN  240
GTGPCTNVST VQCTHGIRPV VSTQLLLNGS LAEEEVVIRS ENFTNNAKTI IVQLNESVEI  300
NCTRPNNNTR KSIHIGPGQA FYTTGEIIGD IRQAHCNISR AKWNNTLKQI VKKLREQFGN  360
KTIVFNQSSG GRPRIVMHSF NCGGEFFYCN TTQLFNSTWN VNGTWNNNTE GNDTITLPCR  420
IKQIINMWQE VGKAMYAPPI RGQIRCSSNI TGLLLTRDGG NNNTNETEIF RPGGGDMRDN  480
WRSELYKYKV VKIEPLGVAP TKAKRRVVQR EKRAVGIGAM FLGFLGAAGS TMGAASMTLT  540
VQARQLLSGI VQQQNNLLRA IEAQQHLLQL TVWGIKQLQA RVLAVERYLK DQQLLGIWGC  600
SGKLICTTTV PWNASWSNKS LDEIWDNMTW MEWEREIDNY TSLIYTLIEE SQNQQEKNEQ  660
ELLELDKWAS LWNWFDITNW LWYIKIFIMI VGGLIGLRIV FAVLSIYPYD VPDYA       715

SEQ ID NO: 139          moltype = DNA  length = 2140
FEATURE                 Location/Qualifiers
misc_feature            1..2140
                        note = Subtype C consensus Envelope DNA sequence construct
source                  1..2140
                        mol_type = other DNA
                        organism = synthetic construct
SEQUENCE: 139
ggatccgcca ccatggattg gacctggatt ctgttcctgg tggccgccgc cacaagagtg  60
cacagcagag tgcggggcat cctgagaaat tgccagcagt ggtggatctg gggcattctg  120
gggttctgga tgctgatgat ctgcaacgtg atgggcaacc tgtgggtgac cgtgtactac  180
ggcgtgcctg tgtggaagga ggccaagacc accctgttct gtgccagcga tgccaaggcc  240
tacgagaccg aggtgcacaa tgtgtgggcc acccacgcct gtgtgcccac cgatcccaac  300
cctcaggaga tggtgctgga gaacgtgacc gagaacttca acatgtggaa gaacgacatg  360
gtggaccaga tgcacgagga catcatcagc ctgtgggacc agagcctgaa gccttgcgtg  420
aagctgaccc ctctgtgcgt gaccctgaac tgccggaaca acgtgaacaa caacaacacc  480
atgaaggagg agatcaagaa ctgcagcttc aacatcacca ccgagctgcg ggacaagaag  540
cagaaggtgt acgccctgtt ctaccggctg gacatcgtgc ccctgaacga gaagaacaac  600
agcaacgact accggctgat caactgcaac accagcgcca tcacccaggc ctgtcccaag  660
gtgtccttcg accccatccc catccactat tgtgcccctg ccggctacgc catcctgaag  720
tgcaacaaca agaccttcaa cggcaccggc ccctgcaata atgtgagcac cgtgcagtgt  780
acccacggca tcaagcctgt ggtgtccacc cagctgctgc tgaatggcag cctggccgag  840
```

```
gaggagatta tcatccggag cgagaacctg accaacaacg ccaagaccat cattgtgcac  900
ctgaatgaga gcgtggagat cgtgtgtacc cggcccaaca acaatacccg gaagagcatc  960
agaatcggcc ctggccagac cttttacgcc accggcgaca tcatcggcga tatcaggcag  1020
gcccactgca atatcagcga ggagaagtgg aacaagaccc tgcagcgggt gtccgagaag  1080
ctgaaggagc acttccccaa taagaccatc aagttcgccc ctagcagcgg cggcagactg  1140
gagatcacca cccacagctt caactgcagg ggcgagttct tctactgcaa taccagcaag  1200
ctgttcaaca gcacctacat gcccaacagc accaacaata ccaacaccac catcaccctg  1260
ccctgccgga tcaagcagat catcaatatg tggcaggaag tgggcagagc catgtacgcc  1320
cctcccatcg agggcaacat cacctgcaag tccaacatca ccggcctgct gctgacaaga  1380
gatggcggca agaacgacac caatgacacc gagaccttca gacctggcgg cggagacatg  1440
agggacaact ggcggagcga gctgtacaag tacaaggtgg tggagatcaa gcctctgggc  1500
gtggccccta ccaaggccaa gaggagagtg gtggagaggg agaagagagc cgtgggcatc  1560
ggcgccgtgt ttctgggctt tctgggagcc gccggatcta caatgggagc cgccagcatc  1620
acactgaccg tgcaggccag acagctgctg agcggcatcg tgcagcagca gagcaatctg  1680
ctgagagcca tcgaggccca gcagcacatg ctgcagctga cagtgtgggg catcaagcag  1740
ctgcagacca gagtgctggc catcgagcgc tacctgaagg atcagcagct gctgggcatc  1800
tggggctgta gcggcaagct gatctgtacc accgccgtgc cttggaatag cagctggagc  1860
aacaagagcc aggaggacat ctgggacaac atgacctgga tgcagtggga ccgggagatc  1920
agcaactaca ccgacaccat ctacaggctg ctggaggaca gccagaacca gcaggagaag  1980
aacgagaagg acctgctggc cctggacagc tggaagaacc tgtggaactg gttcgacatc  2040
accaactggc tgtggtacat caagatcttc atcatgattg tgggcggcct gatcggcctg  2100
agaatcatct tcgccgtgct gagcatctga tagcggccgc                        2140
```

```
SEQ ID NO: 140         moltype = AA  length = 705
FEATURE                Location/Qualifiers
REGION                 1..705
                       note = Subtype C consensus Envelope protein sequence
                        construct
source                 1..705
                       mol_type = protein
                       organism = synthetic construct
SEQUENCE: 140
MDWTWILFLV AAATRVHSRV RGILRNCQQW WIWGILGFWM LMICNVMGNL WVTVYYGVPV  60
WKEAKTTLFC ASDAKAYETE VHNVWATHAC VPTDPNPQEM VLENVTENFN MWKNDMVDQM  120
HEDIISLWDQ SLKPCVKLTP LCVTLNCRNN VNNNNTMKEE IKNCSFNITT ELRDKKQKVY  180
ALFYRLDIVP LNEKNNSNDY RLINCNTSAI TQACPKVSFD PIPIHYCAPA GYAILKCNNK  240
TFNGTGPCNN VSTVQCTHGI KPVVSTQLLL NGSLAEEEII IRSENLTNNA KTIIVHLNES  300
VEIVCTRPNN NTRKSIRIGP GQTFYATGDI IGDIRQAHCN ISEEKWNKTL QRVSEKLKEH  360
FPNKTIKFAP SSGGRLEITT HSFNCRGEFF YCNTSKLFNS TYMPNSTNNT NTTITLPCRI  420
KQIINMWQEV GRAMYAPPIE GNITCKSNIT GLLLTRDGGK NDTNDTETFR PGGGDMRDNW  480
RSELYKYKVV EIKPLGVAPT KAKRRVVERE KRAVGIGAVF LGFLGAAGST MGAASITLTV  540
QARQLLSGIV QQQSNLLRAI EAQQHMLQLT VWGIKQLQTR VLAIERYLKD QQLLGIWGCS  600
GKLICTTAVP WNSSWSNKSQ EDIWDNMTWM QWDREISNYT DTIYRLLEDS QNQQEKNEKD  660
LLALDSWKNL WNWFDITNWL WYIKIFIMIV GGLIGLRIIF AVLSI                  705
```

```
SEQ ID NO: 141         moltype = DNA  length = 2089
FEATURE                Location/Qualifiers
misc_feature           1..2089
                       note = Subtype D consensus Envelope DNA sequence construct
source                 1..2089
                       mol_type = other DNA
                       organism = synthetic construct
SEQUENCE: 141
gggcatcaag cggaattacc agcacctgtg gaagtggggc accatgctgc tgggcatgct  60
gatgacctgc agcgtggccg agaacctgtg ggtgaccgtg tactacggcg tgcctgtgtg  120
gaaggaagcc accaccaccc tgttctgcgc cagcgatgcc aagagctaca agaccgaggc  180
ccacaatatc tgggccaccc acgcctgcgt gcctaccgat cccaaccctc aggagatcga  240
gctggagaac gtgaccgaga acttcaacat gtggaagaac aacatggtgg agcagatgca  300
cgaggacatc atcagcctgt gggaccagag cctgaagcct tgcgtgaagc tgacccctct  360
gtgcgtgacc ctgaactgca ccgacggcat gaggaacgac accaacgata ccaacgtgac  420
catggaggag ggcgagatga agaactgcag cttcaacatc accaccgaag tgcgggacaa  480
gaagaagcag gtgcacgccc tgttctacaa gctggacgtg gtgcccatcg acgacaacaa  540
caccaacaac agcaactacc ggctgatcaa ctgcaacacc agcgccatca cccaggcctg  600
ccccaaagtg accttcgagc ccatccccat ccactactgc gcccctgccg gcttcgccat  660
cctgaagtgc aaggataaga agttcaacgg caccggcccc tgcaagaatg tgagcaccgt  720
gcagtgcacc cacggcatca gacccgtggt gtccacccag ctgctgctga acggcagcct  780
ggccgaggag gagatcatca tccggagcga gaacctgacc aacaacgcca agatcatcat  840
tgtgcagctg aacgagagcg tgaccatcaa ttgcacccgg ccctacaaca atacccggaa  900
gcgcatcccc atcggcctgg gccaggcctt ctacaccacc agaggcatca tcggcgacat  960
cagacaggcc cactgcaata tcagcggagc cgagtggaat aagaccctgc agcaggtggc  1020
caagaagctg ggcgacctgc tgaacaagac caccatcatc ttcaagccta gcagcggcgg  1080
cagacctaga atcaccaccc acagcttcaa ttgtggcggc gagttcttct actgcaatac  1140
cagccggctg ttcaacagca cctggagcaa gaacagcacc agcaactcca ccaaggagaa  1200
caacaccatc accctgccct gccggatcaa gcagatcatc aatatgtggc agggagtggg  1260
caaggccatg tacgcccctc ccatcgaggg cctgatcaag tgcagcagca acatcaccgg  1320
cctgctgctg accagagatg gcggagccaa caactcccac aacgagacct tcagacctgg  1380
cggcggagac atgagggaca actggcggag cgagctgtac aagtacaaag tggtgaagat  1440
cgagcccctg ggcgtggccc ccaccagagc caagagaaga gtggtggagc gggagaagag  1500
agccatcgga ctgggcgcca tgttcctggg cttcctggga gccgccggaa gcaccatggg  1560
```

```
agccgccagc ctgaccctga ccgtgcaggc cagacagctg ctgagcggca tcgtgcagca  1620
gcagaacaac ctgctgagag ccattgaggc ccagcagcac ctgctgcagc tgacagtgtg  1680
gggcattaag cagctgcagg ccaggattct ggccgtggag cgctacctga aggatcagca  1740
gctgctggga atctggggct gcagcggcaa gcacatctgc accaccaccg tgccttggaa  1800
tagcagctgg agcaacaaga gcctggacga gatctggaac aacatgacct ggatggagtg  1860
ggagagggag atcgacaact acaccggcct gatctacagc ctgatcgagg agagccagac  1920
ccagcaggag aagaacgagc aggagctgct ggagctggac aagtgggcca gcctgtggaa  1980
ctggttcagc atcacccagt ggctgtggta catcaagatc ttcatcatga ttgtgggcgg  2040
cctgatcggc ctgagaatcg tgttcgccgt gctgagcctg tgactcgag             2089

SEQ ID NO: 142         moltype = AA  length = 714
FEATURE                Location/Qualifiers
REGION                 1..714
                       note = Subtype D consensus Envelope protein sequence
                        construct
source                 1..714
                       mol_type = protein
                       organism = synthetic construct
SEQUENCE: 142
MDWTWILFLV AAATRVHSRV RGIKRNYQHL WKWGTMLLGM LMTCSVAENL WVTVYYGVPV  60
WKEATTTLFC ASDAKSYKTE AHNIWATHAC VPTDPNPQEI ELENVTENFN MWKNNMVEQM  120
HEDIISLWDQ SLKPCVKLTP LCVTLNCTDG MRNDTNDTNV TMEEGEMKNC SFNITTEVRD  180
KKKQVHALFY KLDVVPIDDN NTNNSNYRLI NCNTSAITQA CPKVTFEPIP IHYCAPAGFA  240
ILKCKDKKFN GTGPCKNVST VQCTHGIRPV VSTQLLLNGS LAEEEIIIRS ENLTNNAKII  300
IVQLNESVTI NCTRPYNNTR KRIPIGLGQA FYTTRGIIGD IRQAHCNISG AEWNKTLQQV  360
AKKLGDLLNK TTIIFKPSSG GRPRITTHSF NCGGEFFYCN TSRLFNSTWS KNSTSNSTKE  420
NNTITLPCRI KQIINMWQGV GKAMYAPPIE GLIKCSSNIT GLLLTRDGGA NNSHNETFRP  480
GGGDMRDNWR SELYKYKVVK IEPLGVAPTR AKRRVVEREK RAIGLGAMFL GFLGAAGSTM  540
GAASLTLTVQ ARQLLSGIVQ QQNNLLRAIE AQQHLLQLTV WGIKQLQARI LAVERYLKDQ  600
QLLGIWGCSG KHICTTTVPW NSSWSNKSLD EIWNNMTWME WEREIDNYTG LIYSLIEESQ  660
TQQEKNEQEL LELDKWASLW NWFSITQWLW YIKIFIMIVG GLIGLRIVFA VLSL        714

SEQ ID NO: 143         moltype = DNA  length = 1049
FEATURE                Location/Qualifiers
misc_feature           1..1049
                       note = Subtype B consensus Nef-Rev DNA sequence construct
source                 1..1049
                       mol_type = other DNA
                       organism = synthetic construct
SEQUENCE: 143
ggatccgcca ccatggactg gacctggatt ctgttcctgg tggccgctgc caccagagtg  60
cacagcagca agagaagcgt ggtgggttgg cctacagtgc gggagaggat gagaagagcc  120
gagcctgccg ccgatggagt gggcgccgtg tctagagatc tggagaagca cggcgccatc  180
accagcagca ataccgccgc caacaatgcc gactgcgcct ggctggaggc ccaggaggag  240
gaggaagtgg gcttccctgt gagagcccag gtggccctga gagccatgac ctacaaggcc  300
gccgtggatc tgagccactt cctgaaggag aagggcggcc tggagggcct gatctacagc  360
cagaagcggc aggacatcct ggatctgtgg gtgtaccaca cccagggcta cttccccgac  420
tggcagaatt acacccctgg ccctggcatc agataccctc tgaccttcgg ctggtgcttc  480
aagctggtgc ctgtggagcc tgagaaagtg gaggaggcca acgagggcga gaacaattct  540
gccgcccacc ctatgagcct gcacggcatg gacgatcccg agagggaagt gctggtgtgg  600
aagttcgaca gcaggctggc cttccaccac atggccagag agctgcaccc cgagtactac  660
aaggactgcc ggggcaggaa gagaagaagc gccggcagaa gcggcgacag cgacgaggag  720
ctgctgaaaa cagtgcggct gatcaagttc ctgtaccaga gcaaccctcc tcccagcccc  780
gagggcacca gacaggcccg gagaaaccgg aggaggcggt ggagagagag gcagcggcag  840
atcagaagca tcagcgagtg gattctgagc acctacctgg gcagacccgc cgagcccgtg  900
cccctgcagc tgcccccct ggagagactg accctggact gcaacgagga ctgcggcacc  960
agcggcaccc agggagtggg cagcccccag atcctggtgg agagccctgc cgtgctggag  1020
agcggcacca aggagtgatg agcggccgc                                   1049

SEQ ID NO: 144         moltype = AA  length = 341
FEATURE                Location/Qualifiers
REGION                 1..341
                       note = Subtype B consensus Nef-Rev protein sequence
                        construct
source                 1..341
                       mol_type = protein
                       organism = synthetic construct
SEQUENCE: 144
MDWTWILFLV AAATRVHSSK RSVVGWPTVR ERMRRAEPAA DGVGAVSRDL EKHGAITSSN  60
TAANNADCAW LEAQEEEEVG FPVRAQVALR AMTYKAAVDL SHFLKEKGGL EGLIYSQKRQ  120
DILDLWVYHT QGYFPDWQNY TPGPGIRYPL TFGWCFKLVP VEPEKVEEAN EGENNSAAHP  180
MSLHGMDDPE REVLVWKFDS RLAFHHMARE LHPEYYKDCR GRKRRSAGRS GDSDEELLKT  240
VRLIKFLYQS NPPPSPEGTR QARRNRRRRW RERQRQIRSI SEWILSTYLG RPAEPVPLQL  300
PPLERLTLDC NEDCGTSGTQ GVGSPQILVE SPAVLESGTK E                     341

SEQ ID NO: 145         moltype = DNA  length = 1863
FEATURE                Location/Qualifiers
misc_feature           1..1863
                       note = Gag consensus DNA sequence of subtype A, B, C and D
```

```
                         construct
source                  1..1863
                        mol_type = other DNA
                        organism = synthetic construct
SEQUENCE: 145
ggatccgcca ccatggactg gacctggatt ctgtttctgg tcgccgccgc cacaagagtg  60
cacagcggcg ccagagccag cgtgctgtcc ggcggcaagc tggacgcctg ggagaagatc  120
agactgaggc ctggcggcaa gaagaagtac cggctgaagc accttgtgtg ggccagcaga  180
gagctggaga gattcgccct gaatcctggc ctgctggaga ccagcgaggg ctgtaagcag  240
atcatcggcc agctgcagcc cgccctgcag accggcagcg aggagctgag aagcctgtac  300
aacaccgtgg ccaccctgta ctgcgtgcac gagaagatcg aggtgaagga caccaaggag  360
gccctggaca agatcgagga ggagcagaac aagagcaagc agaaggccca gcaggccgcc  420
gccgacaccg gcaacagcag ccaggtgtcc cagaactacc ccatcgtgca gaatctgcag  480
ggccagatgg tgcaccaggc catcagcccc agaaccctga atgcctgggt gaaggtgatc  540
gaggagaagg ccttcagccc tgaggtgatc cctatgttca gcgccctgag cgagggcgcc  600
acacctcagg acctgaacac catgctgaac acagtggggg gccaccaggc cgccatgcag  660
atgctgaagg ataccatcaa cgaggaggcc gccgagtggg acagactgca ccccgtgcac  720
gccggaccta tcgcccctgg ccagatgaga gagcccagag gcagcgacat cgccggcacc  780
acctccaccc tgcaagagca gatcggctgg atgaccagca acccccccat ccctgtgggc  840
gacatctaca agcggtggat catcctgggc ctgaacaaga ttgtgaggat gtacagcccc  900
gtgtccatcc tggatatcag gcagggcccc aaggagccct tcagagacta cgtggaccgg  960
ttcttcaaga ccctgagagc cgagcaggcc agccaggacg tgaagaactg gatgaccgag  1020
accctgctgg tgcagaacgc caaccccgac tgtaagacca tcctgagagc cctgggccct  1080
ggcgccaccc tggaggagat gatgaccgcc tgccagggag tgggcggacc cggccacaag  1140
gccagagtgc tggccgaggc catgagccag gccaccaaca gcaacatcat gatgcagcgg  1200
ggcaacttca gaggccccag gaggatcgtg aagtgcttca actgtggcaa ggagggccac  1260
atcgccagaa actgtagggc ccccaggaag aagggctgct ggaagtgtgg caaagagggg  1320
caccagatga aggactgtac cgagcggcag gccaatttcc tggggaagat ctggcccagc  1380
cacaagggca gacccggcaa tttcctgcag agcagacctg agcccaccgc ccctcccgcc  1440
gagagcttcg gcttcggcga ggagatcacc cccagcccca agcaggagcc caaggacaga  1500
gagctgtacc ctctggccag cctgaagagc ctgttcggca acgatcccct gagccagtac  1560
ccctacgacg tgcccgatta cgcctgagaa ttcgtaagta agtgtcatat gggagagctc  1620
gactagactg gacagccaat gacgggtaag agagtgacat ttctcactaa cctaagacag  1680
gagggccgtc aaagctactg cctaatccaa tgacgggtaa tagtgacaag aaatgtatca  1740
ctccaaccta agacaggcgc agcctccgag ggatgtgtct tttgtttttt ataattaaaa  1800
agggtgacat gtccggagcc gtgctgcccg gatgatgtct tggcctctgt ttgctgcggc  1860
cgc                                                                1863

SEQ ID NO: 146          moltype = AA  length = 524
FEATURE                 Location/Qualifiers
REGION                  1..524
                        note = Gag consensus protein sequence of subtype A, B, C
                         and D construct
source                  1..524
                        mol_type = protein
                        organism = synthetic construct
SEQUENCE: 146
MDWTWILFLV AAATRVHSGA RASVLSGGKL DAWEKIRLRP GGKKKYRLKH LVWASRELER  60
FALNPGLLET SEGCKQIIGQ LQPALQTGSE ELRSLYNTVA TLYCVHEKIE VKDTKEALDK  120
IEEEQNKSKQ KAQQAAADTG NSSQVSQNYP IVQNLQGQMV HQAISPRTLN AWVKVIEEKA  180
FSPEVIPMFS ALSEGATPQD LNTMLNTVGG HQAAMQMLKD TINEEAAEWD RLHPVHAGPI  240
APGQMREPRG SDIAGTTSTL QEQIGWMTSN PPIPVGDIYK RWIILGLNKI VRMYSPVSIL  300
DIRQGPKEPF RDYVDRFFKT LRAEQASQDV KNWMTETLLV QNANPDCKTI LRALGPGATL  360
EEMMTACQGV GGPGHKARVL AEAMSQATNS NIMMQRGNFR GPRRIVKCFN CGKEGHIARN  420
CRAPRKKGCW KCGKEGHQMK DCTERQANFL GKIWPSHKGR PGNFLQSRPE PTAPPAESFG  480
FGEEITPSPK QEPKDRELYP LASLKSLFGN DPLSQYPYDV PDYA                  524

SEQ ID NO: 147          moltype = AA  length = 692
FEATURE                 Location/Qualifiers
REGION                  1..692
                        note = Subtype A consensus Envelope protein sequence
source                  1..692
                        mol_type = protein
                        organism = synthetic construct
SEQUENCE: 147
SRVMGIQRNC QHLWRWGTMI LGMIIICSAA ENLWVTVYYG VPVWKDAETT LFCASDAKAY  60
DTEVHNVWAT HACVPTDPNP QEINLENVTE EFNMWKNNMV EQMHTDIISL WDQSLKPCVK  120
LTPLCVTLNC SNVNVTTNIM KGEIKNCSFN MTTELRDKKQ KVYSLFYKLD VVQINKSNSS  180
SQYRLINCNT SAITQACPKV SFEPIPIHYC APAGFAILKC KDKEFNGTGP CKNVSTVQCT  240
HGIKPVVSTQ LLLNGSLAEE EVMIRSENIT NNAKNIIVQL TKPVKINCTR PNNNTRKSIR  300
IGPGQAFYAT GDIIGDIRQA HCNVSRTEWN ETLQKVAKQL RKYFNNKTII FTNSSGGRLR  360
ITTHSFNCGG EFFYCNTSGL FNSTWNGNGT KKKNSTESND TITLPCRIKQ IINMWQRVGQ  420
AMYAPPIQGV IRCESNITGL LLTRDGGDNN SKNETFRPGG GDMRDNWRSE LYKYKVVKIE  480
PLGVAPTKAK RRVVEREKRA VGIGAVFLGF LGAAGSTMGA ASITLTVQAR QLLSGIVQQQ  540
SNLLRAIEAQ QHLLKLTVWG IKQLQARVLA VERYLKDQQL LGIWGCSGKL ICTTNVPWNS  600
SWSNKSQSEI WDNMTWLQWD KEISNYTDII YNLIEESQNQ QEKNEQDLLA LDKWANLWNW  660
FDISNWLWYI KIFIMIVGGL IGLRIVFAVL SV                                692

SEQ ID NO: 148          moltype = AA  length = 697
```

```
FEATURE                 Location/Qualifiers
REGION                  1..697
                        note = Subtype B consensus Envelope protein sequence
source                  1..697
                        mol_type = protein
                        organism = synthetic construct
SEQUENCE: 148
RVKGIRKNYQ HLWRWGTMLL GMLMICSAAE KLWVTVYYGV PVWKEATTTL FCASDAKAYD  60
TEVHNVWATH ACVPTDPNPQ EVVLENVTEN FNMWKNNMVE QMHEDIISLW DQSLKPCVKL  120
TPLCVTLNCT DLSGEKMEKG EIKNCSFNIT TSIRDKVQKE YALFYKLDVV PIDNDNTSYR  180
LISCNTSVIT QACPKVSFEP IPIHYCAPAG FAILKCNDKK FNGTGPCTNV STVQCTHGIR  240
PVVSTQLLLN GSLAEEEVVI RSENFTNNAK TIIVQLNESV EINCTRPNNN TRKSIHIGPG  300
QAFYTTGEII GDIRQAHCNI SRAKWNNTLK QIVKKLREQF GNKTIVFNQS SGGRPRIVMH  360
SFNCGGEFFY CNTTQLFNST WNVNGTWNNN TEGNDTITLP CRIKQIINMW QEVGKAMYAP  420
PIRGQIRCSS NITGLLLTRD GGNNNTNETE IFRPGGGDMR DNWRSELYKY KVVKIEPLGV  480
APTKAKRRVV QREKRAVGIG AMFLGFLGAA GSTMGAASMT LTVQARQLLS GIVQQQNNLL  540
RAIEAQQHLL QLTVWGIKQL QARVLAVERY LKDQQLLGIW GCSGKLICTT TVPWNASWSN  600
KSLDEIWDNM TWMEWEREID NYTSLIYTLI EESQNQQEKN EQELLELDKW ASLWNWFDIT  660
NWLWYIKIFI MIVGGLIGLR IVFAVLSIYP YDVPDYA                          697

SEQ ID NO: 149          moltype = AA  length = 687
FEATURE                 Location/Qualifiers
REGION                  1..687
                        note = Subtype C consensus Envelope protein sequence
source                  1..687
                        mol_type = protein
                        organism = synthetic construct
SEQUENCE: 149
RVRGILRNCQ QWWIWGILGF WMLMICNVMG NLWVTVYYGV PVWKEAKTTL FCASDAKAYE  60
TEVHNVWATH ACVPTDPNPQ EMVLENVTEN FNMWKNDMVD QMHEDIISLW DQSLKPCVKL  120
TPLCVTLNCR NNVNNNNTMK EEIKNCSFNI TTELRDKKQK VYALFYRLDI VPLNEKNNSN  180
DYRLINCNTS AITQACPKVS FDPIPIHYCA PAGYAILKCN NKTFNGTGPC NNVSTVQCTH  240
GIKPVVSTQL LLNGSLAEEE IIIRSENLTN NAKTIIVHLN ESVEIVCTRP NNNTRKSIRI  300
GPGQTFYATG DIIGDIRQAH CNISEEKWNK TLQRVSEKLK EHFPNKTIKF APSSGGRLEI  360
TTHSFNCRGE FFYCNTSKLF NSTYMPNSTN NTNTTITLPC RIKQIINMWQ EVGRAMYAPP  420
IEGNITCKSN ITGLLLTRDG GKNDTNDTET FRPGGGDMRD NWRSELYKYK VVEIKPLGVA  480
PTKAKRRVVE REKRAVGIGA VFLGFLGAAG STMGAASITL TVQARQLLSG IVQQQSNLLR  540
AIEAQQHMLQ LTVWGIKQLQ TRVLAIERYL KDQQLLGIWG CSGKLICTTA VPWNSSWSNK  600
SQEDIWDNMT WMQWDREISN YTDTIYRLLE DSQNQQEKNE KDLLALDSWK NLWNWFDITN  660
WLWYIKIFIM IVGGLIGLRI IFAVLSI                                     687

SEQ ID NO: 150          moltype = AA  length = 696
FEATURE                 Location/Qualifiers
REGION                  1..696
                        note = Subtype D consensus Envelope protein sequence
source                  1..696
                        mol_type = protein
                        organism = synthetic construct
SEQUENCE: 150
RVRGIKRNYQ HLWKWGTMLL GMLMTCSVAE NLWVTVYYGV PVWKEATTTL FCASDAKSYK  60
TEAHNIWATH ACVPTDPNPQ EIELENVTEN FNMWKNNMVE QMHEDIISLW DQSLKPCVKL  120
TPLCVTLNCT DGMRNDTNDT NVTMEEGEMK NCSFNITTEV RDKKKQVHAL FYKLDVVPID  180
DNNTNNSNYR LINCNTSAIT QACPKVTFEP IPIHYCAPAG FAILKCKDKK FNGTGPCKNV  240
STVQCTHGIR PVVSTQLLLN GSLAEEEIII RSENLTNNAK IIIVQLNESV TINCTRPYNN  300
TRKRIPIGLG QAFYTTRGII GDIRQAHCNI SGAEWNKTLQ QVAKKLGDLL NKTTIIFKPS  360
SGGRPRITTH SFNCGGEFFY CNTSRLFNST WSKNSTSNST KENNTITLPC RIKQIINMWQ  420
GVGKAMYAPP IEGLIKCSSN ITGLLLTRDG GANNSHNETF RPGGGDMRDN WRSELYKYKV  480
VKIEPLGVAP TRAKRRVVER EKRAIGLGAM FLGFLGAAGS TMGAASLTLT VQARQLLSGI  540
VQQQNNLLRA IEAQQHLLQL TVWGIKQLQA RILAVERYLK DQQLLGIWGC SGKHICTTTV  600
PWNSSWSNKS LDEIWNNMTW MEWEREIDNY TGLIYSLIEE SQTQQEKNEQ ELLELDKWAS  660
LWNWFSITQW LWYIKIFIMI VGGLIGLRIV FAVLSL                           696

SEQ ID NO: 151          moltype = AA  length = 323
FEATURE                 Location/Qualifiers
REGION                  1..323
                        note = Subtype B consensus Nef-Rev protein sequence
source                  1..323
                        mol_type = protein
                        organism = synthetic construct
SEQUENCE: 151
SKRSVVGWPT VRERMRRAEP AADGVGAVSR DLEKHGAITS SNTAANNADC AWLEAQEEEE  60
VGFPVRAQVA LRAMTYKAAV DLSHFLKEKG GLEGLIYSQK RQDILDLWVY HTQGYFPDWQ  120
NYTPGPGIRY PLTFGWCFKL VPVEPEKVEE ANEGENNSAA HPMSLHGMDD PEREVLVWKF  180
DSRLAFHHMA RELHPEYYKD CRGRKRRSAG RSGDSDEELL KTVRLIKFLY QSNPPPSPEG  240
TRQARRNRRR RWRERQRQIR SISEWILSTY LGRPAEPVPL QLPPLERLTL DCNEDCGTSG  300
TQGVGSPQIL VESPAVLESG TKE                                         323

SEQ ID NO: 152          moltype = AA  length = 506
FEATURE                 Location/Qualifiers
```

-continued

```
REGION                 1..506
                       note = Gag consensus protein sequence of subtype A, B, C
                        and D
source                 1..506
                       mol_type = protein
                       organism = synthetic construct
SEQUENCE: 152
GARASVLSGG KLDAWEKIRL RPGGKKKYRL KHLVWASREL ERFALNPGLL ETSEGCKQII  60
GQLQPALQTG SEELRSLYNT VATLYCVHEK IEVKDTKEAL DKIEEEQNKS KQKAQQAAAD  120
TGNSSQVSQN YPIVQNLQGQ MVHQAISPRT LNAWVKVIEE KAFSPEVIPM FSALSEGATP  180
QDLNTMLNTV GGHQAAMQML KDTINEEAAE WDRLHPVHAG PIAPGQMREP RGSDIAGTTS  240
TLQEQIGWMT SNPPIPVGDI YKRWIILGLN KIVRMYSPVS ILDIRQGPKE PFRDYVDRFF  300
KTLRAEQASQ DVKNWMTETL LVQNANPDCK TILRALGPGA TLEEMMTACQ GVGGPGHKAR  360
VLAEAMSQAT NSNIMMQRGN FRGPRRIVKC FNCGKEGHIA RNCRAPRKKG CWKCGKEGHQ  420
MKDCTERQAN FLGKIWPSHK GRPGNFLQSR PEPTAPPAES FGFGEEITPS PKQEPKDREL  480
YPLASLKSLF GNDPLSQYPY DVPDYA                                      506
```

DNA ANTIBODY CONSTRUCTS FOR USE AGAINST HIV

CROSS-REFERENCE TO RELATED APPLICATIONS

This application is a continuation of U.S. application Ser. No. 16/497,945, filed Sep. 26, 2019, which is a U.S. national phase application filed under 35 U.S.C. § 371 claiming priority to International Patent Application No. PCT/US2018/024520, filed Mar. 27, 2018, which is entitled to priority to U.S. Provisional Application No. 62/477,227, filed Mar. 27, 2017 and U.S. Provisional Application No. 62/477,217, filed Mar. 27, 2017, the contents of each of which are incorporated by reference herein in their entireties.

REFERENCE TO A "SEQUENCE LISTING," SUBMITTED AS AN XML FILE

The Sequence Listing written in the xml file titled: "206193-0109-01US_SequenceListing.xml"; created on Nov. 28, 2023, and 329,503 bytes in size, is hereby incorporated by reference.

TECHNICAL FIELD

The present invention relates to a composition comprising a recombinant nucleic acid sequence for generating one or more synthetic antibodies, and functional fragments thereof, in vivo, and a method of preventing and/or treating viral infection in a subject by administering said composition.

BACKGROUND

The strength of broadly neutralizing antibodies (bNabs) to protect or control HIV-1 is well established in animal models. Though these antibodies are powerful and can prevent infection or control viral loads, the cost of production could severely limit the ability to use these antibodies in the field. Additionally, current vaccine approaches have failed to induce similar antibodies.

Thus there is need in the art for improved therapeutics that prevent and/or treat HIV infection. The current invention satisfies this need.

SUMMARY

The present invention is directed to a nucleic acid molecule encoding one or more synthetic antibodies, wherein the nucleic acid molecule comprises at least one selected from the group consisting of a) a nucleotide sequence encoding an anti-HIV synthetic antibody; and b) a nucleotide sequence encoding a fragment of an anti-HIV synthetic antibody.

In one embodiment, the nucleic acid molecule comprises a nucleotide sequence encoding a cleavage domain.

In one embodiment, the nucleic acid molecule comprises a nucleotide sequence encoding one or more of a variable heavy chain region and a variable light chain region of an anti-HIV antibody.

In one embodiment, the nucleic acid molecule comprises a nucleotide sequence encoding one or more amino acid sequences at least 90% identical to an amino acid sequence as set forth in SEQ ID NO:1, SEQ ID NO:3, SEQ ID NO:5, SEQ ID NO:7, SEQ ID NO:9, SEQ ID NO:11, or SEQ ID NO:13, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39 SEQ ID NO:41, SEQ ID NO:43, SEQ ID NO:45, SEQ ID NO:47, SEQ ID NO:49 SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, or SEQ ID NO:133.

In one embodiment, the nucleic acid molecule comprises a nucleotide sequence at least 95% identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO: 60, SEQ ID NO:62, SEQ ID NO:64, SEQ ID NO:66, SEQ ID NO:68,SEQ ID NO: 70, SEQ ID NO:72, SEQ ID NO:74, SEQ ID NO:76, SEQ ID NO:78, SEQ ID NO: 80, SEQ ID NO:82, SEQ ID NO:84, SEQ ID NO:86, SEQ ID NO:88, SEQ ID NO: 90, SEQ ID NO:92, SEQ ID NO:94, SEQ ID NO:96, SEQ ID NO:98, SEQ ID NO: 100, SEQ ID NO:102, SEQ ID NO:104, SEQ ID NO:106, SEQ ID NO:108, SEQ ID NO: 110, SEQ ID NO:112, SEQ ID NO:114, SEQ ID NO:116, SEQ ID NO:118, SEQ ID NO: 120, SEQ ID NO:122, SEQ ID NO:124, SEQ ID NO:126, SEQ ID NO:128, SEQ ID NO: 130, SEQ ID NO:132, or SEQ ID NO:134.

In one embodiment, the nucleic acid molecule comprises a nucleotide sequence encoding a variable heavy chain region and a variable light chain region of an anti-HIV antibody.

In one embodiment, the nucleic acid molecule comprises a nucleotide sequence encoding a heavy chain comprising an amino acid sequence at least 95% identical to SEQ ID NO:3, SEQ ID NO:11, SEQ ID NO:17, SEQ ID NO:25, SEQ ID NO:39, SEQ ID NO:47, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, or SEQ ID NO:131.

In one embodiment, the nucleotide sequence encoding a heavy chain comprises a nucleotide sequence at least 95% identical to SEQ ID NO:4, SEQ ID NO:12, SEQ ID NO:18, SEQ ID NO:26, SEQ ID NO:40, SEQ ID NO:48, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, or SEQ ID NO:132.

In one embodiment, the nucleic acid molecule comprises a nucleotide sequence encoding a light chain comprising an amino acid sequence at least 95% identical to SEQ ID NO:5, SEQ ID NO:13, SEQ ID NO:19, SEQ ID NO:27, SEQ ID NO:41, SEQ ID NO:49, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO:105, SEQ ID NO:109, SEQ ID NO:113, SEQ ID NO:117, SEQ ID NO:121, SEQ ID NO:125, SEQ ID NO:129, or SEQ ID NO:133.

In one embodiment, the nucleotide sequence encoding a light chain comprises a nucleotide sequence at least 95% identical to SEQ ID NO:6, SEQ ID NO:14, SEQ ID NO:20, SEQ ID NO:28, SEQ ID NO:42, SEQ ID NO:50, SEQ ID NO:58, SEQ ID NO:62, SEQ ID NO:66, SEQ ID NO:70, SEQ ID NO:74, SEQ ID NO:76, SEQ ID NO:82, SEQ ID NO:86, SEQ ID NO:90, SEQ ID NO:94, SEQ ID NO:98, SEQ ID NO:102, SEQ ID NO:106, SEQ ID NO:110, SEQ ID NO:114, SEQ ID NO:118, SEQ ID NO:122, SEQ ID NO:126, SEQ ID NO:130, or SEQ ID NO:134.

In one embodiment, the nucleic acid molecule comprises a nucleotide sequence encoding a polypeptide comprising a variable heavy chain region; an IRES element; and a variable light chain region. In one embodiment, the IRES element is one of a viral IRES or an eukaryotic IRES.

In one embodiment, the nucleotide sequence encodes a leader sequence. In one embodiment, the nucleic acid molecule comprises an expression vector.

The invention further provides a composition comprising any of the nucleic acid molecules described herein.

In one embodiment the composition comprises a pharmaceutically acceptable excipient.

The invention further relates to a method of preventing or treating a disease in a subject, the method comprising administering to the subject a nucleic acid molecule or a composition as described herein.

In one embodiment, the disease is an HIV infection.

In one embodiment, the method further comprises administering an antibiotic agent to the subject. In one embodiment, an antibiotic is administered less than 10 days after administration of the nucleic acid molecule or composition.

In one embodiment, the method further comprises administering an antibiotic agent to the subject. In one embodiment an antibiotic is administered less than 10 days after administration of the nucleic acid molecule or composition.

The invention further relates to a method generating an immune response in a subject, the method comprising administering to the subject a nucleic acid molecule or a composition as described herein.

BRIEF DESCRIPTION OF THE DRAWINGS

FIG. 1, comprising FIG. 1A depicts a schematic of dMAb design. Antibody sequences go through multiple rounds of optimizations to increase dMAb production level including codon and RNA optimization, amino acid sequence modification, changes to the backbone and formulation. FIG. 1B depicts a diagram of dMAb in vivo production. Plasmid DNA expressing the antibody is injected into the muscle followed by electroporation. Muscle cells then product the functional antibody which is secreted into circulation.

FIG. 2, comprising FIG. 2A depicts the expression of HIV dMAB constructs in cell media. FIG. 2B depicts the expression of HIV dMAB constructs in cell lysate. FIG. 2C depicts western blot analysis of media from two constructs to ensure proper processing of the heavy and light chain.

FIG. 5, comprising FIG. 5A through FIG. 5C depicts experimental results demonstrating how different human IgG isotypes can lead to changes in in vivo expression levels of dMAbs.

FIG. 6, comprising of FIG. 6A through FIG. 6B depicts experimental results demonstrating the in vitro expression levels of multiple broadly neutralizing antibodies expressed as either human IgG1 or human IgG4 dMAbs.

FIG. 7, comprising of FIG. 7A through FIG. 7B, depicts experimental results demonstrating the increased expression levels in vivo for multiple HIV dMAbs using IgG4 isotype compared to IgG1.

FIG. 8, comprising of FIG. 8A through FIG. 8B depicts experimental results demonstrating that the S228P mutation in the IgG4 background does not disrupt expression levels.

FIG. 10, comprising FIG. 10A through FIG. 10B depicts experimental results demonstrating the long terms expression of dMAb and how modifications can increase expression levels over time.

FIG. 11, comprising FIG. 11A through FIG. 11B depicts experimental results demonstrating dMAb modifications and optimizations maintains functionality. FIG. 11A depicts reported IC50 concentrations for a panel of tier 2 viruses against numerous bNabs. FIG. 11B depicts neutralization concentration (IC50) for original and modified in vitro produced dMAb to induce functionality after modification.

DETAILED DESCRIPTION

Figures 1A, 1B:
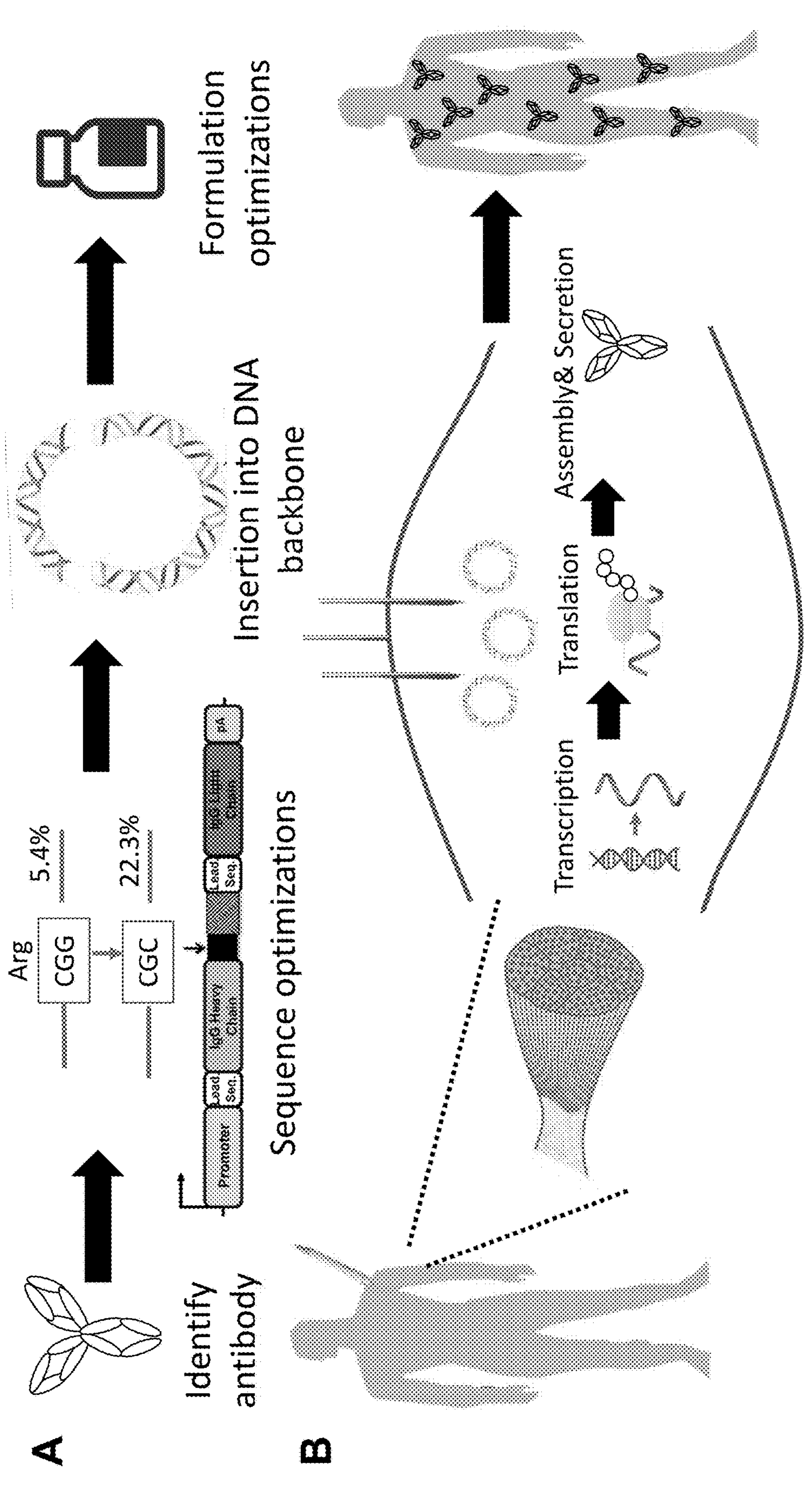
FIG. 1A through FIG. 1B, depicts dMAb concept and design.
Figures 2A, 2B, 2C:
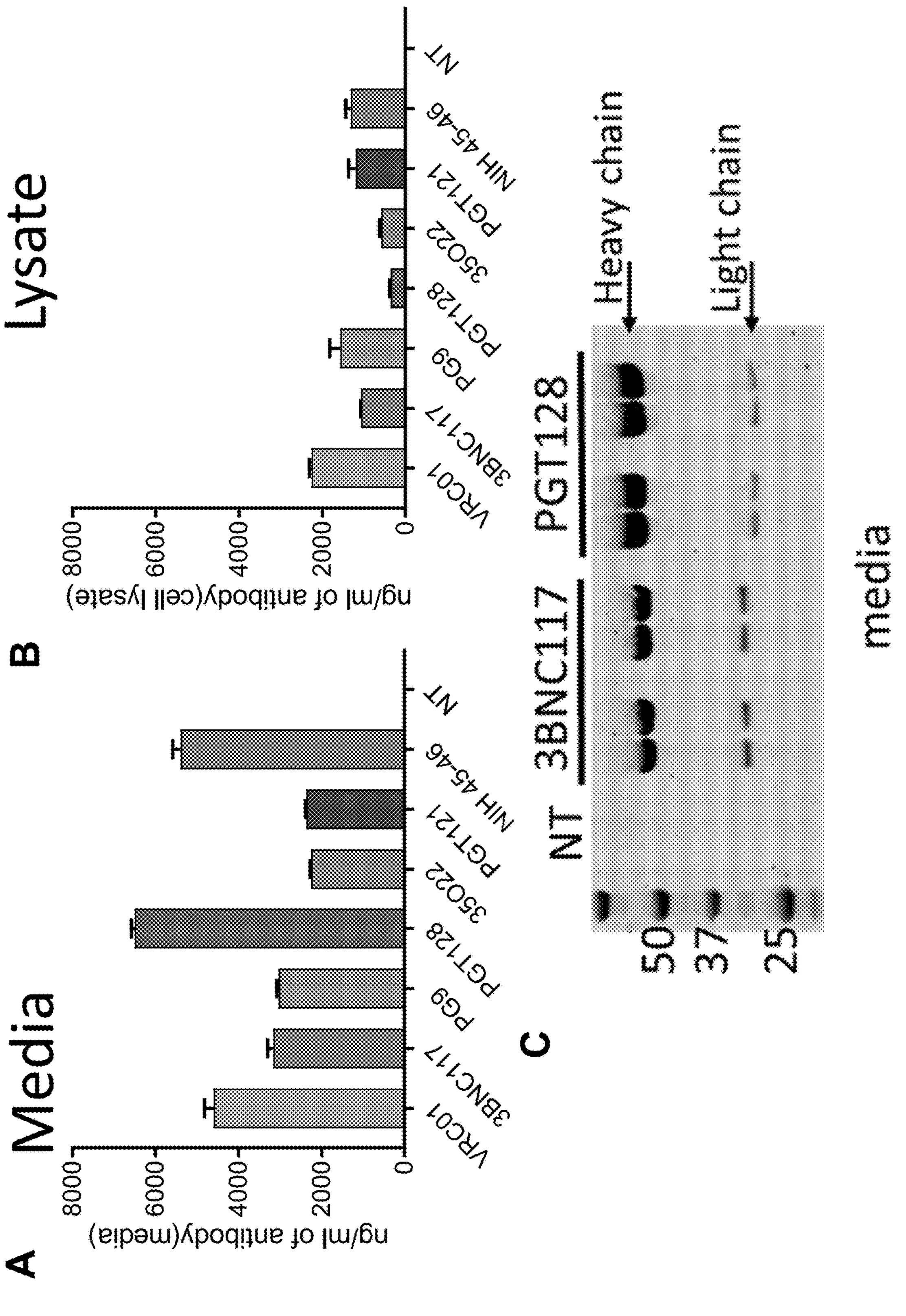
FIG. 2A through FIG. 2C, depicts experimental results demonstrating in vitro expression of HIV IgG1 dMAb constructs. 293T cells were transfected with different HIV dMAb plasmids. Forty-eight hours later cell media or lysate were harvested and quantified via ELISA.

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen induced immune response. The synthetic antibodies are able to effectively bind and neutralize a range of antigens. The synthetic antibodies are also able to effectively protect against and/or promote survival of disease.

A sequence listing provided herewith contains a list of sequences including the following:

SEQ ID NO: 1 is the amino acid sequence of 3BNC117 human IgG1 antibody.
SEQ ID NO: 2 is the nucleotide sequence of 3BNC117 human IgG1 antibody.
SEQ ID NO: 3 is the amino acid sequence of 3BNC117 human IgG1 antibody (heavy chain).
SEQ ID NO: 4 is the nucleotide sequence of 3BNC117 human IgG1 antibody (heavy chain).
SEQ ID NO: 5 is the amino acid sequence of 3BNC117 human IgG1 antibody (light chain).
SEQ ID NO: 6 is the nucleotide sequence of 3BNC117 human IgG1 antibody (light chain).
SEQ ID NO: 7 is the amino acid sequence of 3BNC117 human IgG4.
SEQ ID NO: 8 is the nucleotide sequence of 3BNC117 human IgG4.
SEQ ID NO: 9 is the amino acid sequence of 3BNC117 human IgG4 (S228P).
SEQ ID NO: 10 is the nucleotide sequence of 3BNC117 human IgG4 (S228P).
SEQ ID NO: 11 is the amino acid sequence of 3BNC117 human IgG4 (heavy chain).
SEQ ID NO: 12 is the nucleotide sequence of 3BNC117 human IgG4 (heavy chain).
SEQ ID NO: 13 is the amino acid sequence of 3BNC117 human IgG4 (light chain).
SEQ ID NO: 14 is the nucleotide sequence of 3BNC117 human IgG4 (light chain).
SEQ ID NO: 15 is the amino acid sequence of PGT128 human IgG1.
SEQ ID NO: 16 is the nucleotide sequence of PGT128 human IgG1.
SEQ ID NO: 17 is the amino acid sequence of PGT128 human IgG1-(heavy chain).
SEQ ID NO: 18 is the nucleotide sequence of PGT128 human IgG1-(heavy chain).
SEQ ID NO: 19 is the amino acid sequence of PGT128 human IgG1-(light chain).
SEQ ID NO: 20 is the nucleotide sequence of PGT128 human IgG1-(light chain).
SEQ ID NO: 21 is the amino acid sequence of PGT128 human IgG4.
SEQ ID NO: 22 is the nucleotide sequence of PGT128 human IgG4.
SEQ ID NO: 23 is the amino acid sequence of PGT128 human IgG4mut (S228P).
SEQ ID NO: 24 is the nucleotide sequence of PGT128 human IgG4mut (S228P).
SEQ ID NO: 25 is the amino acid sequence of PGT128 human IgG4-heavy chain.
SEQ ID NO: 26 is the nucleotide sequence of PGT128 human IgG4-heavy chain.
SEQ ID NO: 27 is the amino acid sequence of PGT128 human IgG4-light chain.
SEQ ID NO: 28 is the nucleotide sequence of PGT128 human IgG4-light chain.
SEQ ID NO: 29 is the amino acid sequence of PG9 IgG1.
SEQ ID NO: 30 is the nucleotide sequence of PG9 IgG1.
SEQ ID NO: 31 is the amino acid sequence of PG9 human IgG4.
SEQ ID NO: 32 is the nucleotide sequence of PG9 human IgG4.
SEQ ID NO: 33 is the amino acid sequence of NIH45-46 human IgG1 antibody.
SEQ ID NO: 34 is the nucleotide sequence of NIH45-46 human IgG1 antibody.
SEQ ID NO: 35 is the amino acid sequence of NIH45-46 human IgG4 antibody.
SEQ ID NO: 36 is the nucleotide sequence of NIH45-46 human IgG4 antibody.
SEQ ID NO: 37 is the amino acid sequence of VRC01 human IgG1.
SEQ ID NO: 38 is the nucleotide sequence of VRC01 human IgG1.
SEQ ID NO: 39 is the amino acid sequence of VRC01 human IgG1 (heavy chain).
SEQ ID NO: 40 is the nucleotide sequence of VRC01 human IgG1 (heavy chain).
SEQ ID NO: 41 is the amino acid sequence of VRC01 human IgG1 (light chain).
SEQ ID NO: 42 is the nucleotide sequence of VRC01 human IgG1 (light chain).
SEQ ID NO: 43 is the amino acid sequence of VRC01 human IgG4.
SEQ ID NO: 44 is the nucleotide sequence of VRC01 human IgG4.
SEQ ID NO: 45 is the amino acid sequence of VRC01 human IgG4 mut (S228P).
SEQ ID NO: 46 is the nucleotide sequence of VRC01 human IgG4 mut (S228P).
SEQ ID NO: 47 is the amino acid sequence of VRC01 human IgG4 (heavy chain).
SEQ ID NO: 48 is the nucleotide sequence of VRC01 human IgG4 (heavy chain).
SEQ ID NO: 49 is the amino acid sequence of VRC01 human IgG4 (light chain).

SEQ ID NO: 50 is the nucleotide sequence of VRC01 human IgG4 (light chain).

SEQ ID NO: 51 is the amino acid sequence of VRC01 human IgG2.

SEQ ID NO: 52 is the nucleotide sequence of VRC01 human IgG2.

SEQ ID NO: 53 is the amino acid sequence of VRC01 human IgG3

SEQ ID NO: 54 is the nucleotide sequence of VRC01 human IgG3.

SEQ ID NO: 55 is the amino acid sequence of PGT145 Heavy Chain

SEQ ID NO: 56 is the nucleotide sequence of PGT145 Heavy Chain

SEQ ID NO: 57 is the amino acid sequence of PGT145 Kappa

SEQ ID NO: 58 is the nucleotide sequence of PGT145 Kappa

SEQ ID NO: 59 is the amino acid sequence of PGT151 Heavy Chain

SEQ ID NO: 60 is the nucleotide sequence of PGT151 Heavy Chain

SEQ ID NO: 61 is the amino acid sequence of PGT151 Kappa

SEQ ID NO: 62 is the nucleotide sequence of PGT151 Kappa

SEQ ID NO: 63 is the amino acid sequence of PGDM1400 Heavy Chain

SEQ ID NO: 64 is the nucleotide sequence of PGDM1400 Heavy Chain

SEQ ID NO: 65 is the amino acid sequence of PGDM1400 Kappa

SEQ ID NO: 66 is the nucleotide sequence of PGDM1400 Kappa

SEQ ID NO: 67 is the amino acid sequence of 12A21 Heavy Chain

SEQ ID NO: 68 is the nucleotide sequence of 12A21 Heavy Chain

SEQ ID NO: 69 is the amino acid sequence of 12A21 Kappa

SEQ ID NO: 70 is the nucleotide sequence of 12A21 Kappa

SEQ ID NO: 71 is the amino acid sequence of VRC3401 Heavy Chain

SEQ ID NO: 72 is the nucleotide sequence of VRC3401 Heavy Chain

SEQ ID NO: 73 is the amino acid sequence of VRC3401 Kappa

SEQ ID NO: 74 is the nucleotide sequence of VRC3401 Kappa

SEQ ID NO: 75 is the amino acid sequence of IOMA Heavy Chain

SEQ ID NO: 76 is the nucleotide sequence of IOMA Heavy Chain

SEQ ID NO: 77 is the amino acid sequence of IOMA Lambda

SEQ ID NO: 78 is the nucleotide sequence of IOMA Lambda

SEQ ID NO: 79 is the amino acid sequence of PGT130 Heavy Chain

SEQ ID NO: 80 is the nucleotide sequence of PGT130 Heavy Chain

SEQ ID NO: 81 is the amino acid sequence of PGT130 Lambda

SEQ ID NO: 82 is the nucleotide sequence of PGT130 Lambda

SEQ ID NO: 83 is the amino acid sequence of PGT121 Heavy Chain

SEQ ID NO: 84 is the nucleotide sequence of PGT121 Heavy Chain

SEQ ID NO: 85 is the amino acid sequence of PGT121 Lambda

SEQ ID NO: 86 is the nucleotide sequence of PGT121 Lambda

SEQ ID NO: 87 is the amino acid sequence of 2219 Heavy Chain

SEQ ID NO: 88 is the nucleotide sequence of 2219 Heavy Chain

SEQ ID NO: 89 is the amino acid sequence of 2219 Lambda

SEQ ID NO: 90 is the nucleotide sequence of 2219 Lambda

SEQ ID NO: 91 is the amino acid sequence of 3074 Heavy Chain

SEQ ID NO: 92 is the nucleotide sequence of 3074 Heavy Chain

SEQ ID NO: 93 is the amino acid sequence of 3074 Lambda

SEQ ID NO: 94 is the nucleotide sequence of 3074 Lambda

SEQ ID NO: 95 is the amino acid sequence of 4025 Heavy Chain

SEQ ID NO: 96 is the nucleotide sequence of 4025 Heavy Chain

SEQ ID NO: 97 is the amino acid sequence of 4025 Lambda

SEQ ID NO: 98 is the nucleotide sequence of 4025 Lambda

SEQ ID NO: 99 is the amino acid sequence of 2557 Heavy Chain

SEQ ID NO: 100 is the nucleotide sequence of 2557 Heavy Chain

SEQ ID NO: 101 is the amino acid sequence of 2557 Lambda

SEQ ID NO: 102 is the nucleotide sequence of 2557 Lambda

SEQ ID NO: 103 is the amino acid sequence of F425-B4e8 Heavy Chain

SEQ ID NO: 104 is the nucleotide sequence of F425-B4e8 Heavy Chain

SEQ ID NO: 105 is the amino acid sequence of F425-B4e8 Kappa

SEQ ID NO: 106 is the nucleotide sequence of F425-B4e8 Kappa

SEQ ID NO: 107 is the amino acid sequence of 17b Heavy Chain

SEQ ID NO: 108 is the nucleotide sequence of 17b Heavy Chain

SEQ ID NO: 109 is the amino acid sequence of 17b Kappa

SEQ ID NO: 110 is the nucleotide sequence of 17b Kappa

SEQ ID NO: 111 is the amino acid sequence of F105 Heavy Chain

SEQ ID NO: 112 is the nucleotide sequence of F105 Heavy Chain

SEQ ID NO: 113 is the amino acid sequence of F105 Kappa

SEQ ID NO: 114 is the nucleotide sequence of F105 Kappa

SEQ ID NO: 115 is the amino acid sequence of b12 Heavy Chain

SEQ ID NO: 116 is the nucleotide sequence of b12 Heavy Chain

SEQ ID NO: 117 is the amino acid sequence of b12 Kappa
SEQ ID NO: 118 is the nucleotide sequence of b12 Kappa
SEQ ID NO: 119 is the amino acid sequence of B6 Heavy Chain
SEQ ID NO: 120 is the nucleotide sequence of B6 Heavy Chain
SEQ ID NO: 121 is the amino acid sequence of B6 Kappa
SEQ ID NO: 122 is the nucleotide sequence of B6 Kappa
SEQ ID NO: 123 is the amino acid sequence of 11A Heavy Chain
SEQ ID NO: 124 is the nucleotide sequence of 11A Heavy Chain
SEQ ID NO: 125 is the amino acid sequence of 11A Kappa
SEQ ID NO: 126 is the nucleotide sequence of 11A Kappa
SEQ ID NO: 127 is the amino acid sequence of 12N Heavy Chain
SEQ ID NO: 128 is the nucleotide sequence of 12N Heavy Chain
SEQ ID NO: 129 is the amino acid sequence of 12N Kappa
SEQ ID NO: 130 is the nucleotide sequence of 12N Kappa
SEQ ID NO: 131 is the amino acid sequence of 39F Heavy Chain
SEQ ID NO: 132 is the nucleotide sequence of 39F Heavy Chain
SEQ ID NO: 133 is the amino acid sequence of 39F Lambda pF
SEQ ID NO: 134 is the nucleotide sequence of 39F Lambda pF
SEQ ID NO: 135 is the nucleotide sequence of Subtype A Consensus Envelope with an IgE leader.
SEQ ID NO: 136 is the amino acid sequence of Subtype A Consensus Envelope with an IgE leader.
SEQ ID NO: 137 is the nucleotide sequence of Subtype B Consensus Envelope with an IgE leader.
SEQ ID NO: 138 is the amino acid sequence of Subtype B Consensus Envelope with an IgE leader.
SEQ ID NO: 139 is the nucleotide sequence of Subtype C Consensus Envelope with an IgE leader.
SEQ ID NO: 140 is the amino acid sequence of Subtype C Consensus Envelope with an IgE leader.
SEQ ID NO: 141 is the nucleotide sequence of Subtype D Consensus Envelope with an IgE leader.
SEQ ID NO: 142 is the amino acid sequence of Subtype D Consensus Envelope with an IgE leader.
SEQ ID NO: 143 is the nucleotide sequence of Subtype B Consensus Nef-Rev with an IgE leader.
SEQ ID NO: 144 is the amino acid sequence of Subtype B Consensus Nef-Rev with an IgE leader.
SEQ ID NO: 145 is the nucleotide sequence of Gag Consensus DNA sequence of subtype A, B, C and D with an IgE leader.
SEQ ID NO: 146 is the amino acid sequence of Gag Consensus DNA sequence of subtype A, B, C and D with an IgE leader.
SEQ ID NO: 147 is the amino acid sequence of Subtype A Consensus Envelope without an IgE leader.
SEQ ID NO: 148 is the amino acid sequence of Subtype B Consensus Envelope without an IgE leader.
SEQ ID NO: 149 is the amino acid sequence of Subtype C Consensus Envelope without an IgE leader.
SEQ ID NO: 150 is the amino acid sequence of Subtype D Consensus Envelope without an IgE leader.
SEQ ID NO: 151 is the amino acid sequence of Subtype B Consensus Nef-Rev without an IgE leader.
SEQ ID NO: 152 is the amino acid sequence of Gag Consensus DNA sequence of subtype A, B, C and D without an IgE leader.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes an antibody as set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5× SSC, and 1% SDS, incubating at 42° C., or, 5× SSC, 1% SDS, incubating at 65° C., with wash in 0.2× SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%,or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a composition of the present invention to a subject after induction of the disease but before its clinical appearance. Repressing the disease involves administering a composition of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Composition

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the nucleic acid molecule comprises a nucleotide sequence encoding an anti-HIV antibody. In one embodiment, the anti HIV-antibody is an anti-HIV broadly neutralizing antibody.

In one embodiment, the nucleotide sequence encoding an anti HIV-antibody comprises one or more codon optimized nucleic acid sequences encoding an amino acid sequence at least 95% homologous to an amino acid sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39 SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, or a fragment thereof.

In one embodiment, the nucleotide sequence encoding an anti-HIV antibody comprises one or more RNA sequence transcribed from one or more DNA sequences encoding an amino acid sequence at least 95% homologous to an amino acid sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39 SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, ora fragment thereof.

In one embodiment, the nucleotide sequence encoding an anti-HIV antibody comprises one or more codon optimized nucleic acid sequences at least 95% homologous to a nucleic acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO: 60, SEQ ID NO:62, SEQ ID NO:64, SEQ ID NO:66, SEQ ID NO:68,SEQ ID NO: 70, SEQ ID NO:72, SEQ ID NO:74, SEQ ID NO:76, SEQ ID NO:78, SEQ ID NO: 80, SEQ ID NO:82, SEQ ID NO:84, SEQ ID NO:86, SEQ ID NO:88, SEQ ID NO: 90, SEQ ID NO:92, SEQ ID NO:94, SEQ ID NO:96, SEQ ID NO:98, SEQ ID NO: 100, SEQ ID NO:102, SEQ ID NO:104, SEQ ID NO:106, SEQ ID NO:108, SEQ ID NO: 110, SEQ ID NO:112, SEQ ID NO:114, SEQ ID NO:116, SEQ ID NO:118, SEQ ID NO: 120, SEQ ID NO:122, SEQ ID NO:124, SEQ ID NO:126, SEQ ID NO:128, SEQ ID NO: 130, SEQ ID NO:132, SEQ ID NO:134, or a fragment thereof.

In one embodiment, the nucleotide sequence encoding an anti-HIV antibody comprises one or more RNA sequence transcribed from one or more DNA sequences at least 95% homologous to a nucleic acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO: 60, SEQ ID NO:62, SEQ ID NO:64, SEQ ID NO:66, SEQ ID NO:68,SEQ ID NO: 70, SEQ ID NO:72, SEQ ID NO:74, SEQ ID NO:76, SEQ ID NO:78, SEQ ID NO: 80, SEQ ID NO:82, SEQ ID NO:84, SEQ ID NO:86, SEQ ID NO:88, SEQ ID NO: 90, SEQ ID NO:92, SEQ ID NO:94, SEQ ID NO:96, SEQ ID NO:98, SEQ ID NO: 100, SEQ ID NO:102, SEQ ID NO:104, SEQ ID NO:106, SEQ ID NO:108, SEQ ID NO: 110, SEQ ID NO:112, SEQ ID NO:114, SEQ ID NO:116, SEQ ID NO:118, SEQ ID NO: 120, SEQ ID NO:122, SEQ ID NO:124, SEQ ID NO:126, SEQ ID NO:128, SEQ ID NO: 130, SEQ ID NO:132, SEQ ID NO:134, or a fragment thereof.

In one embodiment, the composition comprises a nucleotide sequence encoding a synthetic anti-HIV heavy chain. In one embodiment, the composition comprises a nucleotide sequence encoding a synthetic anti-HIV light chain. In one embodiment, the composition comprises a nucleotide sequence encoding a synthetic anti-HIV antibody. In one embodiment, the sequence encoding a synthetic anti-HIV antibody comprises a first sequence encoding a synthetic anti-HIV heavy chain and a second sequence encoding a synthetic anti-HIV light chain.

In one embodiment, the first nucleotide sequence encodes an amino acid sequence at least 90% homologous to SEQ ID NO:3 and the second nucleotide sequence encodes an amino acid sequence at least 90% homologous to SEQ ID NO:5. In one embodiment, the first nucleotide sequence encodes SEQ ID NO:3 and the second nucleotide sequence encodes SEQ ID NO:5.

In one embodiment, the first nucleotide sequence encodes an amino acid sequence at least 90% homologous to SEQ ID NO:11 and the second nucleotide sequence encodes an amino acid sequence at least 90% homologous to SEQ ID NO:13. In one embodiment, the first nucleotide sequence encodes SEQ ID NO:11 and the second nucleotide sequence encodes SEQ ID NO:13.

In one embodiment, the first nucleotide sequence encodes an amino acid sequence at least 90% homologous to SEQ ID NO:17 and the second nucleotide sequence encodes an amino acid sequence at least 90% homologous to SEQ ID NO:19. In one embodiment, the first nucleotide sequence encodes SEQ ID NO:17 and the second nucleotide sequence encodes SEQ ID NO:19.

In one embodiment, the first nucleotide sequence encodes an amino acid sequence at least 90% homologous to SEQ ID NO:25 and the second nucleotide sequence encodes an amino acid sequence at least 90% homologous to SEQ ID NO:27. In one embodiment, the first nucleotide sequence encodes SEQ ID NO:25 and the second nucleotide sequence encodes SEQ ID NO:27.

In one embodiment, the first nucleotide sequence encodes an amino acid sequence at least 90% homologous to SEQ ID NO:39 and the second nucleotide sequence encodes an amino acid sequence at least 90% homologous to SEQ ID NO:41. In one embodiment, the first nucleotide sequence encodes SEQ ID NO:39 and the second nucleotide sequence encodes SEQ ID NO:41.

In one embodiment, the first nucleotide sequence encodes an amino acid sequence at least 90% homologous to SEQ ID NO:47 and the second nucleotide sequence encodes an amino acid sequence at least 90% homologous to SEQ ID NO:49. In one embodiment, the first nucleotide sequence encodes SEQ ID NO:47 and the second nucleotide sequence encodes SEQ ID NO:49.

In one embodiment, the first nucleotide sequence encodes an amino acid sequence at least 90% homologous to SEQ ID NO:55 and the second nucleotide sequence encodes an amino acid sequence at least 90% homologous to SEQ ID NO:57. In one embodiment, the first nucleotide sequence encodes SEQ ID NO:55 and the second nucleotide sequence encodes SEQ ID NO:57.

In one embodiment, the first nucleotide sequence encodes an amino acid sequence at least 90% homologous to SEQ ID NO:59 and the second nucleotide sequence encodes an amino acid sequence at least 90% homologous to SEQ ID NO:61. In one embodiment, the first nucleotide sequence encodes SEQ ID NO:59 and the second nucleotide sequence encodes SEQ ID NO:61.

In one embodiment, the first nucleotide sequence encodes an amino acid sequence at least 90% homologous to SEQ ID NO:63 and the second nucleotide sequence encodes an amino acid sequence at least 90% homologous to SEQ ID NO:65. In one embodiment, the first nucleotide sequence encodes SEQ ID NO:63 and the second nucleotide sequence encodes SEQ ID NO:65.

In one embodiment, the first nucleotide sequence encodes an amino acid sequence at least 90% homologous to SEQ ID NO:67 and the second nucleotide sequence encodes an amino acid sequence at least 90% homologous to SEQ ID NO:69. In one embodiment, the first nucleotide sequence encodes SEQ ID NO:67 and the second nucleotide sequence encodes SEQ ID NO:69.

In one embodiment, the first nucleotide sequence encodes an amino acid sequence at least 90% homologous to SEQ ID NO:71 and the second nucleotide sequence encodes an amino acid sequence at least 90% homologous to SEQ ID NO:73. In one embodiment, the first nucleotide sequence encodes SEQ ID NO:71 and the second nucleotide sequence encodes SEQ ID NO:73.

In one embodiment, the first nucleotide sequence encodes an amino acid sequence at least 90% homologous to SEQ ID NO:75 and the second nucleotide sequence encodes an amino acid sequence at least 90% homologous to SEQ ID NO:77. In one embodiment, the first nucleotide sequence encodes SEQ ID NO:75 and the second nucleotide sequence encodes SEQ ID NO:77.

In one embodiment, the first nucleotide sequence encodes an amino acid sequence at least 90% homologous to SEQ ID NO:79 and the second nucleotide sequence encodes an amino acid sequence at least 90% homologous to SEQ ID NO:81. In one embodiment, the first nucleotide sequence encodes SEQ ID NO:79 and the second nucleotide sequence encodes SEQ ID NO:81.

In one embodiment, the first nucleotide sequence encodes an amino acid sequence at least 90% homologous to SEQ ID NO:83 and the second nucleotide sequence encodes an amino acid sequence at least 90% homologous to SEQ ID NO:85. In one embodiment, the first nucleotide sequence encodes SEQ ID NO:83 and the second nucleotide sequence encodes SEQ ID NO:85.

In one embodiment, the first nucleotide sequence encodes an amino acid sequence at least 90% homologous to SEQ ID NO:87 and the second nucleotide sequence encodes an amino acid sequence at least 90% homologous to SEQ ID NO:89. In one embodiment, the first nucleotide sequence encodes SEQ ID NO:87 and the second nucleotide sequence encodes SEQ ID NO:89.

In one embodiment, the first nucleotide sequence encodes an amino acid sequence at least 90% homologous to SEQ ID NO:91 and the second nucleotide sequence encodes an amino acid sequence at least 90% homologous to SEQ ID NO:93. In one embodiment, the first nucleotide sequence encodes SEQ ID NO:91 and the second nucleotide sequence encodes SEQ ID NO:93.

In one embodiment, the first nucleotide sequence encodes an amino acid sequence at least 90% homologous to SEQ ID NO:95 and the second nucleotide sequence encodes an amino acid sequence at least 90% homologous to SEQ ID NO:97. In one embodiment, the first nucleotide sequence encodes SEQ ID NO:95 and the second nucleotide sequence encodes SEQ ID NO:97.

In one embodiment, the first nucleotide sequence encodes an amino acid sequence at least 90% homologous to SEQ ID NO:99 and the second nucleotide sequence encodes an amino acid sequence at least 90% homologous to SEQ ID NO:101. In one embodiment, the first nucleotide sequence encodes SEQ ID NO:99 and the second nucleotide sequence encodes SEQ ID NO:101.

In one embodiment, the first nucleotide sequence encodes an amino acid sequence at least 90% homologous to SEQ ID NO:103 and the second nucleotide sequence encodes an amino acid sequence at least 90% homologous to SEQ ID NO: 105. In one embodiment, the first nucleotide sequence encodes SEQ ID NO:103 and the second nucleotide sequence encodes SEQ ID NO: 105.

In one embodiment, the first nucleotide sequence encodes an amino acid sequence at least 90% homologous to SEQ ID NO: 107 and the second nucleotide sequence encodes an amino acid sequence at least 90% homologous to SEQ ID NO: 109. In one embodiment, the first nucleotide sequence encodes SEQ ID NO: 107 and the second nucleotide sequence encodes SEQ ID NO: 109.

In one embodiment, the first nucleotide sequence encodes an amino acid sequence at least 90% homologous to SEQ ID NO:111 and the second nucleotide sequence encodes an amino acid sequence at least 90% homologous to SEQ ID NO: 113. In one embodiment, the first nucleotide sequence encodes SEQ ID NO:111 and the second nucleotide sequence encodes SEQ ID NO: 113.

In one embodiment, the first nucleotide sequence encodes an amino acid sequence at least 90% homologous to SEQ ID NO: 115 and the second nucleotide sequence encodes an amino acid sequence at least 90% homologous to SEQ ID NO: 117. In one embodiment, the first nucleotide sequence encodes SEQ ID NO: 115 and the second nucleotide sequence encodes SEQ ID NO: 117.

In one embodiment, the first nucleotide sequence encodes an amino acid sequence at least 90% homologous to SEQ ID NO: 119 and the second nucleotide sequence encodes an amino acid sequence at least 90% homologous to SEQ ID NO: 121. In one embodiment, the first nucleotide sequence encodes SEQ ID NO: 119 and the second nucleotide sequence encodes SEQ ID NO: 121.

In one embodiment, the first nucleotide sequence encodes an amino acid sequence at least 90% homologous to SEQ ID NO:123 and the second nucleotide sequence encodes an amino acid sequence at least 90% homologous to SEQ ID NO: 125. In one embodiment, the first nucleotide sequence encodes SEQ ID NO:123 and the second nucleotide sequence encodes SEQ ID NO: 125.

In one embodiment, the first nucleotide sequence encodes an amino acid sequence at least 90% homologous to SEQ ID NO: 1207 and the second nucleotide sequence encodes an amino acid sequence at least 90% homologous to SEQ ID NO: 129. In one embodiment, the first nucleotide sequence encodes SEQ ID NO: 1207 and the second nucleotide sequence encodes SEQ ID NO: 129.

In one embodiment, the first nucleotide sequence encodes an amino acid sequence at least 90% homologous to SEQ ID NO:131 and the second nucleotide sequence encodes an amino acid sequence at least 90% homologous to SEQ ID NO: 133. In one embodiment, the first nucleotide sequence encodes SEQ ID NO:131 and the second nucleotide sequence encodes SEQ ID NO: 133.

In one embodiment, the first nucleotide sequence comprises a nucleotide sequence at least 90% homologous to SEQ ID NO:4 and the second nucleotide sequence comprises a nucleotide sequence at least 90% homologous to SEQ ID NO:6. In one embodiment, the first nucleotide sequence comprises a nucleotide sequence as set forth in SEQ ID NO:4 and the second nucleotide sequence comprises a nucleotide sequence as set forth in SEQ ID NO:6.

In one embodiment, the first nucleotide sequence comprises a nucleotide sequence at least 90% homologous to SEQ ID NO:12 and the second nucleotide sequence comprises a nucleotide sequence at least 90% homologous to SEQ ID NO:14. In one embodiment, the first nucleotide sequence comprises a nucleotide sequence as set forth in SEQ ID NO:12 and the second nucleotide sequence comprises a nucleotide sequence as set forth in SEQ ID NO:14.

In one embodiment, the first nucleotide sequence comprises a nucleotide sequence at least 90% homologous to SEQ ID NO:18 and the second nucleotide sequence comprises a nucleotide sequence at least 90% homologous to SEQ ID NO:20. In one embodiment, the first nucleotide sequence comprises a nucleotide sequence as set forth in SEQ ID NO:18 and the second nucleotide sequence comprises a nucleotide sequence as set forth in SEQ ID NO:20.

In one embodiment, the first nucleotide sequence comprises a nucleotide sequence at least 90% homologous to SEQ ID NO:26 and the second nucleotide sequence comprises a nucleotide sequence at least 90% homologous to SEQ ID NO:28. In one embodiment, the first nucleotide sequence comprises a nucleotide sequence as set forth in SEQ ID NO:26 and the second nucleotide sequence comprises a nucleotide sequence as set forth in SEQ ID NO:28.

In one embodiment, the first nucleotide sequence comprises a nucleotide sequence at least 90% homologous to SEQ ID NO:40 and the second nucleotide sequence comprises a nucleotide sequence at least 90% homologous to SEQ ID NO:42. In one embodiment, the first nucleotide sequence comprises a nucleotide sequence as set forth in SEQ ID NO:40 and the second nucleotide sequence comprises a nucleotide sequence as set forth in SEQ ID NO:42.

In one embodiment, the first nucleotide sequence comprises a nucleotide sequence at least 90% homologous to SEQ ID NO:48 and the second nucleotide sequence comprises a nucleotide sequence at least 90% homologous to SEQ ID NO:50. In one embodiment, the first nucleotide sequence comprises a nucleotide sequence as set forth in SEQ ID NO:48 and the second nucleotide sequence comprises a nucleotide sequence as set forth in SEQ ID NO:50.

In one embodiment, the first nucleotide sequence comprises a nucleotide sequence at least 90% homologous to SEQ ID NO:56 and the second nucleotide sequence comprises a nucleotide sequence at least 90% homologous to SEQ ID NO:58. In one embodiment, the first nucleotide sequence comprises a nucleotide sequence as set forth in SEQ ID NO:56 and the second nucleotide sequence comprises a nucleotide sequence as set forth in SEQ ID NO:58.

In one embodiment, the first nucleotide sequence comprises a nucleotide sequence at least 90% homologous to SEQ ID NO:60 and the second nucleotide sequence comprises a nucleotide sequence at least 90% homologous to SEQ ID NO:62. In one embodiment, the first nucleotide sequence comprises a nucleotide sequence as set forth in SEQ ID NO:60 and the second nucleotide sequence comprises a nucleotide sequence as set forth in SEQ ID NO:62.

In one embodiment, the first nucleotide sequence comprises a nucleotide sequence at least 90% homologous to SEQ ID NO:64 and the second nucleotide sequence comprises a nucleotide sequence at least 90% homologous to SEQ ID NO:66. In one embodiment, the first nucleotide sequence comprises a nucleotide sequence as set forth in SEQ ID NO:64 and the second nucleotide sequence comprises a nucleotide sequence as set forth in SEQ ID NO:66.

In one embodiment, the first nucleotide sequence comprises a nucleotide sequence at least 90% homologous to SEQ ID NO:68 and the second nucleotide sequence comprises a nucleotide sequence at least 90% homologous to SEQ ID NO:70. In one embodiment, the first nucleotide sequence comprises a nucleotide sequence as set forth in SEQ ID NO:68 and the second nucleotide sequence comprises a nucleotide sequence as set forth in SEQ ID NO:70.

In one embodiment, the first nucleotide sequence comprises a nucleotide sequence at least 90% homologous to SEQ ID NO:72 and the second nucleotide sequence comprises a nucleotide sequence at least 90% homologous to SEQ ID NO:74. In one embodiment, the first nucleotide sequence comprises a nucleotide sequence as set forth in SEQ ID NO:72 and the second nucleotide sequence comprises a nucleotide sequence as set forth in SEQ ID NO:74.

In one embodiment, the first nucleotide sequence comprises a nucleotide sequence at least 90% homologous to SEQ ID NO:76 and the second nucleotide sequence comprises a nucleotide sequence at least 90% homologous to SEQ ID NO:78. In one embodiment, the first nucleotide sequence comprises a nucleotide sequence as set forth in SEQ ID NO:76 and the second nucleotide sequence comprises a nucleotide sequence as set forth in SEQ ID NO:78.

In one embodiment, the first nucleotide sequence comprises a nucleotide sequence at least 90% homologous to SEQ ID NO:80 and the second nucleotide sequence comprises a nucleotide sequence at least 90% homologous to SEQ ID NO: 82. In one embodiment, the first nucleotide sequence comprises a nucleotide sequence as set forth in SEQ ID NO:80 and the second nucleotide sequence comprises a nucleotide sequence as set forth in SEQ ID NO:82.

In one embodiment, the first nucleotide sequence comprises a nucleotide sequence at least 90% homologous to SEQ ID NO:84 and the second nucleotide sequence comprises a nucleotide sequence at least 90% homologous to SEQ ID NO: 86. In one embodiment, the first nucleotide sequence comprises a nucleotide sequence as set forth in SEQ ID NO:84 and the second nucleotide sequence comprises a nucleotide sequence as set forth in SEQ ID NO:86.

In one embodiment, the first nucleotide sequence comprises a nucleotide sequence at least 90% homologous to SEQ ID NO:88 and the second nucleotide sequence comprises a nucleotide sequence at least 90% homologous to SEQ ID NO:90. In one embodiment, the first nucleotide sequence comprises a nucleotide sequence as set forth in SEQ ID NO:88 and the second nucleotide sequence comprises a nucleotide sequence as set forth in SEQ ID NO:90.

In one embodiment, the first nucleotide sequence comprises a nucleotide sequence at least 90% homologous to SEQ ID NO:92 and the second nucleotide sequence comprises a nucleotide sequence at least 90% homologous to SEQ ID NO:94. In one embodiment, the first nucleotide sequence comprises a nucleotide sequence as set forth in SEQ ID NO:92 and the second nucleotide sequence comprises a nucleotide sequence as set forth in SEQ ID NO:94.

In one embodiment, the first nucleotide sequence comprises a nucleotide sequence at least 90% homologous to SEQ ID NO:96 and the second nucleotide sequence comprises a nucleotide sequence at least 90% homologous to SEQ ID NO:98. In one embodiment, the first nucleotide sequence comprises a nucleotide sequence as set forth in SEQ ID NO:96 and the second nucleotide sequence comprises a nucleotide sequence as set forth in SEQ ID NO:98.

In one embodiment, the first nucleotide sequence comprises a nucleotide sequence at least 90% homologous to SEQ ID NO:100 and the second nucleotide sequence comprises a nucleotide sequence at least 90% homologous to SEQ ID NO:102. In one embodiment, the first nucleotide sequence comprises a nucleotide sequence as set forth in SEQ ID NO:100 and the second nucleotide sequence comprises a nucleotide sequence as set forth in SEQ ID NO:102.

In one embodiment, the first nucleotide sequence comprises a nucleotide sequence at least 90% homologous to SEQ ID NO:104 and the second nucleotide sequence comprises a nucleotide sequence at least 90% homologous to SEQ ID NO: 106. In one embodiment, the first nucleotide sequence comprises a nucleotide sequence as set forth in SEQ ID NO:104 and the second nucleotide sequence comprises a nucleotide sequence as set forth in SEQ ID NO: 106.

In one embodiment, the first nucleotide sequence comprises a nucleotide sequence at least 90% homologous to SEQ ID NO: 108 and the second nucleotide sequence comprises a nucleotide sequence at least 90% homologous to SEQ ID NO: 110. In one embodiment, the first nucleotide sequence comprises a nucleotide sequence as set forth in SEQ ID NO: 108 and the second nucleotide sequence comprises a nucleotide sequence as set forth in SEQ ID NO: 110.

In one embodiment, the first nucleotide sequence comprises a nucleotide sequence at least 90% homologous to SEQ ID NO:112 and the second nucleotide sequence comprises a nucleotide sequence at least 90% homologous to SEQ ID NO: 114. In one embodiment, the first nucleotide sequence comprises a nucleotide sequence as set forth in SEQ ID NO:112 and the second nucleotide sequence comprises a nucleotide sequence as set forth in SEQ ID NO: 114.

In one embodiment, the first nucleotide sequence comprises a nucleotide sequence at least 90% homologous to SEQ ID NO: 116 and the second nucleotide sequence comprises a nucleotide sequence at least 90% homologous to SEQ ID NO: 118. In one embodiment, the first nucleotide sequence comprises a nucleotide sequence as set forth in SEQ ID NO: 116 and the second nucleotide sequence comprises a nucleotide sequence as set forth in SEQ ID NO: 118.

In one embodiment, the first nucleotide sequence comprises a nucleotide sequence at least 90% homologous to SEQ ID NO: 120 and the second nucleotide sequence comprises a nucleotide sequence at least 90% homologous to SEQ ID NO: 122. In one embodiment, the first nucleotide sequence comprises a nucleotide sequence as set forth in SEQ ID NO: 120 and the second nucleotide sequence comprises a nucleotide sequence as set forth in SEQ ID NO: 122.

In one embodiment, the first nucleotide sequence comprises a nucleotide sequence at least 90% homologous to SEQ ID NO:124 and the second nucleotide sequence comprises a nucleotide sequence at least 90% homologous to SEQ ID NO: 126. In one embodiment, the first nucleotide sequence comprises a nucleotide sequence as set forth in SEQ ID NO:124 and the second nucleotide sequence comprises a nucleotide sequence as set forth in SEQ ID NO: 126.

In one embodiment, the first nucleotide sequence comprises a nucleotide sequence at least 90% homologous to SEQ ID NO: 128 and the second nucleotide sequence comprises a nucleotide sequence at least 90% homologous to SEQ ID NO: 130. In one embodiment, the first nucleotide sequence comprises a nucleotide sequence as set forth in SEQ ID NO: 128 and the second nucleotide sequence comprises a nucleotide sequence as set forth in SEQ ID NO: 130.

In one embodiment, the first nucleotide sequence comprises a nucleotide sequence at least 90% homologous to SEQ ID NO:132 and the second nucleotide sequence comprises a nucleotide sequence at least 90% homologous to SEQ ID NO: 134. In one embodiment, the first nucleotide sequence comprises a nucleotide sequence as set forth in SEQ ID NO:132 and the second nucleotide sequence comprises a nucleotide sequence as set forth in SEQ ID NO: 134.

The composition of the invention can treat, prevent and/or protect against any disease, disorder, or condition associated with HIV infection. In certain embodiments, the composition can treat, prevent, and or/protect against viral infection. In certain embodiments, the composition can treat, prevent, and or/protect against condition associated with HIV infection.

In one embodiment, the present invention relates to a composition comprising a recombinant nucleic acid sequence encoding an IgG4 antibody. In one embodiment the IgG4 antibody comprises an amino acid substitution Ser288Pro. In one embodiment, IgG4 amino acid substitution Ser288Pro prevents IgG4 Fab arm switching. The IgG4 synthetic antibody can be for a foreign antigen or a self antigen. For example, IgG4 synthetic antibody can be for a viral antigen, a bacterial antigen, a parasitic antigen, a fungal antigen or a cancer antigen. Examples foreign and self antigens are described in U.S. Patent Application Publication No. US2015/0284448, the contents of which are incorporated herein in its entirety.

The composition comprising a recombinant nucleic acid sequence encoding an IgG4 antibody, when administered to a subject in need thereof, can result in the generation of a synthetic antibody in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the synthetic antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability and low cost per dose.

3. Recombinant Nucleic Acid Sequence

As described above, the composition can comprise a recombinant nucleic acid sequence. The recombinant nucleic acid sequence can encode the antibody, a fragment thereof, a variant thereof, or a combination thereof. The antibody is described in more detail below.

The recombinant nucleic acid sequence can be a heterologous nucleic acid sequence. The recombinant nucleic acid sequence can include one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; addition of an internal IRES sequence and eliminating to the extent possible cis-acting sequence motifs (i.e., internal TATA boxes).

a. Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can also include a heterologous nucleic acid sequence that encodes an internal ribosome entry site (IRES). An IRES may be either a viral IRES or an eukaryotic IRES. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

In one embodiment, the heavy chain polypeptide comprises an amino acid sequence at least 95% identical to SEQ ID NO:3, SEQ ID NO:11, SEQ ID NO:17, SEQ ID NO:25, SEQ ID NO:39, SEQ ID NO:47, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, or SEQ ID NO:131.

In one embodiment, the heavy chain polypeptide comprises an amino acid sequence as set forth in SEQ ID NO:3, SEQ ID NO:11, SEQ ID NO:17, SEQ ID NO:25, SEQ ID NO:39, SEQ ID NO:47, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, or SEQ ID NO:131.

In one embodiment, the heavy chain polypeptide is encoded by a nucleotide sequence at least 95% identical to SEQ ID NO:4, SEQ ID NO:12, SEQ ID NO:18, SEQ ID NO:26, SEQ ID NO:40, SEQ ID NO:48, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, or SEQ ID NO:132.

In one embodiment, the heavy chain polypeptide is encoded by a nucleotide sequence as set forth in SEQ ID NO:4, SEQ ID NO:12, SEQ ID NO:18, SEQ ID NO:26, SEQ ID NO:40, SEQ ID NO:48, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, or SEQ ID NO:132.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

In one embodiment, the light chain polypeptide comprises an amino acid sequence at least 95% identical to SEQ ID NO:5, SEQ ID NO:13, SEQ ID NO:19, SEQ ID NO:27, SEQ ID NO:41, SEQ ID NO:49, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO:105, SEQ ID NO:109, SEQ ID NO:113, SEQ ID NO:117, SEQ ID NO:121, SEQ ID NO:125, SEQ ID NO:129, or SEQ ID NO:133.

In one embodiment, the light chain polypeptide comprises an amino acid sequence as set forth in SEQ ID NO:5, SEQ ID NO:13, SEQ ID NO:19, SEQ ID NO:27, SEQ ID NO:41, SEQ ID NO:49, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO:105, SEQ ID NO:109, SEQ ID NO:113, SEQ ID NO:117, SEQ ID NO:121, SEQ ID NO:125, SEQ ID NO:129, or SEQ ID NO:133.

In one embodiment, the light chain polypeptide is encoded by a nucleotide sequence at least 95% identical to SEQ ID NO:6, SEQ ID NO:14, SEQ ID NO:20, SEQ ID NO:28, SEQ ID NO:42, SEQ ID NO:50, SEQ ID NO:58, SEQ ID NO:62, SEQ ID NO:66, SEQ ID NO:70, SEQ ID NO:74, SEQ ID NO:76, SEQ ID NO:82, SEQ ID NO:86, SEQ ID NO:90, SEQ ID NO:94, SEQ ID NO:98, SEQ ID NO:102, SEQ ID NO:106, SEQ ID NO:110, SEQ ID NO:114, SEQ ID NO:118, SEQ ID NO:122, SEQ ID NO:126, SEQ ID NO:130, or SEQ ID NO:134.

In one embodiment, the light chain polypeptide is encoded by a nucleotide sequence as set forth in SEQ ID NO:6, SEQ ID NO:14, SEQ ID NO:20, SEQ ID NO:28, SEQ ID NO:42, SEQ ID NO:50, SEQ ID NO:58, SEQ ID NO:62, SEQ ID NO:66, SEQ ID NO:70, SEQ ID NO:74, SEQ ID NO:76, SEQ ID NO:82, SEQ ID NO:86, SEQ ID NO:90, SEQ ID NO:94, SEQ ID NO:98, SEQ ID NO:102, SEQ ID NO:106, SEQ ID NO:110, SEQ ID NO:114, SEQ ID NO:118, SEQ ID NO:122, SEQ ID NO:126, SEQ ID NO:130, or SEQ ID NO:134.

(3) Protease Cleavage Site

The recombinant nucleic acid sequence construct can include heterologous nucleic acid sequence encoding a protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, CA).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

b. Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(1) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide.

For example, in one embodiment, the first recombinant nucleic acid sequence encodes a heavy chain polypeptide having an amino acid sequence at least 95% homologous to SEQ ID NO:3, SEQ ID NO:11, SEQ ID NO:17, SEQ ID NO:25, SEQ ID NO:39, SEQ ID NO:47, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, or SEQ ID NO:131.

In one embodiment, the first recombinant nucleic acid sequence comprises a nucleic acid sequence at least 95% homologous to SEQ ID NO:4, SEQ ID NO:12, SEQ ID NO:18, SEQ ID NO:26, SEQ ID NO:40, SEQ ID NO:48, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, or SEQ ID NO:132.

In one embodiment, the second recombinant nucleic acid sequence encodes a light chain polypeptide having an amino acid sequence at least 95% homologous to SEQ ID NO:5, SEQ ID NO:13, SEQ ID NO:19, SEQ ID NO:27, SEQ ID NO:41, SEQ ID NO:49, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO:105, SEQ ID NO:109, SEQ ID NO:113, SEQ ID NO:117, SEQ ID NO:121, SEQ ID NO:125, SEQ ID NO:129, or SEQ ID NO:133.

In one embodiment, the second recombinant nucleic acid sequence comprises a nucleic acid sequence at least 95% homologous to SEQ ID NO:6, SEQ ID NO:14, SEQ ID NO:20, SEQ ID NO:28, SEQ ID NO:42, SEQ ID NO:50, SEQ ID NO:58, SEQ ID NO:62, SEQ ID NO:66, SEQ ID NO:70, SEQ ID NO:74, SEQ ID NO:76, SEQ ID NO:82, SEQ ID NO:86, SEQ ID NO:90, SEQ ID NO:94, SEQ ID NO:98, SEQ ID NO:102, SEQ ID NO:106, SEQ ID NO:110, SEQ ID NO:114, SEQ ID NO:118, SEQ ID NO:122, SEQ ID NO:126, SEQ ID NO:130, or SEQ ID NO:134.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(2) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A forth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

c. Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

d. Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in Saccharomyces cerevisiae strains of yeast. The plasmid may also be of the MAXBAC™ complete baculovirus expression system (Invitrogen, San Diego, Calif), which may be used for protein production in insect cells. The plasmid may also be pcDNAI or pcDNA3 (Invitrogen, San Diego, Calif), which may be used for protein production in mammalian cells such as Chinese hamster ovary (CHO) cells.

(3) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39 SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, or SEQ ID NO:133, or a variant thereof or a fragment thereof.

In another embodiment, the nucleotide sequence comprises an RNA sequence transcribed by a DNA sequence encoding a polypeptide sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO: 60, SEQ ID NO:62, SEQ ID NO:64, SEQ ID NO:66, SEQ ID NO:68,SEQ ID NO: 70, SEQ ID NO:72, SEQ ID NO:74, SEQ ID NO:76, SEQ ID NO:78, SEQ ID NO: 80, SEQ ID NO:82, SEQ ID NO:84, SEQ ID NO:86, SEQ ID NO:88, SEQ ID NO: 90, SEQ ID NO:92, SEQ ID NO:94, SEQ ID NO:96, SEQ ID NO:98, SEQ ID NO: 100, SEQ ID NO:102, SEQ ID NO:104, SEQ ID NO:106, SEQ ID NO:108, SEQ ID NO: 110, SEQ ID NO:112, SEQ ID NO:114, SEQ ID NO:116, SEQ ID NO:118, SEQ ID NO: 120, SEQ ID NO:122, SEQ ID NO:124, SEQ ID NO:126, SEQ ID NO:128, SEQ ID NO: 130, SEQ ID NO:132, or SEQ ID NO:134, or a variant thereof or a fragment thereof.

Accordingly, in one embodiment, the invention provides an RNA molecule encoding one or more of the DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation

(4) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be perNP. perNP and perMR can be derived from pNP (Puerto Rico/34) and pM2 (New Caledonia/99), respectively.

(5) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(6) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

4. Antibody

As described above, the recombinant nucleic acid sequence can encode the antibody, a fragment thereof, a variant thereof, or a combination thereof. The antibody can bind or react with the antigen, which is described in more detail below.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the $F(ab')_2$ fragment, which comprises both antigen-binding sites. Accordingly, the antibody can be the Fab or $F(ab')_2$. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be an IgG1 antibody, an IgG2 antibody, an IgG3 antibody, or an IgG4 antibody. The antibody can be a chimera of any of an IgG1 antibody, an IgG2 antibody, an IgG3 antibody, or an IgG4 antibody. In some embodiments, the antibody hinge domain is modified. For example, in one embodiment, the antibody includes the amino acid substitution Ser288Pro. In one embodiment, includes the amino acid substitution Ser288Pro prevents IgG4 Fab arm switching.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

a. Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker.

b. Bifunctional Antibody

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

c. Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

d. Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, O-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

5. Antigen

The synthetic antibody is directed to the antigen or fragment or variant thereof. The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

The antigen can be from a virus. The antigen can be associated with viral infection. In one embodiment, the antigen can be associated with an HIV infection. In one embodiment, the antigen can be HIV antigen.

In one embodiment, a synthetic antibody of the invention targets two or more antigens. In one embodiment, at least one antigen of a bispecific antibody is selected from the antigens described herein. In one embodiment, the two or more antigens are selected from the antigens described herein.

a. Viral Antigens

The viral antigen can be a viral antigen or fragment or variant thereof. The virus can be a disease causing virus. The virus can be the Human Immunodeficiency virus.

The antigen may be an HIV viral antigen, or fragment thereof, or variant thereof. The HIV antigen can be from a factor that allows the virus to replicate, infect or survive. Factors that allow HIV to replicate or survive include, but are not limited to structural proteins and non-structural proteins. Such a protein can be an envelope protein or a glycoprotein.

In some embodiments, the HIV antigen can be a subtype A envelope protein, subtype B envelope protein, subtype C envelope protein, subtype D envelope protein, subtype B Nef-Rev protein, Gag subtype A, B, C, or D protein, MPol protein, a nucleic acid or amino acid sequences of Env A, Env B, Env C, Env D, B Nef-Rev, Gag, or any combination thereof. In one embodiment, an envelope protein is an HIV glycoprotein. In one embodiment, the HIV glycoprotein (gp) is HIV gp120, HIV gp41, or gp160.

A synthetic antibody specific for HIV can include a Fab fragment comprising the amino acid sequence of SEQ ID NO:3, which is encoded by the nucleic acid sequence of SEQ ID NO:4, SEQ ID NO: 5, which is encoded by the nucleic acid sequence of SEQ ID NO:6, amino acid sequence of SEQ ID NO:11, which is encoded by the nucleic acid sequence of SEQ ID NO:12, or SEQ ID NO: 13, which is encoded by the nucleic acid sequence of SEQ ID NO:14. The synthetic antibody can comprise the amino acid sequence of SEQ ID NO:1, which is encoded by the nucleic acid sequence of SEQ ID NO:2, the amino acid sequence of SEQ ID NO:7, which is encoded by the nucleic acid sequence of SEQ ID NO:8, or the amino acid sequence of SEQ ID NO:9, which is encoded by the nucleic acid sequence of SEQ ID NO:10.

A synthetic antibody specific for HIV can include a Fab fragment comprising the amino acid sequence of SEQ ID NO:17, which is encoded by the nucleic acid sequence of SEQ ID NO:18, SEQ ID NO: 19, which is encoded by the nucleic acid sequence of SEQ ID NO:20, amino acid sequence of SEQ ID NO:25, which is encoded by the nucleic acid sequence of SEQ ID NO:26, or SEQ ID NO: 27, which is encoded by the nucleic acid sequence of SEQ ID NO:28. The synthetic antibody can comprise the amino acid sequence of SEQ ID NO:15, which is encoded by the nucleic acid sequence of SEQ ID NO:16, the amino acid sequence of SEQ ID NO:21, which is encoded by the nucleic acid sequence of SEQ ID NO:22, or the amino acid sequence of SEQ ID NO:23, which is encoded by the nucleic acid sequence of SEQ ID NO:24.

A synthetic antibody specific for HIV can include a Fab fragment comprising the amino acid sequence of SEQ ID NO:39, which is encoded by the nucleic acid sequence of SEQ ID NO:40, SEQ ID NO: 41, which is encoded by the nucleic acid sequence of SEQ ID NO:42, amino acid sequence of SEQ ID NO:47, which is encoded by the nucleic acid sequence of SEQ ID NO:48, or SEQ ID NO: 49, which is encoded by the nucleic acid sequence of SEQ ID NO:50. The synthetic antibody can comprise the amino acid sequence of SEQ ID NO:37, which is encoded by the nucleic acid sequence of SEQ ID NO:38, the amino acid sequence of SEQ ID NO:43, which is encoded by the nucleic acid sequence of SEQ ID NO:44, the amino acid sequence of SEQ ID NO:45, which is encoded by the nucleic acid sequence of SEQ ID NO:46, the amino acid sequence of SEQ ID NO:51, which is encoded by the nucleic acid sequence of SEQ ID NO:52, or the amino acid sequence of SEQ ID NO:53, which is encoded by the nucleic acid sequence of SEQ ID NO:54.

The synthetic antibody can comprise the amino acid sequence of SEQ ID NO:29, which is encoded by the nucleic acid sequence of SEQ ID NO:30, the amino acid sequence of SEQ ID NO:31, which is encoded by the nucleic acid sequence of SEQ ID NO:32, the amino acid sequence of SEQ ID NO:33, which is encoded by the nucleic acid sequence of SEQ ID NO:34, or the amino acid sequence of SEQ ID NO:35 which is encoded by the nucleic acid sequence of SEQ ID NO:36.

A synthetic antibody specific for HIV can include an Ig comprising the amino acid sequence of SEQ ID NO:1, The Ig can comprise the amino acid sequence of SEQ ID NO:7, which is encoded by the nucleic acid sequence of SEQ ID NO:8. The Ig can comprise the amino acid sequence of SEQ ID NO: 9, which is encoded by the nucleic acid sequence of SEQ ID NO:10. The Ig can comprise the amino acid sequence of SEQ ID NO:15, which is encoded by the nucleic acid sequence of SEQ ID NO:16. The Ig can comprise the amino acid sequence of SEQ ID NO: 21, which is encoded by the nucleic acid sequence of SEQ ID NO:22. The Ig can comprise the amino acid sequence of SEQ ID NO: 23, which is encoded by the nucleic acid sequence of SEQ ID NO: 24. The Ig can comprise the amino acid sequence of SEQ ID NO: 29, which is encoded by the nucleic acid sequence of SEQ ID NO: 30. The Ig can comprise the amino acid sequence of SEQ ID NO:31, which is encoded by the nucleic acid sequence of SEQ ID NO: 32. The Ig can comprise the amino acid sequence of SEQ ID NO:33, which is encoded by the nucleic acid sequence of SEQ ID NO: 34. The Ig can comprise the amino acid sequence of SEQ ID NO:35, which is encoded by the nucleic acid sequence of SEQ ID NO: 36. The Ig can comprise the amino acid sequence of SEQ ID NO:37, which is encoded by the nucleic acid sequence of SEQ ID NO: 38. The Ig can comprise the amino acid sequence of SEQ ID NO:43, which is encoded by the nucleic acid sequence of SEQ ID NO: 44. The Ig can comprise the amino acid sequence of SEQ ID NO:45, which is encoded by the nucleic acid sequence of SEQ ID NO: 46. The Ig can comprise the amino acid sequence of SEQ ID NO:51, which is encoded by the nucleic acid sequence of SEQ ID NO: 52. The Ig can comprise the amino acid sequence of SEQ ID NO:53, which is encoded by the nucleic acid sequence of SEQ ID NO:54. The Ig can comprise the amino acid sequence of SEQ ID NO:55, which is encoded by the nucleic acid sequence of SEQ ID NO: 56. The Ig can comprise the amino acid sequence of SEQ ID NO:57, which is encoded by the nucleic acid sequence of SEQ ID NO: 58. The Ig can comprise the amino acid sequence of SEQ ID NO:59, which is encoded by the nucleic acid sequence of SEQ ID NO: 60. The Ig can comprise the amino acid sequence of SEQ ID NO:61, which is encoded by the nucleic acid sequence of SEQ ID NO: 62. The Ig can comprise the amino acid sequence of SEQ ID NO:63, which is encoded by the nucleic acid sequence of SEQ ID NO: 64. The Ig can comprise the amino acid sequence of SEQ ID NO:65, which is encoded by the nucleic acid sequence of SEQ ID NO: 66. The Ig can comprise the amino acid sequence of SEQ ID NO:67, which is encoded by the nucleic acid sequence of SEQ ID NO: 68. The Ig can comprise the amino acid sequence of SEQ ID NO:69, which is encoded by the nucleic acid sequence of SEQ ID NO: 70. The Ig can comprise the amino acid sequence of SEQ ID NO:71, which is encoded by the nucleic acid sequence of SEQ ID NO: 72. The Ig can comprise the amino acid sequence of SEQ ID NO:73, which is encoded by the nucleic acid sequence of SEQ ID NO: 74. The Ig can comprise the amino acid sequence of SEQ ID NO:75, which is encoded by the nucleic acid sequence of SEQ ID NO: 76. The Ig can comprise the amino acid sequence of SEQ ID NO:77, which is encoded by the nucleic acid sequence of SEQ ID NO: 78. The Ig can comprise the amino acid sequence of SEQ ID NO:79, which is encoded by the nucleic acid sequence of SEQ ID NO: 80. The Ig can comprise the amino acid sequence of SEQ ID NO:81, which is encoded by the nucleic acid sequence of SEQ ID NO: 82. The Ig can comprise the amino acid sequence of SEQ ID NO:83, which is encoded by the nucleic acid sequence of SEQ ID NO: 84. The Ig can comprise the amino acid sequence of SEQ ID NO:85, which is encoded by the nucleic acid sequence of SEQ ID NO: 86. The Ig can comprise the amino acid sequence of SEQ ID NO:87, which is encoded by the nucleic acid sequence of SEQ ID NO: 88. The Ig can comprise the amino acid sequence of SEQ ID NO:89, which is encoded by the nucleic acid sequence of SEQ ID NO: 90. The Ig can comprise the amino acid sequence of SEQ ID NO:91, which is encoded by the nucleic acid sequence of SEQ ID NO: 92. The Ig can comprise the amino acid sequence of SEQ ID NO:93, which is encoded by the nucleic acid sequence of SEQ ID NO: 94. The Ig can comprise the amino acid sequence of SEQ ID NO:95, which is encoded by the nucleic acid sequence of SEQ ID NO: 96. The Ig can comprise the amino acid sequence of SEQ ID NO:97, which is encoded by the nucleic acid sequence of SEQ ID NO: 98. The Ig can comprise the amino acid sequence of SEQ ID NO:99, which is encoded by the nucleic acid sequence of SEQ ID NO: 100. The Ig can comprise the amino acid sequence of SEQ ID NO:101, which is encoded by the nucleic acid sequence of SEQ ID NO: 102. The Ig can comprise the amino acid sequence of SEQ ID NO:103, which is encoded by the nucleic acid sequence of SEQ ID NO: 104. The Ig can comprise the amino acid sequence of SEQ ID NO:105, which is encoded by the nucleic acid sequence of SEQ ID NO: 106. The Ig can comprise the amino acid sequence of SEQ ID NO:107, which is encoded by the nucleic acid sequence of SEQ ID NO: 108. The Ig can comprise the amino acid sequence of SEQ ID NO:109, which is encoded by the nucleic acid sequence of SEQ ID NO: 110. The Ig can comprise the amino acid sequence of SEQ ID NO:111, which is encoded by the nucleic acid sequence of SEQ ID NO: 112. The Ig can comprise the amino acid sequence of SEQ ID NO:113, which is encoded by the nucleic acid sequence of SEQ ID NO: 114. The Ig can comprise the amino acid sequence of SEQ ID NO:115, which is encoded by the nucleic acid sequence of SEQ ID NO: 116. The Ig can comprise the amino acid sequence of SEQ ID NO:117, which is encoded by the nucleic acid sequence of SEQ ID NO: 118. The Ig can comprise the amino acid sequence of SEQ ID NO:119, which is encoded by the nucleic acid sequence of SEQ ID NO: 120. The Ig can comprise the amino acid sequence of SEQ ID NO:121, which is encoded by the nucleic acid sequence of SEQ ID NO: 122. The Ig can comprise the amino acid sequence of SEQ ID NO:123, which is encoded by the nucleic acid sequence of SEQ ID NO: 124. The Ig can comprise the amino acid sequence of SEQ ID NO:125, which is encoded by the nucleic acid sequence of SEQ ID NO: 126. The Ig can comprise the amino acid sequence of SEQ ID NO:127, which is encoded by the nucleic acid sequence of SEQ ID NO: 128. The Ig can comprise the amino acid sequence of SEQ ID NO:129, which is encoded by the nucleic acid sequence of SEQ ID NO: 130. The Ig can comprise the amino acid sequence of SEQ ID NO:131, which is encoded by the nucleic acid sequence of SEQ ID NO: 132. The Ig can comprise the amino acid sequence of SEQ ID NO:133, which is encoded by the nucleic acid sequence of SEQ ID NO: 134.

6. Excipients and Other Components of the Composition

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Ser. No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

7. Method of Generating the Synthetic Antibody

The present invention also relates a method of generating the synthetic antibody. The method can include administering the composition to the subject in need thereof by using the method of delivery described in more detail below. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

8. Method of Identifying or Screening for the Antibody

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

9. Method of Delivery of the Composition

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

a. Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

10. Method of Treatment

Also provided herein is a method of treating, protecting against, and/or preventing disease in a subject in need thereof by generating the synthetic antibody in the subject. The method can include administering the composition to the subject. Administration of the composition to the subject can be done using the method of delivery described above.

In certain embodiments, the invention provides a method of treating protecting against, and/or preventing a HIV infection. In one embodiment, the method treats, protects against, and/or prevents a disease associated with HIV.

Upon generation of the synthetic antibody in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The composition dose can be between 1 μg to 10 mg active component/kg body weight/time, and can be 20 μg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

11. Use in Combination With Antiretrovirals

The present invention also provides a method of treating, protecting against, and/or preventing disease in a subject in need thereof by administering a combination of the synthetic antibody and a therapeutic antiretroviral agent.

The synthetic antibody and an antiretroviral agent may be administered using any suitable method such that a combination of the synthetic antibody and antiretroviral agent are both present in the subject. In one embodiment, the method may comprise administration of a first composition comprising a synthetic antibody of the invention by any of the methods described in detail above and administration of a second composition comprising an antiretroviral agent less than 1, less than 2, less than 3, less than 4, less than 5, less than 6, less than 7, less than 8, less than 9 or less than 10 days following administration of the synthetic antibody. In one embodiment, the method may comprise administration of a first composition comprising a synthetic antibody of the invention by any of the methods described in detail above and administration of a second composition comprising an antiretroviral agent more than 1, more than 2, more than 3, more than 4, more than 5, more than 6, more than 7, more than 8, more than 9 or more than 10 days following administration of the synthetic antibody. In one embodiment, the method may comprise administration of a first composition comprising an antiretroviral agent and administration of a second composition comprising a synthetic antibody of the invention by any of the methods described in detail above less than 1, less than 2, less than 3, less than 4, less than 5, less than 6, less than 7, less than 8, less than 9 or less than 10 days following administration of the antiretroviral agent. In one embodiment, the method may comprise administration of a first composition comprising an antiretroviral agent and administration of a second composition comprising a synthetic antibody of the invention by any of the methods described in detail above more than 1, more than 2, more than 3, more than 4, more than 5, more than 6, more than 7, more than 8, more than 9 or more than 10 days following administration of the antiretroviral agent. In one embodiment, the method may comprise administration of a first composition comprising a synthetic antibody of the invention by any of the methods described in detail above and a second composition comprising an antiretroviral agent concurrently. In one embodiment, the method may comprise administration of a first composition comprising a synthetic antibody of the invention by any of the methods described in detail above and a second composition comprising an antiretroviral agent concurrently. In one embodiment, the method may comprise administration of a single composition comprising a synthetic antibody of the invention and an antiretroviral agent.

Non-limiting examples of antiretrovirals that can be used in combination with the synthetic antibody of the invention include Nucleoside Reverse Transcriptase Inhibitors (NRTIs), Non-Nucleoside Reverse Transcriptase Inhibitors (NNRTIs), Protease Inhibitors (PIs), Fusion Inhibitors, CCRF Antagonists, Integrase Inhibitors, Post-Attachment Inhibitors, Pharmacokinetic Inhibitors, and any combination thereof. Exemplary antiretrovirals include, but are not limited to abacavir, emtricitabine, lamivudine, tenofovir, zidovudine, efavirenz, etravirine, nevirapine, rilpivirine, atazanavir, darunavir, fosamprenavir, ritonavir, saquinavir, tipranavir, enfuvirtide, maraviroc, dolutegravir, raltegravir, ibalizumab, and cobicistat. The present invention has multiple aspects, illustrated by the following non-limiting examples.

12. Generation of Synthetic Antibodies In Vitro and Ex Vivo

In one embodiment, the synthetic antibody is generated in vitro or ex vivo. For example, in one embodiment, a nucleic acid encoding a synthetic antibody can be introduced and expressed in an in vitro or ex vivo cell. Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

13. Use in Combination With Vaccines

The present invention also provides a method of treating, protecting against, preventing disease, and/or inducing an immune response in a subject in need thereof by administering a combination of the synthetic antibody and a vaccine. In one embodiment, the vaccine is a DNA vaccine.

The synthetic antibody and vaccine may be administered using any suitable method such that a combination of the synthetic antibody and vaccine are both present in the subject. In one embodiment, the method may comprise administration of a first composition comprising a synthetic antibody of the invention by any of the methods described in detail above and administration of a second composition comprising an vaccine less than 1, less than 2, less than 3, less than 4, less than 5, less than 6, less than 7, less than 8, less than 9 or less than 10 days following administration of the synthetic antibody. In one embodiment, the method may comprise administration of a first composition comprising a synthetic antibody of the invention by any of the methods described in detail above and administration of a second composition comprising a vaccine more than 1, more than 2, more than 3, more than 4, more than 5, more than 6, more than 7, more than 8, more than 9 or more than 10 days following administration of the synthetic antibody. In one embodiment, the method may comprise administration of a first composition comprising a vaccine and administration of a second composition comprising a synthetic antibody of the invention by any of the methods described in detail above less than 1, less than 2, less than 3, less than 4, less than 5, less than 6, less than 7, less than 8, less than 9 or less than 10 days following administration of the vaccine. In one embodiment, the method may comprise administration of a first composition comprising a vaccine and administration of a second composition comprising a synthetic antibody of the invention by any of the methods described in detail above more than 1, more than 2, more than 3, more than 4, more than 5, more than 6, more than 7, more than 8, more than 9 or more than 10 days following administration of the vaccine. In one embodiment, the method may comprise administration of a first composition comprising a synthetic antibody of the invention by any of the methods described in detail above and a second composition comprising a vaccine concurrently. In one embodiment, the method may comprise administration of a first composition comprising a synthetic antibody of the invention by any of the methods described in detail above and a second composition comprising a vaccine concurrently. In one embodiment, the method may comprise administration of a single composition comprising a synthetic antibody of the invention and a vaccine.

In one embodiment, the vaccine is a DNA vaccine. In one embodiment, the synthetic antibody is a DMAb.

The DNA vaccine and the DMAb may be administered at the same time or at different times. In one embodiment, the DNA vaccine and the DMAb are administered simultaneously. In one embodiment, the DNA vaccine is administered before the DMAb. In one embodiment, the DMAb is administered before the DNA vaccine.

In certain embodiments, the DNA vaccine is administered 1 or more days, 2 or more days, 3 or more days, 4 or more days, 5 or more days, 6 or more days, 7 or more days, 8 or more days, 9 or more days, 10 or more days, 11 or more days, 12 or more days, 13 or more days, or 14 or more days after the DMAb is administered. In certain embodiments, the DNA vaccine is administered 1 or more weeks, 2 or more weeks, 3 or more weeks, 4 or more weeks, 5 or more weeks, 6 or more weeks, 7 or more weeks, 8 or more weeks, 9 or more weeks, or 10 or more weeks after the DMAb is administered. In certain embodiments, the DNA vaccine is administered 1 or more months, 2 or more months, 3 or more months, 4 or more months, 5 or more months, 6 or more months, 7 or more months, 8 or more months, 9 or more months, 10 or more months, 11 or more months, or 12 or more months after the DMAb is administered.

In certain embodiments, the DMAb is administered 1 or more days, 2 or more days, 3 or more days, 4 or more days, 5 or more days, 6 or more days, 7 or more days, 8 or more days, 9 or more days, 10 or more days, 11 or more days, 12 or more days, 13 or more days, or 14 or more days after the DNA vaccine is administered. In certain embodiments, the DMAb is administered 1 or more weeks, 2 or more weeks, 3 or more weeks, 4 or more weeks, 5 or more weeks, 6 or more weeks, 7 or more weeks, 8 or more weeks, 9 or more weeks, or 10 or more weeks after the DNA vaccine is administered. In certain embodiments, the DMAb is administered 1 or more months, 2 or more months, 3 or more months, 4 or more months, 5 or more months, 6 or more months, 7 or more months, 8 or more months, 9 or more months, 10 or more months, 11 or more months, or 12 or more months after the DNA vaccine is administered.

In certain embodiments, the DMAb and DNA vaccine are administered once. In certain embodiments, the DMAb and/or the DNA vaccine are administered more than once. In certain embodiments, administration of the DMAb and DNA vaccine provides a persistent and systemic immune response.

The composition can comprise 1 or more, 2 or more, 3 or more, 4 or more, 5 or more, 6 or more, 7 or more, 8 or more, 9 or more, or 10 or more DNA vaccines encoding an antigen. The composition may comprise 1 or more, 2 or more, 3 or more, 4 or more, 5 or more, 6 or more, 7 or more, 8 or more, 9 or more, or 10 or more DNA encoded synthetic antibodies or fragments thereof.

a. DNA Vaccine

The vaccine can be a DNA vaccine, a peptide vaccine, or a combination DNA and peptide vaccine. The DNA vaccine can include a nucleic acid sequence encoding the antigen. The nucleic acid sequence can be DNA, RNA, cDNA, a variant thereof, a fragment thereof, or a combination thereof. The nucleic acid sequence can also include additional sequences that encode linker, leader, or tag sequences that are linked to the antigen by a peptide bond. The peptide vaccine can include an antigenic peptide, an antigenic protein, a variant thereof, a fragment thereof, or a combination thereof. The combination DNA and peptide vaccine can include the above described nucleic acid sequence encoding the antigen and the antigenic peptide or protein, in which the antigenic peptide or protein and the encoded antigen have the same amino acid sequence The vaccine can induce a humoral immune response in the subject administered the vaccine. The induced humoral immune response can be specific for the antigen. The induced humoral immune response can be reactive with the antigen. The humoral immune response can be induced in the subject administered the vaccine by about 1.5-fold to about 16-fold, about 2-fold to about 12-fold, or about 3-fold to about 10-fold. The humoral immune response can be induced in the subject administered the vaccine by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold.

The humoral immune response induced by the vaccine can include an increased level of neutralizing antibodies associated with the subject administered the vaccine as compared to a subject not administered the vaccine. The neutralizing antibodies can be specific for the antigen. The neutralizing antibodies can be reactive with the antigen. The neutralizing antibodies can provide protection against and/or treatment of infection and its associated pathologies in the subject administered the vaccine.

The humoral immune response induced by the vaccine can include an increased level of IgG antibodies associated with the subject administered the vaccine as compared to a subject not administered the vaccine. These IgG antibodies can be specific for the antigen. These IgG antibodies can be reactive with the antigen. Preferably, the humoral response is cross-reactive against two or more strains of the antigen. The level of IgG antibody associated with the subject administered the vaccine can be increased by about 1.5-fold to about 16-fold, about 2-fold to about 12-fold, or about 3-fold to about 10-fold as compared to the subject not administered the vaccine. The level of IgG antibody associated with the subject administered the vaccine can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to the subject not administered the vaccine.

The vaccine can induce a cellular immune response in the subject administered the vaccine. The induced cellular immune response can be specific for the antigen. The induced cellular immune response can be reactive to the antigen. Preferably, the cellular response is cross-reactive against two or more strains of the antigen. The induced cellular immune response can include eliciting a $CD8^+$ T cell response. The elicited $CD8^+$ T cell response can be reactive with the antigen. The elicited $CD8^+$ T cell response can be polyfunctional. The induced cellular immune response can include eliciting a $CD8^+$ T cell response, in which the $CD8^+$ T cells produce interferon-gamma (IFN-γ), tumor necrosis factor alpha (TNF-α), interleukin-2 (IL-2), or a combination of IFN-γ and TNF-α.

The induced cellular immune response can include an increased $CD8^+$ T cell response associated with the subject administered the vaccine as compared to the subject not administered the vaccine. The $CD8^+$ T cell response associated with the subject administered the vaccine can be increased by about 2-fold to about 30-fold, about 3-fold to about 25-fold, or about 4-fold to about 20-fold as compared to the subject not administered the vaccine. The $CD8^+$ T cell response associated with the subject administered the vaccine can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to the subject not administered the vaccine.

The induced cellular immune response can include an increased frequency of $CD3^+CD8^+$ T cells that produce IFN-γ. The frequency of $CD3^+CD8^+$IFN-$\gamma^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to the subject not administered the vaccine.

The induced cellular immune response can include an increased frequency of $CD3^+CD8^+$ T cells that produce TNF-α. The frequency of $CD3^+CD8^+$TNF-$\alpha^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to the subject not administered the vaccine.

The induced cellular immune response can include an increased frequency of $CD3^+CD8^+$ T cells that produce IL-2. The frequency of $CD3^+CD8^+$IL-$2^+$ T cells associated with the subject administered the vaccine can be increased by at least about 0.5-fold, 1.0-fold, 1.5-fold, 2.0-fold, 2.5-fold, 3.0-fold, 3.5-fold, 4.0-fold, 4.5-fold, or 5.0-fold as compared to the subject not administered the vaccine.

The induced cellular immune response can include an increased frequency of $CD3^+CD8^+$ T cells that produce both IFN-γ and TNF-α. The frequency of $CD3^+CD8^+$IFN-$\gamma^+$ TNF-$\alpha^+$ T cells associated with the subject administered the vaccine can be increased by at least about 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 110-fold, 120-fold, 130-fold, 140-fold, 150-fold, 160-fold, 170-fold, or 180-fold as compared to the subject not administered the vaccine.

The cellular immune response induced by the vaccine can include eliciting a $CD4^+$ T cell response. The elicited $CD4^+$ T cell response can be reactive with the desired antigen. The elicited $CD4^+$ T cell response can be polyfunctional. The induced cellular immune response can include eliciting a $CD4^+$ T cell response, in which the $CD4^+$ T cells produce IFN-γ, TNF-α, IL-2, or a combination of IFN-γ and TNF-α.

The induced cellular immune response can include an increased frequency of $CD3^+CD4^+$ T cells that produce IFN-γ. The frequency of $CD3^+CD4^+$IFN-$\gamma^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to the subject not administered the vaccine.

The induced cellular immune response can include an increased frequency of $CD3^+CD4^+$ T cells that produce TNF-α. The frequency of $CD3^+CD4^+$TNF-$\alpha^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to the subject not administered the vaccine.

The induced cellular immune response can include an increased frequency of $CD3^+CD4^+$ T cells that produce IL-2. The frequency of $CD3^+CD4^+$IL-$2^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 45-fold, 50-fold, 55-fold, or 60-fold as compared to the subject not administered the vaccine.

The induced cellular immune response can include an increased frequency of $CD3^+CD4^+$ T cells that produce both IFN-γ and TNF-α. The frequency of $CD3^+CD4^+$IFN-$\gamma^+$ TNF-$\alpha^+$ associated with the subject administered the vaccine can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to the subject not administered the vaccine.

The vaccine of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The vaccine can further induce an immune response when administered to different tissues such as the muscle or skin. The vaccine can further induce an immune response when administered via electroporation, or injection, or subcutaneously, or intramuscularly b. Antigen

The antigen of the vaccine may be the same antigen across different subtypes of HIV. The vaccine may comprise 1 or more, 2 or more, 3 or more, 4 or more, or 5 or more DNA sequences encoding a particular protein sequence isolated from HIV subtypes A, B, C, D, or other HIV subtypes, or a combination or variant thereof. The antigen of the vaccine may be the same antigen across different subtypes of HIV. The vaccine may comprise 1 or more, 2 or more, 3 or more, 4 or more, or 5 or more consensus DNA sequences encoding a particular protein sequence isolated from HIV subtypes A, B, C, D, or other HIV subtypes, or a combination or variant thereof. The vaccine may comprise a DNA sequence encoding a particular protein sequence isolated from HIV subtype A, a second DNA sequence encoding a particular protein sequence isolated from HIV subtype B, a third DNA sequence encoding a particular protein sequence isolated from HIV subtype C, a fourth DNA sequence encoding a particular protein sequence isolated from HIV subtype D, or a combination thereof. The vaccine may comprise a consensus DNA sequence encoding a particular protein sequence isolated from HIV subtype A, a second consensus DNA sequence encoding a particular protein sequence isolated from HIV subtype B, a third consensus DNA sequence encoding a particular protein sequence isolated from HIV subtype C, a fourth consensus DNA sequence encoding a particular protein sequence isolated from HIV subtype D, or a combination thereof. The vaccine may comprise a consensus DNA sequence or variant thereof encoding a particular HIV subtype A protein sequence or variant thereof, a second consensus DNA sequence or variant thereof encoding a particular HIV subtype B protein sequence or variant thereof, a third consensus DNA sequence or variant thereof encoding a particular HIV subtype C protein sequence or variant thereof, a fourth consensus DNA sequence or variant thereof encoding a particular HIV subtype D protein sequence or variant thereof.

In some embodiments, the HIV antigen can be a subtype A consensus envelope DNA sequence construct, an IgE leader sequence linked to a consensus sequence for Subtype A envelope protein, or a subtype A consensus Envelope protein sequence.

In other embodiments, the HIV antigen can be a subtype B consensus envelope DNA sequence construct, an IgE leader sequence linked to a consensus sequence for Subtype B envelope protein, or a subtype B consensus Envelope protein sequence.

In still other embodiments, the HIV antigen can be a subtype C consensus envelope DNA sequence construct, an IgE leader sequence linked to a consensus sequence for subtype C envelope protein, or a subtype C consensus envelope protein sequence.

In further embodiments, the HIV antigen can be a subtype D consensus envelope DNA sequence construct, an IgE leader sequence linked to a consensus sequence for Subtype D envelope protein, or a subtype D consensus envelope protein sequence.

In some embodiments, the HIV antigen can be a subtype A Nef-Rev consensus envelope DNA sequence construct, an IgE leader sequence linked to a consensus sequence for Subtype A Nef-Rev protein, or a Subtype A Nef-Rev consensus protein sequence.

In some embodiments, the HIV antigen can be a subtype B Nef-Rev consensus envelope DNA sequence construct, an IgE leader sequence linked to a consensus sequence for Subtype B Nef-Rev protein, or a Subtype B Nef-Rev consensus protein sequence.

In some embodiments, the HIV antigen can be a subtype C Nef-Rev consensus envelope DNA sequence construct, an IgE leader sequence linked to a consensus sequence for Subtype C Nef-Rev protein, or a Subtype C Nef-Rev consensus protein sequence.

In some embodiments, the HIV antigen can be a subtype D Nef-Rev consensus envelope DNA sequence construct, an IgE leader sequence linked to a consensus sequence for Subtype D Nef-Rev protein, or a Subtype D Nef-Rev consensus protein sequence.

In other embodiments, the HIV antigen can be a Gag consensus DNA sequence of subtype A, B, C and D DNA sequence construct, an IgE leader sequence linked to a consensus sequence for Gag consensus subtype A, B, C and D protein, or a consensus Gag subtype A, B, C and D protein sequence.

In still other embodiments, the HIV antigen can be a MPol DNA sequence or a MPol protein sequence. The HIV antigen can be nucleic acid or amino acid sequences of Env A, Env B, Env C, Env D, B Nef-Rev, Gag, MPol, or any combination thereof.

In other embodiments, the HIV antigen may be a DNA sequence or consensus sequence of subtype A, B, C, or D encoding gp140 or consensus gp140 protein. In other embodiments, the HIV antigen may be a DNA sequence or consensus sequence of subtype A, B, C, or D encoding gp140 or consensus gp120 protein. In other embodiments, the HIV antigen gp140 peptide sequence or gp140 consensus peptide sequence of subtype A, B, C, or D. In other embodiments, the HIV antigen gp120 peptide sequence or gp140 consensus peptide sequence of subtype A, B, C, or D.

Examples of DNA vaccines encoding HIV antigens include those described in U.S. Pat. No. 8,168,769 and WO2015/073291, the contents of each are fully incorporated by reference In some embodiments, a DNA vaccine encoding a HIV antigen may include a nucleic acid sequence encoding an amino acid sequence comprising one of SEQ ID NO: 136, SEQ ID NO: 138, SEQ ID NO: 140, SEQ ID NO: 142, SEQ ID NO: 144, SEQ ID NO: 146, SEQ ID NO: 147, SEQ ID NO: 148, SEQ ID NO: 149, SEQ ID NO: 150, SEQ ID NO: 151, or SEQ ID NO: 152. In some embodiments, the DNA vaccine encoding a HIV antigen may include a nucleic acid sequence comprising the sequence of one of SEQ ID NO: 135, SEQ ID NO: 137, SEQ ID NO: 139, SEQ ID NO: 141, SEQ ID NO: 143, or SEQ ID NO: 145.

The antigen can affect a mammal, which can be a human, chimpanzee, dog, cat, horse, cow, mouse, or rat. The antigen can be contained in a protein from a mammal, which can be a human, chimpanzee, dog, cat, horse, cow, pig, sheep, mouse, or rat.

c. DNA

The composition may comprise the DNA. Also provided herein is a DNA that encodes the antigen as described above. The DNA can include an encoding sequence that encodes the antigen. The DNA can also include additional sequences that encode linker or tag sequences that are linked to the antigen by a peptide bond.

d. Vector

The composition may comprise a vector that includes the DNA encoding the antigen. The vector can be capable of expressing the antigen. The vector may be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

i. Expression Vectors

The vector may be circular plasmid or a linear nucleic acid vaccine. The circular plasmid and linear nucleic acid are capable of directing expression of a particular nucleotide sequence in an appropriate subject cell. The vector may have a promoter operably linked to the antigen-encoding nucleotide sequence, which may be operably linked to termination signals. The vector may also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

ii. Circular and Linear Vectors

The vector may be circular plasmid, which may transform a target cell by integration into the cellular genome or exist extrachromosomally (e.g. autonomous replicating plasmid with an origin of replication).

The vector can be pVAX, pcDNA3.0, or provax, or any other expression vector capable of expressing the DNA and enabling a cell to translate the sequence to a antigen that is recognized by the immune system. The vector can be combined with antigen at a mass ratio of between 5:1 and 1:5, or of between 1:1 and 2:1.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid may be pNP (Puerto Rico/34) or pM2 (New Caledonia/99). See FIG. 1. The plasmid may be pVAX, pcDNA3.0, or provax, or any other expression vector capable of expressing the DNA and enabling a cell to translate the sequence to a antigen that is recognized by the immune system.

The LEC may be perM2. The LEC may be perNP. perNP and perMR may be derived from pNP (Puerto Rico/34) and pM2 (New Caledonia/99), respectively. See FIG. 34. The LEC may be combined with antigen at a mass ratio of between 5:1 and 1:5, or of between 1:1 to 2:1.

iii. Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

e. Other Components of Vaccine-Adjuvants, Excipients

The composition may further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate is may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in alternative plasmid or are delivered as proteins in combination with the plasmid above in the vaccine. The adjuvant may be selected from the group consisting of: a-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80,CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFP, GM-CSF, epidermal growth factor (EGF), IL-1, IL-2, IL-4, IL-5, IL-6, IL-10, IL-12, IL-18, or a combination thereof.

Other genes that can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, pl50.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

14. Examples

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

The studies presented herein demonstrate in vivo production of broadly neutralizing and non-neutralizing antibodies against HIV-1 by novel DNA encoded mAb technology.

As described herein, an optimized, synthetic DNA vector platform (dMAb) to deliver encoding broadly neutralizing antibodies (bNabs) and non-neutralizing antibodies (non-Nabs) against HIV was designed. Plasmids encoding the heavy and light chain of numerous bNabs were designed. Using various optimization strategies including sequence, formulation, structural and delivery modifications, high levels (1-100 μg/ml) of serum bNabs are generated in mice. Antibody levels are detectable in the serum as early as two days after DNA injection with electroporation. Furthermore, these antibodies from the serum retain functional capabilities including binding to Env and neutralization as measured by the TZM-bl neutralization assay. To lower the possibility of viral escape in a clinical scenario, multiple HIV-1 bNabs can be encoded and expressed simultaneously.

Example 2—DMABs Encoding HIV bnAbs

The studies presented herein demonstrate DNA monoclonal antibodies are able to encode HIV bNabs and non-Nabs.

Figure 3:
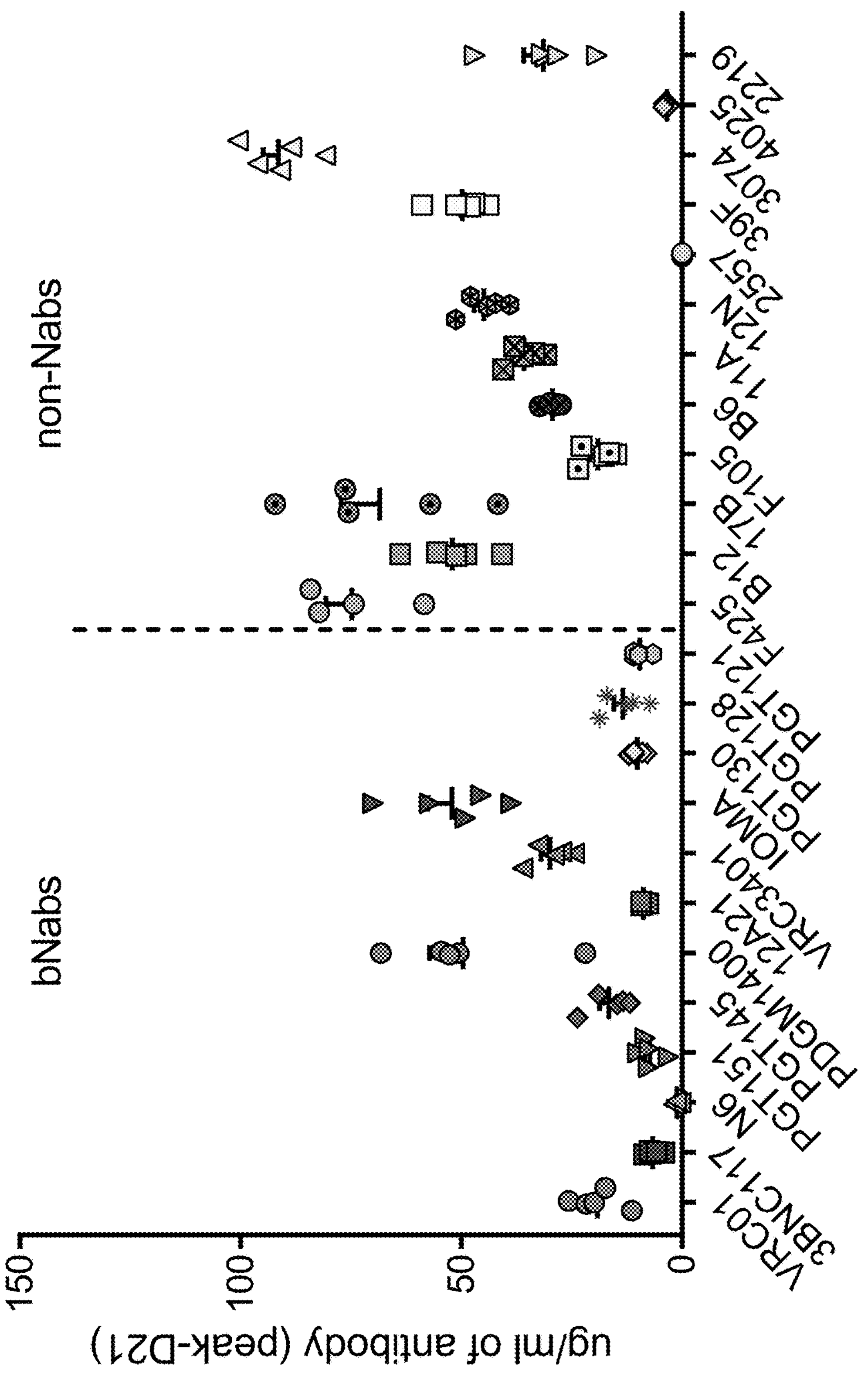
FIG. 3, depicts experimental results demonstrating in vivo expression of HIV dMAb constructs. BalbC mice were injected followed by electroporation with HIV dMAb constructs. Both broadly neutralizing antibodies and non-neutralizing antibodies express in mice.
Figure 4:
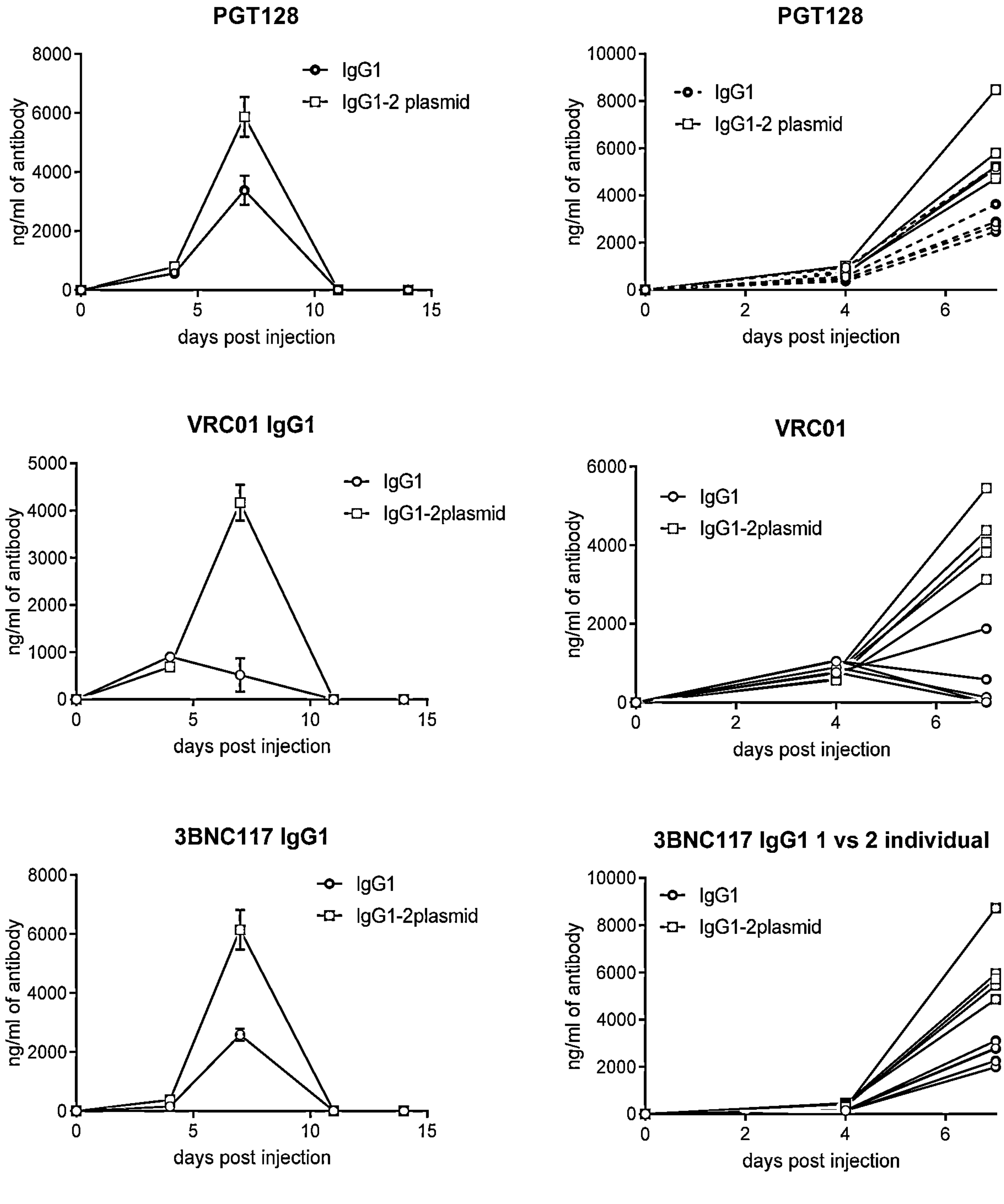
FIG. 4 depicts experimental results demonstrating how two plasmids expressing the heavy and light chain of the IgG1 on separate plasmids can increase expression levels over a single plasmid expressing both the heavy and light chain IgG1 across multiple HIV dMAbs.

Some HIV dMAbs express at very low levels (FIG. 3) thus we initially looked to determine if dMAb levels could be increases when the heavy and light change were encoded on separate plasmids. Encoding the heavy and light chain on two separate plasmids increases in vivo dMAb production of various HIV bNabs over that of single plasmid injection (FIG. 4).

Figures 5A, 5B, 5C:
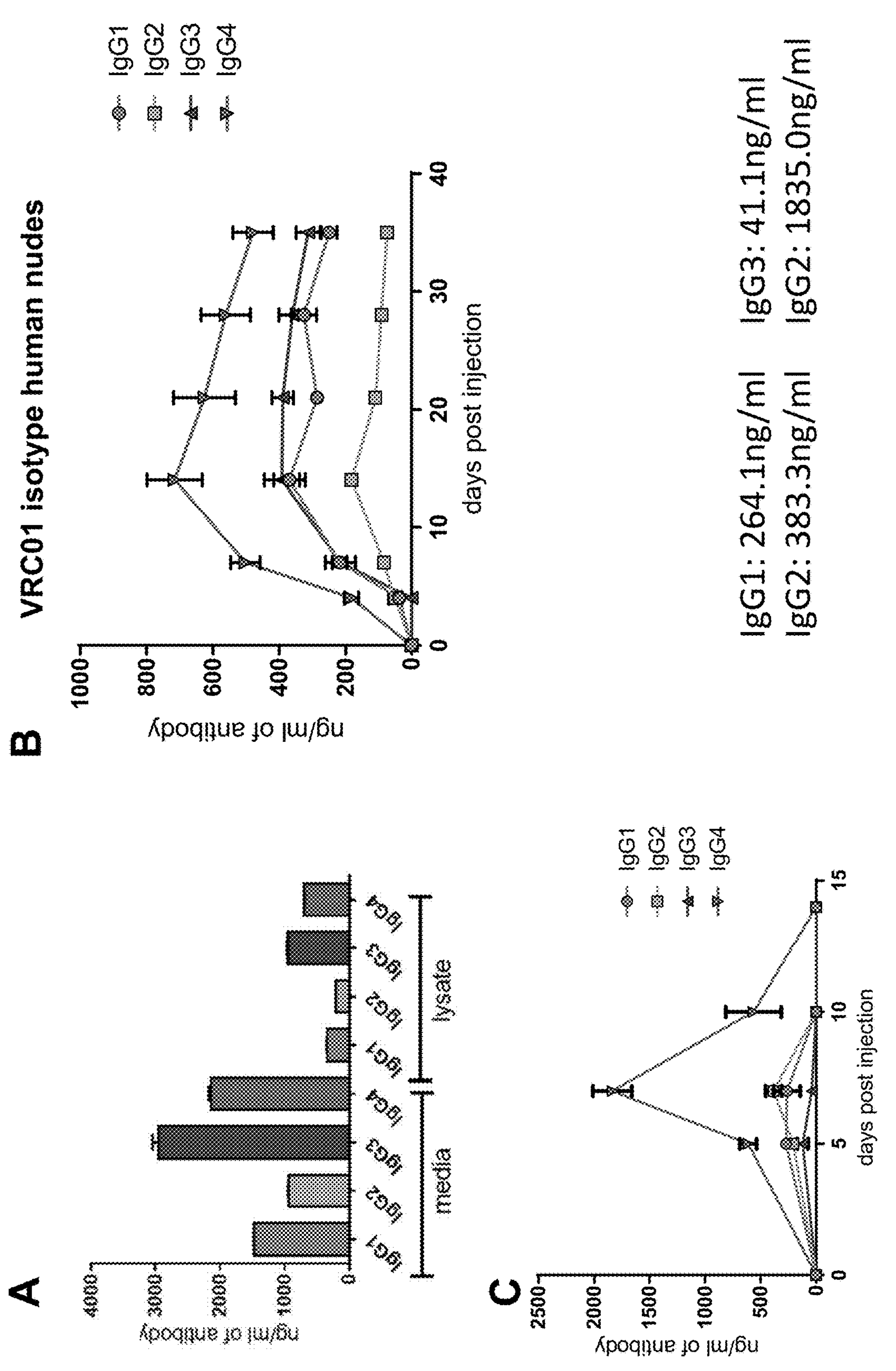
FIG. 5A depicts in vitro expression levels of human IgG1, IgG2, IgG3 and IgG4 isotypes for broadly neutralizing antibody VRC01 for both media and lysate.
FIG. 5B depicts expression levels of human IgG isotypes for VRC01 dMAbs in immune incompetent mice over the course of more than a month.
FIG. 5C depicts expression levels of human IgG isotypes for VRC01 dMAbs in immune competent balbC mice.
Figures 6A, 6B:
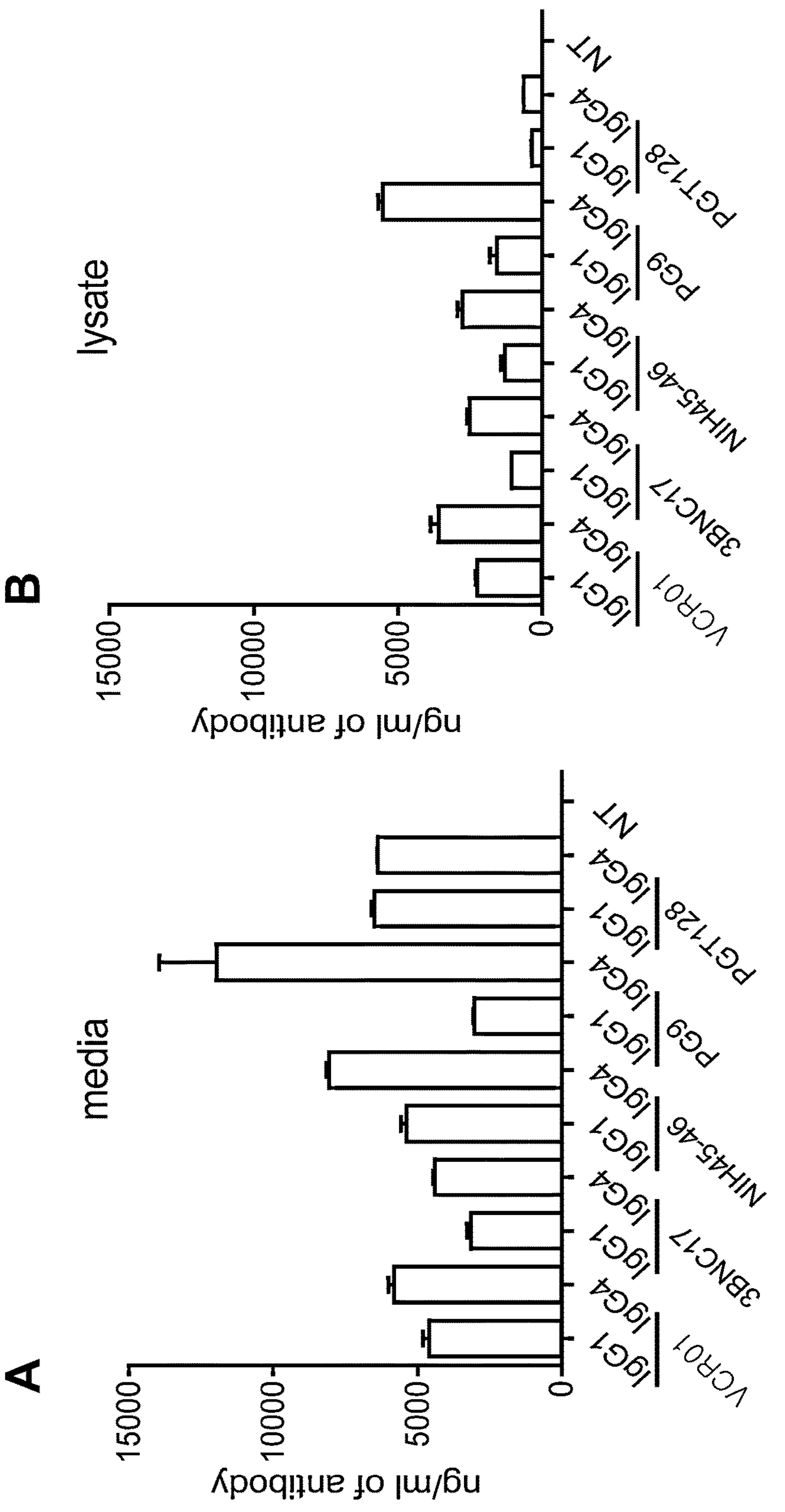
FIG. 6A depicts in vitro expression levels in 293T transfected cell media.
FIG. 6B depicts in vitro expression levels in 293T transfected cell lysate.
Figure 7A:
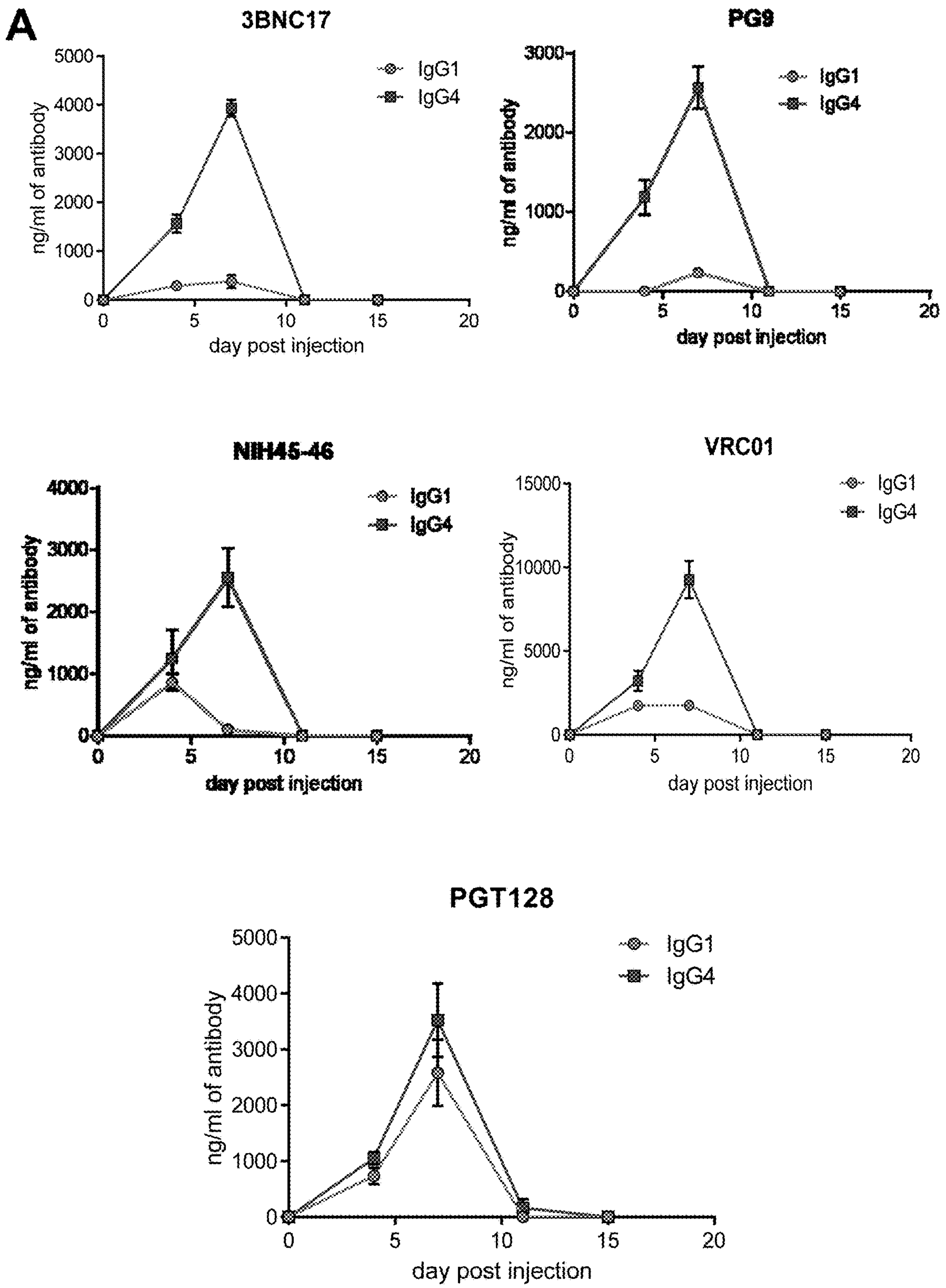
FIG. 7A depict in vivo expression levels over time for 5 HIV dMAbs, PG9, PGT128, 3BNC117, NIH45-46 and VRC01 comparing balbC mice injected with plasmids expressing either the IgG1 or IgG4 isoform.
Figure 7B:
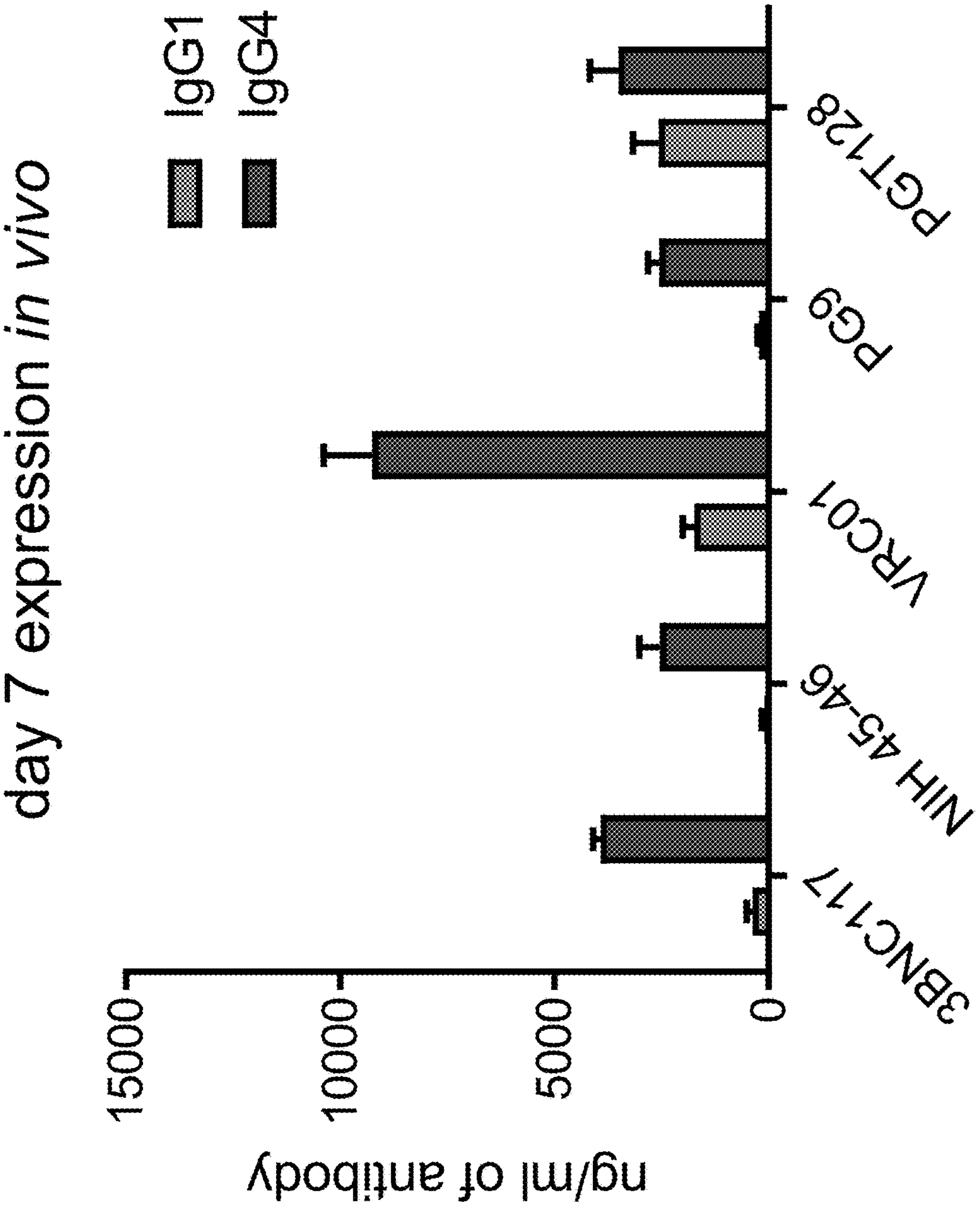
FIG. 7B, depicts peak expression levels on Day 7.

Different IgGs have different effector functions and distributions. Therefore, it was determined whether dMAbs expressing various IgGs have differential expression as well as effector functions. All isotypes of VRCOI express in vitro (FIG. 5A). In nude mice, IgG4 has the highest expression level (FIG. 5B). In BALB/c mice, IgG4 significantly increases VRCOI expression (FIG. 5C). Due to the limited expression in vivo of HIV dMAbs and the increase in VRCOI with IgG4 isotype, we next looked to see IgG4 optimization could be broadly applied to increase the levels of dMAb expression. All IgG4 constructs expressed in vitro in both the cell lysate and media of 293T transfected cells (FIG. 6). Futhermore, IgG4 increased the expression of each of PG9, 3BNC17, NIH 45-46, VRC01, PGT218 over IgG1 (FIGS. 7).

Figure 8A:
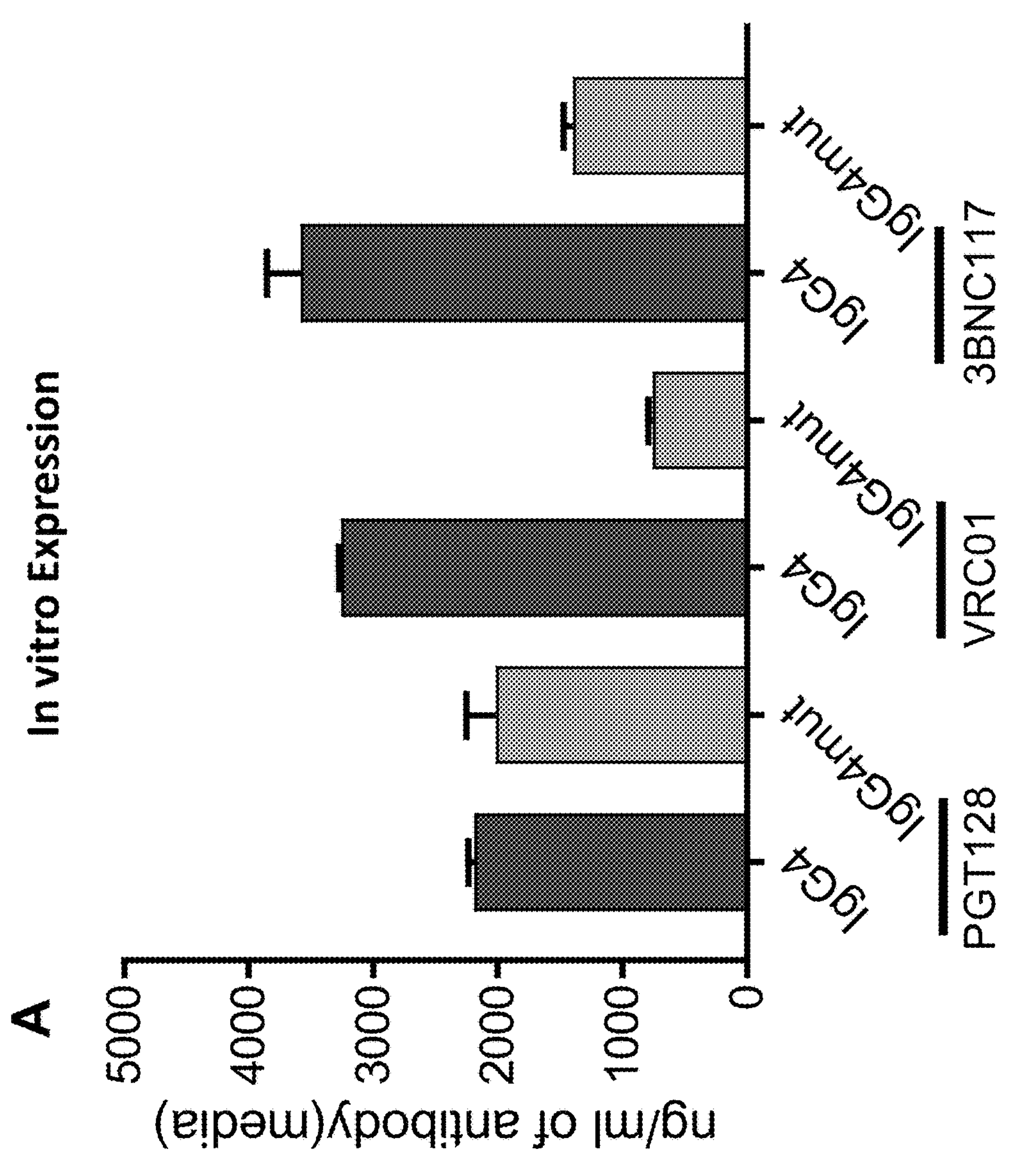
FIG. 8A depicts expression levels of IgG4 and IgG4mut (S228P) in vitro after 293T cells transfection.
Figure 8B:
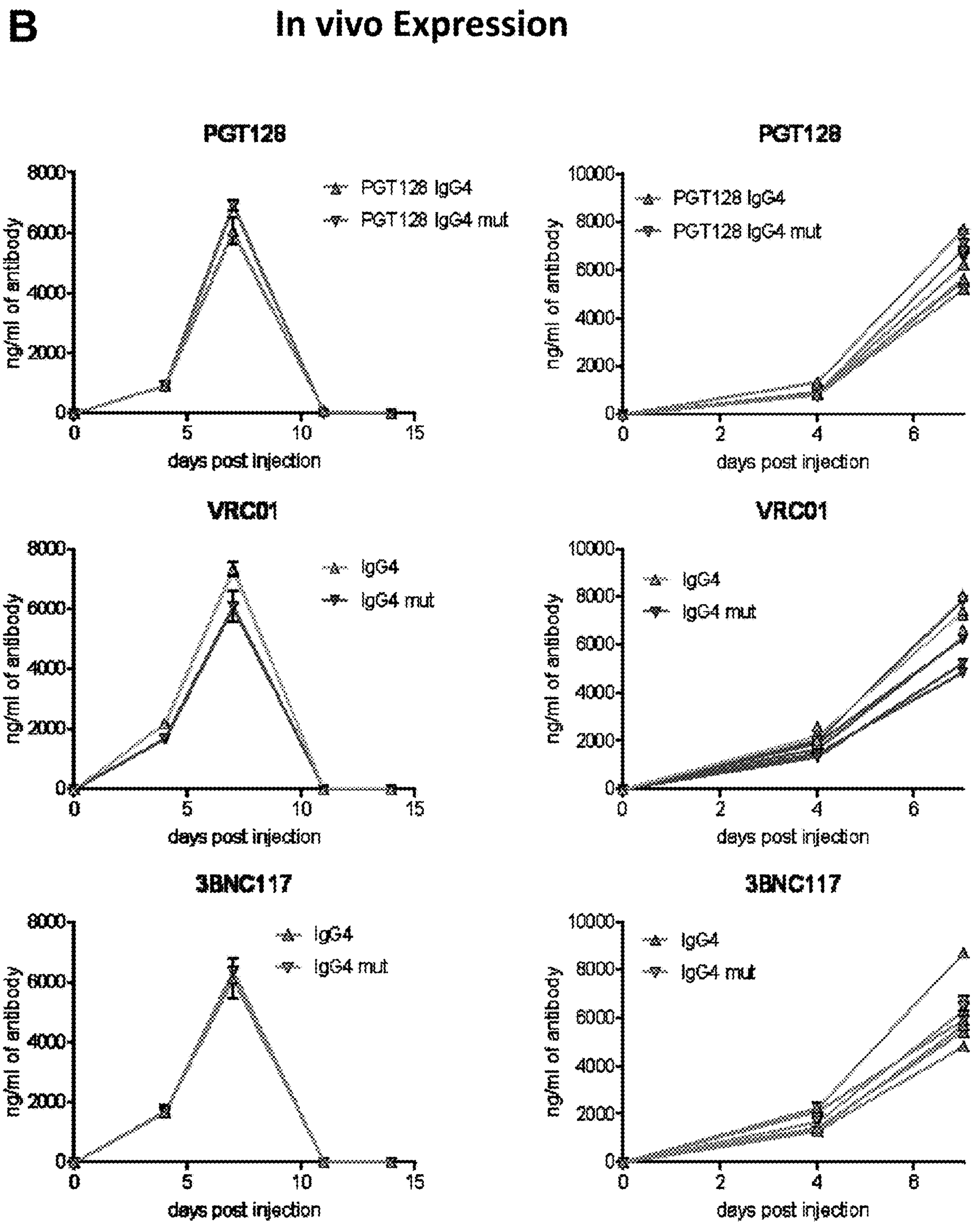
FIG. 8B depicts expression levels in vivo in balbC mice injected with either IgG4 or IgG4mut(S228P) plasmids for PGT128, VRC01, or 3BNC117.
Figure 9:
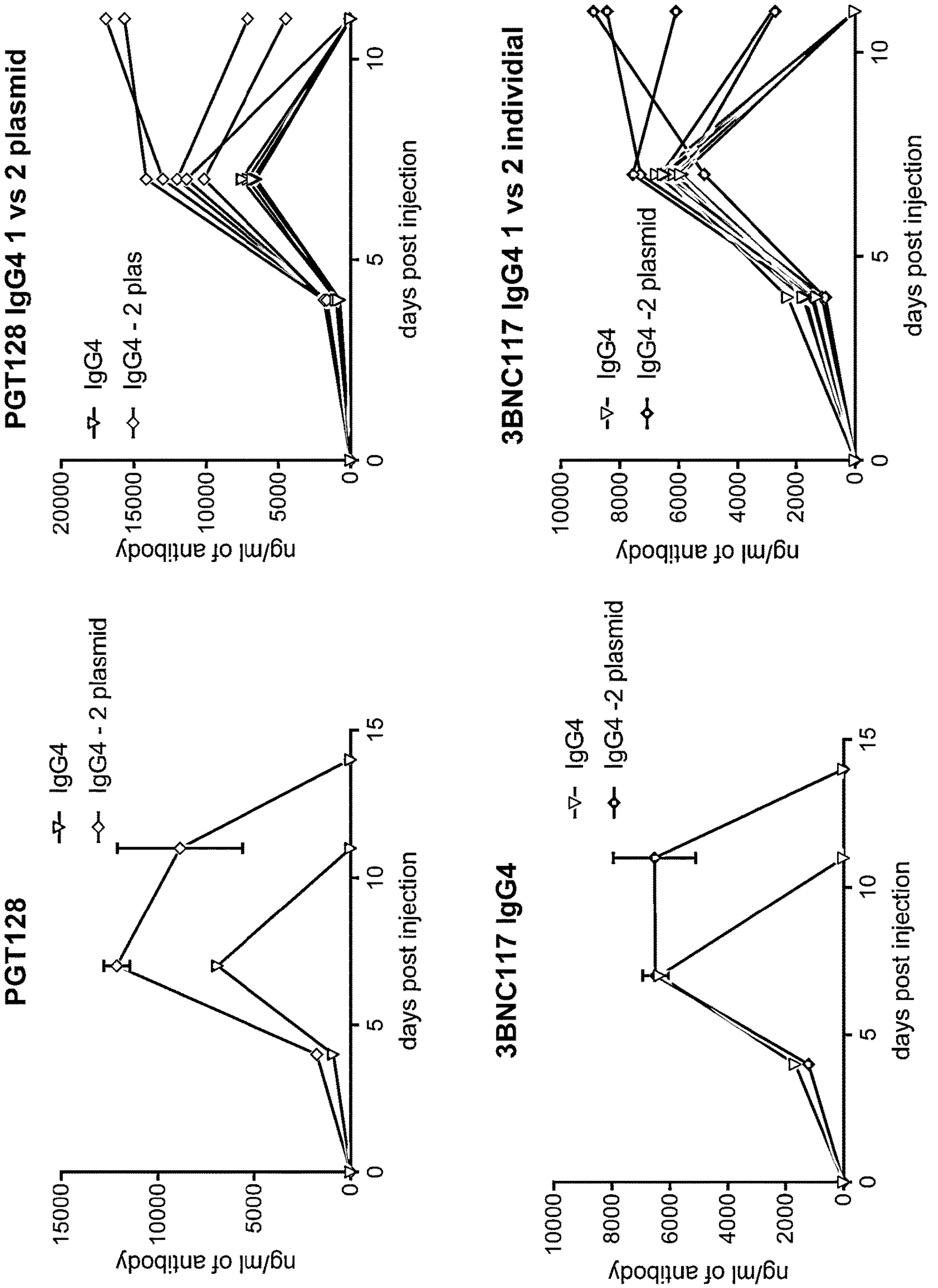
FIG. 9 depicts experimental results demonstrating that two plasmid system increases in vivo dMAb levels over that of single plasmid IgG4.
Figures 10A, 10B:
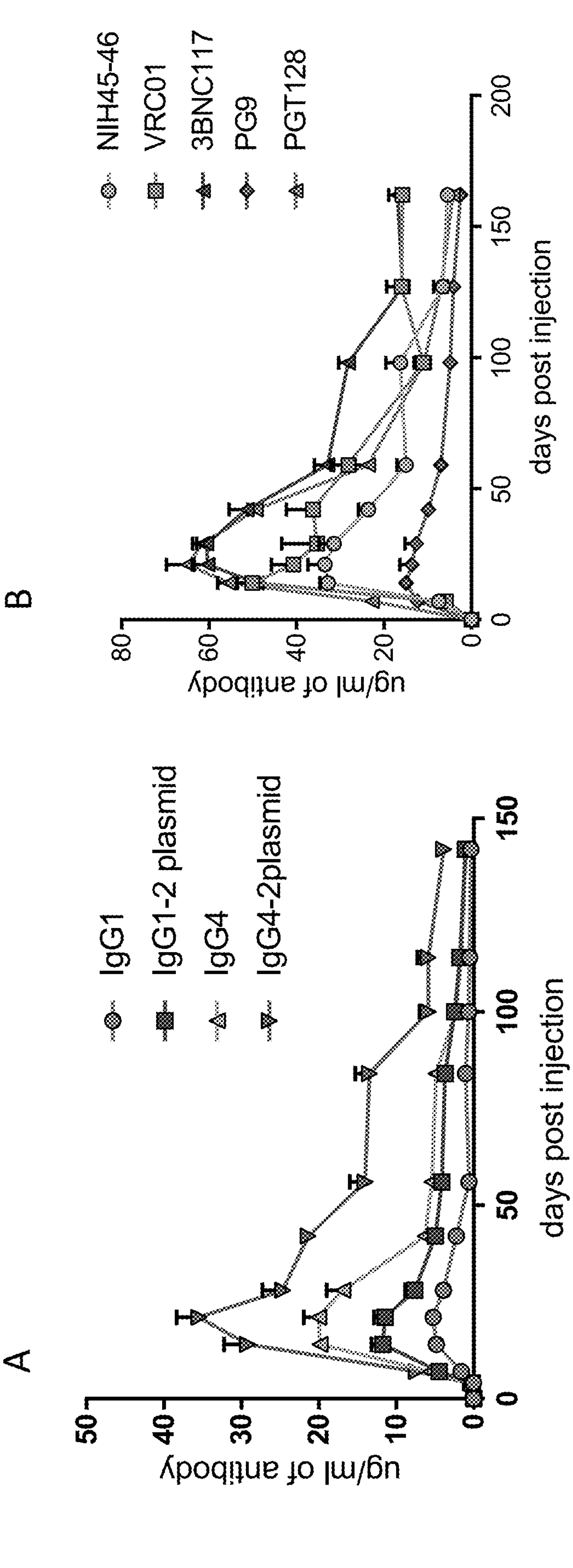
FIG. 10A depicts dMAb expression levels in vivo when balb C mice are immunocompromised and injected with plasmid expressing PGT128 on the IgG1 or IgG4 backbone delivered as either 1 or 2 plasmids.
FIG. 10B shows the generalization of IgG4 2 plasmid expression across 5 HIV dMAbs.
Figure 12:
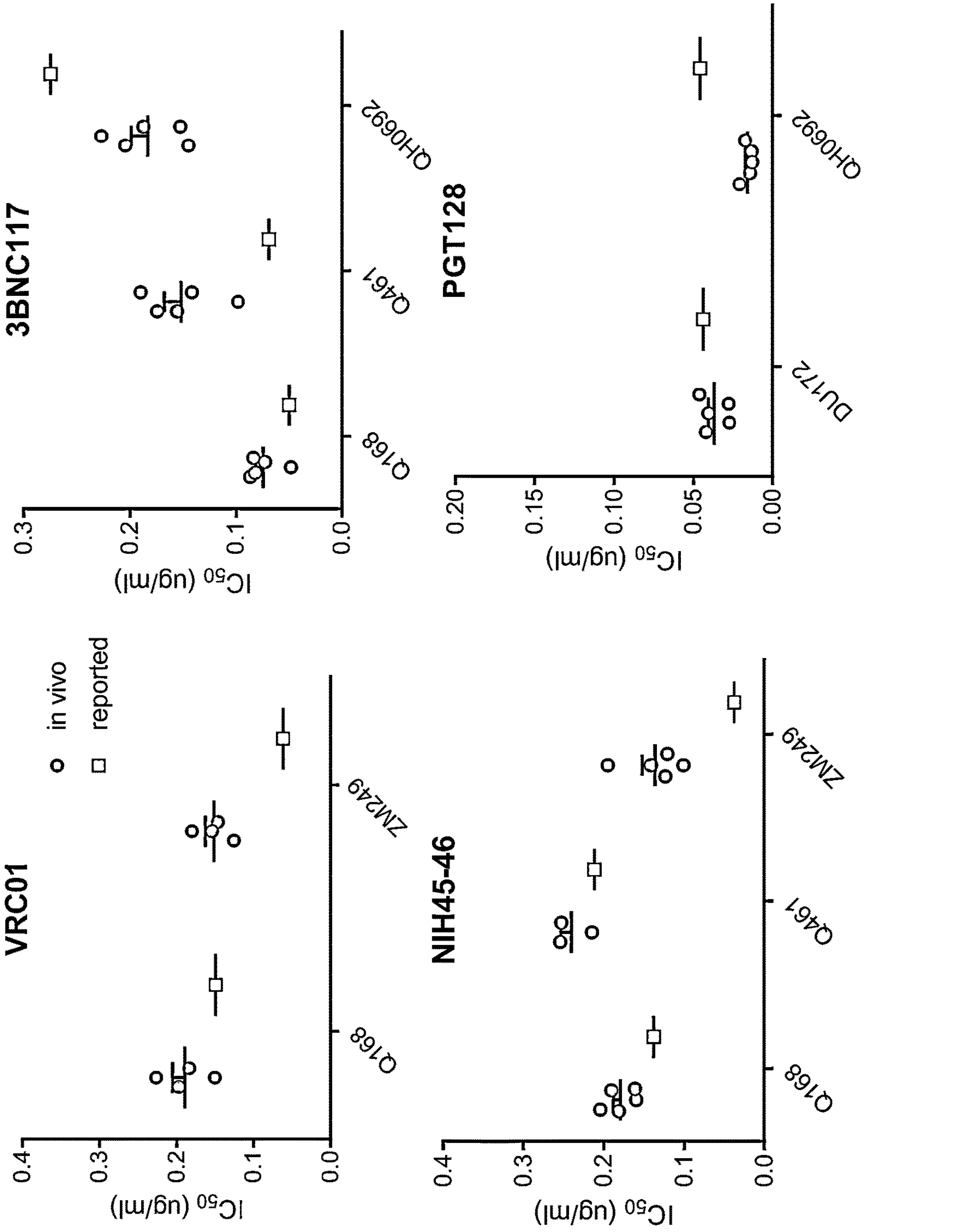
FIG. 12 depicts experimental results demonstrating that in vivo produced IgG4 HIV dMAbs are functional as measured by neutralization capacity in the TzmBl assay. Serum from balbC mice injected with VRC01, 3BNC117, NIH45-46 or PGT128 are able to neutralize multiple pseudotype viruses to similar levels as reported in the literature.

To further increase the level of dMAbs expression, a mutation was made the core-hinge region, Ser228Pro, to block Fab-arm exchange. FIG. 8 demonstrates, that the S228P mutation does not disrupt expression levels. Additionally, encoding the IgG4 heavy and light chain on separate plasmids further increased expression levels and kinetics of HIV dMAbs (FIG. 9). Importantly there was no change in the functionality of these antibodies when testing in the TzmBL assay (FIG. 11 and FIG. 12)

Figure 13:
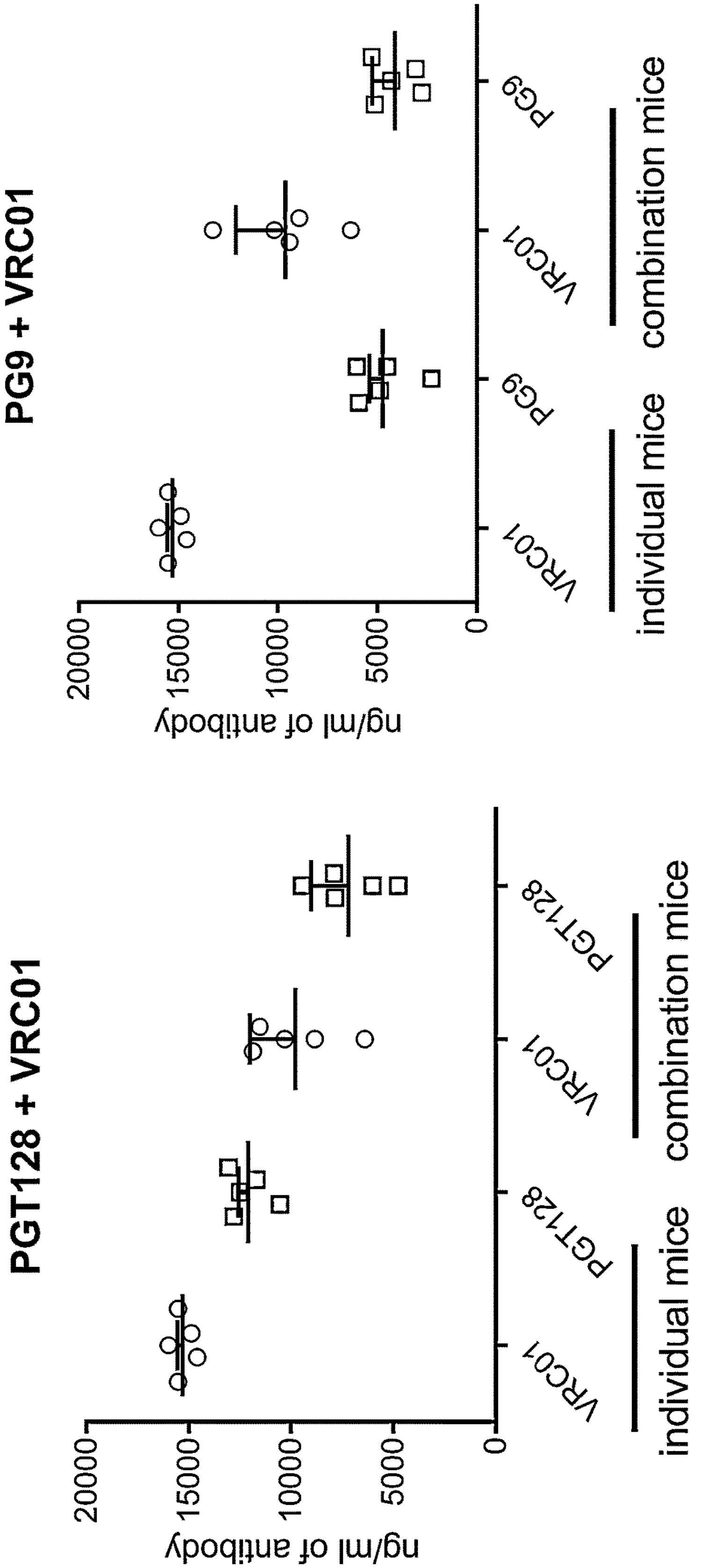
FIG. 13 depicts expression of multiple HIV dMAb in a single mouse. Mice were injected with single plasmid or two plasmids expressing different antibodies. Expression of hIgG was determined on day 7.

It may be beneficial to express multiple HIV bnAbs to have more than 1 site targeted which may decrease the likelihood of viral escape. We have demonstrated that multiple dMAbs expressing two different HIV bNab can be expressed in a single mouse (FIG. 13).

Example 3—Engineering HIV-1 Antibodies and Immunoadhesins for Increased In Vivo Production Using DNA Encoded Monoclonal Antibody Technology The ability of HIV specific broadly neutralizing antibodies (bNabs) to protect or control HIV-1 is well-established in animal models. Though these antibodies are powerful and can prevent infection or control viral loads, the cost of production could severely limit the ability to use these antibodies in the field. Additionally, current vaccine approaches have failed to induce similar antibodies. A novel way to encode and produce bNabs in vivo is described herein using a synthetic DNA encoded monoclonal antibody (dMab) platform.

Engineered plasmids encoding the heavy and light chain of over 20 HIV Envelope (Env) specific antibodies were produced and delivered intramuscularly to mice via electroporation. Initial production levels of many of the antibodies were low; however, using numerous optimization strategies including sequence, formulation, structural modifications and delivery, we can generate high levels (over 80 ug/ml) of serum dMabs in mice. dMabs are detectable in the serum as early as two days after injection and are sustained for over half a year. Additionally, these antibodies retain functional capabilities including binding to Env and neutralization as measured by the TZM-bl neutralization assay. The in vivo produced dMabs have similar neutralization profile and potency as reported with the recombinant purified monoclonal bNabs. To lower the possibility of viral escape, using the dMab platform, we can encode and express multiple HIV-1 bNabs simultaneously in a single mouse. Furthermore, we are exploring the ability to encode and produce bispecific antibodies or other immunoadhesins to increase potency and prevent escape.

The dMab platform represents a novel technique for in vivo antibody production against HIV-1 and possibly other immune targets.

Example 4—Rapid and Long-Term Immunity Elicited by DNA Encoded Antibody Prophylaxis and DNA Vaccination Against HIV Vaccination is known to exhibit a lag phase before generation of immunity; thus, there is a gap of time during infection before an immune response is in effect. The following provides specific novel approaches that utilize the benefit of vaccines and the native immune response along with a rapid generation of effective immunity using the DNA synthetic antibodies or dMabs.

An antibody-based prophylaxis/therapy entailing the electroporation mediated delivery of synthetic plasmids, encoding biologically active anti-Human Immunodeficiency virus (HIV) mAb (designated dMAb), is designed and evaluated for anti-viral efficacy as well as for the ability to overcome shortcomings inherent with conventional active vaccination by a novel passive immune-based strategy. One intramuscular injection of the HIV-dMAb produces antibodies in vivo more rapidly than active vaccination with an HIV-DNA vaccine. This dMAb neutralized diverse HIV clinical isolates and protected mice from viral challenge. Combinations of both afford rapid as well as long-lived protection.

A DNA based dMAb strategy induces rapid protection against an emerging viral infection, which can be combined with DNA vaccination providing a uniquely both short term and long-term protection against this emerging infectious disease. These studies have implications for pathogen treatment and control strategies.

dMAb IgG Quantification and Binding Assays

ELISA assays are performed with sera from subjects administered an HIV-dMAb to quantify expression kinetics and target antigen binding.

Analysis of dMAb Generated IgG

IgG expression of HIV infected cells are analyzed by western blot. For immunofluorescence analysis HIV infected cells are visually evaluated by confocal microscopy and quantitatively or semi-quantitatively analyzed.

dMAb DNA Plasmid Administration and In Vivo Analysis

Expression kinetics and functionality were evaluated in subjects following injection of control or HIV-dMAb. For studies that include the DNA vaccine, the HIV-DNA vaccine plasmid is administered.

Challenge Study

Subjects receive electroporation-enhanced injection of HIV-dMAb or control plasmids. The HIV-DNA vaccine was delivered as described above. After DNA delivery, subjects are challenged with HIV. The animals are monitored for survival and signs of infection. Serum samples are collected for cytokine quantification and other immune analysis. Blood samples are collected from after infection and viremia levels are measured.

Neutralizing Antibody Analysis

Anti-HIV neutralizing antibody titers from subjects administered HIV-dMAb are determined. Neutralization titers may be calculated as the reciprocal of the highest dilution mediating 100% reduction of the cytopathic effects in the cells.

Cytokine Quantitative Analysis

Sera is collected from HIV-dMAb, and HIV-DNA vaccine injected subjects as well as HIV challenged subjects. TNF-α, IL-1β and IL-6 sera cytokine levels are measured.

Anti-HIV dMAbs Design and Confirmation of Expression

The optimized synthetic plasmids constructed from the anti-HIV-neutralizing mAb were designed for the IgG and Fab antibodies. Cells are transfected with either the HIV-IgG plasmid or the HIV-Fab (VL, VH, or combined) plasmids to validate expression in vitro. The HIV-Fab and HIV-IgG expressed antibodies in the muscle that appeared to be properly assembled and biologically functional in vitro.

In Vivo Expression and Quantification of Anti-HIV dMAb

Following confirmation of in vitro expression, the ability of HIV-Fab or HIV-IgG to produce anti-HIV antibodies in vivo is measured. Both constructs generate mAbs. Subjects are administered either HIV-IgG or HIV-Fab, and sera antibody levels are evaluated through a binding ELISA. Sera collected after injection from both HIV-IgG and HIV-Fab bind to HIV protein but not to an unrelated control antigen. These data indicate that in vivo produced anti-HIV antibodies from HIV-IgG or HIV-Fab constructs have similar biological characteristics to conventionally produced antigen specific antibodies.

In Vivo Specificity and Broadly Neutralizing Activity in Sera from Anti-HIV dMAb Injected Subjects The anti-HIV dMAb generated mAbs are tested for binding specificity and anti-HIV neutralizing activity. Sera antibodies bind to HIV-infected cells. There is a strong specificity of the antibody generated from the anti-HIV dMAb plasmid.

Furthermore, the anti-HIV neutralizing activity in sera from subjects that received anti-HIV dMAb is measured against that in HIV strains. Sera from anti-HIV dMAb-injected subjects effectively neutralize HIV isolates, demonstrating that a single injection can produce significant neutralizing levels of human anti-HIV IgG. Thus, antibodies produced in vivo by anti-HIV dMAb constructs have relevant biological activity (i.e., binding and neutralizing activity against HIV).

Anti-HIV dMAb Injection Protects Mice from Lethal HIV Challenge

To determine whether antibodies generated from anti-HIV dMAb provide protection against early exposure to HIV, groups of 10 subjects receive of a control or anti-HIV dMAb on day 0. Each group subsequently is challenged subcutaneously with virus to mimic natural HIV infection. Subject survival and weight changes are subsequently recorded. Anti-HIV dMAb plasmids confer protective immunity.

The longevity of immune protection is next evaluated. A second group of subjects was challenged with HIV after injection with anti-HIV dMAb, or control plasmid on day 0. Subjects are monitored for survival. Anti-HIV dMAb provides a more durable degree of immune protection.

Anti-HIV dMAb protects subjects from both subcutaneous viral challenge and intranasal viral challenge compared with control-injected subjects, demonstrating that anti-HIV dMAbs can protect against systemic and mucosal infection.

An efficacy study comparing the protective efficacy of anti-HIV dMAb administration vs a HIV-DNA vaccine (HIV-DNA) is next performed. A novel consensus-based DNA vaccine was developed by our laboratory and is capable of providing protection against HIV challenge. The DNA vaccine also induced both measurable cellular immune responses, as well as potent neutralizing antibody responses. Groups of subjects are administered a single injection of anti-HIV dMAb, HIV-DNA, or the pVaxl, followed by viral challenge. Anti-HIV dMAb confers protective immunity more rapidly than the HIV-DNA vaccine.

Comparison between In Vivo Protective Immunity Conferred by Anti-HIV dMAb Administration and HIV-DNA Vaccination Next, a long-term HIV challenge protection study was performed following vaccination with the HIV-DNA vaccine or administration of anti-HIV dMAb on day 0. HIV-DNA confers longer protective immunity than anti-HIV dMAb.

Co-Delivery of Anti-HIV dMAb and the HIV-DNA Vaccine Produces Systemic Humoral Immunity, Cell-Mediated Immunity, and Protection In Vivo One potential issue of combining antibody delivery with vaccination approaches is that the antibodies can neutralize many traditional vaccines and thus are incompatible platforms. The effect of co-administration of anti-HIV dMAb and HIV-DNA on subject survival in the context of HIV challenge was is evaluated. Subjects are administered at day 0 anti-HIV dMAb and HIV-DNA. Subsequently, some animals are challenged with HIV at day 2 and the others at day 35. Survival in these groups is followed as a function of time. Anti-HIV dMAb mediates protection from infection, with the survival percentage decreasing to approximately 30% by 4 days after challenge in control (pVax1) animals. Both IgG induced by anti-HIV dMAb and HIV-DNA vaccine are detected. Anti-HIV dMAb mediates rapid protection from infection and death after HIV challenge.

Furthermore, T-cell responses induced in subjects injected with Anti-HIV dMAb, HIV-DNA, or anti-HIV dMAb plus HIV-DNA are evaluated. HIV-DNA elicits strong T-cell responses irrespective of co-delivery with anti-HIV dMAb, showing the lack of interference of these approaches. Conversely, animals administered only anti-HIV dMAb do not develop T-cell responses. Both anti-HIV dMAb and HIV-DNA vaccine can be administered simultaneously without reciprocal interference, providing immediate and long-lived protection via systemic humoral and cellular immunity.

Electroporation-Mediated Delivery of Optimized DNA Plasmids for the In Vivo Rapid Production of Biologically Functional mAbs Subjects administered anti-HIV dMAbs are fully protected from viral challenge shortly after administration, whereas subjects do not survive infection following a single immunization with HIV-DNA vaccine, owing presumably to an insufficient time to mount protective immunity. However, HIV-DNA provides complete protection after an immunization regimen followed by challenge at later time points. A similar level of protection occurs in subjects administered a single dose of anti-HIV dMAbs, although protection wanes over time. Notably, the co-delivery of anti-HIV dMAbs and HIV-DNA produces rapid and persistent humoral and cellular immunity, suggesting that a combination approach can have additive or synergistic effects. Importantly, co-delivery of anti-HIV dMAbs and HIV-DNA are not antagonistic in terms of the development of short- or long-term protective immune responses.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A composition comprising:

a) a nucleic acid molecule encoding a consensus HIV antigen; and b) at least one nucleic acid molecule encoding one or more synthetic antibodies, wherein the at least one nucleic acid molecule comprises at least one of i) a nucleotide sequence encoding an antibody heavy chain comprising an amino acid sequence at least 96% homologous to an amino acid sequence selected from the group consisting of SEQ ID NO:3, SEQ ID NO:11, SEQ ID NO:17, SEQ ID NO:25, SEQ ID NO:39, SEQ ID NO:47, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, and SEQ ID NO:131, and ii) a nucleotide sequence encoding an antibody light chain comprising an amino acid sequence at least 90% homologous to an amino acid sequence selected from the group consisting of SEQ ID NO:5, SEQ ID NO:13, SEQ ID NO:19, SEQ ID NO:27, SEQ ID NO:41, SEQ ID NO:49, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO:105, SEQ ID NO:109, SEQ ID NO:113, SEQ ID NO:117, SEQ ID NO:121, SEQ ID NO:125, SEQ ID NO:129, and SEQ ID NO:133.

2. The composition of claim 1, wherein the composition comprises a single nucleic acid molecule encoding the antibody heavy chain and the antibody light chain and wherein the nucleic acid molecule further comprises a nucleotide sequence encoding a cleavage domain.

3. The composition of claim 1, comprising a combination of a first nucleic acid molecule encoding the antibody heavy chain and a second nucleic acid molecule encoding the antibody light chain.

4. The composition of claim 1, wherein the composition comprises at least one nucleotide sequence encoding one or more amino acid sequences selected from the group consisting of SEQ ID NO:1, SEQ ID NO:3, SEQ ID NO:5, SEQ ID NO:7, SEQ ID NO:9, SEQ ID NO:11, or SEQ ID NO:13, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39 SEQ ID NO:41, SEQ ID NO:43, SEQ ID NO:45, SEQ ID NO:47, SEQ ID NO:49 SEQ ID NO:51, SEQ ID NO:53, SEQ ID NO:55, SEQ ID NO:57, SEQ ID NO:59, SEQ ID NO:61, SEQ ID NO:63, SEQ ID NO: 65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, and SEQ ID NO:133.

5. The composition of claim 1, wherein the composition comprises at least one nucleic acid molecule comprising a nucleotide sequence at least 95% homologous to a nucleic acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, and SEQ ID NO:134.

6. The composition of claim 5, wherein the composition comprises at least one nucleic acid molecule comprising a nucleotide sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, and SEQ ID NO:134.

7. The composition of claim 1, wherein the first nucleotide sequence encodes an amino acid sequence at least 96% homologous to SEQ ID NO:3 and the second nucleotide sequence encodes an amino acid sequence at least 90% homologous to SEQ ID NO:5;

the first nucleotide sequence encodes an amino acid sequence at least 96% homologous to SEQ ID NO:11 and the second nucleotide sequence encodes an amino acid sequence at least 90% homologous to SEQ ID NO:13;

the first nucleotide sequence encodes an amino acid sequence at least 96% homologous to SEQ ID NO:17 and the second nucleotide sequence encodes an amino acid sequence at least 90% homologous to SEQ ID NO:19;

the first nucleotide sequence encodes an amino acid sequence at least 96% homologous to SEQ ID NO:25 and the second nucleotide sequence encodes an amino acid sequence at least 90% homologous to SEQ ID NO:27;

the first nucleotide sequence encodes an amino acid sequence at least 96% homologous to SEQ ID NO:39 and the second nucleotide sequence encodes an amino acid sequence at least 90% homologous to SEQ ID NO:41;

the first nucleotide sequence encodes an amino acid sequence at least 96% homologous to SEQ ID NO:47 and the second nucleotide sequence encodes an amino acid sequence at least 90% homologous to SEQ ID NO:49;

the first nucleotide sequence encodes an amino acid sequence at least 96% homologous to SEQ ID NO:55 and the second nucleotide sequence encodes an amino acid sequence at least 90% homologous to SEQ ID NO:57;

the first nucleotide sequence encodes an amino acid sequence at least 96% homologous to SEQ ID NO:59 and the second nucleotide sequence encodes an amino acid sequence at least 90% homologous to SEQ ID NO:61;

the first nucleotide sequence encodes an amino acid sequence at least 96% homologous to SEQ ID NO:63 and the second nucleotide sequence encodes an amino acid sequence at least 90% homologous to SEQ ID NO:65;

the first nucleotide sequence encodes an amino acid sequence at least 96% homologous to SEQ ID NO:67 and the second nucleotide sequence encodes an amino acid sequence at least 90% homologous to SEQ ID NO:69;

the first nucleotide sequence encodes an amino acid sequence at least 96% homologous to SEQ ID NO:71 and the second nucleotide sequence encodes an amino acid sequence at least 90% homologous to SEQ ID NO:73;

the first nucleotide sequence encodes an amino acid sequence at least 96% homologous to SEQ ID NO:75 and the second nucleotide sequence encodes an amino acid sequence at least 90% homologous to SEQ ID NO:77;

the first nucleotide sequence encodes an amino acid sequence at least 96% homologous to SEQ ID NO:79 and the second nucleotide sequence encodes an amino acid sequence at least 90% homologous to SEQ ID NO:81;

the first nucleotide sequence encodes an amino acid sequence at least 96% homologous to SEQ ID NO:83 and the second nucleotide sequence encodes an amino acid sequence at least 90% homologous to SEQ ID NO:85;

the first nucleotide sequence encodes an amino acid sequence at least 96% homologous to SEQ ID NO:87 and the second nucleotide sequence encodes an amino acid sequence at least 90% homologous to SEQ ID NO:89;

the first nucleotide sequence encodes an amino acid sequence at least 96% homologous to SEQ ID NO:91 and the second nucleotide sequence encodes an amino acid sequence at least 90% homologous to SEQ ID NO:93;

the first nucleotide sequence encodes an amino acid sequence at least 96% homologous to SEQ ID NO:95 and the second nucleotide sequence encodes an amino acid sequence at least 90% homologous to SEQ ID NO:97;

the first nucleotide sequence encodes an amino acid sequence at least 96% homologous to SEQ ID NO:99 and the second nucleotide sequence encodes an amino acid sequence at least 90% homologous to SEQ ID NO:101;

the first nucleotide sequence encodes an amino acid sequence at least 96% homologous to SEQ ID NO:103 and the second nucleotide sequence encodes an amino acid sequence at least 90% homologous to SEQ ID NO:105;

the first nucleotide sequence encodes an amino acid sequence at least 96% homologous to SEQ ID NO:107 and the second nucleotide sequence encodes an amino acid sequence at least 90% homologous to SEQ ID NO:109;

the first nucleotide sequence encodes an amino acid sequence at least 96% homologous to SEQ ID NO:111 and the second nucleotide sequence encodes an amino acid sequence at least 90% homologous to SEQ ID NO:113;

the first nucleotide sequence encodes an amino acid sequence at least 96% homologous to SEQ ID NO:115 and the second nucleotide sequence encodes an amino acid sequence at least 90% homologous to SEQ ID NO:117;

the first nucleotide sequence encodes an amino acid sequence at least 96% homologous to SEQ ID NO:119 and the second nucleotide sequence encodes an amino acid sequence at least 90% homologous to SEQ ID NO:121;

the first nucleotide sequence encodes an amino acid sequence at least 96% homologous to SEQ ID NO:123 and the second nucleotide sequence encodes an amino acid sequence at least 90% homologous to SEQ ID NO:125;

the first nucleotide sequence encodes an amino acid sequence at least 96% homologous to SEQ ID NO:1207 and the second nucleotide sequence encodes an amino acid sequence at least 90% homologous to SEQ ID NO:129; or the first nucleotide sequence encodes an amino acid sequence at least 96% homologous to SEQ ID NO:131 and the second nucleotide sequence encodes an amino acid sequence at least 90% homologous to SEQ ID NO:133.

8. The composition of claim 7, wherein the first nucleotide sequence comprises a nucleotide sequence at least 90% homologous to SEQ ID NO:4 and the second nucleotide sequence comprises a nucleotide sequence at least 90% homologous to SEQ ID NO:6;

the first nucleotide sequence comprises a nucleotide sequence at least 90% homologous to SEQ ID NO:12 and the second nucleotide sequence comprises a nucleotide sequence at least 90% homologous to SEQ ID NO:14;

the first nucleotide sequence comprises a nucleotide sequence at least 90% homologous to SEQ ID NO:18 and the second nucleotide sequence comprises a nucleotide sequence at least 90% homologous to SEQ ID NO:20;

the first nucleotide sequence comprises a nucleotide sequence at least 90% homologous to SEQ ID NO:26 and the second nucleotide sequence comprises a nucleotide sequence at least 90% homologous to SEQ ID NO:28;

the first nucleotide sequence comprises a nucleotide sequence at least 90% homologous to SEQ ID NO:40 and the second nucleotide sequence comprises a nucleotide sequence at least 90% homologous to SEQ ID NO:42;

the first nucleotide sequence comprises a nucleotide sequence at least 90% homologous to SEQ ID NO:48 and the second nucleotide sequence comprises a nucleotide sequence at least 90% homologous to SEQ ID NO:50;

the first nucleotide sequence comprises a nucleotide sequence at least 90% homologous to SEQ ID NO:56 and the second nucleotide sequence comprises a nucleotide sequence at least 90% homologous to SEQ ID NO:58;

the first nucleotide sequence comprises a nucleotide sequence at least 90% homologous to SEQ ID NO:60 and the second nucleotide sequence comprises a nucleotide sequence at least 90% homologous to SEQ ID NO:62;

the first nucleotide sequence comprises a nucleotide sequence at least 90% homologous to SEQ ID NO:64 and the second nucleotide sequence comprises a nucleotide sequence at least 90% homologous to SEQ ID NO:66;

the first nucleotide sequence comprises a nucleotide sequence at least 90% homologous to SEQ ID NO:68 and the second nucleotide sequence comprises a nucleotide sequence at least 90% homologous to SEQ ID NO:70;

the first nucleotide sequence comprises a nucleotide sequence at least 90% homologous to SEQ ID NO:72 and the second nucleotide sequence comprises a nucleotide sequence at least 90% homologous to SEQ ID NO:74;

the first nucleotide sequence comprises a nucleotide sequence at least 90% homologous to SEQ ID NO:76 and the second nucleotide sequence comprises a nucleotide sequence at least 90% homologous to SEQ ID NO:78;

the first nucleotide sequence comprises a nucleotide sequence at least 90% homologous to SEQ ID NO:80 and the second nucleotide sequence comprises a nucleotide sequence at least 90% homologous to SEQ ID NO:82;

the first nucleotide sequence comprises a nucleotide sequence at least 90% homologous to SEQ ID NO:84 and the second nucleotide sequence comprises a nucleotide sequence at least 90% homologous to SEQ ID NO:86;

the first nucleotide sequence comprises a nucleotide sequence at least 90% homologous to SEQ ID NO:88 and the second nucleotide sequence comprises a nucleotide sequence at least 90% homologous to SEQ ID NO:90;

the first nucleotide sequence comprises a nucleotide sequence at least 90% homologous to SEQ ID NO:92 and the second nucleotide sequence comprises a nucleotide sequence at least 90% homologous to SEQ ID NO:94;

the first nucleotide sequence comprises a nucleotide sequence at least 90% homologous to SEQ ID NO:96 and the second nucleotide sequence comprises a nucleotide sequence at least 90% homologous to SEQ ID NO:98;

the first nucleotide sequence comprises a nucleotide sequence at least 90% homologous to SEQ ID NO:100 and the second nucleotide sequence comprises a nucleotide sequence at least 90% homologous to SEQ ID NO:102;

the first nucleotide sequence comprises a nucleotide sequence at least 90% homologous to SEQ ID NO:104 and the second nucleotide sequence comprises a nucleotide sequence at least 90% homologous to SEQ ID NO:106;

the first nucleotide sequence comprises a nucleotide sequence at least 90% homologous to SEQ ID NO:108 and the second nucleotide sequence comprises a nucleotide sequence at least 90% homologous to SEQ ID NO:110;

the first nucleotide sequence comprises a nucleotide sequence at least 90% homologous to SEQ ID NO:112 and the second nucleotide sequence comprises a nucleotide sequence at least 90% homologous to SEQ ID NO:114;

the first nucleotide sequence comprises a nucleotide sequence at least 90% homologous to SEQ ID NO:116 and the second nucleotide sequence comprises a nucleotide sequence at least 90% homologous to SEQ ID NO:118;

the first nucleotide sequence comprises a nucleotide sequence at least 90% homologous to SEQ ID NO:120 and the second nucleotide sequence comprises a nucleotide sequence at least 90% homologous to SEQ ID NO:122;

the first nucleotide sequence comprises a nucleotide sequence at least 90% homologous to SEQ ID NO:124 and the second nucleotide sequence comprises a nucleotide sequence at least 90% homologous to SEQ ID NO:126;

the first nucleotide sequence comprises a nucleotide sequence at least 90% homologous to SEQ ID NO:128 and the second nucleotide sequence comprises a nucleotide sequence at least 90% homologous to SEQ ID NO:130; or the first nucleotide sequence comprises a nucleotide sequence at least 90% homologous to SEQ ID NO:132 and the second nucleotide sequence comprises a nucleotide sequence at least 90% homologous to SEQ ID NO:134.

9. The composition of claim 1, wherein the composition comprises a combination of expression vectors.

10. The composition of claim 1, further comprising a pharmaceutically acceptable excipient.

11. A method of inducing an immune response in a subject, the method comprising administering to the subject the composition of claim 1.

12. A nucleic acid molecule encoding one or more synthetic antibodies, wherein the nucleic acid molecule comprises a nucleotide sequence encoding an IgG4 synthetic antibody, wherein the IgG4 antibody comprises a Ser288Pro amino acid substitution.

13. The nucleic acid molecule of claim 12, wherein the Ser288Pro amino acid substitution prevents IgG4 Fab arm switching.

* * * * *